US007122361B2

(12) United States Patent
Liu et al.

(10) Patent No.: US 7,122,361 B2
(45) Date of Patent: Oct. 17, 2006

(54) COMPOSITIONS EMPLOYING A NOVEL HUMAN KINASE

(75) Inventors: Wei Liu, Sudbury, MA (US); Leeying Wu, Lexington, MA (US)

(73) Assignee: Wyeth, Madison, NJ (US)

( * ) Notice: Subject to any disclaimer, the term of this patent is extended or adjusted under 35 U.S.C. 154(b) by 398 days.

(21) Appl. No.: 10/684,190

(22) Filed: Oct. 10, 2003

(65) Prior Publication Data

US 2004/0096889 A1    May 20, 2004

Related U.S. Application Data

(60) Provisional application No. 60/417,209, filed on Oct. 10, 2002.

(51) Int. Cl.
*C12N 9/12* (2006.01)
(52) U.S. Cl. ............... 435/194; 435/252.3; 435/320.1; 536/23.2
(58) Field of Classification Search ................ 435/194, 435/252.3, 320.1; 536/23.2
See application file for complete search history.

(56) References Cited

U.S. PATENT DOCUMENTS

| | | | |
|---|---|---|---|
| 4,489,710 A | 12/1984 | Spitler | |
| 4,522,811 A | 6/1985 | Eppstein et al. | |
| 4,569,789 A | 2/1986 | Blattler et al. | |
| 4,625,014 A | 11/1986 | Senter et al. | |
| 4,638,045 A | 1/1987 | Kohn et al. | |
| 4,671,958 A | 6/1987 | Rodwell et al. | |
| 4,751,180 A | 6/1988 | Cousens et al. | |
| 4,935,233 A | 6/1990 | Bell et al. | |
| 5,459,039 A | 10/1995 | Modrich et al. | |
| 5,498,531 A | 3/1996 | Jarrell | |
| 5,919,619 A | 7/1999 | Tullis | |
| 6,506,559 B1 | 1/2003 | Fire et al. | |
| 6,759,222 B1 | 7/2004 | Meyers | |
| 2004/0038881 A1 | 2/2004 | Bandman et al. | |

FOREIGN PATENT DOCUMENTS

| | | |
|---|---|---|
| WO | WO 89/10134 | 11/1989 |
| WO | WO 97/07668 | 3/1997 |
| WO | WO 97/07669 | 3/1997 |
| WO | WO 99/14346 | 3/1999 |
| WO | WO 99/27132 | 6/1999 |
| WO | WO 00/44895 | 8/2000 |
| WO | WO 00/63364 | 10/2000 |
| WO | WO 00/73469 A2 | 12/2000 |
| WO | WO 01/29058 | 4/2001 |
| WO | WO 01/36646 | 5/2001 |
| WO | WO 01/66594 A2 | 9/2001 |
| WO | WO 01/68836 | 9/2001 |
| WO | WO 01/70949 | 9/2001 |
| WO | WO 01/75067 A2 | 10/2001 |
| WO | WO 01/75164 | 10/2001 |
| WO | WO 01/92513 | 12/2001 |
| WO | WO 02/08399 | 1/2002 |
| WO | WO 02/18557 A2 | 3/2002 |
| WO | WO 02/24924 | 3/2002 |
| WO | WO 02/24924 A2 | 3/2002 |
| WO | WO 02/46384 A2 | 6/2002 |
| WO | WO 02/081731 A2 | 10/2002 |
| WO | WO 03/050084 A2 | 6/2003 |
| WO | 2004/032877 | 4/2004 |

OTHER PUBLICATIONS

Altschul et al.; "*Gapped Blast and Psi-Blast: A New Generation of Protein Database Search Programs*", Nucleic Acids Research, 1997, pp. 3389-3402, vol. 25, No. 17, Oxford University Press.
Berger P. et al.; "*Loss of Phosphatase Activity in Myotubularin-Related Protein 2 is Associated with Charcot-Marie Tooth Disease Type 4B1*", Human Molecular Genetics, 2002, pp. 1569-1579, vol. 11, No. 13, Oxford University Press.
Boe R. et al.; "*The Protein Phosphatase Inhibitor Okadaic Acid Induces Morphological Changes Typical of Apoptosis in Mammalian Cells*", Experimental Cell Research 195, 1991, pp. 237-246, Academic Press, Inc.
Bottini N. et al.; "*Low-Molecular-Weight Protein Tyrosine Phosphatase and Human Disease: In Search of Biochemical Mechanisms*", Archivum Immunologiae et Therapiae Experimentalis, 2002 pp. 95-104, vol. 50.
Brown-Shimer, et al.; "*Effect of Protein Tyrosine Phosphatase 1b Expression on Transformation by the Human neu Oncogene*", Cancer Research, 52, 1992, pp. 478-480.
Chen et al.; "*The Myotonic Dystrophy Kinase-Related Cdc42-Binding Kinase is Involved in the Regulation of Neurite Outgrowth in PC12 Cells*", The Journal of Biological Chemistry 1999, pp. 19901-19905, vol. 274, No. 28, The American Society for Biochemistry and Molecular Biology, Inc.
Delagrave et al.; "*Recursive Ensemble Mutagenesis*", Protein Engineering, 1993, pp. 327-331, vol. 6 No. 3, Oxford University Press.
Dong et al.; "*Cdc42 Antagonizes Inductive Action of cAMP on Cell Shape, via Effects of the Myotonic Dystropht Kinase-Related Cdc42-Binding Kinase (MRCK) on Myosin Light Chain Phosphorylation*", European Journal of Cell Biology Apr. 2002, pp. 231-242, vol. 81.
Engleman et al.; "*Identifying Nonpolar Transbilayer Helices in Amino Acid Sequences of Membrane Proteins*", Ann. Rev. Biophys. Chem. 1986, pp. 321-353, vol. 15, Annual Reviews Inc.
Florea et al.; "*A Computer Program for Aligning a cDNA Sequence with a Genomic DNA Sequence*", Genome Research 1998, pp. 967-974, vol. 8, Cold Spring Harbor Laboratory Press.

(Continued)

Primary Examiner—Tekchand Saidha
(74) Attorney, Agent, or Firm—Kirkpatrick & Lockhart Nicholson Graham LLP

(57) ABSTRACT

This invention provides compositions, organisms and methodologies employing a novel human protein kinase, HPK3P23. The novel human kinase has sequence homology to the catalytic domains of several protein kinases. The gene encoding this novel protein kinase is localized in or near the 3p23 locus of the human chromosome 3. The sequence similarity between the novel human protein and the catalytic domain of protein kinases indicates that the novel human protein may function as a protein kinase.

2 Claims, 3 Drawing Sheets

OTHER PUBLICATIONS

Gossen et al.; "*Transcriptional Activation by Tetracyclines in Mammalian Cells*", Science Jun. 23, 1995, pp. 1766-1769, vol. 268.

Guatelli et al.; "*Isothermal, In Vitro Amplification of Nucleic Acids by a Multienzyme Reaction Modeled After Retroviral Replication*", Pro. Natl. Acad. Sci. USA, Mar. 1990, pp. 1874-1878, vol. 87.

Haseloff et al.; "*Simple RNA Enzymes with New and Highly Specific Endoribonuclease Activities*", Nature, Aug. 18, 1988, pp. 585-591, vol. 334.

Hyrup et al.; "*Peptide Nucleic Acids (PNA): Synthesis, Properties and Potential Applications*", Bioorganic & Medicinal Chemistry, 1996, pp. 5-23, vol. 4, No. 1, Elsevier Science Ltd., Great Britain.

Ishida et al.; "*Treatment of Myeloid Leukemic Cells with the Phosphatase Inhibitor Okadaic Acid Induces Cell Cycle Arrest at Either G1/S or G2/M Depending on Dose*", Journal of Cellular Physiology, 1992, pp. 484-492.

Janssens et al.; "*Protein Phosphatase 2A: A Highly Regulated Family of Serine/Threonine Phosphatases Implicated in Cell Growth and Signaliing,*" Biochem, J., 353, 2001, pp. 417-43.

Kedra et al.; "*The Germinal Center Kinase Gene and a Novel CDC25-Like Gene are Located in the Vicinity of the PYGM Gene on 11q13*", Hum. Genet., 1997, pp. 611-619, vol. 100.

Keen et al.; *Rapid Detection of Single Base Mismatches as Heteroduplexes on Hydrolink Gels*, Trends in Genetics, 1997, p. 5, vol. 7.

Kwoh et al.; "*Transcription-Based Amplification System and Detection of Amplified Human Immunodeficiency Virus Type 1 with a Bead-Based Sandwich Hybridization Format*", Proc. Natl., Acad. Sci. USA, Feb. 1989, pp. 1173-1177, vol. 86.

Lam et al.; "*Characterization of a Monoclonal Antibody Panel Shows that the Myotonic Dystrophy Protein Kinase, DMPK, is Expressed Almost Exclusively in Muscle and Heart*", Human Molecular Genetics, 2000, pp. 2167-2173, vol. 9, No. 4, Oxford University Press.

Lee et al.; "*Expression of Small Interfering RNAs Targeted Against HIV-1 rev Transcripts in Human Cells*", Nature Biotechnology, May 2002, pp. 500505, vol. 19.

Leung et al.; "*Myotonic Dystrophy Kinase-Related Cdc42-Binding Kinase Acts as a Cdc42 Effector in Promoting Cytoskeletal Reorganization*", Molecular and Cellular Biology, Jan. 1998, pp. 130-140, vol. 18, No. 1, American Society for Microbiology.

Lizardi et al.; "*Exponential Amplification of Recombinant-RNA Hybridization Probes*", Biotechnology, Oct. 1988, pp. 1197-1202, vol. 6.

Maratea et al.; "*Deletion and Fusion Analysis of the Phage Øx174 Lysis Gene E*", Gene, 1985, pp. 39-46, vol. 40, Elsevier Science Publishers.

Meyers et al.; "*Optimal Alignments in Linear Space*", Cabios, 1988, pp. 11-17, vol. 4, No. 1, Press Limited, Oxford England.

Murphy et al.; "*Genetic Construction, Expression, and Melanoma-Selective Cytotoxicity of a Diphtheria Toxin-Related α-Melanoma-Stimulating Hormone Fusion Protein*", Proc. Natl. Aca. Sci. USA, Nov. 1986, pp. 8258-8262, vo. 83.

Needleman et al.; "*A General Method Applicable to the Search for Similarities in the Amino Acid Sequence of Tow Proteins*", J. Mol. Bio., 1970, pp. 443-453, vol. 48.

No et al.; "*Ecdysone-Inducible Gene Expression in Mammalian Cells and Transgenic Mice*", Proc. Natl. Acad. Sci. USA, Apr. 1996, pp. 3346-3351, vol. 93.

Nomura et al.; "*Enhancement by Cyclosporin A of Taxol-Induced Apoptosis of Human Urinary Bladder Cancer Cells*", Urol Res, 2002, pp. 102-111, vol. 30.

O'Gorman et al.; "*Recombinase-Mediated Gene Activation and Site-Specific Integration in Mammalian Cells*", Science, Mar. 1991, pp. 1351-1355.

Rosenbaum et al.; "*Temperature-Gradient Gel Electrophoresis*", Biophysical Chemistry, 1987, pp. 235-246, vol. 26.

Saiki et al.; "*Genetic Analysis of Amplified DNA with Immobilized Sequence-Specific Oligonucleotide Probes*", Proc. Natl. Acad. Sci. USA, Aug. 1989, pp. 6230-6234, vol. 86.

Straub et al.; "*Genome-Wide Scans of Three Independent Sets of 90 Irish Multiplex Schizophrenia Families and Follow-Up of Selected Regions in All Families Provides Evidence for Multiple Susceptibility Genes*", Mol. Psychiatry, 2002, pp. 542-559, vol. 7, No. 6.

Sui et al.; "*A DNA Vector-Based RNAi Technology to Suppress Gene Expression in Mammalian Cells*", Proc. Natl. Acad. Sci., Apr. 16, 2002, pp. 5515-5520, vol. 99, No. 8.

Tan et al.; "*Phosphorylation of a Novel Myosin Binding Subunit of Protein Phosphatase 1 Reveals a Conserved Mechanism in the Regulation of Actin Cytoskeleton*", The Journal of Biological Chemistry, 2001, pp. 21209-21216, vol. 276, No. 24.

Tan et al.; "*Intermolecular and Intramolecular Interactions Regulate Catalytic Activity of Myotonic Dystrophy Kinase-Related Cdc42-Binding Kinase α*", Molecular and Cellular Biology, Apr. 2001, pp. 2767-2778, vol. 21, No. 8.

Wang et al.; "*Ligand-Inducible and Liver-Specific Target Gene Expression in Transgenic Mice*", Nature Biotechnology, Mar. 1997, pp. 239-243, vol. 15.

Wary et al.; "*A Homozygous Deletion Within the Carbonic Anhydrase-Like Domain of the Ptprg Gene in Murine L-Cells*", Cancer Research, Apr. 1, 1993, pp. 478-482, vol. 53.

Wilmut et al.; "*Viable Offspring Derived from Fetal and Adult Mammalian Cells*", Letters to Nature, Feb. 1997, 810-813, vol. 385.

Ye et al.; "*Regulated Delivery of Therapeutic Proteins After In Vivo Somatic Cell Gene Transfer,* " Science, Jan. 1999, pp. 88-91, vol. 283.

Zhao et al.; "*Reversible Modification of Tissue-Type Plasminogen Activator by Methyphosphonate Esters,*" Bioorganic & Medicinal Chemistry, 1996, pp. 523-529, vol. 4.

Zy; "*Protein Tyrosine Phosphatases: Structure and Function, Substrate Specificity, and Inhibitor Development,*" Annu Rev Pharmacol Toxicol, 2002, pp. 209-234, vol. 42.

Hayashi, K. et al., "Activity and substrate specificity of the murine STK2 Serine/Threonine kinase that is structurally related to the mitotic regulator protein NIMA of *Aspergillus nidulans,*" Biochem. Biophys. Res. Commun., 264(2):449-56 (1999).

Aravind, L. and Koonin, E.V., "Phosphoesterase domains associated with DNA polymerases of diverse origins," Nucleic Acids Res., 26(16):3746-52 (1998).

Myers, R.M. et al., "Detection of single base substitutions by ribonuclease cleavage at mismatches in RNA: DNA duplexes," Science, vol. 230 (4731):1242-1246 (1985).

Database GenEmbl, on STN, AN AF021935, Leung, T. et al., "*Myotonic Dystrophy Kinase-Related Cdc42-Binding Kinase Acts as a Cdc42 Effector in Promoting Cytoskeletal Reorganization,*" Sequence Comparison, pp. 18-21.

Collins, F.S., "Generation and initial analysis of more than 15,000 full-length human and mouse cDNA sequences," Proc. Natl. Acad. Sci. USA, 99(26):16899-16903 (2002).

Database GenCore on STN, AN AAD34299, Bandman, O. et al., Database N Geneseq Jan. 29, 2004 (WO 02/18557-A2), Mar. 7, 2002, Sequence Comparison, pp. 1-4.

Copy of International Search Report mailed on Jun. 23, 2005, for WO 2004/032877, and associated sequence search alignments.

```
Query:  369  LGSGAFGCVYK---VRKHSGQNLLAMKEVNLHNPAFGKDKDRDSSVRNIVSELTIIKEQ      425
Sbjct:    7  LGEGAFGEVYKGTLKGKGGKEVEVAVKT--LKEDASEQQIEE------FLREAKIMR-K      56

Query:  426  LYHPNIVRYYKTFLENDRLYIVMELIEGAPLGEHFSSLKEKHHHFTEERLWKIFIQLCLA    485
Sbjct:   57  LDHPNIVKLLGVCTEEEPLMIVMEYMEGGDLLDYLR--KNRPKELSLSDLLSFALQIARG    114

Query:  486  LRYLHKEKRIVHRDLTPNNIMLGDKDKVTVTDFGLAKQKQENSKLTSVVG--TILYSCPE    543
Sbjct:  115  MEYLE-SKNFVHRDLAARNCLVGENKTVKIADFGLSRDLYSDDYYKVKGGKLPIRWMAPE    173

Query:  544  VLKSEPYGEKADVWAVGCILYQMATL-SPPFYSTNMLSLATKIVEAVYEPVPEGIYSEKV    602
Sbjct:  174  SLKEGKFTSKSDVWSFGVLLWEIFTLGESPYPGMSNEEVLEYLKKGYRLPQPPNC-PDEI    232

Query:  603  TDTISRCLTPDAEARPDIVEVSSMI    627
Sbjct:  233  YDLMLQCWAEDPEDRPSFSELVERL    257
```

FIG. 1

```
Query:  363  YAILDHLGSGAFGCVYKVRKHSGQNLLAMKEVNLHNPAFGKDKDRDSSVRNIVSELTII      422
Sbjct:    1  YELGEKLGSGSFGKVYKGKHKNTGEIVAIKKL--------KKESIKEKKRFLREIRIL      50

Query:  423  KEQLYHPNIVRYYKTFLENDRLYIVMELIEGAPLGEHFSSLKEKHHHFTEERLWKIFIQL    482
Sbjct:   51  R-RLSHPNIVRLIGVFEEDDHLYLVMEYMEGGDL---FDYLRRNGLLLSEKEAKKIALQI    106

Query:  483  CLALRYLHKEKRIVHRDLTPNNIMLGDKDKVTVTDFGLAKQ-KQENSKLTSVVGTILYSC    541
Sbjct:  107  LRGLEYLH-SRGIVHRDLKPENILLDENGTVKIADFGLARLLKSSYSKLTTFVGTPEYMA    165

Query:  542  PEVLKSEPYGEKADVWAVGCILYQMATLSPPFYSTNMLSLATKIVEAVYEPVPEGIYSEK    601
Sbjct:  166  PEVLEGRGYSSKVDVWSLGVVLYELLTGKPPFSGIDPLEELFRIIKRGLRLPPNCSEE    225

Query:  602  VTDTISRCLTPDAEARPDIVEV    623
Sbjct:  226  LKDLIKKCLNKDPEKRPTAKEI    247
```

FIG. 2

```
Query:  363  YAILDHLGSGAFGCVYKVRKHSGQNLLAMKEVNLHNPAFGKDKKDRDSSVRNIVSELTII   422
Sbjct:  1    YELLEVLGKGAFGKVYLARDKKTGKLVAIKVIKK------EKLKKKKRERILREIKIL    52

Query:  423  KEQLYHPNIVRYYKTFLENDRLYIVMELIEGAPLGEHFSSLKEKHHFTEERLWKIFIQL   482
Sbjct:  53   K--KLDHPNIVKLYDVFEDKDKLYLVMEYCEGGDLFDLL----KKRGRLSEDEARFYARQI  107

Query:  483  CLALRYLHKEKRIVHRDLTPNNIMLGDKDKVTVTDFGLAKQKQENS-KLTSVVGTILYSC   541
Sbjct:  108  LSALEYLHS-NGIIHRDLKPENILLDSDGHVKLADFGLAKQLDSGGTLLTTFVGTPEYMA   166

Query:  542  PEVLKSEPYGEKADVWAVGCILYQMATLSPPFYSTNMLSLATKIVEAVYEPVP--EGIYS   599
Sbjct:  167  PEVLLGKGYGKAVDIWSLGVILYELLTGKPPFPGDDQLDALFKKIGKPPPPFPPPEWKIS   226

Query:  600  EKVTDTISRCLTPDAEARPDIVEV   623
Sbjct:  227  PEAKDLIKKLLVKDPEKRLTAEEA   250
```

FIG. 3

```
Query:  369  LGSGAFGCVYKVRKHSGQNLLAMKEVNLHNPAFGKDKKDRDSSVRNIVSELTIIKEQLYH   428
Sbjct:  48   LDGSGNERAVKIYKTGTLEFKRRDRYVDGDFRFKYRKINP-----RKLVRLWAEKE---F    99

Query:  429  PNIVRYYKTFL------ENDRLYIVMELIEGAPLGEHFSSLKEKHHFTEERLWKIFIQL   482
Sbjct:  100  RNLQRLYEAGVPVPKPIAWRRNVLVMEFIGG----DGLPAPRLKDVEPEEEEDELYDDI   155

Query:  483  CLALRYLHKEKRIVHRDLTPNNIMLGDKDKVTVTDFGLAKQKQE   526
Sbjct:  156  LEEMRKLYKEGELVHGDLSEYNILVHD-GKVVIIDVSQSVELDH   198
```

FIG. 4

COMPOSITIONS EMPLOYING A NOVEL HUMAN KINASE

The present application incorporates by reference U.S. Provisional Application Ser. No. 60/417,209 filed Oct. 10, 2002 and entitled "Composition, Organisms and Methodologies Employing a Novel Human Kinase."

FIELD OF THE INVENTION

The present invention relates to compositions, organisms and methodologies employing a novel human protein kinase, HPK3P23, which has sequence homology to the catalytic domain of tyrosine protein kinases and serine/threonine protein kinases. This invention can be used for diagnosing, prognosing, and treating kinase-related diseases and, in particular, diseases associated with aberrant expression of HPK3P23.

BACKGROUND OF THE INVENTION

Protein kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1,000 of the 10,000 proteins active in a typical mammalian cell are phosphorylated. The high energy phosphate, which drives activation, is generally transferred from adenosine triphosphate molecules (ATP) to a particular protein by protein kinases and removed from that protein by protein phosphatases. Phosphorylation occurs in response to extracellular signals (hormones, neurotransmitters, growth and differentiation factors, etc.), cell cycle checkpoints, and environmental or nutritional stresses. The phosphorylation process is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups: those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250–300 amino acid catalytic domain. The primary structure of the kinase domains is conserved and can be further subdivided into 11 subdomains. The N-terminal of the kinase domain, which contains subdomains I–IV, generally folds into a lobe-like structure that binds and orients the ATP (or GTP) donor molecule. The C terminal of the kinase domain forms a larger lobe, which contains subdomains VI–XI, binds the protein substrate and carries out the transfer of the gamma phosphate from ATP to the hydroxyl group of a serine, threonine, or tyrosine residue. Subdomain V spans the two lobes. Each of the 11 subdomains contains specific residues and motifs or patterns of amino acids that are characteristic of that subdomain and are highly conserved.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein.

The presence of a phosphate moiety modulates protein function in multiple ways. A common mechanism involves changes in the catalytic properties (Vmax and Km) of an enzyme, leading to its activation or inactivation.

A second widely recognized mechanism involves promoting protein-protein interactions. An example of this is the tyrosine autophosphorylation of the ligand-activated EGF receptor tyrosine kinase. This event triggers the high-affinity binding to the phosphotyrosine residue on the receptor's C-terminal intracellular domain to the SH2 motif of an adaptor molecule Grb2. Grb2, in turn, binds through its SH3 motif to a second adaptor molecule, such as SHC. The formation of this complex activates the signaling events that are responsible for the biological effects of EGF. Serine and threonine phosphorylation events also have been recently recognized to exert their biological function through protein-protein interaction events that are mediated by the high-affinity binding of phosphoserine and phosphothreonine to the WW motifs present in a large variety of proteins.

A third important outcome of protein phosphorylation is changes in the subcellular localization of the substrate. As an example, nuclear import and export events in a large diversity of proteins are regulated by protein phosphorylation.

Many kinases are involved in regulatory cascades wherein their substrates may include other kinases whose activities are regulated by their phosphorylation state. Ultimately the activities of some downstream effectors are modulated by phosphorylation resulting from activation of such a pathway.

SUMMARY OF THE INVENTION

The present invention discloses compositions, organisms and methodologies employing a novel human protein kinase. The new human protein kinase shares sequence homology with the catalytic domain of tyrosine protein kinases and serine/threonine protein kinases. The gene encoding this new protein is localized in or near locus 3P23 of human chromosome 3. This new gene is hereinafter referred to as human protein kinase 3P23 (HPK3P23) gene, and its encoded protein(s) is referred to as HPK3P23 or HPK3P23 kinase.

The kinase domain in HPK3P23 shows 97.7% sequence alignment with the consensus sequences of the catalytic domain of tyrosine kinases, 97.6% sequence alignment with the consensus sequence of the pkinase domain, and 97.7% sequence alignment with the consensus sequences of the catalytic domains of serine/threonine protein kinases. The utilities of various kinase domains are known in the art. The unique peptide sequences, and nucleic acid sequences that encode the peptides, can be used as models for the development of human therapeutic targets, aid in the identification of therapeutic proteins, and serve as targets for the development of human therapeutic agents that modulate kinase activity in cells and tissues that express the kinase.

In one aspect, the invention provides isolated polynucleotides comprising a nucleotide sequence encoding HPK3P23 or a variant of HPK3P23.

In another aspect, the invention provides isolated polypeptides comprising the amino acid sequence of HPK3P23 or a variant of HPK3P23.

In yet another aspect, the invention provides agents that modulate expression level of the HPK3P23 gene or an activity of HPK3P23.

The invention also provides methods for (a) detecting polynucleotides comprising a nucleotide sequence encoding HPK3P23 or a variant of HPK3P23 and (b) detecting polypeptides comprising an amino acid sequence of HPK3P23 or a variant of HPK3P23 in a biological sample.

The invention further provides methods for screening agents that modulate expression level of the HPK3P23 gene or an activity of HPK3P23.

The invention further provides cell lines harboring the HPK3P23 gene, animals transgenic for the HPK3P23 gene, and animals with an interrupted HPK3P23 gene (HPK3P23 knockout animals). These cell lines and animals can be used to study the functions of HPK3P23.

In still another aspect, the invention provides polynucleotides capable of inhibiting HPK3P23 gene expression by RNA interference.

The invention further provides methods of inhibiting HPK3P23 gene expression by introducing siRNAs or other RNAi sequences into target cells.

The preferred embodiments of the inventions are described below in the Detailed Description of the Invention. Unless specifically noted, it is intended that the words and phrases in the specification and claims be given the ordinary and accustomed meaning to those of ordinary skill in the applicable art or arts. If any other meaning is intended, the specification will specifically state that a special meaning is being applied to a word or phrase.

It is further intended that the inventions not be limited only to the specific structure, material or methods that are described in the preferred embodiments, but include any and all structures, materials or methods that perform the claimed function, along with any and all known or later-developed equivalent structures, materials or methods for performing the claimed function.

Further examples exist throughout the disclosure, and it is not applicant's intention to exclude from the scope of his invention the use of structures, materials, or methods that are not expressly identified in the specification, but nonetheless are capable of performing a claimed function.

BRIEF DESCRIPTION OF THE DRAWINGS

The inventions of this application are better understood in conjunction with the following drawings, in which:

FIG. 1 shows the sequence alignment between amino acid residues 369 to 627 of HPK3P23 (SEQ ID NO:2) and the catalytic domain of a family of tyrosine kinases (SEQ ID NO:87).

FIG. 2 shows the sequence alignment between amino acid residues 363 to 623 of HPK3P23 (SEQ ID NO:2) and the protein kinase domain of pkinases (SEQ ID NO:88).

FIG. 3 compares amino acid residues 363 to 623 of HPK3P23 (SEQ ID NO:2) to the catalytic domain of a family of Ser/Thr protein kinases (SEQ ID NO:89).

FIG. 4 illustrates the sequence alignment between amino acid residues 369 to 526 of HPK3P23 (SEQ ID NO:2) and a consensus sequence of RIO-like kinases (SEQ ID NO:90).

DETAILED DESCRIPTION OF THE INVENTION

Figure 5:
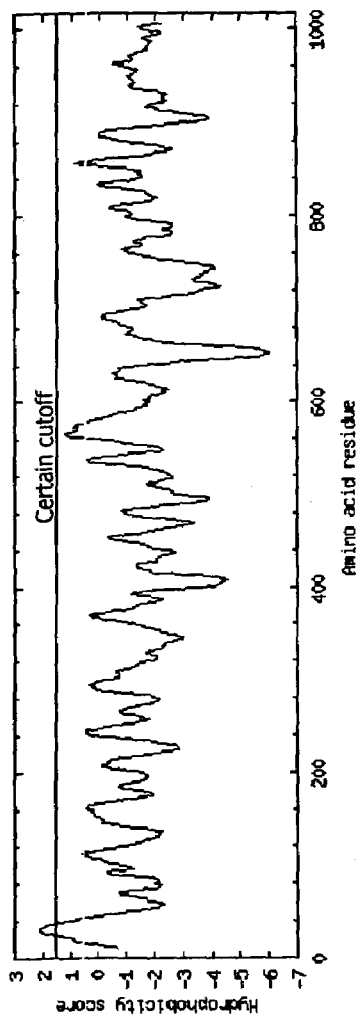
FIG. 5 shows the hydrophobicity profile of HPK3P23.

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the spirit and scope of the invention. The present invention is not intended to be limited to the embodiments shown, but is to be accorded the widest possible scope consistent with the principles and features disclosed herein.

The present invention is based on the sequence information obtained from a newly developed genomic prediction pipeline. Briefly, the X-ray crystal structures of the catalytic domains of protein kinases were collected and aligned together according to their structural identity/similarities. The alignment was converted into a "scoring matrix" which carried the structural profile of the kinase catalytic domains. This scoring matrix was then used to search the Celera Human Genome database and pull out sequences that have kinase catalytic domains.

Based on this analysis, the present invention provides the amino acid sequence of a human kinase peptide containing a kinase domain that is highly homologous to the consensus sequences of the catalytic domain of several protein kinases, as well as the cDNA sequences and genomic sequences that encode the kinase peptide. The present invention also provides information about the closest art known protein/peptide/domain that has structural or sequence homology to the kinase of the present invention.

The peptide of the present invention may be used for the development of commercially important products and services. Various aspects of the invention are described in detail in the following subsections. The use of subsections is not meant to limit the invention. Each subsection applies to any aspect of the invention.

Definitions and Terms

To facilitate the understanding of the present invention, a number of terms and phrases are defined below:

As used herein, a polynucleotide or a polypeptide is "isolated" if it is removed from its native environment. For instance, a polynucleotide or a polypeptide is isolated through a purification process such that the polynucleotide or polypeptide is substantially free of cellular material or free of chemical precursors. The polynucleotide/polypeptide of the present invention can be purified to homogeneity or other degrees of purity. The level of purification will be based on the intended use. As appreciated by one of ordinary skill in the art, a polynucleotide/polypeptide can perform its desired function(s) even in the presence of considerable amounts of other components or molecules.

In some uses, a polynucleotide/polypeptide that is "substantially free of cellular material" includes preparations which have less than about 30% (by weight) other polynucleotides/polypeptides including contaminating polynucleotides/polypeptides. For instance, the preparations can have less than about 20%, less than about 10%, or less than about 5% other polynucleotides/polypeptides. If a polynucleotide/polypeptide preparation is recombinantly produced, it can be substantially free of culture medium, i.e., culture medium components representing less than about 20% by weight of the polynucleotide/polypeptide preparation.

The language "substantially free of chemical precursors" includes preparations in which the polynucleotide/polypeptide is separated from chemical precursors or other chemicals that are involved in the synthesis of the polynucleotide/polypeptide. In one embodiment, the language "substantially free of chemical precursors" includes kinase preparations having less than about 30% (by weight), less than about 20% (by weight), less than about 10% (by weight), or less than about 5% (by weight) chemical precursors or other chemicals used in the synthesis.

As used in the present invention, a polynucleotide introduced into a cell is an isolated polynucleotide. Likewise, a polypeptide expressed from an introduced vector in a cell is also an isolated polypeptide.

A "polynucleotide" can include any number of nucleotides. For instance, a polynucleotide can have at least 10, 20, 25, 30, 40, 50, 100 or more nucleotides. A polynucleotide can be DNA or RNA, double-stranded or single-stranded. A polynucleotide encodes a polypeptide if the polypeptide is capable of being transcribed and/or translated from the polynucleotide. Transcriptional and/or translational regulatory sequences, such as promoter and/or enhancer(s), can be added to the polynucleotide before said transcription and/or translation occurs. Moreover, if the polynucleotide is singled-stranded, the corresponding double-stranded DNA containing the original polynucleotide and its complementary sequence can be prepared before said transcription and/or translation.

As used herein, "a variant of a polynucleotide" refers to a polynucleotide that differs from the original polynucleotide by one or more substitutions, additions, and/or deletions. For instance, a variant of a polynucleotide can have 1, 2, 5, 10, 15, 20, 25 or more nucleotide substitutions, additions or deletions. Preferably, the modification(s) is in-frame, i.e., the modified polynucleotide can be transcribed and translated to the original or intended stop codon. If the original polynucleotide encodes a polypeptide with a biological activity, the polypeptide encoded by a variant of the original polynucleotide variants substantially retains such activity.

Preferably, the biological activity is reduced/enhanced by less than 50%, or more preferably, less than 20%, relative to the original activity.

A variant of a polynucleotide can be a polynucleotide that is capable of hybridizing to the original polynucleotide, or the complementary sequence thereof, under reduced stringent conditions, preferably stringent conditions, or more preferably, highly stringent conditions. Examples of conditions of different stringency are listed in Table 1. Highly stringent conditions are those that are at least as stringent as conditions A–F; stringent conditions are at least as stringent as conditions G-L; and reduced stringency conditions are at least as stringent as conditions M–R. As used in Table 1, hybridization is carried out under a given hybridization condition for about 2 hours, followed by two 15-minute washes under the corresponding washing condition(s).

TABLE 1

Stringency Conditions

| Stringency Condition | Polynucleotide Hybrid | Hybrid Length (bp)[1] | Hybridization Temperature and Buffer[H] | Wash Temp. and Buffer[H] |
| --- | --- | --- | --- | --- |
| A | DNA:DNA | >50 | 65° C.; 1 × SSC -or- 42° C.; 1 × SSC, 50% formamide | 65° C.; 0.3 × SSC |
| B | DNA:DNA | <50 | $T_B$*; 1 × SSC | $T_B$*; 1 × SSC |
| C | DNA:RNA | >50 | 67° C.; 1 × SSC -or- 45° C.; 1 × SSC, 50% formamide | 67° C.; 0.3 × SSC |
| D | DNA:RNA | <50 | $T_D$*; 1 × SSC | $T_D$*; 1 × SSC |
| E | RNA:RNA | >50 | 70° C.; 1 × SSC -or- 50° C.; 1 × SSC, 50% formamide | 70° C.; 0.3 × SSC |
| F | RNA:RNA | <50 | $T_F$*; 1 × SSC | $T_F$*; 1 × SSC |
| G | DNA:DNA | >50 | 65° C.; 4 × SSC -or- 42° C.; 4 × SSC, 50% formamide | 65° C.; 1 × SSC |
| H | DNA:DNA | <50 | $T_H$*; 4 × SSC | $T_H$*; 4 × SSC |
| I | DNA:RNA | >50 | 67° C.; 4 × SSC -or- 45° C.; 4 × SSC, 50% formamide | 67° C.; 1 × SSC |
| J | DNA:RNA | <50 | $T_J$*; 4 × SSC | $T_J$*; 4 × SSC |
| K | RNA:RNA | >50 | 70° C.; 4 × SSC -or- 50° C.; 4 × SSC, 50% formamide | 67° C.; 1 × SSC |
| L | RNA:RNA | <50 | $T_L$*; 2 × SSC | $T_L$*; 2 × SSC |
| M | DNA:DNA | >50 | 50° C.; 4 × SSC -or- 40° C.; 6 × SSC, 50% formamide | 50° C.; 2 × SSC |
| N | DNA:DNA | <50 | $T_N$*; 6 × SSC | $T_N$*; 6 × SSC |
| O | DNA:RNA | >50 | 55° C.; 4 × SSC -or- 42° C.; 6 × SSC, 50% formamide | 55° C.; 2 × SSC |
| P | DNA:RNA | <50 | $T_P$*; 6 × SSC | $T_P$*; 6 × SSC |
| Q | RNA:RNA | >50 | 60° C.; 4 × SSC -or- 45° C.; 6 × SSC, 50% formamide | 60° C.; 2 × SSC |
| R | RNA:RNA | <50 | $T_R$*; 4 × SSC | $T_R$*; 4 × SSC |

[1]The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.
[H]SSPE (1 × SSPE is 0.15 M NaCl, 10 mM $NaH_2PO_4$, and 1.25 mM EDTA, pH 7.4) can be substituted for SSC (1 × SSC is 0.15 M NaCl and 15 mM sodium citrate) in the hybridization and wash buffers.
$T_B$*–$T_R$*: The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m$(° C.) = 2(# of A + T bases) + 4(# of G + C bases). For hybrids between 18 and 49 base pairs in length, $T_m$(° C.) = 81.5 + 16.6($\log_{10}Na^+$) + 0.41(% G + C) − (600/N), where N is the number of bases in the hybrid, and $Na^+$ is the concentration of sodium ions in the hybridization buffer ($Na^+$ for 1 × SSC = 0.165 M).

It will be appreciated by those of ordinary skill in the art that, as a result of the degeneracy of the genetic code, there are many polynucleotide variants that encode the same polypeptide. Some of these polynucleotide variants bear minimal sequence homology to the original polynucleotide. Nonetheless, polynucleotides that vary due to differences in codon usage are specifically contemplated by the present invention.

As used herein, a "polypeptide" can include any number of amino acid residues. For instance, a polypeptide can have 5, 10, 15, 20, 30, 40, 50 or more amino acid residues.

As used herein, a "variant of a polypeptide" is a polypeptide that differs from the original polypeptide by one or more substitutions, deletions, and/or insertions. Preferably, these modifications do not substantially change (e.g., reduce or enhance) the original biological function of the polypeptide. For instance, a variant can reduce or enhance or maintain the biological activities of the original polypeptide. Preferably, the biological activities of the variant is reduced or enhanced by less than 50%, or more preferably, less than 20%, relative to the original polypeptide.

Similarly, the ability of a variant to react with antigen-specific antisera can be enhanced or reduced by less than 50%, preferably less than 20%, relative to the original polypeptide. These variants can be prepared and evaluated by modifying the original polypeptide sequence and then determining the reactivity of the modified polypeptide with the antigen-specific antibodies or antisera.

Preferably, a variant polypeptide contains one or more conservative substitutions. A "conservative substitution" is one in which an amino acid is substituted for another amino acid which has similar properties, such that one skilled in the art would expect that the secondary structure and hydropathic nature of the substituted polypeptide will not be substantially changed. Conservative amino acid substitutions can be made on the basis of similarity in polarity, charge, solubility, hydrophobicity, hydrophilicity and/or the amphipathic nature of the residues. Negatively charged amino acids include aspartic acid and glutamic acid, and positively charged amino acids include lysine and arginine. Amino acids having uncharged polar head groups and similar hydrophilicity values include leucine, isoleucine and valine, or glycine and alanine, or asparagine and glutamine, or serine, threonine, phenylalanine and tyrosine. Other groups of amino acids that can produce conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A polypeptide variant can also contain nonconservative changes.

Polypeptide variants can be prepared by the deletion and/or addition of amino acids that have minimal influence on the biological activity, immunogenicity, secondary structure and/or hydropathic nature of the polypeptide. Variants can be prepared by, for instance, substituting, modifying, deleting or adding one or more amino acids residues in the original sequence. Polypeptide variants preferably exhibit at least about 70%, more preferably at least about 90%, and most preferably at least about 95% sequence homology to the original polypeptide.

Polypeptide variants include polypeptides that are modified from the original polypeptides either by a natural process, such as a post-translational modification, or by a chemical modification. These modifications are well known in the art. Modifications can occur anywhere in the polypeptide, including the backbone, the amino acid side-chains and the amino or carboxyl termini. It will be appreciated that the same type of modification can be present in the same or varying degrees at several sites in a given polypeptide. Also, a given polypeptide can contain many types of modifications. Polypeptides may be branched, for example, as a result of ubiquitination, and they may be cyclic, with or without branching. Cyclic, branched, and branched cyclic polypeptides can result from natural post-translational processes or be made through synthetic methods. Suitable modifications for this invention include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination.

As used herein, the term "modulation" includes up-regulation, induction, stimulation, potentiation, inhibition, down-regulation or suppression, or relief of inhibition.

A nucleotide sequence is "operably linked" to another nucleotide sequence if the two sequences are placed into a functional relationship. For example, a coding sequence is operably linked to a 5' regulatory sequence if the 5' regulatory sequence can initiate transcription of the coding sequence in an in vitro transcription/translation system or in a host cell. "Operably linked" does not require that the DNA sequences being linked are contiguous to each other. Intervening sequences may exist between two operably linked sequences.

As used herein, a "disease-free" human refers to a human who does not have HPK3P23-related diseases. Disease-free cells, tissues or samples refer to cells, tissues or samples obtained from such disease-free human(s).

A polynucleotide is "capable of hybridizing" to a gene if the polynucleotide can hybridize to at least one of the following sequences: (1) the sequence of an RNA transcript of the gene, (2) the complementary sequence of an RNA transcript of the gene, (3) the cDNA sequence of an RNA transcript of the gene, (4) the complementary sequence of the cDNA sequence of an RNA transcript of the gene, (5) a genomic sequence of the gene, and (6) the complementary sequence of a genomic sequence of the gene.

As used herein, sequence "identity" in an alignment can be determined by the standard protein-protein BLAST program (blastp), the standard nucleotide-nucleotide BLAST program (blastn) or the BLAST2 Sequence program. Suitable BLAST programs can be found at the web site maintained by the National Center of Biotechnology Information (NCBI), National Library of Medicine, Washington, D.C., USA.

Human HPK3P23 Gene and HPK3P23 Kinase

The present invention identifies a new human gene (HPK3P23 gene) that encodes a protein containing sequences highly homologous to the consensus sequences of the catalytic domain of tyrosine protein kinases and serine/threonine protein kinases. The nucleotide sequence encoding HPK3P23 and the amino acid sequence of HPK3P23 are depicted in SEQ ID NOS: 1 and 2, respectively. HPK3P23 gene is localized in or near locus 3p23 of human chromosome 3. Specifically, the HPK3P23 gene is located between loci LOC1131717 and LOC1131721, and overlaps with loci LOC1152109, LOC1152110, and LOC 166046.

Human chromosome locus 3p23 and the neighboring regions have been associated with multiple diseases, including but are not limited to, small cell lung cancer, ovarian cancer, esophageal cancer, colorectal cancer, chronic myeloid leukemia, arrhythomgenic right ventricular dysplasia, and polycystic kidney disease. Recurrent deletions of 3p23 were found in a number of tumor cells, suggesting the existence of a tumor suppressor gene in the region.

Human HPK3P23 gene has 32 exons. The exons are mapped to the nucleotide sequences of human chromosome 3 in Celera genomic database (SEQ ID NO:3). Exons 1-29,31 and 32 are also mapped to nucleotides 2719783 to 2940912 of human chromosome 3 in the Entrez Human Genome Sequence Database maintained by NCBI. Table 2 lists the location of each of these 32 exons the location of each of these 32 exons in the genomic sequence SEQ ID NO:3. Table 2 also illustrates the corresponding location of each exon in the HPK3P23-coding sequence SEQ ID NO:1.

TABLE 2

Exons in Human HPK3P23 Gene

| Exon Numbers | Corresponding Sequence in SEQ ID NO:3 | Corresponding Sequence in SEQ ID NO:1 |
| --- | --- | --- |
| 1 | 1–208 | 1–208 |
| 2 | 1291–1358 | 209–276 |
| 3 | 3303–3382 | 277–356 |
| 4 | 7339–7563 | 357–581 |
| 5 | 10475–10614 | 582–721 |
| 6 | 15070–15131 | 722–783 |
| 7 | 16620–16755 | 784–919 |
| 8 | 20738–20826 | 920–1008 |
| 9 | 20920–21048 | 1009–1137 |
| 10 | 21548–21685 | 1138–1275 |
| 11 | 24559–24604 | 1276–1321 |
| 12 | 27341–27462 | 1322–1443 |
| 13 | 27598–27700 | 1444–1546 |
| 14 | 55923–55998 | 1547–1622 |
| 15 | 109494–109623 | 1623–1752 |
| 16 | 110472–110542 | 1753–1823 |
| 17 | 119802–120015 | 1824–2037 |
| 18 | 137212–137395 | 2038–2221 |
| 19 | 137520–137606 | 2222–2308 |
| 20 | 140172–140226 | 2309–2363 |
| 21 | 149307–149344 | 2364–2401 |
| 22 | 149444–149584 | 2402–2542 |
| 23 | 168572–168601 | 2543–2572 |
| 24 | 170464–170564 | 2573–2673 |
| 25 | 180056–180166 | 2674–2784 |
| 26 | 192178–192286 | 2785–2893 |
| 27 | 195919–195971 | 2894–2946 |
| 28 | 196051–196106 | 2947–3002 |
| 29 | 200725–201051 | 3003–3329 |
| 30 | 209064–209145 | 3330–3411 |
| 31 | 210747–210809 | 3412–3474 |
| 32 | 220691–220860 | 3475–3644 |

A conserved domain search using RPS-BLAST program (RPS-BLAST 2.2.3 [Apr. 24, 2002], available at the BLAST web site maintained by NCBI), showed that HPK3P23 contains sequences homologous to the consensus sequences of several protein kinase domains.

Specifically, the amino acid residues 369 to 627 of HPK3P23 are highly homologous to a catalytic domain of a family of Tyr protein kinases (smart00219). This family includes the tyrosine kinase domain of fibroblast growth factor receptor 1, tyrosine-protein kinase (KIN15/KIN16 subfamily), and a *Drosophila* receptor protein-tyrosine kinase family member (dr1-P1). FIG. 1 shows that the amino acid residues 369–627 in HPK3P23's kinase domain has 97.7% sequence identities to smart00219, with a score of 137 bits and a E value of $2 \times 10^{-33}$. As used in other figures of this invention, "Query" denotes to the sequence of HPK3P23, and "Sbjct" refers to the sequence being compared to the HPK3P23 sequence.

FIG. 2 shows that the amino acid residues 363 to 623 of HPK3P23 also aligned 97.6% with the protein kinase domain of pkinases (pfam00069). The alignment has a score of 222 bits, and an E value of $3 \times 10^{-59}$. This pkinase family includes protein kinase Ck2, wee1-like protein kinase (WEE1hu), and tyrosine-protein kinase RYK.

FIG. 3 shows the sequence alignment between amino acid residues 369 to 627 of HPK3P23 and the catalytic domain of a family of serine/threonine kinases (smart00220). The amino acid residues 369 to 627 of HPK3P23 are highly homologous to a catalytic domain of a family of serine/threonine protein kinases (smart00220). This kinase family includes C-Jun N-terminal kinase (JNK3), abelson tyrosine kinase, a calmodulin-binding, vesicle-associated, protein kinase-like protein (1G5), serine/threonine protein kinase prp4, Cdc2/Cdc28 subfamily of serine/threonine protein kinases in *C. elegans*, and ribosomal S6 kinase of *C elegans*. The two sequences share 97.7% alignment with a score of 230 bits and an E value of $2 \times 10^{-61}$.

FIG. 4 illustrates the sequence alignment between amino acid residues 369 to 526 of HPK3P23 and the consensus sequence of RIO-like-kinases (smart00090). The two sequences share 64.3% sequence identities with a score of 42.9 bits and an E value of $5 \times 10^{-5}$. The RIO-like-kinase family of protein kinases includes several uncharacterized proteins such as yeast protein RIO1, *C. elegans* hypothetical protein ZK632.3, *Methanococcus jannaschii* hypothetical protein MJ0444; and *Thermoplasma acidophilum* hypothetical protein in rpoA23' region. These proteins were found to be evolutionary related. The eukaryotic members of this family are proteins of about 55 to 60 kd, while the archebacterial ones are half that size. The central part of these proteins is highly conserved.

FIG. 5 shows the hydrophobicity profile of HPK3P23. The hydrophobicity analysis indicates that HPK3P23 kinase is not likely a membrane or transmembrane protein.

HPK3P23 shows significant sequence homology to a human protein kinase-like protein SGK237 (Entrez accession number: AX250157, SEQ ID NOS:4 and 5), which was disclosed in PCT Patent Application No. WO01/66594. Analysis using pairwise BLAST algorithm revealed that HPK3P23 and SGK237 share 91% sequence identities at the amino acid level (blastp, matrix: BLOSUM62, gap open: 11, Gap extension: 1, x_dropoff: 50, expect: 10.0, wordsize: 3, filter: unchecked), and 90% sequence identities at nucleotide level (blastn, match: 1, mismatch: -2, gap open: 5, gap extension: 0, x_dropoff: 50, expect: 10.0, wordsize: 11, filter: unchecked).

The existence and expression of the HPK3P23 gene in humans are supported by various EST sequences. For instance, nucleotides 365–861 of SEQ ID NO:1 are supported by the EST sequences disclosed under Incyte accession numbers 5026615H1, 5026615F6, 2509577H1, 6097133H1 and 6097133F6; nucleotides 919–1260 of SEQ ID NO:1 are supported by the EST sequence disclosed under GenBank accession numbers BM976173, AA430250, and AI149647, as well as Incyte accession number 6097133F6; nucleotides 1164–1623 of SEQ ID NO:1 are supported by the EST sequences disclosed under GenBank accession numbers BM976126, BM976173, AI149647, and AW372558; nucleotides 1624–2042 of SEQ ID NO: 1 are supported by the EST sequences disclosed under GenBank accession number BG717420; nucleotides 1798–2327 of SEQ ID NO:1 are supported by the EST sequences disclosed under Incyte accession numbers 5546336H1, 5546336F8, 6999077H1, 4123469H1; nucleotides 2783–3329 of SEQ ID NO:1 are supported by the EST sequences disclosed under GenBank accession numbers AI652681, AI962584, AA954906, AA889152, AI611061, and AA843473, as well as Incyte accession numbers 5576248H1, 5547612H1, and 6444587H1.

Utility of the HPK3P23 Gene and HPK3P23 Kinase

Protein kinases are involved in the regulation of many critical biological processes such as signal transduction pathways. Malfunctions of cellular signaling have been associated with many diseases. Regulation of signal transduction by cytokines and association of signal molecules with protooncogenes and tumor suppressor genes have been the subjects of intense research. Many therapeutic strategies can now be developed through the synthesis of compounds which activate or inactivate protein kinases.

The importance of kinases in the etiology of diseases has been well established. Kinase proteins are a major target for drug action and development. A January 2002 survey of ongoing clinical trials in the USA revealed more than 100 clinical trials involving the modulation of kinases. Trials are ongoing in a wide variety of therapeutic indications including asthma, Parkinson's, inflammation, psoriasis, rheumatoid arthritis, spinal cord injuries, muscle conditions, osteoporosis, graft versus host disease, cardiovascular disorders, autoimmune disorders, retinal detachment, stroke, epilepsy, ischemia/reperfusion, breast cancer, ovarian cancer, glioblastoma, non-Hodgkin's lymphoma, colorectal cancer, non-small cell lung cancer, brain cancer, Kaposi's sarcoma, pancreatic cancer, liver cancer, and other tumors. Numerous kinds of modulators of kinase activity are currently in clinical trials including antisense molecules, antibodies, small molecules, and even gene therapy. Accordingly, it is valuable to the field of pharmaceutical development to identify and characterize previously unknown members of the kinase family proteins. The present invention advances the state of the art by providing previously unidentified human kinase proteins.

Many therapeutic strategies are aimed at critical components in signal transduction pathways. Approaches for regulating kinase gene expression include specific antisense oligonucleotides for inhibiting post-transcriptional processing of the messenger RNA, naturally occurring products and their chemical derivatives to inhibit kinase activity and monoclonal antibodies to inhibit receptor linked kinases. In some cases, kinase inhibitors also allow other therapeutic agents additional time to become effective and act synergistically with current treatments.

Among the areas of pharmaceutical research that are currently receiving a great deal of attention are the role of phosphorylation in transcriptional control, apoptosis, protein degradation, nuclear import and export, cytoskeletal regulation, and checkpoint signaling. The accumulating knowledge about signaling networks and the proteins involved will be put to practical use in the development of potent and specific pharmacological modulators of phosphorylation-dependent signaling. The rational structure-based design and development of highly specific kinase modulators is becoming routine and drugs that intercede in signaling pathways are becoming a major class of drug. The functions of some of the kinases are described below.

The second messenger dependent protein kinases primarily mediate the effects of second messengers such as cyclic AMP (cAMP), cyclic GMP, inositol triphosphate, phosphatidylinositol, 3,4,5-triphosphate, cyclic-ADPribose, arachidonic acid, diacylglycerol and calcium-calmodulin. The cyclic-AMP dependent protein kinases (PKA) are important members of the STK family. Cyclic-AMP is an intracellular mediator of hormone action in all prokaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic-AMP in most of these cells. Altered PKA expression is implicated in a variety of disorders and diseases including cancer, thyroid disorders, diabetes, atherosclerosis, and cardiovascular disease.

Calcium-calmodulin (CaM) dependent protein kinases are also members of the STK family. Calmodulin is a calcium receptor that mediates many calcium regulated processes by binding to target proteins in response to the binding of calcium. The principle target protein in these processes is CaM dependent protein kinases. CaM-kinases are involved in regulation of smooth muscle contraction (MLC kinase), glycogen breakdown (phosphorylase kinase), and neurotransmission (CaM kinase I and CaM kinase II). CaM kinase I phosphorylates a variety of substrates including the neurotransmitter related proteins synapsin I and II, the gene transcription regulator, CREB, and the cystic fibrosis conductance regulator protein, CFTR. CaM II kinase also phosphorylates synapsin at different sites, and controls the synthesis of catecholamines in the brain through phosphorylation and activation of tyrosine hydroxylase. Many of the CaM kinases are activated by phosphorylation in addition to binding to CaM. The kinase may autophosphorylate itself, or be phosphorylated by another kinase as part of a "kinase cascade".

Another ligand-activated protein kinase is 5'-AMP-activated protein kinase (AMPK). Mammalian AMPK is a regulator of fatty acid and sterol synthesis through phosphorylation of the enzymes acetyl-CoA carboxylase and hydroxymethylglutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues, such as brain, heart, spleen, and lung, than expected. This distribution suggests that AMPK's functions may extend beyond regulation of lipid metabolism alone.

The mitogen-activated protein kinases (MAP) are also members of the STK family. MAP kinases also regulate intracellular signaling pathways. They mediate signal transduction from the cell surface to the nucleus via phosphorylation cascades. Several subgroups have been identified, and each manifests different substrate specificities and responds to distinct extracellular stimuli. MAP kinase signaling pathways are present in mammalian cells as well as in yeast. The extracellular stimuli that activate mammalian pathways include epidermal growth factor (EGF), ultraviolet light, hyperosmolar medium, heat shock, endotoxic lipopolysaccharide (LPS), and pro-inflammatory cytokines, such as tumor necrosis factor (TNF) and interleukin-1 (IL-1).

EGF receptor is found in over half of breast tumors unresponsive to hormone. EGF is found in many tumors, and EGF may be required for tumor cell growth. Antibodies to EGF blocked the growth of tumor xenografts in mice. An antisense oligonucleotide for amphiregulin inhibited growth of a pancreatic cancer cell line.

Tamoxifen, a protein kinase C inhibitor with anti-estrogen activity, is currently a standard treatment for hormone-dependent breast cancer. The use of this compound may increase the risk of developing cancer in other tissues such as the endometrium. Raloxifene, a related compound, has been shown to protect against osteoporosis. The tissue specificity of inhibitors must be considered when identifying therapeutic targets.

Signal transduction to the nucleus in response to extracellular stimulus by a growth factor involves the mitogen activated protein (MAP) kinases. MAP kinases are a family of protein serine/threonine kinases which mediate signal transduction from extracellular receptors or heat shock, or UV radiation. Cell proliferation and differentiation in normal cells are under the regulation and control of multiple MAP kinase cascades. Aberrant and deregulated functioning of MAP kinases can initiate and support carcinogenesis. Insulin and IGF-1 also activate a mitogenic MAP kinase pathway that may be important in acquired insulin resistance occurring in type 2 diabetes.

Many cancers become refractory to chemotherapy by developing a survival strategy involving the constitutive activation of the phosphatidylinositol 3-kinase-protein kinase B/Akt signaling cascade. This survival signaling pathway thus becomes an important target for the development of specific inhibitors that would block its function. PI-3 kinase/Akt signaling is equally important in diabetes. The pathway activated by RTKs subsequently regulates glycogen synthase 3 (GSK3) and glucose uptake. Since AKT has decreased activity in type 2 diabetes, it provides a therapeutic target.

Protein kinase inhibitors provide much of our knowledge about in vivo regulation and coordination of physiological functions of endogenous peptide inhibitors. A pseudosubstrate sequence within PKC acts to inhibit the kinase in the absence of its lipid activator. A PKC inhibitor, such as chelerythrine, acts on the catalytic domain to block substrate interaction, while calphostin acts on the regulatory domain to mimic the pseudosubstrate sequence and block ATPase activity, or to inhibit cofactor binding.

Although some protein kinases have, to date, no known system of physiological regulation, many are activated or inactivated by autophosphorylation or phosphorylation by upstream protein kinases. The regulation of protein kinases also occurs during the transcription, post-transcription, and post-translation processes. The mechanism of post-transcriptional regulation is alternative splicing of precursor mRNA. For example, protein kinase C $\beta$I and $\beta$II are two isoforms of a single PKC$\beta$ gene derived from differences in the splicing of the exon encoding the C-terminal 50–52 amino acids. Splicing can be regulated by a kinase cascade in response to peptide hormones, such as insulin and IGF-1. PKC $\beta$I and $\beta$II have different specificities for phosphorylating members of the mitogen activated protein (MAP) kinase family, for glycogen synthase 3$\beta$, for nuclear transcription factors, such as TLS/Fus, and for other nuclear kinases. By inhibiting the post-transcriptional alternative splicing of PKC $\beta$II mRNA, PKC $\beta$II-dependent processes are inhibited.

The development of antisense oligonucleotides to inhibit the expression of various protein kinases has been successful. Antisense oligonucleotides are short lengths of synthetically manufactured, chemically modified DNA or RNA designed to specifically interact with mRNA transcripts encoding target proteins. The interaction of the antisense moiety with mRNA inhibits protein translation and, in some cases, post-transcriptional processing (e.g., alternative splicing and stability) of mRNA. Antisense oligonucleotides have been developed to alter alternative splicing of mRNA forms for inhibiting the translation of PKC$\alpha$.

Protein kinase C isoforms have been implicated in cellular changes observed in the vascular complications of diabetes. Hyperglycemia is associated with increased levels of PKC$\alpha$ and $\beta$ isoforms in renal glomeruli of diabetic rats. Oral administration of a PKC$\beta$ inhibitor prevented the increased mRNA expression of TGF-$\beta$1 and extracellular matrix component genes. Administration of the specific PKC$\beta$ inhibitor (LY333531) also normalized levels of cytokines, caldesmon, and hemodynamics of retinal and renal blood flow. Overexpression of the PKC$\beta$ isoform in the myocardium resulted in cardiac hypertrophy and failure. The use of LY333531 to prevent adverse effects of cardiac PKC$\beta$ overexpression in diabetic subjects is under investigation. The compound is also in Phase I/II clinical trials for diabetic retinopathy and diabetic macular edema indicating that it may be pharmacodynamically active.

PRK (proliferation-related kinase) is a serum/cytokine inducible STK that is involved in regulation of the cell cycle and cell proliferation in human megakaroytic cells. PRK is related to the polo (derived from humans polo gene) family of STKs implicated in cell division. PRK is down-regulated in lung tumor tissue and may be a proto-oncogene whose deregulated expression in normal tissue leads to oncogenic transformation. Altered MAP kinase expression is implicated in a variety of disease conditions including cancer, inflammation, immune disorders, and disorders affecting growth and development.

DNA-dependent protein kinase (DNA-PK) is involved in the repair of double-strand breaks in mammalian cells. This enzyme requires ends of double stranded DNA or transitions from single-stranded to double-stranded DNA in order to act as a serine/threonine kinase. Cells with defective or deficient DNA-PK activity are unable to repair radiation induced DNA double-strand breaks and are consequently very sensitive to the lethal effects of ionizing radiation. Inhibition of DNA-PK has the potential to increase the efficacy of anti-tumor treatment with radiation or chemotherapeutic agents.

The cyclin-dependent protein kinases (CDKs) are another group of STKs that control the progression of cells through the cell cycle. Cyclins are small regulatory proteins that act by binding to and activating CDKs that then trigger various phases of the cell cycle by phosphorylating and activating selected proteins involved in the mitotic process. CDKs are unique in that they require multiple inputs to become activated. In addition to the binding of cyclin, CDK activation requires the phosphorylation of a specific threonine residue and the dephosphorylation of a specific tyrosine residue.

Cellular inhibitors of CDKs also play a major role in cell cycle progression. Alterations in the expression, function, and structure of cyclin and CDK are encountered in the cancer phenotype. Therefore, CDKs may be important targets for new cancer therapeutic agents.

Chemotherapy resistant cells tend to escape apoptosis. Under certain circumstances, inappropriate CDK activation may even promote apoptosis by encouraging the progression of the cell cycle under unfavorable conditions, i.e., attempting mitosis while DNA damage is largely unrepaired.

Purines and purine analogs act as CDK inhibitors. Flavopiridol is a flavonoid that causes 50% growth inhibition of tumor cells at 60 nM. It also inhibits EGFR and protein kinase A. Flavopiridel induces apoptosis and inhibits lymphoid, myeloid, colon, and prostate cancer cells grown in vivo as tumor xenografts in nude mice.

Staurosporine and its derivative, UCN-01, in addition to inhibiting protein kinase C, inhibit cyclin B/CDK (IC50=3 to 6 nM). Staurosporine is toxic, but its derivative 7-hydroxystaurosporine (UCN-01) has anti-tumor properties and is in clinical trials. UCN-01 affects the phosphorylation of CDKs and alters the cell cycle checkpoint functioning. These compounds illustrate that multiple intracellular targets may be affected as the concentration of an inhibitor is increased within cells.

Protein tyrosine kinases, PTKs, specifically phosphorylate tyrosine residues on their target proteins and may be divided into transmembrane, receptor PTKs and non-transmembrane, non-receptor PTKs. Transmembrane protein tyrosine kinases are receptors for most growth factors.

Binding of a growth factor to the receptor activates the transfer of a phosphate group from ATP to selected tyrosine side chains of the receptor and other specific proteins. Growth factors (GF) associated with receptor PTKs include; epidermal GF, platelet-derived GF, fibroblast GF, hepatocyte GF, insulin and insulin-like GFs, nerve GF, vascular endothelial GF, and macrophage colony stimulating factor.

Since RTKs stimulate tumor cell proliferation, inhibitors of RTKs may inhibit the growth and proliferation of such cancers. Inhibitors of RTKs are also useful in preventing tumor angiogenesis and can eliminate support from the host tissue by targeting RTKs located on vascular cells, such as blood vessel endothelial cells and stromal fibroblasts. For example, VEGF stimulates endothelial cell growth during angiogenesis, and increases the permeability of tumor vasculature so that proteins and other growth factors become accessible to the tumor. Broad-spectrum antitumor efficacy of an oral dosage form of an inhibitor of VEGF signaling has been reported. Thus, inhibition of VEGF receptor signaling presents an important therapeutic target. An extracellular receptor can also be a target for inhibition. For example, the EGF receptor family and its ligands are overexpressed and exist as an autocrine loop in many tumor types.

Increasing knowledge of the structure and activation mechanism of RTKs and the signaling pathways controlled by tyrosine kinases provided the possibility for the development of target specific drugs and new anti-cancer therapies. Approaches towards the prevention or interception of deregulated RTK signaling include the development of selective components that target either the extracellular ligand-binding domain or the intracellular substrate binding region.

The most successful strategy to selectively kill tumor cells is the use of monoclonal antibodies (mAbs) that are directed against the extracellular domain of RTKs, which are critically involved in cancer and are expressed at the surface of tumor cells. In the past years, recombinant antibody technology has made an enormous progress in the design, selection and production of newly engineered antibodies. It is also possible to generate humanized antibodies, human-mouse chimeric or bispecific antibodies for targeted cancer therapy. Mechanistically, anti-RTK mAbs might work by blocking the ligand-receptor interaction and therefore inhibiting ligand-induced RTK signaling and increasing RTK down-regulation and internalization. In addition, binding of mAbs to certain epitopes on the cancer cells may induce immune-mediated responses, such as opsonization and complement-mediated lysis, and trigger antibody-dependent cellular cytotoxicity by macrophages or natural killer cells. In recent years, it became evident that mAbs control tumor growth by altering the intracellular signaling pattern inside the targeted tumor cell, leading to growth inhibition and/or apoptosis. In addition, bispecific antibodies can bridge selected surface molecules on a target cell with receptors on an effector cell, thus triggering cytotoxic responses against the target cell. Despite the toxicity that has been seen in clinical trials of bispecific antibodies, advances in antibody engineering, characterization of tumor antigens and immunology might help to produce rationally designed bispecific antibodies for anti-cancer therapy.

Another promising approach to inhibiting aberrant RTK signaling is to develop small molecule drugs that selectively interfere with the intrinsic tyrosine kinase activity and thereby block receptor autophosphorylation and activation of downstream signal transducers. The tyrphostins, which belong to the quinazolines, are one important group of such inhibitors that compete with ATP for the ATP binding site at the receptor's tyrosine kinase domain and some members of the group have been shown to specifically inhibit the EGFR. Potent and selective inhibitors of receptors involved in neovascularization have been developed and are now undergoing clinical evaluation. New classes of tyrosine kinase inhibitors (TKIs) with increased potency and selectivity, higher in vitro and in vivo efficacy and decreased toxicity have been developed using the advantages of structure-based drug design, crystallographic structure information, combinatorial chemistry and high-throughput screening.

Recombinant immunotoxins provide another possibility of target-selective drug design. Recombinant immunotoxins are composed of a bacterial or plant toxin either fused or chemically conjugated to a specific ligand, such as the variable domains of the heavy and light chains of mAbs or to a growth factor. Immunotoxins may contain bacterial toxins, such as Pseudomouas exotoxin A or diphtheria toxin, or plant toxins, such as ricin A or clavin. These recombinant molecules can selectively kill their target cells when internalized after binding to cell surface receptors of the target cells.

The use of antisense oligonucleotides represents another strategy to inhibit the activation of receptor tyrosine kinase (RTKs). Antisense oligonucleotides are short pieces of synthetic DNA or RNA that are designed to interact with the mRNA to block the transcription and thus the expression of the target proteins. Antisense oligonucleotides interact with the mRNA by Watson-Crick base-pairing and are therefore highly specific to the target protein. Several preclinical and clinical studies suggest that antisense therapy might be therapeutically useful for the treatment of solid tumors.

The potential of RTKs and their relevant signaling as selective anti-cancer targets for therapeutic intervention has been recognized. As a consequence, a variety of successful target specific drugs such as mAbs and RTK inhibitors have been developed and are currently being evaluated in clinical trials. Table 3 summarizes the most successful drugs against receptor tyrosine kinase signaling which are currently evaluated in clinical phases or have already been approved by the FDA.

TABLE 3

RTK Drugs Currently Under Clinical Evaluation

| RTK | Drug | Company | Description | Status |
|---|---|---|---|---|
| EGFR | ZA18539 Iressa | AstraZeneca | TKI that inhibits EGFR signaling | Phase III |
| EGFR | Cetuximab C225 | ImClone Systems | Mab directed against EGFR | Phase III |
| EGFR | EGF fusion protein | Seragen | Recombinant diphtheria toxin-hEGF fusion protein | Phase II |
| HER2 | Trastuzumab Herceptin | Genetech | Mab directed against HER2 | Approved by the FDA in 1998 |
| IGF-IR | INX-4437 | INEX USA | Antisense oligo-nucleotides targeting IGR-IR | Phase I |
| VEGFR | SU5416 | SUGEN | TKI that inhibits VEGFR2 | Phase II |
| VEGFR/ FGFR/ PDGFR | SU6668 | SUGEN | RTK inhibition of VEGFR, FGFR, and PDGFR | Phase I |

Non-receptor PTKs lack transmembrane regions and, instead, form complexes with the intracellular regions of cell surface receptors. Receptors that function through non-receptor PTKs include those for cytokines, hormones (growth hormone and prolactin) and antigen-specific receptors on T and B lymphocytes.

Many of the PTKs were first identified as the products of mutant oncogenes in cancer cells where their activation was no longer subject to normal cellular controls. In fact, about one third of the known oncogenes encode PTKs, and it is well known that cellular transformation (oncogenesis) is often accompanied by increased tyrosine phosphorylation activity.

Many tyrosine kinase inhibitors, such as flavopiridol, genistem, erbstatin, lavendustin A, staurosporine, and UCN-01, are derived from natural products. Inhibitors directed to the ATP binding site are also available. Signals from RTKs can also be inhibited at other target sites such as nuclear tyrosine kinases, membrane anchors (inhibition of farnesylation) and transcription factors.

Targeting the signaling potential of growth promoting tyrosine kinases such as EGFR, HER2, PDGFR, src, and abl, will block tumor growth while blocking IGF-I and TRK will interfere with tumor cell survival. Inhibition of these kinases will lead to tumor shrinkage and apoptosis. FklI/KDR and src are kinases necessary for neovascularization (angiogenesis) of tumors. Inhibition of these kinases will slow tumor growth and decrease metastases.

Inhibitors of RTKs suppress tumor development by preventing cell migration, invasion and metastases. These drugs are likely to increase the time required for tumor progression, and may inhibit or attenuate the aggressiveness of the disease but may not initially result in measurable tumor regression.

An example of cancer arising from a defective tyrosine kinase is a class of ALK positive lymphomas referred to as "ALKomas" which display inappropriate expression of a neural-specific tyrosine kinase, anaplastic lymphoma kinase (ALK).

Iressa (ZD1839) is an orally active selective EGF-R inhibitor. This compound disrupts signaling involved in cancer cell proliferation. The clinical efficacy of this agent shows that it is well tolerated by patients undergoing Phase I/II clinical trials. The compound has shown promising cytotoxicity towards several cancer cell lines.

Since the majority of protein kinases are expressed in the brain, often in a neuron-specific fashion, protein phosphorylation must play a key role in the development and function of the vertebrate central nervous system. Thus neuron-specific kinases are well established as targets for the development of pharmacologically active modulators.

In summary, kinase proteins are a major target for drug action and development. Accordingly, it is valuable to the field of pharmaceutical development to identify and characterize previously unknown members of kinase proteins. The present invention advances the state of the art by providing a previously unidentified human kinase protein that has sequence and structure similarities to several protein kinases. Specifically, the kinase domain in HPK3P23 shares high sequence identity with the corresponding domains in serine/threonine kinases, tyrosine kinases, and pkinases. This domain, either in the native form or in the mutant form, can be used to affect the function of the corresponding domain in other kinases. The kinase domain in HPK3P23 can be used to phosphorylate suitable substrates. The substrate peptides can be conjugated to antibodies, and the phosphate groups added to the substrate peptides can be radioactively or fluorescently labeled. Antibodies thus labeled can be used in various detection assays, as appreciated by one of ordinary skill in the art.

HPK3P23 gene and the gene product can be used as a molecular marker for diagnosing, prognosing, and monitoring the treatment of disorders related to the aberrant expression of HPK3P23. In addition, the HPK3P23 gene can be used to screen for potential agents or drugs capable of enhancing or inhibiting the HPK3P23 gene expression in human cells. the HPK3P23 gene products (polynucleotide and polypeptide) can be used to screen for potential agents or drugs capable of enhancing or inhibiting HPK3P23 activity. Furthermore, various therapeutic methods for treating disorders related to the aberrant expression of HPK3P23 can be designed based on the HPK3P23 gene, its variants, or the agents/drugs that affect the expression of the HPK3P23 gene or the activity of the HPK3P23 gene products.

The following subsections illustrate examples of the utilities of human HPK3P23 gene and HPK3P23 kinase. Various changes and modifications within the spirit and scope of the present invention will become apparent to those skilled in the art from the present description.

Polynucleotides and Variants Thereof

One aspect of the invention pertains to isolated polynucleotide probes capable of hybridizing to the HPK3P23 gene or its transcripts, such as HPK3P23 mRNAs. These probes can be used to detect the expression level of the HPK3P23 gene in human tissue or cells. The present invention also contemplates polynucleotide fragments for use as PCR primers for the amplification or mutation of the HPK3P23 gene or the HPK3P23 kinase-coding sequences. Another aspect of the invention pertains to isolated polynucleotides that encode HPK3P23, or a fragment or mutant thereof. These polynucleotides can be used for expressing HPK3P23, or a fragment or mutant thereof. The protein products thus expressed can be used to screen for agents/drugs that modulate an activity of HPK3P23. In addition, these polynucleotides can be used to designing gene therapy vectors which target the expression of the HPK3P23 gene or an activity of HPK3P23 in humans.

A polynucleotide comprising SEQ ID NO:1 or SEQ ID NO:3 can be prepared using standard molecular biology techniques as appreciated by one of ordinary skill in the art. For instance, primers derived from the 5' and 3' ends of SEQ ID NO:1 can be used to amplify mRNAs isolated from human tissues. The cDNA thus produced contains SEQ ID NO:1. Likewise, primers for amplifying the human genomic sequence containing SEQ ID NO:3 can be designed and used to prepare the genomic sequence of the HPK3P23 gene. A variant (such as a homolog) or a fragment of SEQ ID NO:1 or SEQ ID NO:3 can be similarly prepared. Alternatively, probes can be designed to screen for cDNA or genomic sequence libraries in order to identify polynucleotide molecules comprising the full-length or fragments of SEQ ID NO:1 or SEQ ID NO:3. The molecules thus identified can be used to create suitable vectors comprising the full-length SEQ ID NO:1 or SEQ ID NO:3.

Polynucleotides capable of hybridizing to the HPK3P23 gene can be prepared by standard synthetic techniques, e.g., using an automated DNA synthesizer. Preferably, the polynucleotide probes can hybridize to the HPK3P23 gene under reduced stringent conditions, stringent conditions, or highly stringent conditions. In one embodiment, the polynucleotides comprise at least 15, 20, 25, 30, 50, 100, 150, 200, 250, 300, 350, 400, 450, 500, 550, 600, 650, 700, 750, 800, 850, 900, 950, 1000 or more consecutive nucleotides of SEQ ID NO:1. Any fragments of SEQ ID NO:1 and SEQ ID NO:3 may be used as hybridization probes or PCR primers for the HPK3P23 gene or its transcripts. The probes/primers can be substantially purified.

In a preferred embodiment, the hybridization probes for the HPK3P23 gene comprise a label group. The label group can be a radioisotope, a fluorescent compound, an enzyme, or an enzyme co-factor. Probes thus labeled can be used as part of a diagnostic kit for determining the expression level of the HPK3P23 gene in human tissues.

This invention encompasses human HPK3P23 gene homologs in other species. These homologs can be determined by search different sequence databases, such as the Entrez/GenBank sequence databases maintained by the NCBI. The invention also encompasses polynucleotide molecules which are structurally different from the molecules described above, but have the substantially same properties as the molecules described above. Such molecules include allelic variants, which will be described below in greater detail.

DNA sequence polymorphism in human HPK3P23 gene exists among different individuals due to natural allelic variations. An allele is one of a group of genes which occur alternatively at a given genetic locus. DNA polymorphisms that affect the RNA expression level of the HPK3P23 gene can also exist, e.g through affecting the regulation or degradation of expression of the gene. The present invention contemplates all allelic variants of human HPK3P23 gene. Allelic variants and other homologs of the HPK3P23 gene can be isolated using probes/primers derived from SEQ ID NO:1 or SEQ ID NO:3.

It should, of course, be understood that SEQ ID NO:1 and SEQ ID NO:3 can be modified. The modified polynucleotides can comprise one or more mutations. These mutations can be substitutions, additions or deletions of 1, 2, 3, 5, 10, 15, 20 or more nucleotide residues in SEQ ID NO:1 or SEQ ID NO:3. Standard techniques can be used, such as site-directed mutagenesis or PCR-mediated mutagenesis. Preferably, these mutations create conservative amino acid substitutions. Alternatively, mutations can be introduced randomly along all or part of the HPK3P23 gene or its cDNA, such as by saturation mutagenesis. Following mutagenesis, the encoded proteins can be expressed recombinantly and their activities can be determined.

In one embodiment, nucleotide substitutions leading to amino acid substitutions at "non-essential" amino acid residues can be introduced. A "non-essential" amino acid residue is a residue that can be altered without changing the biological activity of the protein. In contrast, an "essential" amino acid residue is required for the biological activity of the protein. Amino acid residues that are conserved among allelic variants or homologs of the HPK3P23 gene from different species preferably are not changed in the present invention.

Accordingly, another aspect of the invention pertains to HPK3P23 proteins that contain changes in amino acid residues that are not essential for the biological activity of HPK3P23. These proteins differ in amino acid sequence from the original human HPK3P23 kinase, but retain its biological activity. In one embodiment, the modified protein comprises an amino acid sequence at least about 92%, 94%, 96%, 98% or more homologous to SEQ ID NO:2.

In another embodiment, HPK3P23 proteins contain mutations in amino acid residues which result in inhibition of HPK3P23 activity. These mutated HPK3P23 proteins can be used to inhibit HPK3P23 activity in patients with disorders related to the aberrant expression of HPK3P23.

A polynucleotide of this invention can be further modified to increase its stability in vivo. Possible modifications include, but are not limited to, the addition of flanking sequences at the 5' and/or 3' ends; the use of phosphorothioate or 2-o-methyl rather than phosphodiester linkages in the backbone; and/or the inclusion of nontraditional bases such as inosine, queosine and wybutosine, as well as acetyl-methyl-, thio- and other modified forms of adenine, cytidine, guanine, thymine and uridine.

Polynucleotide molecules which are antisense to the HPK3P23 gene can be prepared. An "antisense" polynucleotide comprises a nucleotide sequence which is complementary to a "sense" polynucleotide which encodes a protein. An antisense polynucleotide can bind via hydrogen bonds to the sense polynucleotide.

Antisense polynucleotides of the invention can be designed according to the rules of Watson and Crick base pairing. The antisense polynucleotide molecule can be complementary to the entire coding region or part of the coding region of the HPK3P23 gene. The antisense polynucleotide molecule can also be complementary to a "non-coding region" in the coding strand of the HPK3P23 gene. Preferably, the antisense polynucleotide is an oligonucleotide which is antisense to only a portion of the HPK3P23 gene. An antisense polynucleotide can be, for example, about 5, 10, 15, 20, 25, 30, 35, 40, 45 or 50 nucleotides in length. An antisense polynucleotide of the invention can be constructed using chemical synthesis and enzymatic ligation reactions as appreciated by one of ordinary skill in the art. For example, an antisense polynucleotide can be chemically synthesized using naturally occurring nucleotides or variously modified nucleotides designed to increase the biological stability of the molecules or to increase the physical stability of the duplex formed between the antisense and sense polynucleotides. Examples of modified nucleotides which can be used to generate the antisense polynucleotide include 5-fluorouracil, 5-bromouracil, 5-chlorouracil, 5-iodouracil, hypoxanthine, xantine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-6-isopentenyl adenosine, uracil-5-oxyacetic acid, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, (acp3)w, and 2,6-diaminopurine. Phosphorothioate derivatives and acridine substituted nucleotides can also be used. Alternatively, the antisense polynucleotide can be produced biologically using an expression vector into which a polynucleotide has been subcloned in an antisense orientation (i.e., RNA transcribed from the inserted polynucleotide will be of an antisense orientation to the target polynucleotide of interest).

The antisense polynucleotides of the invention can be administered to a subject or applied in situ such that they hybridize or bind to cellular mRNAs and/or genomic DNAs that encode HPK3P23 kinase, thereby inhibiting the expression of HPK3P23 kinase. The hybridization can result in a stable duplex via conventional nucleotide complementarity. An example route for administering antisense polynucleotides includes direct injection at a tissue site. Antisense polynucleotides can also be modified first, and then administered systemically. For example, for systemic administration, antisense molecules can be modified such that they specifically bind to receptors or antigens expressed on a selected cell surface. Suitable modifications include linking the antisense polynucleotides to peptides or antibodies which bind to the cell surface receptors or antigens. In addition, the antisense polynucleotides can be delivered to cells using vectors. To achieve sufficient intracellular concentrations of the antisense molecules, strong pol II or pol III promoters may be used in the vectors.

In one embodiment, the antisense polynucleotides are α-anomeric polynucleotides. An α-anomeric polynucleotide molecule forms specific double-stranded hybrid with a complementary RNA in which, contrary to the usual β-units, the strands run parallel to each other. The antisense polynucleotide molecule can also comprise a 2-o-methylribonucleotide or a chimeric RNA-DNA analogue.

In another embodiment, the antisense polynucleotide is a ribozyme. Ribozymes are catalytic RNA molecules with ribonuclease activity which are capable of cleaving a single-stranded polynucleotide, such as an mRNA, to which they have a complementary region. Thus, ribozymes (e.g., hammerhead ribozymes described in Haselhoif and Gerlach, Nature 334:585–591, 1988) can be used to catalytically cleave mRNA transcripts of HPK3P23 in order to inhibit its expression. A ribozyme having specificity for the HPK3P23 gene or its transcripts can be designed based upon SEQ ID NO:1 or 3. mRNAs transcribed from the HPK3P23 gene can be used to select from a pool of RNA molecules a catalytic RNA having a specific ribonuclease activity.

Alternatively, the expression of the HPK3P23 gene can be inhibited by using nucleotide sequences complementary to the regulatory region (e.g., the promoter and/or enhancers). These nucleotide sequences can form triple helical structures that prevent transcription of the gene in the target cells.

Expression of the HPK3P23 gene can also be inhibited using RNA interference ("RNAi"). RNAi is a phenomenon in which the introduction of double-stranded RNA (dsRNA) into certain organisms or cell types causes degradation of the homologous mRNA. First discovered in the nematode *Caenorhabditis elegans*, RNAi has since been found to operate in a wide range of organisms. For example, in mammalian cells, introduction of long dsRNA (>30 nt) can initiate a potent antiviral response, exemplified by non-specific inhibition of protein synthesis and RNA degradation. RNA interference provides a mechanism of gene silencing at the mRNA level. In recent years, RNAi has become an endogenous and potent gene-specific silencing technique that uses double-stranded RNAs (dsRNA) to mark a particular transcript for degradation in vivo. It also offers an efficient and broadly applicable approach for gene knock-out. In addition, RNAi technology can be used for therapeutic purposes. For example, RNAi targeting Fas-mediated apoptosis has been shown to protect mice from fulminant hepatitis. RNAi technology has been disclosed in numerous publications, such as U.S. Pat. Nos. 5,919,619, 6,506,559 and PCT Publication Nos. WO99/14346, WO01/70949, WO01/36646, WO00/63364, WO00/44895, WO01/75164, WO01/92513, WO01/68836 and WO01/29058.

In a preferred embodiment, short interfering RNAs (siRNA) are used. siRNAs are dsRNAs having 19–25 nucleotides. siRNAs can be produced endogenously by degradation of longer dsRNA molecules by an RNase III-related nuclease called Dicer. siRNAs can also be introduced into a cell exogenously or by transcription of an expression construct. Once formed, the siRNAs assemble with protein components into endoribonuclease-containing complexes known as RNA-induced silencing complexes (RISCs). An ATP-generated unwinding of the siRNA activates the RISCs, which in turn target the complementary mRNA transcript by Watson-Crick base-pairing, thereby cleaving and destroying the mRNA. Cleavage of the mRNA takes place near the middle of the region bound by the siRNA strand. This sequence specific mRNA degradation results in gene silencing.

At least two ways can be employed to achieve siRNA-mediated gene silencing. First, siRNAs can be synthesized in vitro and introduced into cells to transiently suppress gene expression. Synthetic siRNA provides an easy and efficient way to achieve RNAi. siRNA are duplexes of short mixed oligonucleotides which can include, for example, 19 nucleotides with symmetric 2 dinucleotide 3' overhangs. Using synthetic 21 bp siRNA duplexes (19 RNA bases followed by a UU or dTdT 3' overhang), sequence specific gene silencing can be achieved in mammalian cells. These siRNAs can specifically suppress targeted gene translation in mammalian cells without activation of DNA-dependent protein kinase (PKR) by longer dsRNA, which may result in non-specific repression of translation of many proteins.

Second, siRNAs can be expressed in vivo from vectors. This approach can be used to stably express siRNAs in cells or transgenic animals. In one embodiment, siRNA expression vectors are engineered to drive siRNA transcription from polymerase III (pol III) transcription units. Pol III transcription units are suitable for hairpin siRNA expression, since they deploy a short AT rich transcription termination site that leads to the addition of 2 bp overhangs (UU) to hairpin siRNAs—a feature that is helpful for siRNA function. The Pol III expression vectors can also be used to create transgenic mice that express siRNA.

In another embodiment, siRNAs can be expressed in a tissue-specific manner. Under this approach, long double-stranded RNAs (dsRNAs) are first expressed from a promoter (such as CMV (pol II)) in the nuclei of selected cell lines or transgenic mice. The long dsRNAs are processed into siRNAs in the nuclei (e.g., by Dicer). The siRNAs exit from the nuclei and mediate gene-specific silencing. A similar approach can be used in conjunction with tissue-specific (pol II) promoters to create tissue-specific knock-down mice.

Any 3' dinucleotide overhang, such as UU, can be used for siRNAs. In some cases, G residues in the overhang may be avoided because of the potential for the siRNA to be cleaved by RNase at single-stranded G residues.

With regard to the siRNA sequence itself, it has been found that siRNAs with 30–50% GC content can be more active than those with a higher G/C content in certain cases. Moreover, since a 4–6 nucleotide poly(T) tract may act as a termination signal for RNA pol III, stretches of>4 Ts or As in the target sequence may be avoided in certain cases when designing sequences to be expressed from an RNA pol III promoter. In addition, some regions of mRNA may be either highly structured or bound by regulatory proteins. Thus, it may be helpful to select siRNA target sites at different positions along the length of the gene sequence. Finally, the potential target sites can be compared to the appropriate genome database (human, mouse, rat, etc.). Any target sequences with more than 16–17 contiguous base pairs of homology to other coding sequences may be eliminated from consideration in certain cases.

In one embodiment, siRNA can be designed to have two inverted repeats separated by a short spacer sequence and end with a string of Ts that serve as a transcription termination site. This design produces an RNA transcript that is predicted to fold into a short hairpin siRNA. The selection of siRNA target sequence, the length of the inverted repeats that encode the stem of a putative hairpin, the order of the inverted repeats, the length and composition of the spacer sequence that encodes the loop of the hairpin, and the presence or absence of 5'-overhangs, can vary to achieve desirable results.

The siRNA targets can be selected by scanning an mRNA sequence for AA dinucleotides and recording the 19 nucleotides immediately downstream of the AA. Other methods can also been used to select the siRNA targets. In one example, the selection of the siRNA target sequence is purely empirically determined (see e.g., Sui et al., Proc. Natl. Acad. Sci. USA 99: 5515–5520, 2002), as long as the target sequence starts with GG and does not share significant sequence homology with other genes as analyzed by BLAST search. In another example, a more elaborate method is employed to select the siRNA target sequences. This procedure exploits an observation that any accessible site in endogenous mRNA can be targeted for degradation by synthetic oligodeoxyribonucleotide/RNase H method (Lee et al., Nature Biotechnology 20:500–505, 2002).

In another embodiment, the hairpin siRNA expression cassette is constructed to contain the sense strand of the target, followed by a short spacer, the antisense strand of the target, and 5–6 Ts as transcription terminator. The order of the sense and antisense strands within the siRNA expression constructs can be altered without affecting the gene silencing activities of the hairpin siRNA. In certain instances, the reversal of the order may cause partial reduction in gene silencing activities.

The length of nucleotide sequence being used as the stem of siRNA expression cassette can range, for instance, from 19 to 29. The loop size can range from 3 to 23 nucleotides. Other lengths and/or loop sizes can also be used.

In yet another embodiment, a 5' overhang in the hairpin siRNA construct can be used, provided that the hairpin siRNA is functional in gene silencing. In one specific example, the 5' overhang includes about 6 nucleotide residues.

In a preferred embodiment, the target sequence for RNAi is a 21-mer sequence fragment selected from SEQ ID NO:1. The 5' end of the target sequence has dinucleotide "NA," where "N" can be any base and "A" represents adenine. The remaining 19-mer sequence has a GC content of between 45% and 55%. In addition, the remaining 19-mer sequence does not include (1) any three consecutive identical bases (i.e., GGG, CCC, TTT, or AAA); (2) seven "GC" in a role; and (3) any palindrome sequence with 5 or more bases. Furthermore, the target sequence has low sequence homology to other human genes. In one specific example, potential target sequences are searched by BLASTN against NCBI's human UniGene cluster sequence database. The human UniGene database contains non-redundant sets of gene-oriented clusters. Each UniGene cluster includes sequences that represent a unique gene. Fragments of SEQ ID NO: 1 that produce no hit to other human genes under BLASTN search are selected as the preferred candidate sequences for RNAi. During the search, the e-value may be set at a stringent value (such as "1"). Table 4 lists exemplary HPK3P23 gene target sequences for RNAi prepared using the above-described criteria. The siRNA sequences for each target sequence (the sense strand and the antisense strand) are also disclosed. In addition, the 5' end location of each target sequence in SEQ ID NO:1 is identified ("5 End").

TABLE 4

Exemplary RNAi Target Sequences of the HPK3P23 Gene and the Corresponding siRNAs

| Target Sequence (SEQ ID NO) | 5' End | siRNA Sense Strand (SEQ ID NO) | siRNA Antisense Strand (SEQ ID NO) |
|---|---|---|---|
| AATGAGTACCTCGGCTATGGA (SEQ ID NO:9) | 147 | UGAGUACCUCGGCUAUGGAUU (SEQ ID NO:10) | UUACUCAUGGAGCCGAUACCU (SEQ ID NO:11) |
| AAGACTAACAGCGGAGTTGCT (SEQ ID NO:12) | 353 | GACUAACAGCGGAGUUGCUUU (SEQ ID NO:13) | UUCUGAUUGUCGCCUCAACGA (SEQ ID NO:14) |
| AAGATCGAGACAGCAGCGTAA (SEQ ID NO:15) | 1216 | GAUCGAGACAGCAGCGUAAUU (SEQ ID NO:16) | UUCUAGCUCUGUCGUCGCAUU (SEQ ID NO:17) |
| AACTCACGTCTGTGGTTGGAA (SEQ ID NO:18) | 1585 | CUCACGUCUGUGGUUGGAAUU (SEQ ID NO:19) | UUCUAGCUCUGUCGUCGCAUU (SEQ ID NO:20) |
| AATAGTGGAGGCGGTATATGA (SEQ ID NO:21) | 1751 | UAGUGGAGGCGGUAUAUGAUU (SEQ ID NO:22) | UUAUCACCUCCGCCAUAUACU (SEQ ID NO:23) |
| AAGCTCGTCCAGATATTGTAG (SEQ ID NO:24) | 1843 | GCUCGUCCAGAUAUUGUAGUU (SEQ ID NO:25) | UUCGAGCAGGUCUAUAACAUC (SEQ ID NO:26) |
| AACACCGTCACATGTCACCAT (SEQ ID NO:27) | 1995 | CACCGUCACAUGUCACCAUUU (SEQ ID NO:28) | UUGUGGCAGUGUACAGUGGUA (SEQ ID NO:29) |
| AATAGAGGCTGAGTTAGTGAC (SEQ ID NO:30) | 2465 | UAGAGGCUGAGUUAGUGACUU (SEQ ID NO:31) | UUAUCUCCGACUCAAUCACUG (SEQ ID NO:32) |
| AATTGCTAGTGCATTGGTGAG (SEQ ID NO:33) | 3529 | UUGCUAGUGCAUUGGUGAGUU (SEQ ID NO:34) | UUAACGAUCACGUAACCACUC (SEQ ID NO:35) |
| CAATGAGTACCTCGGCTATGG (SEQ ID NO:36) | 146 | AUGAGUACCUCGGCUAUGGUU (SEQ ID NO:37) | UUUACUCAUGGAGCCGAUACC (SEQ ID NO:38) |

TABLE 4-continued

Exemplary RNAi Target Sequences of the HPK3P23 Gene
and the Corresponding siRNAs

| Target Sequence (SEQ ID NO) | 5' End | siRNA Sense Strand (SEQ ID NO) | siRNA Antisense Strand (SEQ ID NO) |
|---|---|---|---|
| CAGCTGTGCTTAGCTCTTCGA (SEQ ID NO:39) | 1440 | GCUGUGCUUAGCUCUUCGAUU (SEQ ID NO:40) | UUCGACACGAAUCGAGAAGCU (SEQ ID NO:41) |
| CAGCACTAACATGCTGTCCTT (SEQ ID NO:42) | 1721 | GCACUAACAUGCUGUCCUUUU (SEQ ID NO:43) | UUCGUGAUUGUACGACAGGAA (SEQ ID NO:44) |
| CAAGCATCAGCAGGAATTGCT (SEQ ID NO:45) | 2568 | AGCAUCAGCAGGAAUUGCUUU (SEQ ID NO:46) | UUUCGUAGUCGUCCUUAACGA (SEQ ID NO:47) |
| CAGGATGTCAGAGCTACCAG (SEQ ID NO:48) | 3266 | GGAUGUCAGAGCUACCAGUUU (SEQ ID NO:49) | UUCCUACAGUCUCGAUGGUCA (SEQ ID NO:50) |
| GAGACAGCAGCGTAAGGAATA (SEQ ID NO:51) | 1222 | GACAGCAGCGUAAGGAAUAUU (SEQ ID NO:52) | UUCUGUCGUCGCAUUCCUUAU (SEQ ID NO:53) |
| GAGGCGGTATATGAACCAGTC (SEQ ID NO:54) | 1758 | GGCGGUAUAUGAACCAGUCUU (SEQ ID NO:55) | UUCCGCCAUAUACUUGGUCAG (SEQ ID NO:56) |
| GAACACCGTCACATGTCACCA (SEQ ID NO:57) | 1994 | ACACCGUCACAUGUCACCAUU (SEQ ID NO:58) | UUUGUGGCAGUGUACAGUGGU (SEQ ID NO:59) |
| GATCTCCAGAACCGATTGAG (SEQ ID NO:60) | 2794 | UCUCCAGAACCGAUUGAGCUU (SEQ ID NO:61) | UCUCCAGAACCGAUUGAGCUU (SEQ ID NO:62) |
| GACTTCAGCCGCTATTGCAAG (SEQ ID NO:63) | 3102 | CUUCAGCCGCUAUUGCAAGUU (SEQ ID NO:64) | UUGAAGUCGGCGAUAACGUUC (SEQ ID NO:65) |
| GAGTATATGACAGCTGCGGTA (SEQ ID NO:66) | 3212 | GUAUAUGACAGCUGCGGUAUU (SEQ ID NO:67) | UUCAUAUACUGUCGACGCCAU (SEQ ID NO:68) |
| GAGGATTGAGCATCGAATGGT (SEQ ID NO:69) | 3325 | GGAUUGAGCAUCGAAUGGUUU (SEQ ID NO:70) | UUCCUAACUCGUAGCUUACCA (SEQ ID NO:71) |
| GAGTTCGCATCACACCAGATC (SEQ ID NO:72) | 3393 | GUUCGCAUCACACCAGAUCUU (SEQ ID NO:73) | UUCAAGCGUAGUGUGGUCUAG (SEQ ID NO:74) |
| TAGTGGAGGCGGTATATGAAC (SEQ ID NO:75) | 1753 | GUGGAGGCGGUAUAUGAACUU (SEQ ID NO:76) | UUCACCUCCGCCAUAUACUUG (SEQ ID NO:77) |
| TATTACATCGTTCATCCGGTG (SEQ ID NO:78) | 2842 | UUACAUCGUUCAUCCGGUGUU (SEQ ID NO:79) | UUAAUGUAGCAAGUAGGCCAC (SEQ ID NO:80) |
| TATATGACAGCTGCGGTACTT (SEQ ID NO:81) | 3215 | UAUGACAGCUGCGGUACUUUU (SEQ ID NO:82) | UUUAUACUGUCGACGCCAUGAA (SEQ ID NO:83) |
| TATGACAGCTGCGGTACTTGA (SEQ ID NO:84) | 3217 | UGACAGCUGCGGUACUUGAUU (SEQ ID NO:85) | UUACUGUCGACGCCAUGAACU (SEQ ID NO:86) |

In yet another embodiment, the polynucleotides of the present invention can be modified at the base moiety, sugar moiety or phosphate backbone to improve the stability, hybridization, or solubility of the molecules. For instance, the deoxyribose phosphate backbone of the polynucleotide molecules can be modified to generate peptide polynucleotides (see Hyrup B. et al. Bioorganic & Medicinal Chemistry 4:523, 1996). As used herein, the terms "peptide polynucleotides" or "PNAs" refer to polynucleotide mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. PNA oligomers can be synthesized using standard solid phase peptide synthesis protocols.

PNAs can be used in therapeutic and diagnostic applications. For example, PNAs can be used as antisense agents for sequence-specific modulation of the HPK3P23 gene expression. PNAs can also be used in the analysis of single base pair mutations in a gene, (e.g., by PNA-directed PCR clamping); as artificial restriction enzymes when used in combination with other enzymes, (e.g., S1 nucleases); or as probes or primers for DNA sequencing or hybridization.

In one embodiment, PNAs can be modified to enhance their stability or cellular uptake by attaching lipophilic or other helper groups to PNA, by the formation of PNA-DNA chimeras, or by the use of liposomes or other drug delivery techniques known in the art. For example, PNA-DNA chimeras of the polynucleotides of the invention can be generated. These chimeras allow DNA recognition enzymes, such as RNase H and DNA polymerases, to interact with the DNA portion while the PNA portion provides high binding affinity and specificity. PNA-DNA chimeras can be linked using linkers of appropriate lengths which are selected based on base stacking, number of bonds between the nucleobases, and orientations. The PNA-DNA chimeras can be synthesized as follows. A DNA chain is synthesized on a solid support using standard phosphoramidite coupling chemistry and modified nucleoside analogs. PNA monomers are then coupled in a stepwise manner to produce a chimeric molecule with a 5' PNA segment and a 3' DNA segment. Alternatively, chimeric molecules can be synthesized with a 5' DNA segment and a 3' PNA segment.

In other embodiments, the polynucleotides of this invention may include other appended groups such as peptides (e.g., for targeting host cell receptors in vivo), or agents facilitating transportation across the cell membrane or the blood-kidney barrier (see, e.g., PCT Publication No. W089/10134). In addition, polynucleotides can be modified using hybridization-triggered cleavage agents or intercalating agents. To this end, the polynucleotides can be conjugated to another molecule (e.g., a peptide, hybridization triggered cross-linking agent, transport agent, or hybridization-triggered cleavage agent). Furthermore, the polynucleotide can be detectably labeled.

Polypeptides and Variants Thereof

Several aspects of the invention pertain to isolated HPK3P23 polypeptides and mutated HPK3P23 polypeptides capable of inhibiting normal HPK3P23 activity. The present invention also contemplates immunogenic polypeptide fragments suitable for raising anti-HPK3P23 antibodies.

In one embodiment, native HPK3P23 polypeptides can be isolated from cells or tissue sources by using standard protein purification techniques. Standard purification methods include electrophoresis, molecular, immunological and chromatographic techniques. Specific examples include ion exchange, hydrophobic, affinity or reverse-phase HPLC chromatography, and chromatofocusing. In one embodiment, HPK3P23 polypeptides are purified using a standard affinity column coupled with anti-HPK3P23 antibodies. Ultrafiltration and diafiltration techniques can also be used. The degree of purification depends on the purpose of the use of the HPK3P23 polypeptides. In some instances, purification is not necessary.

In another embodiment, HPK3P23 polypeptides or mutated HPK3P23 polypeptides capable of inhibiting normal HPK3P23 activity are produced by recombinant DNA techniques. Alternative to recombinant expression, HPK3P23 polypeptides or mutated HPK3P23 polypeptides can be synthesized chemically using standard peptide synthesis techniques.

The invention provides HPK3P23 polypeptides encoded by the human HPK3P23 gene, or homologs thereof. The polypeptides of this invention can be substantially homologous to human HPK3P23 kinase (SEQ ID NO:2). Preferably, these polypeptides retain the biological activity of the native HPK3P23 kinase. In one embodiment, the polypeptides comprise an amino acid sequence which is at least about 92%, 94%, 96%, 98% or more homologous to SEQ ID NO:2.

Comparison of sequences and determination of percent identity between two sequences can be accomplished using a mathematical algorithm. The percent identity between two amino acid sequences can be determined using the Needleman and Wunsch (J. Mol. Biol. 48:444–453, 1970) algorithm, or the GAP program in the GCG software package which uses either a Blossom 62 matrix or a PAM250 matrix, and a gap weight of 16, 14, 12, 10, 8, 6, or 4 and a length weight of 1, 2, 3, 4, 5, or 6. The percent identity between two nucleotide sequences can be determined using the GAP program in the GCG software package, which uses a NWSgapdna. CMP matrix and a gap weight of 40, 50, 60, 70, or 80 and a length weight of 1, 2, 3, 4, 5, or 6. The percent identity between two amino acid or nucleotide sequences can also be determined using the algorithm of E. Meyers and W. Miller (CABIOS, 4:11–17, 1989) which has been incorporated into the ALIGN program (version 2.0), or the pairwise BLAST program available at NCBI's BLAST web site.

The polypeptide and polynucleotide sequences of the present invention can be used as query sequences for searching public databases in order to identify similar sequences. The search can be conducted using BLAST programs, such as the protein BLAST, nucleotide BLAST, pairwise BLAST, and genomic BLAST, that are available at the BLAST web site maintained by the NCBI. When using BLAST programs, the default parameters of the respective programs can also be used.

The invention further provides chimeric or fusion HPK3P23 polypeptides. A fusion HPK3P23 polypeptide contains an HPK3P23-related polypeptide and a non-HPK3P23 polypeptide. The HPK3P23-related polypeptides include all or a portion of SEQ ID NO:2 or its variant. A peptide linker sequence can be employed to separate the HPK3P23-related polypeptide from the non-HPK3P23 polypeptide components by a distance sufficient to ensure that each polypeptide folds into its native secondary and tertiary structures. Such a peptide linker sequence is incorporated into the fusion protein using standard techniques well known in the art. Suitable peptide linker sequences can be chosen based on the following factors: (1) their ability to adopt a flexible extended conformation; (2) their inability to adopt a secondary structure that could interact with functional epitopes on the HPK3P23-related polypeptide and non-HPK3P23 polypeptide; and (3) the lack of hydrophobic or charged residues that might react with the polypeptide functional epitopes. Preferred peptide linker sequences contain Gly, Asn and Ser residues. Other near neutral amino acids, such as Thr and Ala can also be used in the linker sequence. Amino acid sequences suitable as linkers include those disclosed in Maratea et al., Gene 40:39–46, 1985; Murphy et al., Proc. Natl. Acad. Sci. USA 83:8258–8262, 1986; U.S. Pat. No. 4,935,233 and U.S. Pat. No. 4,751,180. The linker sequences may be from 1 to about 50 amino acids in length. Linker sequences are not required when the HPK3P23-related polypeptide or the non-HPK3P23 polypeptide has non-essential N-terminal amino acid regions that can be used to separate the respective functional domains and thereby prevent steric interference.

In one embodiment, the fusion protein is a GST-HPK3P23 fusion protein in which an HPK3P23-related sequence, such as SEQ ID NO:2, is fused to the C-terminus of the GST sequence. This fusion protein can facilitate the purification of the recombinant HPK3P23.

The HPK3P23-fusion proteins of the invention can be incorporated into pharmaceutical compositions and administered to a subject. The HPK3P23-fusion proteins can be used to affect the bioavailability of an HPK3P23 substrate. The HPK3P23-fusion proteins can also be used for the treatment or prevention of damages caused by (i) aberrant modification or mutation of HPK3P23, or (ii) aberrant post-translational modification of HPK3P23. It is also conceivable that a fusion protein containing a normal or mutated HPK3P23 polypeptide, or a fragment thereof, can be used to inhibit HPK3P23 activity in a human subject.

Moreover, the HPK3P23-fusion proteins can be used as immunogens to produce anti-HPK3P23 antibodies. They can also be used to purify HPK3P23 ligands and to screen for molecules capable of inhibiting the interaction between HPK3P23 and its substrates.

Preferably, the HPK3P23-chimeric or fusion proteins of the invention are produced using standard recombinant DNA techniques. Commercially available expression vectors which encode a fusion moiety (e.g., a GST polypeptide) can be used.

A signal sequence can be used to facilitate secretion and isolation of the secreted protein or other proteins of interest. Signal sequences are typically characterized by a core of hydrophobic amino acids which are generally cleaved from the mature protein. Such signal peptides contain processing sites that allow cleavage of the signal sequence from the mature proteins as they pass through the secretory pathway. The present invention encompasses HPK3P23 polypeptides having a signal sequence, or the polynucleotide sequences encoding the same.

The present invention also pertains to HPK3P23 mutants which function as antagonists to HPK3P23. In one embodiment, antagonists of HPK3P23 are used as therapeutic agents. For example, a mutant of HPK3P23 that forms a non-functional dimer with a wide-type HPK3P23 (the so-called dominant negative mutant) can decrease the activity of HPK3P23 and may ameliorate diseases in a subject wherein HPK3P23 are abnormally increased in level or activity. Dominant negative HPK3P23 mutants can be generated by mutagenesis, as appreciated by one skilled in the art.

HPK3P23 mutants which function as either HPK3P23 agonists or antagonists can be identified by screening combinatorial libraries of mutants. A variegated library of HPK3P23 mutants can be produced by, for example, enzymatically ligating a mixture of synthetic oligonucleotides into gene sequences such that a degenerate set of potential HPK3P23 sequences is expressible as individual polypeptides, or alternatively, as a set of larger fusion proteins containing the set of HPK3P23 sequences therein. There are a variety of methods which can be used to produce libraries of potential HPK3P23 mutants from a degenerate oligonucleotide sequence. A degenerate gene sequence can be chemically synthesized using an automatic DNA synthesizer. The synthetic gene can then be ligated into an appropriate expression vector.

In one embodiment, a library of coding sequences can be generated using nucleases. For instance, double stranded PCR fragments of the HPK3P23 coding sequence can be treated by a nuclease which produces about one nick per molecule. The double-stranded DNAs then are subject to a cycle of denaturing and re-naturing. The newly reformed DNAs, which may include sense/antisense pairs from different nicked products, are treated with S1 nuclease to remove single stranded portions. Using this method, an expression library which encodes N-terminal, C-terminal or internal fragments of HPK3P23 can be derived.

In addition, recursive ensemble mutagenesis (REM), a technique which enhances the frequency of functional mutants in the libraries, can be used to prepare HPK3P23 mutants (Delgrave et al, Protein Engineering 6:327–331, 1993).

HPK3P23 fragments, or variants thereof, can also be generated using synthetic means, such as solid-phase synthesis methods. Preferably, the synthesized fragment has less than about 100 amino acids, or preferably, less than about 50 amino acids.

Antibodies

In accordance with another aspect of the present invention, antibodies specific to HPK3P23 or its variants are prepared. An antibody is considered to bind "specifically" to an antigen if the binding affinity between the antibody and the antigen is equal to, or greater than 105 M-1. The antibodies can be monoclonal or polyclonal. Preferably, the antibodies are monoclonal. More preferably, the antibodies are humanized antibodies.

Polyclonal anti-HPK3P23 antibodies can be prepared by immunizing a suitable subject with HPK3P23 or fragments thereof. The anti-HPK3P23 antibody titer in the immunized subject can be monitored over the time using standard techniques, such as ELISA. The anti-HPK3P23 antibody can be isolated from the immunized subject using well known techniques.

In one embodiment, hybridomas capable of producing anti-HPK3P23 antibodies are prepared. Purified HPK3P23 or its variants, or fragments thereof, are used to immunize a vertebrate, such as a mammal. Suitable mammals include mice, rabbits and sheep. Preferably, the fragment used for immunization comprises at least 8 amino acid residues, more preferably at least 12 amino acid residues, highly preferably at least 16 amino acid residues, and most preferably at least 20 amino acid residues.

Immunogenic fragments (epitopes) of HPK3P23 can be identified using well known techniques. In general, any fragment of SEQ ID NO:2 can be used to raise antibodies specific to HPK3P23. Preferred epitopes are regions that are located on the surface of HPK3P23. These regions are usually hydrophilic.

Splenocytes are isolated from the immunized vertebrate and fused with an immortalized cell line (such as a myeloma) to form hybridomas. Preferably, the immortal cell line is derived from the same mammalian species as the lymphocytes. For example, murine hybridomas can be made by fusing an immortalized mouse cell line with lymphocytes isolated from a mouse that is immunized with an immunogenic preparation of the present invention. Preferred immortalized cell lines include mouse myeloma cell lines that are sensitive to culture medium containing hypoxanthine, aminopterin and thymidine ("HAT medium"). Suitable myeloma cell lines include, but are not limited to, the P3-NS1/1-Ag4-1, P3-x63-Ag8.653 or Sp210-Ag14 myeloma lines, all of which are available from ATCC. In one embodiment, HAT-sensitive mouse myeloma cells are fused to mouse splenocytes using polyethylene glycol ("PEG"). Hybridoma cells thus produced are selected against HAT medium, which kills unfused or unproductively fused myeloma cells. Hybridoma cells which produce monoclonal anti-HPK3P23 antibodies are then detected by screening the hybridoma culture supernatants.

A monoclonal anti-HPK3P23 antibody can also be prepared by screening a recombinant combinatorial immunoglobulin library (e.g., an antibody phage display library). Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612).

The anti-HPK3P23 antibodies of the present invention also include "single-chain Fv" or "scFv." The scFv fragments comprise the VH and VL domains of an antibody. Generally, the scFv polypeptide further comprises a polypeptide linker between the VH and VL domains. The polypeptide linker enables the scFv to form the desired structure for antigen binding. Additionally, recombinant anti-HPK3P23 antibodies, such as chimeric and humanized monoclonal antibodies, can be prepared, as appreciated by one of ordinary skill in the art.

Humanized antibodies are particularly desirable for therapeutic treatment of human subjects. Humanized forms of non-human (e.g., murine) antibodies are chimeric immunoglobulins, immunoglobulin chains, or fragments thereof (such as Fv, Fab, Fab', F(ab')2 or other antigen-binding subsequences of antibodies) which contain minimal sequence derived from non-human immunoglobulin. Humanized antibodies are derived from human immunoglobulins in which the residues forming the complementary determining regions (CDRs) are replaced by the residues from CDRs of a non-human antibody, such as a mouse, rat or rabbit antibody having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. The humanized antibody can comprise at least one or two variable domains, in which all or substantially all of the CDR regions correspond to those of a non-human immunoglobulin and all or substantially all of the constant regions are those of a human immunoglobulin consensus sequence. The humanized antibody preferably comprises at least a portion of an immunoglobulin constant region (Fc) of a human immunoglobulin.

Humanized antibodies can be produced using transgenic mice which are incapable of expressing endogenous immunoglobulin heavy and light chains but can express human heavy and light chains. The transgenic mice are immunized in the normal fashion with a selected antigen. Monoclonal antibodies directed against the antigen can be obtained using conventional hybridoma technology. The human immunoglobulin transgenes harbored in the transgenic mice rearrange during B cell differentiation, and subsequently undergo class switching and somatic mutation. Using this technique, therapeutically useful IgG, IgA and IgE antibodies can be prepared.

In addition, humanized antibodies which recognize a selected epitope can be generated using a technique referred to as "guided selection." In this approach a selected non-human monoclonal antibody, e.g., a murine antibody, is used to guide the selection of a humanized antibody recognizing the same epitope.

In a preferred embodiment, the antibodies to HPK3P23 are capable of reducing or eliminating the biological function of HPK3P23. Preferably, the antibodies reduce at least 25% of HPK3P23 activity. More preferably, the antibodies reduce at least about 50% of the activity. Highly preferably, the antibodies reduce about 95–100% of HPK3P23 activity.

Anti-HPK3P23 antibodies can be used to isolate HPK3P23. Suitable methods include affinity chromatography and immunoprecipitation. Moreover, anti-HPK3P23 antibodies can be used to evaluate the expression level of HPK3P23. Anti-HPK3P23 antibodies can also be used to monitor HPK3P23 level as part of a clinical testing procedure, or to determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive materials include 125I, 131I, 35S or 3H.

Anti-HPK3P23 antibodies are also useful for targeting a therapeutic agent/drug to a particular cell or tissue. The therapeutic agent/drug may be coupled to an antibody, either covalently or non-covalently. For instance, a therapeutic agent can be coupled to an antibody via a linker group. A linker group can function as a spacer to separate the antibody from the agent so as to avoid interference with antibody's binding capabilities. The linker group can also serve to increase the chemical reactivity of a substituent on the agent or the antibody, and thus increase the coupling efficiency. A variety of bifunctional or polyfunctional reagents, either homo- or hetero-functional (such as those described in the catalog of the Pierce Chemical Co., Rockford, Ill.), can be employed as the linker group. Coupling may be effected, for example, through amino groups, carboxyl groups, sulfhydryl groups or oxidized carbohydrate residues. There are numerous references describing this methodology. See e.g., U.S. Pat. No. 4,671,958.

Where a therapeutic agent is more potent when free from the antibody, it may be desirable to use a linker group which is cleavable during or upon internalization into the target cell. A number of different cleavable linker groups have been described. The mechanisms for the intracellular release of an agent from these linker groups include cleavage by reduction of a disulfide bond (e.g., U.S. Pat. No. 4,489,710), by irradiation of a photolabile bond (e.g., U.S. Pat. No. 4,625,014), by hydrolysis of derivatized amino acid side chains (e.g., U.S. Pat. No. 4,638,045), by serum complement-mediated hydrolysis (e.g., U.S. Pat. No. 4,671,958), or by acid-catalyzed hydrolysis (e.g., U.S. Pat. No. 4,569,789).

It may also be desirable to couple more than one agent to an antibody. In one embodiment, multiple agents are coupled to one antibody molecule. In another embodiment, at least two different types of agents are coupled to one antibody. Regardless of the particular embodiment, immunoconjugates coupled with more than one agent can be prepared in a variety of ways, as appreciated by one of ordinary skill in the art.

Vectors, Expression Vectors and Gene Delivery Vectors

Another aspect of the invention pertains to vectors containing a polynucleotide encoding HPK3P23 or a portion thereof. One type of vector is a "plasmid," which includes a circular double stranded DNA into which additional DNA segments can be introduced. Vectors also include expression vectors and gene delivery vectors.

The expression vectors of the present invention comprise a polynucleotide encoding HPK3P23 or a portion thereof. The expression vectors also include one or more regulatory sequences operably linked to the polynucleotide being expressed. These regulatory sequences are selected based on the type of host cells. It will be appreciated by those skilled in the art that the design of the expression vector depends on such factors as the choice of the host cells and the desired expression levels. HPK3P23 can be expressed in bacterial cells such as E. coli, insect cells (using baculovirus expression vectors), yeast cells or mammalian cells. The expression vector can also be transcribed and translated in vitro, for example, by using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of the recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Suitable cleavage enzymes include Factor Xa, thrombin and enterokinase. Examples of fusion expression vectors include pGEX (Pharmacia Piscataway, N.J.), pMAL (New England Biolabs, Beverly, Mass.) and pRITS (Pharmacia, Piscataway, N.J.). Purified fusion proteins can be utilized in HPK3P23 activity assays, or to generate antibodies specific for HPK3P23.

Examples of suitable inducible non-fusion *E. coli* expression vectors include pTrc and pET 11d. Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL221(DE3) or HSLE174(DE3) from a resident prophage harboring a T7 gn1 gene under the transcriptional control of the lacUV 5 promoter.

One strategy to maximize recombinant protein expression in *E. coli* is to express the protein in host bacteria that have an impaired capacity to proteolytically cleave the recombinant protein. Another strategy is to alter the polynucleotide sequence encoding the protein so that the individual codons for each amino acid are those preferentially utilized in *E. coli*.

In another embodiment, the HPK3P23 expression vector is a yeast expression vector. Examples of yeast expression vectors include pYepSec1, pMFa, pJRY88, pYES2 (Invitrogen Corporation, San Diego, Calif.), and picZ (Invitrogen Corp, San Diego, Calif.).

Alternatively, HPK3P23 or its variant can be expressed in insect cells using baculovirus expression vectors. Suitable baculovirus vectors include the pAc series and the pVL series.

In yet another embodiment, HPK3P23 or its variant is expressed in mammalian cells using a mammalian expression vector. Examples of mammalian expression vectors include pCDM8 and pMT2PC. When used in mammalian cells, the expression vector's control functions are often provided by viral regulatory elements. For example, commonly used promoters are derived from polyoma, adenovirus 2, cytomegalovirus and Simian Virus 40.

In another embodiment, the mammalian expression vector contains tissue-specific regulatory elements. Examples of suitable tissue-specific promoters include the liver-specific albumin promoter, lymphoid-specific promoters, promoters of T cell receptors and immunoglobulins, neuron-specific promoters (e.g., the neurofilament promoter), pancreas-specific promoters, and mammary gland-specific promoters (e.g., milk whey promoter). Developmentally-regulated promoters are also contemplated, which include, for example, the α-fetoprotein promoter.

The present invention also provides a recombinant expression vector comprising a polynucleotide which encodes HPK3P23 but is cloned into the expression vector in an antisense orientation. Regulatory sequences that are operatively linked to the antisense-oriented polynucleotide can be chosen to direct continuous expression of the antisense RNA molecule in a variety of cell types. Suitable regulatory sequences include viral promoters and/or enhancers. Regulatory sequences can also be chosen to direct constitutive, tissue specific or cell type specific expression of the antisense RNA. The antisense expression vector can be in the form of a recombinant plasmid, phagemid, or attenuated virus in which antisense polynucleotides are produced under the control of a highly efficient regulatory region.

The present invention further provides gene delivery vehicles for delivering polynucleotides to mammals. A polynucleotide sequence of the invention can be administered either locally or systemically via a gene delivery vehicle. Expression of the polynucleotide can be induced using endogenous mammalian or heterologous promoters. Expression of the polynucleotide in vivo can be either constituted or regulated. The gene delivery vehicles preferably are viral vectors, including retroviral, lentiviral, adenoviral, adeno-associated viral (AAV), herpes viral, or alphavirus vectors. The viral vectors can also be astrovirus, coronavirus, orthomyxovirus, papovavirus, paramyxovirus, parvovirus, picomavirus, poxvirus, or togavirus vectors.

Delivery of gene therapy constructs is not limited to the above mentioned viral vectors. Other delivery methods can also be employed. These methods include nucleic acid expression vectors, polycationic condensed DNA linked or unlinked to killed adenovirus, ligand linked DNA, liposome-DNA conjugates, gene guns, ionizing radiation, nucleic charge neutralization, or fusion with cell membranes. Naked DNA can also be employed. Uptake efficiency of the naked DNA may be improved using biodegradable latex beads. This method can be further improved by treating the beads to increase their hydrophobicity.

Regulatable Expression Systems

Another aspect of the present invention pertains to the use of regulatable expression systems to express desirable polynucleotides or polypeptides in cells. Systems suitable for this invention are briefly described below:

Tet-on/off system. The Tet-system is based on two regulatory elements derived from the tetracycline-resistance operon of the *E. coli* Tn10 transposon: the tet repressor protein (TetR) and the Tet operator DNA sequence (tetO) to which TetR binds (Gossen et al., Science 268: 1766–1769, 1995). The system consists of two components, a "regulator" and a "reporter" plasmid. The "regulator" plasmid encodes a hybrid protein containing a mutated Tet repressor (rtetR) fused to the VP 16 activation domain of herpes simplex virus. The "reporter" plasmid contains a tet-responsive element (TRE), which controls the "reporter" gene of choice. The rtetR-VP16 fusion protein can only bind to the TRE, therefore activating the transcription of the "reporter" gene in the presence of tetracycline. The system has been incorporated into a number of viral vectors including retrovirus, adenovirus and AAV.

Ecdysone system. The Ecdysone system is based on the molting induction system found in *Drosophila*, but modified for inducible expression in mammalian cells. The system uses an analog of the *Drosophila* steroid hormone ecdysone, muristerone A, to activate expression of the gene of interest via a heterodimeric nuclear receptor. Expression levels have been reported to exceed 200-fold over basal levels with no effect on mammalian cell physiology (No et al., Proc. Natl. Acad. Sci. USA 93: 3346–3351, 1996).

Progesterone-system. The progesterone receptor is normally stimulated to bind to a specific DNA sequence and to activate transcription through an interaction with its hormone ligand. Conversely, the progesterone antagonist mifepristone (RU486) is able to block hormone-induced nuclear transport and subsequent DNA binding. A mutant form of the progesterone receptor that can be stimulated to bind through an interaction with RU486 has been generated. To generate a specific, regulatable transcription factor, the RU486-binding domain of the progesterone receptor has been fused to the DNA-binding domain of the yeast transcription factor GAL4 and the transactivation domain of the HSV protein VP16. The chimeric factor is inactive in the absence of RU486. The addition of hormone, however, induces a conformational change in the chimeric protein, and this change allows binding to a GAL4-binding site and the activation of transcription from promoters containing the GAL4-binding site (Wang et al., Nat. Biotech 15: 239–243, 1997).

Rapamycin-system. Immunosuppressive agents, such as FK506 and rapamycin, act by binding to specific cellular proteins and facilitating their dimerization. For example, the binding of rapamycin to FK506-binding protein (FKBP) results in its heterodimerization with another rapamycin binding protein FRAP, which can be reversed by removal of the drug. The ability to bring two proteins together by addition of a drug potentiates the regulation of a number of biological processes, including transcription. A chimeric DNA-binding domain has been fused to the FKBP, which enables binding of the fusion protein to a specific DNA-binding sequence. A transcriptional activation domain also has been fused to FRAP. When these two fusion proteins are co-expressed in the same cell, a fully functional transcription factor can be formed by heterodimerization mediated by addition of rapamycin. The dimerized chimeric transcription factor can then bind to a synthetic promoter sequence containing copies of the synthetic DNA-binding sequence. This system has been successfully integrated into adenoviral and AAV vectors. Long term regulatable gene expression has been achieved in both mice and baboons (Ye et al., Science 283: 88–91, 1999).

Detection Methods

In patients with disorders related to the aberrant expression of HPK3P23. The expression level of HPK3P23 can be used as an indicator for detecting the presence of HPK3P23-related diseases in humans. Detection and measurement of the relative amount of the HPK3P23 gene product can be carried out using various methods known in the art.

Typical methodologies for detecting the transcription level of a gene include extracting RNA from a cell or tissue sample, hybridizing a labeled probe to the extracted RNA or derivative thereof (such as cDNA or cRNA), and detecting the probe. Suitable methods include Northern Blot and quantitative RCR or RT-PCR. In situ hybridization can also be used to detect the transcription level of the HPK3P23 gene in human tissues.

Typical methodologies for detecting a polypeptide include extracting proteins from a cell or tissue sample, binding an antibody to the target polypeptide and detecting the antibody. Suitable methods include enzyme linked immunosorbent assays (ELISAs), Western blots, immunoprecipitations, and immunofluorescence. The antibody can be polyclonal, or preferably, monoclonal. The antibody can be an intact antibody, or a fragment thereof (e.g. Fab or F(ab')2). The antibody can be labeled with a radioisotope, a fluorescent compound, an enzyme, an enzyme co-factor, or a detectable ligand. The term "labeled," with regard to a probe or antibody, is intended to encompass direct labeling such as through covalent coupling, as well as indirect labeling such as being mediated by another reagent which is directly labeled. Examples of indirect labeling include labeling a primary antibody using a fluorescently labeled secondary antibody, or attaching a DNA probe with a biotin which can be detected, for example, by a fluorescence-labeled streptavidin.

Preferably, the binding affinity of the antibody to HPK3P23 is at least 105 M-1. More preferably, the binding affinity is at least 106 M-1. Other methods such as electrophoresis, chromatography or direct sequencing can also be used to detect the amount of a polypeptide in a biological sample. Anti-HPK3P23 antibodies can also be directly introduced into a subject. The antibody can be labeled with a radioactive marker whose presence and location in the subject can be detected using standard imaging techniques.

In one embodiment, the genomic copies of the HPK3P23 gene in the genome of a human subject may indicate the presence or predisposition of a disease. Detection of the presence or number of copies of the HPK3P23 gene in the genome can be performed using methods known in the art. For instance, it can be assessed using Southern Blot. The probes for Southern Blot can be labeled with a radioisotope, a fluorescent compound, an enzyme, or an enzyme co-factor.

In the field of diagnostic assays, the above-described detection methods can be used to determine the severity of HPK3P23-related diseases. A biological sample is isolated from a test subject, and the presence, quantity and/or activity of HPK3P23 in the sample relative to a disease-free or control sample is evaluated. The expression level of HPK3P23 in the biological sample can indicate the presence or severity of HPK3P23-related diseases in the test subject. The term "biological sample" is intended to include tissues, cells or biological fluids isolated from the subject. A preferred biological sample is a serum sample isolated from the subject using conventional means.

Screening Methods

The present invention also provides methods for identifying HPK3P23 modulators. Suitable modulators include compounds or agents comprising therapeutic moieties, such as peptides, peptidomimetics, peptoids, polynucleotides, small molecules or other drugs. These moieties can either bind to HPK3P23, or have a modulatory (e.g., stimulatory or inhibitory) effect on the activity of HPK3P23. In one embodiment, the moieties have a modulatory effect on the interactions of HPK3P23 with one or more of its natural substrates. These moieties can also exert a modulatory effect on the expression of HPK3P23. The screen assays of the present invention comprise detecting the interactions between HPK3P23 and test components.

The test compounds of the present invention can be either small molecules or bioactive agents. In a preferred embodiment, the test compound is a small organic or inorganic molecule. In another preferred embodiment, the test compounds are polypeptides, oligopeptides, polysaccharides, nucleotides or polynucleotides.

In accordance with one aspect of this invention, methods for screening for compounds that inhibit the biological activities of HPK3P23 are provided. Pharmaceutical compositions comprising these compounds can subsequently be prepared. The screening method comprises (1) contacting a sample with a compound, and (2) comparing expression profile or biological activity of HPK3P23 in the sample to determine whether the compound substantially decreases the expression level or activities of HPK3P23. The screening method can be carried out either in vivo or in vitro.

The present invention further includes a method for screening for compounds capable of modulating the binding between HPK3P23 and a binding partner. As used herein, the term "binding partner" refers to a bioactive agent which serves as either a substrate for HPK3P23, or a ligand having a binding affinity to HPK3P23. The bioactive agent may be selected from a variety of naturally-occurring or synthetic compounds, proteins, peptides, polysaccharides, nucleotides or polynucleotides.

Inhibitors of the expression, activity or binding ability of HPK3P23 may be used as therapeutic compositions. These inhibitors can be formulated in suitable pharmaceutical compositions, as described herein below.

The present invention also provides methods for conducting high-throughput screening for compounds capable of inhibiting activity or expression of HPK3P23. In one embodiment, the high-throughput screening method involves contacting test compounds with HPK3P23, and then detecting the effect of the test compounds on HPK3P23. Functional assays, such as cytosensor microphysiometer-based assays, calcium flux assays (e.g., FLIPR®, Molecular Devices Corp, Sunnyvale, Calif.), or the TUNEL assay, can be employed to measure HPK3P23 cellular activity. Fluorescence-based techniques can be used for high-throughput and ultra high-throughput screening. They include, but are not limited to, BRET® and FRET® (both by Packard Instrument Co., Meriden, Conn.).

In a preferred embodiment, the high-throughput screening assay uses label-free plasmon resonance technology as provided by BIACORE® systems (Biacore International AB, Uppsala, Sweden). Plasmon free resonance occurs when surface plasmon waves are excited at a metal/liquid interface. By reflecting directed light from the surface as a result of contact with a sample, the surface plasmon resonance causes a change in the refractive index at the surface layer. The refractive index change for a given change of mass concentration at the surface layer is similar for many bioactive agents (including proteins, peptides, lipids and polynucleotides), and since the BIACORE® sensor surface can be functionalized to bind a variety of these bioactive agents, detection of a wide selection of test compounds can thus be accomplished.

Monitoring Efficacy of a Drug During Clinical Trials

Using the HPK3P23 detection methods of this invention, the efficacy of a therapeutic agent for HPK3P23-related diseases can be monitored during clinical trials. The therapeutic agent may be a drug, small molecule, agonist, antagonist, peptidomimetic, protein, peptide, or polynucleotide. The changes in the expression or activity of the HPK3P23 gene in response to the treatment of the agent can be used to evaluate the therapeutic effect of the agent on patients with HPK3P23-related diseases. In addition, the expression or activity of HPK3P23 in response to the agent can be measured at various points during the clinical trial.

In a preferred embodiment, the method for monitoring the effectiveness of the therapeutic agent includes the steps of (i) obtaining a pre-administration sample from a subject; (ii) detecting the level of expression or activity of HPK3P23 in the pre-administration sample; (iii) obtaining one or more post-administration samples from the subject; (iv) detecting the level of expression or activity of HPK3P23 in the post-administration samples; (v) comparing the level of expression or activity of HPK3P23 in the pre-administration sample to the level of expression or activity of HPK3P23 in the post administration samples. The dose or frequency of the administration of the agent may be adjusted based on the effectiveness of the agent in a particular patient. Therefore, HPK3P23 expression or activity can be used as an indicator of the effectiveness of a therapeutic agent for HPK3P23-related diseases, even if the agent does not produce an observable phenotypic response.

Prognostic Assays

The detection methods described herein can be used to identify subjects having or at risk of developing HPK3P23-related diseases. In addition, the detection methods can be used to determine whether an agent (e.g., an agonist, antagonist, peptidomimetic, protein, peptide, polynucleotide, small molecule, or other drug candidate) can be administered to a subject for effectively treating or preventing HPK3P23-related diseases.

HPK3P23 expression profiles at different progression stages of HPK3P23-related diseases can be established. In addition, HPK3P23 expression profiles in different patients who have different responses to a drug treatment are determined. A pattern may emerge such that a particular expression profile may be correlated to an increased likelihood of a poor prognosis. Therefore, the prognostic assay of the present invention may be used to determine whether a subject undergoing a treatment for a HPK3P23-related disease has a poor outlook for long term survival or disease progression. Preferably, prognosis is performed shortly after diagnosis, such as within a few days after diagnosis. The result of prognosis can then be used to devise individualized treatment program, thereby enhancing the effectiveness of the treatment as well as the likelihood of long-term survival and well being.

The method of the invention can also be used to detect genetic alterations in the HPK3P23 gene, thereby determining if a subject with the altered gene is at risk for damages characterized by aberrant regulation in HPK3P23 activity or expression. In a preferred embodiment, the method includes detecting the presence or absence of a genetic alteration that affects the integrity of the HPK3P23 gene, or detecting the aberrant expression of the HPK3P23 gene. The genetic alteration can be detected by ascertaining the existence of at least one of the following: 1) deletion of one or more nucleotides from the HPK3P23 gene; 2) addition of one or more nucleotides to the HPK3P23 gene; 3) substitution of one or more nucleotides of the HPK3P23 gene, 4) a chromosomal rearrangement in the HPK3P23 gene; 5) alteration in the level of a messenger RNA transcript of the HPK3P23 gene, 6) aberrant modification of the HPK3P23 gene, 7) the presence of a non-wild type splicing pattern of a messenger RNA transcript of the HPK3P23 gene, 8) non-wild type level HPK3P23, 9) allelic loss of an HPK3P23 gene, and 10) inappropriate post-translational modification of HPK3P23.

In one embodiment, detection of the alteration involves the use of a probe/primer in a polymerase chain reaction (such as anchor PCR or RACE PCR) or alternatively, in a ligation chain reaction (LCR). LCR can be particularly useful for detecting point mutations in the HPK3P23 gene. This method includes the steps of collecting a sample from a subject, isolating polynucleotides (e.g., genomic DNA, mRNA, or both) from the sample, contacting the polynucleotide with one or more primers which specifically hybridize to the HPK3P23 gene or gene product, and detecting the presence or absence of an amplification product, or detecting the size of the amplification product and comparing its length to a control. It is understood that PCR and/or LCR can be used as a preliminary amplification step in conjunction with any other techniques described herein.

Alternative amplification methods include: self sustained sequence replication (Guatelli et al., Proc. Natl. Acad. Sci. USA 87:1874–1878, 1990), transcriptional amplification system (Kwoh et al., Proc. Natl. Acad. Sci. USA 86:1173–1177, 1989), and Q-Beta Replicase (Lizardi et al. Bio-Technology 6:1197, 1988).

In another embodiment, mutations in the HPK3P23 gene can be identified using restriction enzymes. Differences in restriction enzyme digestion patterns indicate mutation(s) in the HPK3P23 gene or its transcripts. Moreover, sequence specific ribozymes can be used to detect the presence of specific mutations. See, for example, U.S. Pat. No. 5,498,531.

In yet another embodiment, genetic mutations in the HPK3P23 gene can be identified using high density arrays which contain a large number of oligonucleotides probes. For example, genetic mutations in the HPK3P23 gene can be identified in two dimensional arrays. In this example, a first hybridization array of probes is used to scan through long stretches of DNA in a sample and a control in order to identify base changes between the two sequences. This step allows the identification of point mutations. This step is followed by a second hybridization array that allows the characterization of specific mutations by using smaller and specialized probe arrays which are complementary to all variants or mutations detected. Each mutation array is composed of parallel probe sets, one complementary to the wild-type gene and the other complementary to the mutant gene.

In still another embodiment, any sequencing reactions known in the art can be used to directly sequence the HPK3P23 gene in order to detect mutations. It is contemplated that any automated sequencing procedures can be utilized, including sequencing by mass spectrometry.

In one embodiment, protection from cleavage agents is used to detect mismatched bases in RNA/RNA or RNA/DNA heteroduplexes. In general, the "mismatch cleavage" technique involves forming heteroduplexes by hybridizing an RNA or DNA (labeled) containing the wild-type HPK3P23 gene sequence to a potentially mutant RNA or DNA obtained from a tissue sample. The double-stranded duplexes are treated with an agent which cleaves single-stranded regions of the duplex. The agent may be RNase (for RNA/DNA duplexes), or S1 nuclease (for DNA/DNA hybrids). In one case, either DNA/DNA or RNA/DNA duplexes are treated with piperidine and hydroxylamine, or piperidine and osmium tetroxide, in order to digest mismatched regions. After the digestion, the resulting material is separated by size on a denaturing polyacrylamide gel from which the site(s) of mutation may be determined.

In a preferred embodiment, the mismatch cleavage reaction employs one or more proteins that recognize mismatched base pairs in double-stranded DNA. Examples of these proteins include "DNA mismatch repair" enzymes. For instance, the mutY enzyme of E. coli cleaves A at G/A mismatches, and the thymidine DNA glycosylase from HeLa cells cleaves T at G/T mismatches. In one case, cDNAs are prepared from mRNAs isolated from test cells. The cDNAs are then hybridized to a probe derived from the HPK3P23 gene. The duplex thus formed is treated with a DNA mismatch repair enzyme, and the cleavage products, if any, can be detected from electrophoresis protocols or the like. See, for example, U.S. Pat. No. 5,459,039.

In another embodiment, alterations in electrophoretic mobility are used to identify mutations in the HPK3P23 gene. Differences in electrophoretic mobility between mutant and wild type polynucleotides can be detected using single strand conformation polymorphism (SSCP). The resulting alteration in electrophoretic mobility enables the detection of a single base change. The DNA fragments can be labeled or detected with probes. In one case, the sensitivity of the assay is enhanced by using RNA, in which the secondary structure is more sensitive to a change in sequence. In a preferred embodiment, the assay utilizes heteroduplex analysis to separate double stranded heteroduplex molecules on the basis of changes in electrophoretic mobility (Keen et al., Trends Genet 7:5, 1991).

In yet another embodiment, the movement of mutant or wild-type fragments is evaluated using denaturing gradient gel electrophoresis (DGGE). For this purpose, DNA fragments can be modified to insure that they do not completely denature. For instance, a GC clamp of approximately 40 GC-rich base pairs can be added to the DNA fragment using PCR. In a further embodiment, a temperature gradient is used in place of a denaturing gradient (Rosenbaum and Reissner, Biophys Chem 265:12753, 1987).

Examples of other techniques for detecting point mutations include, but are not limited to, selective oligonucleotide hybridization, selective amplification, or selective primer extension. In one embodiment, oligonucleotide primers for specific amplification carry the mutation of interest in the center of the molecule (so that amplification depends on differential hybridization) or at the extreme 3' end of one primer where, under appropriate conditions, mismatch can prevent or reduce polymerase extension. See, for example, Saiki et al., Proc. Natl. Acad. Sci USA 86:6230, 1989. In addition, it may be desirable to introduce a novel restriction site in the region of the mutation to create cleavage-based detection.

The methods described herein can be performed using prepackaged diagnostic kits which comprise at least one polynucleotide probe or one antibody of the present invention. These kits can be used in clinical settings to diagnose subjects exhibiting symptoms or family history of a HPK3P23-related disease. Any cell type or tissue in which HPK3P23 is expressed can be used for prognostic or diagnostic purposes.

Prophylactic Methods

This invention also provides methods for preventing diseases associated with aberrant HPK3P23 expression or activity. The methods comprise administering to a target subject an agent which modulates HPK3P23 expression or activity.

Subjects at risk of diseases which are caused by or attributed to aberrant HPK3P23 expression or activity can be identified using the diagnostic or prognostic assays described herein. A prophylactic agent can be administered prior to the manifestation of HPK3P23-related disease symptoms in order to prevent or delay HPK3P23-related diseases. Suitable prophylactic agents include mutant HPK3P23 proteins, HPK3P23 antagonist agents, or HPK3P23 antisense polynucleotides.

The prophylactic methods of this invention can be specifically tailored or modified based on knowledge obtained from the study of pharmacogenomics. Pharmacogenomics includes the application of genomics technologies, such as gene sequencing, statistical genetics, and gene expression analysis, to drugs which are either in clinical development or on the market. Pharmacogenomics can be used to determine a subject's response to a drug (e.g., a subject's "drug response phenotype" or "drug response genotype"). Thus, another aspect of this invention is to provide methods for tailoring an individual's prophylactic or therapeutic treatment using HPK3P23 modulators according to the individual's drug response genotype. Pharmacogenomics allows a clinician or physician to target prophylactic or therapeutic treatments to subjects who will most benefit from the treatment and to avoid treatment of subjects who will experience toxic drug-related side effects.

One pharmacogenomics approach to identify genes that predict drug response, known as "a genome-wide association," relies primarily on a high-resolution map of the human genome consisting of already known gene-related sites (e.g., a "bi-allelic" gene marker map which consists of 60,000–100,000 polymorphic or variable sites on the human genome, each of which has two variants). Such a high-resolution genetic map can be compared to a map of the genome of each of a statistically substantial number of subjects taking part in a Phase II/III drug trial in order to identify genes associated with a particular observed drug response or side effect. Alternatively, such a high resolution map can be generated from a combination of some ten-million known single nucleotide polymorphisms (SNPs) in the human genome. A "SNP" is a common alteration that occurs in a single nucleotide base in a stretch of DNA. For example, a SNP may occur once per every 1000 bases of DNA. A SNP may be involved in a disease process. However, the vast majority of SNPs may be not related to diseases. Given a genetic map based on the occurrence of SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals. Thus, mapping of the HPK3P23 gene to SNP maps of patients with HPK3P23-related diseases may facilitate the identification of drug-response-prediction genes.

Alternatively, the "candidate gene approach" can be utilized to identify genes that predict drug response. According to this method, if a gene that encodes a drug target is known, all common variants of that gene can be easily identified in the population. It then can be determined if a particular drug response is associated with one version of the gene versus another.

The activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYPZC19) has provided an explanation as to why some subjects do not obtain the expected drug effects or show exaggerated drug response and serious toxicity after taking the standard and safe dose of a drug. These polymorphisms are expressed in two phenotypes in the population, extensive metabolizer and poor metabolizer. The prevalence of poor metabolizer phenotypes is different among different populations. For example, the gene coding for CYP2D6 is highly polymorphic and several mutations have been identified in poor metabolizers, which all lead to the absence of functional CYP2D6. Poor metabolizers of CYP2D6 and CYP2C19 quite frequently experience exaggerated drug response and side effects when they receive standard doses. If a metabolite is the active therapeutic moiety, poor metabolizers show no therapeutic response. The other extreme are the so called ultra-rapid metabolizers who do not respond to standard doses. Recently, the molecular basis of ultra-rapid metabolism has been identified to be due to CYP2D6 gene amplification.

In one embodiment, the "gene expression profiling" method can be utilized to identify genes that predict drug response. In this regard, the gene expression profile of an animal dosed with a drug can give an indication of whether the gene pathways related to toxicity have been turned on.

Information generated from the above pharmacogenomics approaches can be used to determine the appropriate dosage or treatment regimen suitable for a particular individual. This knowledge can avoid adverse reactions or therapeutic failure, and therefore enhance therapeutic or prophylactic efficiency when treating a subject with an HPK3P23 modulator.

Therapeutic Methods

As described above, the present invention includes therapeutic methods for treating a subject at risk for, susceptible to, or diagnosed with HPK3P23-related diseases. The therapeutic methods can be individually tailored based on the subject's drug response genotype. Typically, the therapeutic methods comprise modulating the expression or activity of HPK3P23 in the subject. In one embodiment, the method comprises contacting a plurality of cells in the subject with an agent that inhibits the expression or activity of HPK3P23. Suitable agents include polynucleotides (e.g., an antisense oligonucleotides of HPK3P23), polypeptides (e.g., a dominant negative mutant of HPK3P23), or polysaccharides, naturally-occurring target molecules of HPK3P23 protein (e.g., an HPK3P23 protein substrate or receptor), anti-HPK3P23 antibodies, HPK3P23 antagonists, or other small organic and inorganic molecule. They may also include vectors comprising polynucleotides encoding HPK3P23 inhibitors or antisense sequences. Moreover, the agents can be anti-HPK3P23 antibodies conjugated with therapeutic moieties. Suitable agents can be identified using the screening assays of the present invention.

Pharmaceutical Compositions

The present invention is further directed to pharmaceutical compositions comprising an HPK3P23 modulator and a pharmaceutically acceptable carrier. As used herein, a "pharmaceutically acceptable carrier" is intended to include any and all solvents, solubilizers, fillers, stabilizers, binders, absorbents, bases, buffering agents, lubricants, controlled release vehicles, diluents, emulsifying agents, humectants, lubricants, dispersion media, coatings, antibacterial or antifungal agents, isotonic and absorption delaying agents, and the like, compatible with pharmaceutical administration. The use of such media and agents for pharmaceutically active substances is well-known in the art. Except insofar as any conventional media or agent is incompatible with the active compound, use thereof in the compositions is contemplated. Supplementary agents can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the injectable composition should be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active modulator (e.g., an anti-HPK3P23 antibody, an HPK3P23 activity inhibitor, or a gene therapy vector expressing antisense nucleotide to HPK3P23) in the required amount in an appropriate solvent, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active, ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Stertes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the bioactive compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the therapeutic moieties, which may contain a bioactive compound, are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from e.g. Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein includes physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The pharmaceutical compositions can be included in a container, pack, or dispenser together with instructions for administration.

Kits

The invention also encompasses kits for detecting the presence of an HPK3P23 gene product in a biological sample. An example kit comprises reagents for assessing expression of HPK3P23 at mRNA or protein level. Preferably, the reagents include an antibody or fragment thereof, wherein the antibody or fragment specifically binds to HPK3P23. Optionally, the kits may comprise a polynucleotide probe capable of specifically binding to a transcript of the HPK3P23 gene. The kit may also contain means for determining the amount of HPK3P23 protein or mRNA in the test sample, and/or means for comparing the amount of HPK3P23 protein or mRNA in the test sample to a control or standard. The compound or agent can be packaged in a suitable container.

The invention further provides kits for assessing the suitability of each of a plurality of compounds for inhibiting HPK3P23-related diseases in cells or human subjects. Such kits include a plurality of compounds to be tested, and a reagent (such as an antibody specific to HPK3P23 proteins, or a polynucleotide probe or primer capable of hybridizing to the HPK3P23 gene) for assessing expression of HPK3P23.

It should be understood that the above-described embodiments are given by way of illustration, not limitation. Various changes and modifications within the scope of the present invention will become apparent to those skilled in the art from the present description.

Host Cells

Another aspect of the invention pertains to host cells into which a polynucleotide molecule of the invention is introduced, e.g., an HPK3P23 gene or homolog thereof, within an expression vector, a gene delivery vector, or a polynucleotide molecule of the invention containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an HPK3P23 gene can be expressed in bacterial cells such as E. coli, insect cells, yeast or mammalian cells (such as Chinese hamster ovary cells (CHO), COS cells, Fischer 344 rat cells, HLA-B27 rat cells, HeLa cells, A549 cells, or 293 cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign polynucleotide (e.g., DNA) into a host cell, including calcium phosphate or calcium chloride co-precipitation, DAKD-dextran-mediated transfection, lipofection, or electroporation.

For stable transfection of mammalian cells, it is known that, depending upon the expression vector and transfection technique used, only a small fraction of cells may integrate the foreign DNA into their genome. In order to identify and select these integrants, a gene that encodes a selectable flag (e.g., resistance to antibiotics) is generally introduced into the host cells along with the gene of interest. Preferred selectable flags include those which confer resistance to drugs, such as G418, hygromycin and methotrexate. A polynucleotide encoding a selectable flag can be introduced into a host cell by the same vector as that encoding HPK3P23 or can be introduced by a separate vector. Cells stably transfected with the introduced polynucleotide can be identified by drug selection (e.g., cells that have incorporated the selectable flag gene will survive, while the other cells die).

A host cell of the invention, such as a prokaryotic or eukaryotic host cell in culture, can be used to produce (i.e., express) HPK3P23. Accordingly, the invention further provides methods for producing HPK3P23 using the host cells of the invention. In one embodiment, the method comprises culturing the host cell of invention (into which a recombinant expression vector containing an HPK3P23 gene has been introduced) in a suitable medium such that HPK3P23 is produced. In another embodiment, the method further comprises isolating HPK3P23 from the medium or the host cell.

Transgenic and Knockout Animals

The host cells of the invention can also be used to produce non-human transgenic animals. For example, in one embodiment, a host cell of the invention is a fertilized oocyte or an embryonic stem cell into which HPK3P23-coding sequences have been introduced. Such host cells can then be used to create non-human transgenic animals in which exogenous sequences encoding HPK3P23 have been introduced into their genome or homologous recombinant animals in which endogenous sequences encoding HPK3P23 have been altered. Such animals are useful for studying the function and/or activity of HPK3P23 and for identifying and/or evaluating modulators of HPK3P23 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" or "knockout animal" is a non-human animal, preferably a mammal, more preferably a mouse, in which an endogenous HPK3P23 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing an HPK3P23-encoding polynucleotide into the mate pronuclei of a fertilized oocyte, e.g., by microinjection or retroviral infection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to a transgene to direct expression of HPK3P23 to particular cells. Methods for generating transgenic animals via embryo manipulation and microinjection, particularly animals such as mice, have become conventional in the art. Similar methods are used for production of other transgenic animals. A transgenic founder animal can be identified based upon the presence of a transgene of the invention in its genome and/or expression of mRNA corresponding to a gene of the invention in tissues or cells of the animals. A transgenic founder animal can then be used to breed additional animals carrying the transgene. Moreover, transgenic animals carrying a transgene encoding HPK3P23 can further be bred to other transgenic animals carrying other transgenes.

To create a homologous recombinant animal (knockout animal), a vector is prepared which contains at least a portion of a gene of the invention into which a deletion, addition or substitution has been introduced to thereby alter, e.g., functionally disrupt, the gene. The gene can be a human gene, but more preferably, is a non-human homolog of a human gene of the invention (e.g., a homolog of the HPK3P23 gene). For example, a mouse gene can be used to construct a homologous recombination polynucleotide molecule, e.g., a vector, suitable for altering an endogenous gene of the invention in the mouse genome. In a preferred embodiment, the homologous recombination polynucleotide molecule is designed such that, upon homologous recombination, the endogenous gene of the invention is functionally disrupted (i.e., no longer encodes a functional protein; also referred to as a "knockout" vector). Alternatively, the homologous recombination polynucleotide molecule can be designed such that, upon homologous recombination, the endogenous gene is mutated or otherwise altered but still encodes functional protein (e.g., the upstream regulatory region can be altered to thereby alter the expression of the endogenous HPK3P23 gene). In the homologous recombination polynucleotide molecule, the altered portion of the gene of the invention is flanked at its 5' and 3' ends by additional polynucleotide sequence of the gene of the invention to allow for homologous recombination to occur between the exogenous gene carried by the homologous recombination polynucleotide molecule and an endogenous gene in a cell, e.g., an embryonic stem cell. The additional flanking polynucleotide sequence is of sufficient length for successful homologous recombination with the endogenous gene. Typically, several kilobases of flanking DNA (both at the 5' and 3' ends) are included in the homologous recombination polynucleotide molecule. The homologous recombination polynucleotide molecule is introduced into embryonic stem cells by electroporation. The cells in which the introduced gene has homologously recombined with the endogenous gene are selected. The selected cells can then be injected into a blastocyst of an animal (e.g., a mouse) to form aggregation chimeras. A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the homologously recombined DNA. Methods for constructing homologous recombination polynucleotide molecules, e.g., vectors, or homologous recombinant animals are well known in the art.

In another embodiment, transgenic non-human animals can be produced which contain selected systems which allow for regulated expression of the transgene. One example of such a system is the cre/loxP recombinase system of bacteriophage P1. Another example of a recombinase system is the FLP recombinase system of *Saccharomyces cerevisiae* (see e.g., O'Gorman et al., Science 251: 1351–1355, 1991). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al,. Nature 385:810–813, 1997, and PCT International Publication Nos. WO97/07668 and WO97/07669. In brief, a cell, e.g., a somatic cell, from the transgenic animal can be isolated and induced to exit the growth cycle and enter G0 phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

EXAMPLES

Example 1

Identification of the HPK3P23 Sequence in Human Genome Database

The nucleic acid sequence of HPK3P23 is obtained from a newly developed genomic prediction pipeline. Briefly, the X-ray crystal structures of the catalytic domains of protein kinases were collected and aligned together according to their structural identity/similarities. The alignment was converted into a "scoring matrix" which carried the structural profile of the kinase catalytic domains. This scoring matrix was then used to search the Celera Human Genome database for sequences that have kinase catalytic domains.

Example 2

BLAST and Hydrophobicity Analysis

Sequence alignments between HPK3P23 and other sequences in GenBank database were performed using the standard protein-protein BLAST (blastp), standard nucleotide-nucleotide BLAST (blastn), BLAST2 Sequences, and human genome BLAST programs. The programs are available at NCBI's BLAST website.

A standard protein-protein BLAST search in the "nr" database (available at NCBI's BLAST website) with "Filter" setting unchecked, "Expect" setting at 10.0, "Word Size" setting at 3, "Matrix" setting at BLOSUM62, "Gap costs" setting at Existence: 11 and Extension: 1, identified partial amino acid sequence similarities between HPK3P23 and a number of proteins. These proteins include, but are not limited to, a human protein similar to putative ser/thr protein kinase D1044.3 in chromosome 3 (Entrez accession numbers: XM_087381100% alignment to amino acid residues 542–1016 of HPK3P23), a mouse protein similar to putative ser/thr protein kinase D1044.3 in chromosome 3 (Entrez accession number: XM_138903, 76% alignment to amino acid residues 45–516 of HPK3P23), and an unnamed human protein (Entrez accession number: BAC05427.1, 100% sequence alignment to amino acid residues 448–848 of HPK3P23).

A conserved domain search was performed within the standard protein-protein BLAST search with the RPS-BLAST 2.2.3 [Apr-24-2002] program. The amino acid residues 363–627 of HPK3P23 share high homologies to the consensus sequences of the catalytic domain of tyrosine kinase, the kinase domain of pkinase, and the catalytic domain of serine/threonine protein kinase.

A standard nucleotide-nucleotide BLAST search in database nr (available at NCBI's BLAST website) with "Filter" setting unchecked, "Expect" setting at 10.0, "Word Size" setting at 3, identified several nucleotide sequences that showed significant homology to HPK3P23. These sequences include, but are not limited to, a human cDNA coding a protein similar to putative ser/thr protein kinase D1044.3 in chromosome 3 (LOC152110) (Entrez accession numbers: XM_087381.4, SEQ ID NO:6, 100% alignment to nucleotides 1623–3329 of HPK3P23), human cDNA FLJ32685 fis, clone TEST12000154 (Entrez accession numbers: AK057247.1, SEQ ID NO:7, 99% alignment to nucleotides 1623–3329 of HPK3P23), and human cDNA FLJ25966 fis, clone TEST05207 (Entrez accession numbers: AK098832.1, SEQ ID NO:8, 99% alignment to nucleotides 1274–2543 of HPK3P23).

A standard nucleotide-nucleotide BLAST search in the "pat" database (available at NCBI's BLAST website) with "Filter" setting unchecked, "Expect" setting at 10.0, "Word Size" setting at 3, identified significant nucleotide sequence similarities between HPK3P23 with a human protein kinase-like protein SGK237 (Entrez accession number: AX250157, SEQ ID NOS:4 and 5), which was disclosed in PCT patent application WO01/66594. Further analysis using pairwise BLAST algorithm revealed that HPK3P23 and SGK237 share 91% sequence identities at the amino acid level (blastp, matrix: BLOSUM62, gap open: 11, Gap extension: 1, x_dropoff: 50, expect: 10.0, wordsize:3, filter: unchecked), and 90% sequence identities at nucleotide level (blastn, match: 1, mismatch: −2, gap open: 5, gap extension: 0, x_dropoff: 50, expect: 10.0, wordsize: 11, filter: unchecked).

A human genome search was carried out using blastn program with Expect setting at 0.01, Filter setting at default, Descriptions setting at 100, and Alignment settings at 100. The HPK3P23 gene was mapped to or near loci 3P23 of human chromosome 3. Specifically, the HPK3P23 gene is located between loci LOC131717 and LOC131721, and overlaps with loci LOC152109, LOC152110, and LOC166046. Thirty-one of the thirty-two exons of the HPK3P23 gene were mapped to nucleotides 2719783 to 2940912 in human chromosome 3 of the Entrez Human Genome Sequence Database maintained by NCBI. All thirty-two exons were mapped to Celera genomic database (SEQ ID NO: 3). The exons/introns in the HPK3P23 gene were determined using the program "sim4" described by Florea et al. in "A computer program for aligning a cDNA sequence with a genomic DNA sequence." Genome Res. 8:967–974, 1998.

Example 3

Hydrophobicity Analysis

The hydrophobicity profile of HPK3P23 sequence (FIG. 5) was generated using the GES (Goldman, Engelman and Steitz) hydrophobicity scale (Engelman, D. M. et al.,. Ann. Rev. Biophys. Biophys.Chem. 15:321–353, 1986). Briefly, the GES scale is used to identify nonpolar transbilayer helices. The curve is the average of a residue-specific hydrophobicity scale over a window of 20 residues. When the line is in the upper half of the frame (positive), it indicates a hydrophobic region and when it is in the lower half (negative), a hydrophilic region.

In FIG. 5, the X-axis represents the length of the protein in amino acids (aa), while the Y-axis represents the GES score. The curve line shows the GES pattern of the entire protein, while the strait line represent certain cutoff for potential membrane spanning domains. The hydrophobicity profile indicates that HPK3P23 is probably not a membrane protein.

Having described the preferred embodiments of compositions, organisms and methodologies employing a novel human gene HPK3P23 (which are intended to be illustrative and not limiting), it is noted that modifications and variations can be made by persons skilled in the art in light of the above teachings. Therefore, it is understood that changes may be made in the particular embodiments disclosed which are within the scope of what is described as defined by the appended claims.

What is claimed is:

1. An isolated polypeptide comprising a fragment of SEQ ID NO:2, wherein said fragment comprising at least 500 consecutive amino acid residues of SEQ ID NO:2.

2. An isolated polypeptide comprising SEQ ID NO:2.

* * * * *

UNITED STATES PATENT AND TRADEMARK OFFICE
CERTIFICATE OF CORRECTION

PATENT NO. : 7,122,361 B2
APPLICATION NO. : 10/684190
DATED : October 17, 2006
INVENTOR(S) : Liu et al.

It is certified that error appears in the above-identified patent and that said Letters Patent is hereby corrected as shown below:

Col. 277, Claim 1, line 40, after "fragment" delete "comprising" and replace with --comprises--.

Col. 277, Claim 1, line 41, after "residues of SEQ ID NO:2", insert --, and wherein said fragment has kinase activity--.

Signed and Sealed this

Third Day of April, 2007

JON W. DUDAS
*Director of the United States Patent and Trademark Office*

SEQUENCE LISTING

```
<160> NUMBER OF SEQ ID NOS: 86

<210> SEQ ID NO 1
<211> LENGTH: 3644
<212> TYPE: DNA
<213> ORGANISM: Homo sapiens
```

-continued

```
<400> SEQUENCE: 1
atgagagtat tatttgatga atctgttttg ccacctacag tttattttaa gaactgcagc      60
atcttgttcc ttgcttcctt gggtgctttt ggtgtcctga ctggcttgtt ggtttggtcc     120
ttcatgcagt atatggagat tgtagccaat gagtacctcg gctatggaga agagcagcac     180
actgtggaca agctggtcaa catgacatat attttttcaaa aacttgctgc agtcaaagat     240
caaagagaat gggtcaccac aagtggagcc acaagacat tagtaaattt acttggtgcc      300
cgagatacta atgttctatt gggttcctt ctggctctgg ctagtttagc agaaagacta      360
acagcggagt tgctgcgcct actttgtgca gagccccagg tgaaagagca ggtgaagctc     420
tatgagggga taccggtcct cctcagtctg ctccactctg accacttgaa gctcctctgg     480
agcattgtct ggattctggt acaggtttgt gaggaccctg agaccagcgt ggaaattcgc     540
atttggggag gcatcaaaca gcttcttcat attttacaag agacagaaa ttttgtttct      600 gatcactcct ccattggaag cctgtccagt gcaaatgctg caggccgaat ccagcagctt     660
catttatcag aagacttgag ccctagggaa atacaagaaa atactttctc acttcaagca     720
gcctgctgtg ctgccctcac tgagctggtg ctcaatgaca ccaatgccca ccaggtggtt     780
caggaaaatg gtgtatatac aatagcaaaa ttaattttac caaataagca aaagaatgca     840
gcaaaaagta atctattaca ggtaataaac atgtctcttg tccttcagta tcaagttatt     900
gaaatcttgg gtaactatga cttgtttgag atcttcattg acatagggca ttatgtacgt     960
gatatcagtc ttatgaaga attggtatcc aagctgaatt tattagtgga ggatgaactg    1020
aagcaaattg ctgaaaatat tgaaagcatt aatcagaaca aagctccttt gaaatatata    1080
ggcaactatg caattttgga tcatcttgga agtggagctt ttggctgtgt ttacaaggtt    1140
agaaagcata gtggtcaaaa tctttttagca atgaaagagg tcaatttaca taacccagca    1200
tttggaaagg ataagaaaga tcgagacagc agcgtaagga atattgtttc tgaattaaca    1260
ataattaaag agcagctta tcatcccaac attgtacgtt attacaaaac atttctggaa    1320
aatgataggt tgtacatagt tatgagctg atagaaggag ccccgcttgg agagcatttc    1380
agttctttga aggaaaaaca tcaccatttt actgaagaaa gactatggaa atatttata     1440 cagctgtgct agctcttcg atacttacac aaggagaaga ggattgtcca tagagatctg    1500
acaccaaaca acattatgtt gggggataag gacaaagtaa ccgttactga ctttggcctg    1560
gcaaagcaaa aacaagaaaa cagtaaactc acgtctgtgg ttggaacaat cctgtattct    1620
tgccccgagg tactgaagag tgagccgtat ggggagaagg ctgatgtctg ggcagtaggc    1680
tgcatccttt atcagatggc gactttgagt cccccttct acagcactaa catgctgtcc    1740
ttggctacaa aaatagtgga ggcggtatat gaaccagtcc cagaaggtat ctactctgaa    1800
aaagtaacag acaccatcag caggtgcctc actcctgatg cggaagctcg tccagatatt    1860
gtagaagtca gttcgatgat atcagatgtc atgatgaat atttagacaa cttatctaca    1920
tcccagttgt ccttggaaaa gaagctagaa cgggaacgaa gacgcacaca aggtatttt    1980 atggaagcca accggaacac cgtcacatgt caccatgagc tggctgttct atctcacgag    2040
acctttgaga aggcaagttt gagtagcagc agcagtggag cagccagcct gaaaagtgaa    2100
ctttcagaaa gcgcagacct gccccctgaa ggcttccagg cctcctatgg taaagacgaa    2160 gacaggcct gtgacgaaat cctgtcagat gataacttca acctggaaaa tgctgagaaa    2220 gatacatat cagaggtaga tgatgaattg gacatttcgg ataactccag cagctccagt    2280
tcaagccctc tgaaagaatc tacattcaac atttttaaga gaagttttag tgcttcagga    2340
```

```
ggagaaagac aatcccaaac aagggacttc actggaggaa caggatcaag accaagacca    2400
gctttgctgc ctcttgacct gcttctgaaa gtgccacccc acatgctcag ggcccacatt    2460
aaggaaatag aggctgagtt agtgacaggg tggcagtccc atagccttcc tgctgtgatt    2520
cttcgaaatc tcaaagatca tgggccacag atgggcacat tcttgtggca agcatcagca    2580
ggaattgctg tgtcccagag gaaagtgcgt cagatcagtg atcctattca gcagatatta    2640
attcagctgc acaaaataat ctatatcaca cagcttcctc cagctttgca ccacaatttg    2700
aaaagaaggg ttatagagag attcaagaaa tccctcttca gccagcagag taacccttgt    2760
aatttgaaat ctgaaattaa aaagttatct cagggatctc agaaccgat tgagcccaac     2820 tttttcacag cagattacca tttattacat cgttcatccg gtggaaacag cctgtcccca    2880
aatgacccta caggtttacc aaccagcatt gaattggagg aaggaataac atatgaacag    2940
atgcagactg tgattgaaga gtccttgag gaaagtggct attacaattt tacatctaac     3000
aggtatcatt cctatccatg ggggaccaag aatcacccaa ccaaaagatg aaaatgctgc    3060
attttgagtg gacttgattt tctcagtgaa gttcaagttc tggacttcag ccgctattgc    3120
aagatgccca aggattgggt gctgctagag ggtgtggaaa agaccaagat gccatggggc    3180
ctgcaggact tctttctggg ggtcctgtgc tggagtatat gacagctgcg gtacttgagg    3240
gcttcattgc cagaacacat tatatacagg atgtcagagc taccagtgtg ctgctgggag    3300
aaaatgctgc aaaattcatc ttttggagga ttgagcatcg aatggtatct tcattctaca    3360
ttcgctacga tgcggcatca acaaggcggg tgggagttcg catcacacca gatcaaggtg    3420
gggtcagaat ccaaaaaaaa gatgtcacag gaactgggga gacccctaaa acagttgaga    3480
gacacccagg tgaagagtcc aagttttgga ctggatacga agattttgga attgctagtg    3540
cattggtgag agtagactct aacaatgtgc atgaaagtgg aaagaaagag aagactccag    3600
aaataagggc ctatcctgaa gaacacccat gcggaatcca ctag                     3644
```

<210> SEQ ID NO 2
<211> LENGTH: 1016
<212> TYPE: PRT
<213> ORGANISM: Homo sapiens

<400> SEQUENCE: 2

```
Met Arg Val Leu Phe Asp Glu Ser Val Leu Pro Pro Thr Val Tyr Phe
1               5                   10                  15

Lys Asn Cys Ser Ile Leu Phe Leu Ala Ser Leu Gly Ala Phe Gly Val
            20                  25                  30

Leu Thr Gly Leu Leu Val Trp Ser Phe Met Gln Tyr Met Glu Ile Val
        35                  40                  45

Ala Asn Glu Tyr Leu Gly Tyr Gly Glu Glu Gln His Thr Val Asp Lys
    50                  55                  60

Leu Val Asn Met Thr Tyr Ile Phe Gln Lys Leu Ala Ala Val Lys Asp
65                  70                  75                  80

Gln Arg Glu Trp Val Thr Thr Ser Gly Ala His Lys Thr Leu Val Asn
                85                  90                  95

Leu Leu Gly Ala Arg Asp Thr Asn Val Leu Leu Gly Ser Leu Leu Ala
            100                 105                 110

Leu Ala Ser Leu Ala Glu Arg Leu Thr Ala Glu Leu Leu Arg Leu Leu
        115                 120                 125

Cys Ala Glu Pro Gln Val Lys Glu Gln Val Lys Leu Tyr Glu Gly Ile
    130                 135                 140
```

```
Pro Val Leu Leu Ser Leu Leu His Ser Asp His Leu Lys Leu Leu Trp
145                 150                 155                 160

Ser Ile Val Trp Ile Leu Val Gln Val Cys Glu Asp Pro Glu Thr Ser
                165                 170                 175

Val Glu Ile Arg Ile Trp Gly Gly Ile Lys Gln Leu Leu His Ile Leu
            180                 185                 190

Gln Gly Asp Arg Asn Phe Val Ser Asp His Ser Ser Ile Gly Ser Leu
        195                 200                 205

Ser Ser Ala Asn Ala Ala Gly Arg Ile Gln Gln Leu His Leu Ser Glu
210                 215                 220

Asp Leu Ser Pro Arg Glu Ile Gln Glu Asn Thr Phe Ser Leu Gln Ala
225                 230                 235                 240

Ala Cys Cys Ala Ala Leu Thr Glu Leu Val Leu Asn Asp Thr Asn Ala
                245                 250                 255

His Gln Val Val Gln Glu Asn Gly Val Tyr Thr Ile Ala Lys Leu Ile
            260                 265                 270

Leu Pro Asn Lys Gln Lys Asn Ala Ala Lys Ser Asn Leu Leu Gln Val
        275                 280                 285

Ile Asn Met Ser Leu Val Leu Gln Tyr Gln Val Ile Glu Ile Leu Gly
290                 295                 300

Asn Tyr Asp Leu Phe Glu Ile Phe Ile Asp Ile Gly His Tyr Val Arg
305                 310                 315                 320

Asp Ile Ser Ala Tyr Glu Glu Leu Val Ser Lys Leu Asn Leu Leu Val
                325                 330                 335

Glu Asp Glu Leu Lys Gln Ile Ala Glu Asn Ile Glu Ser Ile Asn Gln
            340                 345                 350

Asn Lys Ala Pro Leu Lys Tyr Ile Gly Asn Tyr Ala Ile Leu Asp His
        355                 360                 365

Leu Gly Ser Gly Ala Phe Gly Cys Val Tyr Lys Val Arg Lys His Ser
370                 375                 380

Gly Gln Asn Leu Leu Ala Met Lys Glu Val Asn Leu His Asn Pro Ala
385                 390                 395                 400

Phe Gly Lys Asp Lys Lys Asp Arg Asp Ser Ser Val Arg Asn Ile Val
                405                 410                 415

Ser Glu Leu Thr Ile Ile Lys Glu Gln Leu Tyr His Pro Asn Ile Val
            420                 425                 430

Arg Tyr Tyr Lys Thr Phe Leu Glu Asn Asp Arg Leu Tyr Ile Val Met
        435                 440                 445

Glu Leu Ile Glu Gly Ala Pro Leu Gly Glu His Phe Ser Ser Leu Lys
450                 455                 460

Glu Lys His His His Phe Thr Glu Glu Arg Leu Trp Lys Ile Phe Ile
465                 470                 475                 480

Gln Leu Cys Leu Ala Leu Arg Tyr Leu His Lys Glu Lys Arg Ile Val
                485                 490                 495

His Arg Asp Leu Thr Pro Asn Asn Ile Met Leu Gly Asp Lys Asp Lys
            500                 505                 510

Val Thr Val Thr Asp Phe Gly Leu Ala Lys Gln Lys Gln Glu Asn Ser
        515                 520                 525

Lys Leu Thr Ser Val Val Gly Thr Ile Leu Tyr Ser Cys Pro Glu Val
530                 535                 540

Leu Lys Ser Glu Pro Tyr Gly Glu Lys Ala Asp Val Trp Ala Val Gly
545                 550                 555                 560
```

-continued

```
Cys Ile Leu Tyr Gln Met Ala Thr Leu Ser Pro Pro Phe Tyr Ser Thr
            565                 570                 575
Asn Met Leu Ser Leu Ala Thr Lys Ile Val Glu Ala Val Tyr Glu Pro
            580                 585                 590
Val Pro Glu Gly Ile Tyr Ser Glu Lys Val Thr Asp Thr Ile Ser Arg
            595                 600                 605
Cys Leu Thr Pro Asp Ala Glu Ala Arg Pro Asp Ile Val Glu Val Ser
610                 615                 620
Ser Met Ile Ser Asp Val Met Met Lys Tyr Leu Asp Asn Leu Ser Thr
625                 630                 635                 640
Ser Gln Leu Ser Leu Glu Lys Lys Leu Glu Arg Glu Arg Arg Arg Thr
                645                 650                 655
Gln Arg Tyr Phe Met Glu Ala Asn Arg Asn Thr Val Thr Cys His His
            660                 665                 670
Glu Leu Ala Val Leu Ser His Glu Thr Phe Glu Lys Ala Ser Leu Ser
        675                 680                 685
Ser Ser Ser Ser Gly Ala Ala Ser Leu Lys Ser Glu Leu Ser Glu Ser
    690                 695                 700
Ala Asp Leu Pro Pro Glu Gly Phe Gln Ala Ser Tyr Gly Lys Asp Glu
705                 710                 715                 720
Asp Arg Ala Cys Asp Glu Ile Leu Ser Asp Asp Asn Phe Asn Leu Glu
                725                 730                 735
Asn Ala Glu Lys Asp Thr Tyr Ser Glu Val Asp Asp Glu Leu Asp Ile
            740                 745                 750
Ser Asp Asn Ser Ser Ser Ser Ser Ser Pro Leu Lys Glu Ser Thr
        755                 760                 765
Phe Asn Ile Leu Lys Arg Ser Phe Ser Ala Ser Gly Gly Glu Arg Gln
    770                 775                 780
Ser Gln Thr Arg Asp Phe Thr Gly Gly Thr Gly Ser Arg Pro Arg Pro
785                 790                 795                 800
Ala Leu Leu Pro Leu Asp Leu Leu Lys Val Pro Pro His Met Leu
                805                 810                 815
Arg Ala His Ile Lys Glu Ile Glu Ala Glu Leu Val Thr Gly Trp Gln
            820                 825                 830
Ser His Ser Leu Pro Ala Val Ile Leu Arg Asn Leu Lys Asp His Gly
        835                 840                 845
Pro Gln Met Gly Thr Phe Leu Trp Gln Ala Ser Ala Gly Ile Ala Val
    850                 855                 860
Ser Gln Arg Lys Val Arg Gln Ile Ser Asp Pro Ile Gln Gln Ile Leu
865                 870                 875                 880
Ile Gln Leu His Lys Ile Ile Tyr Ile Thr Gln Leu Pro Pro Ala Leu
                885                 890                 895
His His Asn Leu Lys Arg Arg Val Ile Glu Arg Phe Lys Lys Ser Leu
            900                 905                 910
Phe Ser Gln Gln Ser Asn Pro Cys Asn Leu Lys Ser Glu Ile Lys Lys
        915                 920                 925
Leu Ser Gln Gly Ser Pro Glu Pro Ile Glu Pro Asn Phe Phe Thr Ala
    930                 935                 940
Asp Tyr His Leu Leu His Arg Ser Ser Gly Gly Asn Ser Leu Ser Pro
945                 950                 955                 960
Asn Asp Pro Thr Gly Leu Pro Thr Ser Ile Glu Leu Glu Glu Gly Ile
                965                 970                 975
Thr Tyr Glu Gln Met Gln Thr Val Ile Glu Glu Val Leu Glu Glu Ser
```

```
                   980              985              990
Gly Tyr Tyr Asn Phe Thr Ser Asn Arg Tyr His Ser Tyr Pro Trp Gly
       995             1000            1005

Thr Lys Asn His Pro Thr Lys Arg
   1010            1015

<210> SEQ ID NO 3
<211> LENGTH: 220860
<212> TYPE: DNA
<213> ORGANISM: Homo sapiens
<220> FEATURE:
<221> NAME/KEY: misc_feature
<222> LOCATION: (44415)..(44535)
<223> OTHER INFORMATION: Can be any one of A, T, C and G.
<220> FEATURE:
<221> NAME/KEY: misc_feature
<222> LOCATION: (106884)..(107279)
<223> OTHER INFORMATION: Can be any one of A, T, C and G.
<220> FEATURE:
<221> NAME/KEY: misc_feature
<222> LOCATION: (217784)..(218607)
<223> OTHER INFORMATION: Can be any one of A, T, C and G.

<400> SEQUENCE: 3
atgagagtat tatttgatga atctgttttg ccacctacag tttattttaa gaactgcagc      60
atcttgttcc ttgcttcctt gtgtgctttt ggtgtcctga ctggcttgtt ggtttggtcc     120
ttcatgcagt atatggagat tgtagccaat gagtacctcg gctatggaga agagcagcac     180
actgtggaca agctggtcaa catgacatgt aagtgttatt gcagggacac agccattttt     240
gtggacttgc tagaaaaagc agtatggtgt ttgcagcagg aaacaaggat actttaaata     300
tttattaatg ttcgcacaca cagctcaggt gttgagcatc caggccaatt gttatattca     360
gtggcaacat acagccagaa gaaagatgtt tagattacaa cctttacctt gaaaagcaca     420
atttatttaa tgcaagagag gcttccataa agcaaatttt tggtaaaatc tattttttgcg     480
tcttttttatt tctgttaaaa tgtcagagac tatccagttt ttttttctata aagttgggtt     540
aatcatgatt gcctacctca tagaatctga aacatccaga gcatgaaaaa gaaaaataac     600
aacaaacctt atctgatgct gcgaatgtga aaacattgga ctgtgagtgt gaggtattcc     660
ttagtcactc aatcttctcc cgttggaggc tcttcccagc cctgctgtcc tgcactccag     720
cttttgatgag tcacagacgt cctgccgtgt gggatgcctg tccgttttct ttgtgtgact     780
ggactggctc ttcatatctg cttgtggagc agcacagtga ttctcagatc caggagaga     840
agagtttatg gcaagccctg ggcactagga agtctctttg aggatgacta ttttcctcag     900
ctgaggaaac gtgcaggttc ctctcatttg ctggccttcc ctctcttctt tataagttga     960
aatcttcaca gagaggatct ttgaagaata ggcctcactt tgaactggta atgatgttaa    1020
ggaacttcaa gtggaaagag aggtttgcct ttttggtat ttttatattt cattattaca    1080
ataatattag aaaataaata ccagtggagc ttgaggagta attcttgggg taaaaaagta    1140
gccatgctgc tcctgcatct gttgttcctt ttgtgctgtg ttccctttga cctttctctg    1200
cctgcccata tgcactgcag atctgtgctc tggaagtac tccccctta atctctggat    1260
gcctctttgc gctctttctt tcctttatag atattttca aaaacttgct gcagtcaaag    1320
atcaaagaga atgggtcacc acaagtggag cccacaaggt gagtggcccc tgaaagagtt    1380
aatgcttcag ctccctatgg caatagttca cattagggaa gttcagagcc tttgcggtta    1440
agtcatgtgt aattagaatc cacaaaccta ccagcctggc ctgagattgt ggatctttgt    1500
caacccttttt atattcttta ccagcattac aagttaatag agatataata aatacaagtt    1560
```

-continued

```
ttctggaact ctcttctttt ttttcctatg ccatttaata ccaactaggt ttattactta    1620
aatattattt gaaaagcccc agctatgtat aaattcaccc taggtgtgca tttataaata    1680
agtcaacaga aataaacaaa atgtacatat gtatacatat aaattccata tggcatgtgg    1740
ggctatatta gtttgaacca tatatgattg ccattgtagg tcaaaacaga ctatatttat    1800
agcaaaactg tttagactgt agccatgtgg agccaagttt cagaaacctg ttgagtttca    1860
tatcccggga agccactttc tagtgtatat gggagcaaga ttgcctaaaa tgtgttaaca    1920
catgctgctc atggtctaga ggatgattct aggtgataca caggtcaaca ttttttgttt    1980
cagtagccag ctatttcaca ggtattattg cttacaattg gaaaaatttt ttttgagtta    2040
acattaaaga tgttagttga atatggcaaa aaatgtgaaa atgatatgta atggattgaa    2100
gtttgggaaa cattagaaga cagagaagaa agagagaaga aaagaggaa aggatcagac     2160
aaataaagat aatgataact tcattaagat aaaatgaaat cataaaggca aaaaatccat    2220
atactggaaa cataaaaatt accttagccg ttgttgcgca ggttgcagct ctgacctgag    2280
acatttgggg aggcactttt caggggcact ccgcattctg aaaatgtaga aattttccca    2340
aataagaaaa tttgccttaa cgagaattca gggaaagcca ctgacaagct acagacttcc    2400
agctaagtca tgttagttag gatgatgctt gggagcatca gtgatgcact ttcaacatca    2460
attagaaatc tgggaggcaa atggaatgct cgatagtatt catatcttgt ttagtttggc    2520
aaaagaatga aagtttcaat attttgttga aaaatcgttt cataatttgg aaagtgccta    2580
gcacaatgcc tggctcaaag tgagttctca atggctgatc actaccacta ttgtaattta    2640
tgtcattaat cttcctggtt cttcccagcg tgggatcaga agggggagag aatacttggg    2700
cacatggaaa tagaaggatg tatgagaacc aggctggtca tgtagcttga tgccttttct    2760
tcctgtcctg ggcaaggaat ggctacaaga ggttactgtc aagagttcca agtaaggag     2820
agatggactc ctgccatctg taaagaactg gatattttga atgtttaata aaactctttt    2880
taagataaac ttttatattg actgcaaaaa ataaaaagga agctgcataa ggcttgatag    2940
ggcataattt ttttcactat tctatgggta aagccataat aaaataaaca acttgattat    3000
attgacaaaa agtgtttata aagatatatt taatgccatg aaaaaatttc agtagataac    3060
attaagaaaa aaacataaga gagagcagct ttaacattat atatagtttg tgcttaattg    3120
tatatgcaca tacattataa actactaagc aaaaaaaaaa aaacagttaa gcctatatga    3180
tcttaagagg gaagcatttt gtcattcaag cagctggtaa tggaaaataa attaatgtta    3240
atgttgaaaa aagaagcttg tagtacttat ataattaaac tttattttac ttcattttc     3300
agacattagt aaatttactt ggtgcccgag atactaatgt tctattgggt tcccttctgg    3360
ctctggctag tttagcagaa aggtaagtag tgtattctaa tatactttcc agttctgcta    3420
ctatagcaat ttaggtggta aggatgcaaa ataatcagtt actttgtcaa ctacttaata    3480
caatttcttg ataaataagt gtgaaataac atgttgaaga gaatcctgga tagaaggcat    3540
tatttaaaaa tttaaactgg aaaggcaaat tgcagtttaa aattttcttt ttatttcctg    3600
actggaaata tttagtcttt tcatctaacc ctcagttact tctaatttca aaattaccat    3660
aatatttctt tggcagttga atcttctga ccatcttaat tcattcttac ctgtgaattt      3720
taacatacag aacgttttca aacatctgtg ggctttgaaa aattttcaag aagatctttc    3780
ctcttataaa tgtcatgatt attttaaatg ttttttatgac aataagtgga ccattgcttt   3840
tctgtgaata acatatgatt cctttttgttt tttgatctct tctcccaaga taatattgga   3900
```

-continued

```
gctaggatat taaataaata aatttatatg gttaggcttt gtgtccccac ccaaatctca    3960
tcttgaattg taatccctgt aatccccata attccctcat gtcaagggag agaccaggtg    4020
gaggtcattg aatcatgggg ccatttcctc catgctgttc tcatgatagt gagtgagttc    4080
tcatgagagc tgatggtttt ataagggggct cttccccctt ggctcggcac ttatccttcc    4140
tgctgccttg tgaagaaggt gccttgcttc tcctttatct tccaccatga ctgtaagttt    4200
cctgaggcct ccctagccat gctgaactgt gagtcaagta aacctctttc ctttataaat    4260
cacccagtct caggcagttc tttataccag tttgaaaaag gactaataca tggatctagc    4320
aaaatatgct tttagtaatt gctaatattt ttcaatttat agtcaagaat gtagggagaa    4380
gataagtgaa ctcaacattg tagaaaatct gttgatgatt ttacatgaat atgacttgct    4440
ttctaaaagg taggattgct aacagtagaa aaagacaatg cagtgccttt atttgacaga    4500
tacacttgtt attattttta ttacgtcatg ttatttacat tgtaactgaa tatgatgagt    4560
cagcttggca tttattttct gtttaagttt atataaagaa aatagagcaa agaagtatat    4620
ccatttatgt ttagtcctgc attacttcta gatctgggca tagaagctga tgaaataaat    4680
ttttgtgata tcatttttaa tgttttgttt attgcattta tttatatcct gccttttag    4740 ggaaagaaac tctgaggtgg ctctagtttt agtaatttca aattgtatat tacaataagt    4800
gattaggttg ctaaaatcca tttgcatgaa ggcaagtaaa ataagatagc aactgacttg    4860
ttttgtgatc acctgctacg ataactcaaa atctagagta aaatggattc attttactt    4920 gaactgcata ttgttctaat aactatccag atagttatta gattgtactt aaatagagtt    4980
gcaatctata tcatttgata tttagttgag taattttcta aagaggcaaa atagataaaa    5040
agaaatctcc agcaatggag ccctgacact taactcatag taaatccttt tggattcttc    5100
ttcaaaactc tcataaaaga gcattaaata tagataatac ttatagactt ggttatctga    5160
acaaacaagg ttccaagctt ggtaccaggt gttgaaaacc aaagatgaat aagttataaa    5220
tatgtagtgt agaagagggt caaacagtgc tataactgat acggtagaca gatgcacagg    5280
gtactctggg aacatggagc agagacttcc caattagaat gtggagtcat gcaaagtttc    5340
ctggaggaaa gagaagatat ctaggcagag agagagagac aacataaaaa cagtatgtgc    5400
ttggacatgg aggcatgaaa ttgggtgtgt tagaggaatg tgatggttgg gcacagcagg    5460
accataagaa caaaagtgcc agagaactag aacagatagt taatgataaa tttaaaatgt    5520
agctaacttt gatcagtgtt ttctatatgc caagacctgc tctaagcact ttgcttatta    5580
actcatgtga tctgcacatt aaccctattt ttcccgtatt ttatagataa ggcaacaaga    5640
cacctttatc caggtcatga tggtctctga taaataacga tgtgaatttt atcatgaaca    5700
ttatggggac tcatgggaac attttaagca tgatcaaatt tgttttttga aagatcactt    5760
tgatagcagt gtatgtggga gtgaggtggg ggtgtttgtt tatatccaca cattgagatc    5820
cacttacaac aaagagaggc tgggaaagtt cgtgaaggta aagaatacta tttatcaagg    5880
aacatttatt attaatgtca gagcacaaaa tttgggaggg agaggagcca taggtaatca    5940 gctcaggggga aaggaatgag aaagccgtat gagaatgaga atattggaga ggtagatgaa    6000
agagggattt atatcttgag catgacaaag gattacaagg atgggaggag cagtgggggtt    6060 acctagctgc ctggtgttca aaagaatccc aacgttgccc aggaaataga aaacactaag    6120
agctcttgat tgacagtgga gggagtgtgaa aagaggagta tgtgtcttga tgactcccag    6180
tcttgtggct tggaagactg aaaatatgt ggtgccatga acaagatcg gggatataag    6240 gtgaagaata gacctgggga ggaggctaat gactttgagt ttagggtag tatggagagt    6300
```

```
acttgtggaa tatccatgtg gctaaaactt ctggaagtta ggagcaatgc ctgggctgag    6360
atcatgatga cagggttgaa agagtgtttg aaatcatggg aatggatgac accatccagg    6420
aggggagtgt ttagagtatg aaactggagg actaaggatg attctataaa acgtttatca    6480
tcataatatt tcatggcaca gctgaacctt gtgtctttac catcaattta atgcactttg    6540
cactgagtat atagtaactg agtgcttttgc ccttaactta cctgcattgt agtgtttttg    6600
acattttcta agaatgtctt attttgcaat tacatagtaa gtttctgaag actagaataa    6660
ggcttttatt attattatta ttatttttt tttttagtct ttagcacaat gcagatgtca    6720
ttgtttgtcc ttgatacccta tttgctggtc agtaggtttg ttttttgttt ttgttttttgt    6780 tttttaaaca gagtctcgct ctgtcaccca ggctggagtg cagtggcaag tgacctcggc    6840
tcactgcaac ctctgcctcc tgggttcaag caattcttct gcctcagcct cccaagtggc    6900
tgggattaca ggcacacacc accacgcct gccaatgctg gtcagtaggt ttttaatcag    6960
accaacgatg atgcaacgag cctataattt agaacagtgg tctgcaaact atgacctaca    7020
gtctaagttt attccactgc ttattttgt aaataaagat ttattttaac atagggatgc    7080
gaatttattt ttatatgttg tctatggctg cttcatgct atctcagcat agctgagtag    7140
ttgtgacaca gattgtacag ttagtaaagc taaaagtgtt tggctttgat cgggctcctt    7200
acagaaaatg gcacattgac ccatgactta caaaatgtta gggttatatt tcatgcactg    7260
atgatagctt tagtcttaat gtaaagtaat caactcatga tgctgtgatt ctcaccccac    7320
cctctgtacc ccttttcagac taacagcgga gttgctgcgc ctactttgtg cagagcccca    7380
ggtgaaagag caggtgaagc tctatgaggg gataccggtc ctcctcagtc tgctccactc    7440
tgaccacttg aagctcctct ggagcattgt ctggattctg gtacaggttt gtgaggaccc    7500
tgagaccagc gtggaaattc gcatttgggg aggcatcaaa cagcttcttc atattttaca    7560
agggtgagta aaagtgggct ttggcctact ttgccctgtt tgttgaagtc tggggactct    7620
gtgacaagat ggcagattgg tgtgtgtcac ctcattccct cctgctttgg gatttctttg    7680
gtaattcatg ctttccaaag tcatctagac ttgtcacaag catgttctaa atcaatgtca    7740
ggggcattca tcttttaaat tccttgggga cccagatata tttatctttg catcaccaac    7800
ctccagtaca gtgctgggaa tgtagaaggc catcaatctg caaatataat gaaggctgaa    7860
tggaaatcca gtaacctaaa aaaaacctt gtcttgccac cttttccttg aattagtata    7920
tgcattttgt cattccaagt ataatgatta ctaatatttt cctaaaatgt ttgtgtgtgc    7980
acatatgtta ttatctataa agagaaaaca aagcctatat gaaaggagca ggtgtacaat    8040
ccttgttttt gaaagatgat atcattaatc aagtggttgc catgttacta actctagtcc    8100
agttctctac tttctctct aatcttcatt acggtcctct aaggtgggca ttatctctct    8160
tttaaaagta gaattccagt gacattctaa gtcaggagca cggagaatgg atagttttgt    8220
tcccaattga aattctctag aagtacgttg caaactaact tctgtatttt ctgaattaaa    8280
tagattgaag tatttaataa taatatcttg tggtaccatc catgggaaga ttctattacc    8340
taatattgtt ataaagtata attcagttct atgggtgctg aaccaaagtt aaaaatgagt    8400
atgtctcctt gaactggatc gtctttatga tctgcagtac ataaataaag ctcattctaa    8460
taaaagcaga gggacttatc aattttcata taactagata ttatcaaatc aatgttgtta    8520
tgactttgta tttgttatgc ttccagcgat attgcagaac tgtgtgttac caacttcatt    8580
ttctcttaag gaacattcag aagcataaga atagactgta cagacatgaa cagtagcttt    8640
```

-continued

```
gttaacaata tttgtcatta cctaaacaaa ggaaaaattt atagactgtt gacaacctac    8700
ttgcttcatg aatgtgacat aaaaatatca attactttat agtataaatt ataagtcatt    8760
cattagtgct gtgacataat aagccagccc cttggtcaaa ataattacaa ttgccaaagg    8820
ttttttattt aggtttgcag gatgacgatg gtaatgatga tcatggtggt ggttattctt    8880
tattattgga caatcatacc tattataata ggtatgggtt gccctcttgg agaacagcta    8940
ttttcataag gataaaatga aattctgtaa tagttaagca gaatttcaaa gacaaaacct    9000
gccttttcct catatagaat tgaatctagc tttcttcttt tgctgaagtc ataactatcc    9060
ttggtaaaaa agaggtcttt cacatctaaa gtatcatttt ccagtccatt ttgatggtgc    9120
aatgttagca aacttttccc caggacaatg acatattta actcttattc tatgttaaat    9180
atgtactggt gctttgggag aatttattac cccagctgga taaacagttt cttttcagag    9240
cttgtgcctg accctgggct gactgcagct ggcattaggg gtagacgttt ccaggctgtc    9300
ttgtggctgg agtatgaaga acactgtttt cagggcagtt tctgggacac tttctcatgc    9360
ctgttcacct gccatctcaa actcaaaggc agctcccaaa gggctctctt gatcaggtga    9420
agagatccct acaatttgag ttttaagaga atcatgttga cagataagat caccacctgt    9480
gactgtccct aggcctagct ccattacctt ccccatgctc attgcaggga ggacactagt    9540
ggacccagat gacatgagag ggaagtcaag gaaactccat ccatgttaca tttaggcaca    9600
gagaaatcca ggtagagttg ctgctataaa aaataaatac atggaaaaaa atggtaacta    9660
tgtaaaacaa aagggaacaa agcaggtgaa agacagatga agaactatta tggaagaaag    9720
tgtactgagt aaacagaaaa gccaatgctt tatttcatca aagacattaa gcagagcatg    9780
aatttatgaa atgagattaa agatgaaaca aattttggga cacaaaaaag ggagaagact    9840
gcagagctag gaaagaaaac aaggactgaa taacacctac agaaccgata aattgctaga    9900
tcaccagaaa aaaatggaaa tagtaaaatg tagggtaagc ttgaaaaaaa ttacatataa    9960
tgcagaagaa aaagaccaat gaataaaaga aattagaaaa tgaaagatac gcccaataga   10020
agaagacagg ttttcaacat gtggacaatt gagatccctg aagtacagag taaaatgaaa   10080
agggccaaac atttccaaga tatgataggg gagaactttc ttaaaataaa ggaagattga   10140
aagttcatgg aaaagaaaa ctgagaataa tcaagactga gatgtattca ggtgaatcaa   10200
ctccaggaaa atagaaaatt caaaacaaa ggtggccatg tagagcagtg gggagaggac   10260
acttttcaat aaatagtgag aaatcagtaa ccataaaaaa atggttctta ccacacacca   10320
tacacaaaaa tcaattccag gtggattgga aagtgaaaca ataatgatgc cttcatgacc   10380
tgagggaggc aaagatttct taaatgtgac acagaaagga ctgacggtga agggaaattg   10440
ataaatggtc tatgcattaa cttttctttt tcagagacag aaattttgtt tctgatcact   10500
cctccattgg aagcctgtcc agtgcaaatg ctgcaggccg aatccagcag cttcatttat   10560
cagaagactt gagccctagg gaaatacaag aaaatacttt ctcacttcaa gcaggtattt   10620
atgttttatt atttgatatg ctataattta ttgtgttgta ttattattca ctatcataga   10680
ttagtgtagt agtgttaagt aggcaaaatt tagaagttta caaaaatgta aagtgaaatc   10740
cacatggatg ccagaaactt cttggtccca gtgttggact tgcagatgaa tgatacaaca   10800
aatgtttctt tgtcttctgt gttctgaacc tagcaagaga taaacacaga agtcagagat   10860
aaggatacaa aacgttagct ttattatgag gaaagctgga ttagggatg cagcttgatc   10920
tgtggccaga atcatgcttt ctagaatttt ctagatccca gggcaccta cataaggggg   10980
aatctacagt gcacacactt gtctcaccag gtgcaagaga gtaccttccc catgcttctt   11040
```

```
gagctccaaa gagaagactg aaagatgctg ccctgtctag gattttcaca tgcaagcagg    11100
agcagcaatg catcaatgct ttttggcagg gccaccttga gcagtcatgc agtttgtgcc    11160
ctgcctgggg gcacctggcc tttgggacaa ctggagctac agtgccgtct gagtgctatt    11220
ggccaatttg ggtgccctag agcggcccac agaaagggag cagagaggtg tggtatgggc    11280
cagcaggaga cagggagact ctgaggggaa agagcagact gcaggagagg gaatgaggga    11340
gtggggaagt gggagagggc aggctttcct tgctgtctac tattttctcc tgaagaatac    11400
agaagatatt tcttcataga tggtgtgaaa acaaggacat aggagctcct cctcaaagtg    11460
ccatttctgc ttactctgaa aggcccctgt ctcagtacaa ggtcttgtgc tgggggttta    11520
ctgtttgaag actccccaga agtctaatcc agtggaatct cagagctctg agtgtttcta    11580
gcaatcattc aaagagtgga tgagattgac ggtgatagaa ttcagaagaa cagttactta    11640
gatgtggaat tataggagag tgagtgcctg agaaggggca caaggagcct ttgagaactg    11700
gaaatatagc ctacacattc ctctgggtgg aggatggtta cagggcacat agatatgtag    11760
tatctcattg agccttacac ttaagatgtg tttacgttac atagcttatt ctatacccgt    11820
attagtccat tttcacgctg ctgctaaaga catacccaag acagggcaat ttacaaaaga    11880
aagaggttta atggacttac agttccacat ggttggggaa gcctcacaat catggtggaa    11940
ggcaaggaga agcaagtcac atcttacatg gatgatggca ggcaagagag ggcttgtgca    12000
gggaaactcc acgcactttc aatggtttta caaaaaaaac attttaaaaa caatcagatc    12060
tcaagtgaga ctcattcact atcatgagaa cagcacagga aagacccacc cccataattc    12120
aatcccctct cactgggttc ctcccatgac acatgaaaat tgtgggagtt acaattcaag    12180
attgagattt gggtggggac acagtcaaac catatcattt tgctcccggc ccctcccaaa    12240
tcgtatgtcc tcacatttca aaaccagtca tgccttccca acagtccccc aaagtcttaa    12300
ctcatttcag cattaactca gaagtccaca gtccaacatc tcatctgaga caaggcaagt    12360
cccttttgcc tgtgagcctg taaaatcaaa agcaagtcag ttacttccta gatacaatgg    12420
ggtacagaca ttggataaat acagctgttc caaatgggag aaattggcca aaacaaaggg    12480
gggctacagg ccccaagcaa gtccagaatc cagcagggca gtcaaatctt aaagctccaa    12540
aatgatctcc tttgactcca tgtcttgcat ctgggtcacg ctgatgctat aagtgggttc    12600
ccatgatctt gggcagctcc gcccctgtgg ctatgtgagg tacagcttcc ctctcggctg    12660 cttttcatggg ttgatgttga gttcttttgg cttttccagg tacactgtgc acacttgtca    12720
gtggatctgc cattctactg gaggacagtg gcctgcttct tacagctcca ctaggcagta    12780
ccccagcagg gactctgtgt gggggctctg accccacatt tcccttctga actgccctag    12840
cagatgttct ccatgagagc cccgcccctg cagcaaactt ctgcctgggc atccaggcat    12900
ttccatacat cctctgaaat ctaggcagag gttcccaaac cctaattctt gacttttgtg    12960
tacaagcaga ctcaacacca catggaagct gccaaggctt ggggcttcca ccctctgaag    13020
caacagccta agctgtacct tggcccctt tagtcatgac tgaagtggct gggatgcagg    13080
gcaccaagtc cctagactgc gcacagcaga gggaccctgg gtccagtcca tgaaaccgtt    13140
tttccctctg aaacctccag gcctgtgatg ggagggactg ccacaaaggt ctctgacaca    13200
ccctggagaa attttctcca ttgtttgggg ggttaacatt tggctcctca ttacttatgc    13260
aaatttctgc agcaggcttg aatttctttt cagaaaatta gattttcttt tctattgcat    13320
tgtcagatgg caaatttttcc aaacttttat gctgtgttcc tcttttaaaa ctcaatgcct    13380
```

| | | | | |
|---|---|---|---|---|
|ttaatagcat|tcaagtcacc|ccttgaatgc|tttgctgctt|agaaatttct tctgccaggt 13440|
|accctaaatc|atttctctca|agttcaaagt|tccacagatc|tctagggcag gggcaaaatg 13500|
|ccaccaatct|ctttgctaaa|acatagcaag|agtcaccttg|gctccagtta ccaacaattt 13560|
|cctcatctcc|atctgagacc|acctcggcct|ggatttcatt|gtccatatca ttatcagcat 13620|
|ttggtcaaag|ccattcaaca|agcctctagg|gagttccaaa|cttcccaca ttttcctgtc 13680|
|ttcttgtgag|ccctccaaat|tgttccaagc|tctgcttgtt|acccagttcc aaagtcactt 13740|
|tcacaatttc|tgttatcttt|tcagcaaagc|ccgactctac|tggtaccaat ttactctatt 13800|
|agtccatttt|catgctgctg|ataaagacat|acctgagact|gggcaatttc caaaagaaag 13860|
|gggtttaatg|gacttacagt|tccacatggc|tggggaggcc|tcacaatcat ggcggaaggc 13920|
|aaggaggagc|aagtcatatc|ttaagtggat|ggcagcaggc|aaagagggg cttgtgcaag 13980|
|gaaactccca|tttttaaaac|catcagatct|tgtgagactc|attcactatc acaagaacag 14040|
|tgcaggaaag|accaccccc|ataattcaat|cacttcacac|cgggttcctc ctatgacatg 14100|
|tgggaattgt|ggggattaca|attcatgatg|agatttgggt|ggggacacag ccaaaccatg 14160|
|ttaataccta|aataaaaatg|gaaaataaa|aattaaaaac|ataaacggtt aagagtaggg 14220|
|tctgagtttt|ggctccaccc|tcattgatgg|ctatatggcc|ttgggaaagt tccttaattt 14280|
|ctccaagctc|cagttttgct|tatgtaaaat|ggtgatgata|atcatggtat caatgataga 14340|
|agatcattgt|gagaattatg|tgggaatata|tgtaaaatct|tcagcacagt aaaatggaat 14400|
|tatccttat|aggagctctg|tgctatagag|tctggcatac|ttctgagagc acaagtatct 14460|
|cagtgcaaaa|taccaccaaa|ggctgccaca|gtggctgtca|ggaggcaaga gtggtgctgc 14520|
|ttagggctgg|ggatttaacg|tctggcagac|tggggctgca|ctcctggtca tttccactta 14580|
|ctggttgtgt|ggcctagtct|agtaactctt|tgaaactgtt|ttctcaccag taacagtggt 14640|
|aatcacagtg|catactctta|ttataaggat|tgagttgaat|aatatattta aagcattctt 14700|
|ttattatca|accattatag|atatatttgt|tgagcacctg|ctaagtgcca ggcatgtttt 14760|
|gggcactggg|gattacaatg|aaatggacag|atgcaatact|tgcctcctgg tacgaagaaa 14820|
|gtgctcaata|aatggttgca|gtggaataga|cacgcacatg|aattacatgg ggaggagaat 14880|
|tagaagccat|tacaagtcaa|cttcttttct|tccagagctg|tgccaaaagg aaaattagtg 14940|
|tttcttgaga|agttactttg|ctaataaaaa|tagcaaaata|ataaaaatac cctgtggagt 15000|
|aagagtattt|atgtgatagt|atatttattg|taatgatgca|cactatgcat ttgattgttg 15060|
|tcattccagc|ctgctgtgct|gccctcactg|agctggtgct|caatgacacc aatgcccacc 15120|
|aggtggttca|ggtgagagca|ctccttctca|aggtcaggtc|tccataacca ttcataatca 15180|
|actcaccttg|tggtgcagtc|tgtatcccag|aacataggtt|ttgggattcc catcatgtga 15240|
|ttttaaaact|attttaacat|ttctcgttta|actaataaag|ttccactta tattcttctc 15300|
|cttcctcctt|taactcattt|gacttaaaaa|ggactgacat|gtggttaatt gatgtttctt 15360|
|cattatgtta|tgtgcggtcc|cttttatttt|ttctttctaa|agggatact ctgaattgca 15420|
|ttaattctgg|gtgtatagaa|taccataagg|taaggacagc|aatcattttg attaagacta 15480|
|tgcatcagat|tattaagtta|aaaatgatga|ttgagacaca|gcaaacaaaa tatttattgc 15540|
|caagaaactg|attttgcaaa|gtataatcca|ctaattaatc|tactatatgt acagctatat 15600|
|atacatgttt|gtgtgtgtat|gtatatatac|acataaatat|aaattaatag atctatatta 15660|
|ataaacatac|acatgtatat|gtacaaccct|tgtatgggtt|tctatcacaa aagttacctc 15720|
|ctacttagtg|aattttacag|agaaaacatt|tttggttgtg|tcattacaat atccaacttc 15780|

```
aagatccgta catgttagta agggatcagc tcatcaatga ttaaattagg acataagaga    15840
aactcagcag atcagggggt agttgataga acagggcatc tgaagttggc cagattgagg    15900
ttcaattcct ggaattatta cttcttggct tggcttctaa aaaaataatg tatccactct    15960
aagtattggt tttctcatgt ataaaacaag gaaattatag actaatttca cagagttgtt    16020
acagagatta gatgcaataa ggcaaataaa gctctttgca gttataatat gaatgcctgc    16080
acacagtaaa gatcagtaca ttatatattt actagataat agaaaagtgg ctgtaaggta    16140
ttattatttg ttcattcctt catgtgtata tttcaattaa aaaatctaga aagatgtcaa    16200
gattataata aagacataaa ttaataactg gaatataatt tctcccttta tggttgtggt    16260
aattaaggat ataaataaat atcaaagata taaatctaag atattgggac acctttactc    16320
tgtccctttt taatctctca ttgttttttaa ggtatttgaa tcactttacg tttatgtact    16380
ttattataat cttgattctc cacagacagt tgaaatttta agattgtagt tgtactcttt    16440
ggtgtttaaa agtgttatgt tgacatttta aatattgtcc tgtaatgttt acttcaaggt    16500
ccatagttat actaatattt cttctttgat attaatgttt gagattgttt atttgcctct    16560
ttttgcttgt gtatcactac agtgttgtca ctcatagtat gacccctttta ttctttcagg    16620 aaaatggtgt atatacaata gcaaaattaa ttttaccaaa taagcaaaag aatgcagcaa    16680
aaagtaatct attacaggta ataaacatgt ctcttgtcct tcagtatcaa gttattgaaa    16740
tcttgggtaa ctatggtaaa atgatctatg atttttagaa tgtttaggtt agtactggtc    16800
cctgtactga ctatgaggga aaaatatctg gcaaggaaga ctggcatgga atcaaataat    16860
attaaaacaa tacagaaggc ttaacagtgg tttctctgtg tgggagaatt aggtgattta    16920
tttaggtgtt tctttgctta tcaataagtt ctatttttt aaaaaaatat gcattcctta    16980
tgtatcagaa tataacaaca gggggaaaat tatttgccat catggatctt gatggatgag    17040
aagggacttg ccaagtggat aagggggatat tgggtgggc accaatggca tctgctgcag    17100
ggtggaaggg cattccatgc agagggaaca gcatgcacca agtgtgaaag ctgtgagctt    17160
agagtgtgct gagggaagtg tgagctgctc agtggggttg gggtgtgtgg ttgtgggggc    17220
cagtgctcca gcagatgagg cctcacatgt aagaaagggg aacagttagg caggttctac    17280
attcattttt gaggagtggg tgttgggaga gctgagtaaa gggtgagctg ctcagtggaa    17340
ctggggtgtg tggtttgggg aggcagtgct ccaggagttg agggctcaca tgtaagaaag    17400
gggaacagtt acgcagggtt ctatgttcgt ttttgaggag tgggtattgg cagagtgggg    17460
gcggggggca gtggcgctaa tgtcaaaatc tgatttaaag ttagtctttg caatagttgt    17520
agctcatctt ttttttttccc ccaagtcatt ttgaaaagga agaaagaaac aacctttgtc    17580
tccaatctga tttaagagtt atcatccaaa atgatggcca aacccagcag actctttcgg    17640
ggtgtctctg tgctggcagg caggggtttt tggagcgcta ccaacgggaa ggtgcaggca    17700
tgggacttga tttcttcagt gcatcacaga tatatgacac tgtgctgtta aacagataaa    17760
gacaaaccca tcctgcagag acatttcgtt aagccagtag agggttttttt agaattccag    17820 atggagggct tttgaggaat atgcatgctc tcccttctc acagtctcca ctgctctcac    17880
ctggctcctt catgtcattt tgttaccggc ctcacctctc tgggcaattt tgtatgggac    17940
ccttctgtgt tcagatcact gatttaggaa atgatcccaa gatttgattc accaaaccct    18000
gatcactcca atggtggcct attgtgcagg cacagctgca ggctgggcac actctttttt    18060
ctcagtactg caaaatgtca gatgtttatt tttcctaggt aaaggctcac aggcctcttt    18120
```

```
ctgagcgttc tagggagtta gtgtagattg ttctatttgg ggaatgctta agactctttta   18180 ctcaagagac caatttgtca agtttgaatc cagtgtgcct gcggctattt ttatatgtca   18240
tcatttctag tgtttatttt ctcacagaaa ccatataaat attgaggtat gcatagcagg   18300
ctagaaacaa ataaaccttt gagctcctgg aaatctttag acatttggtt ttctcagcat   18360 cggaattttta tttcttgtct ctgtactcat tttgtacttt ctagaaagaa attaatgacg   18420
agtaccaagt gaagcaaggc caatattccc agcattctac aacataaaca ctttttaaat   18480
acaggaatga ccccaggtgt tggtgttttt tgttttcagt tagaagcttt ggctccaact   18540
tggaccagcc acttacaata aagtcacgtt aatgtttact tcctgttaat tctttcctga   18600
aaatgtttta atttgttgag ctaccatttg agaatcacat atccttttgt tttctagtgt   18660
tatgctttca gagccttgag atttctcttc agtatggaaa gaaacagacc actctttaaa   18720
aggtatgagg ttagagaaat ataagtgatc attaggttta ggagatcatt agattgaact   18780
gttttcacat acttggctta gatgcaacag aaggaaaata atgcgtcagt atgcaaacca   18840
tgtgtcttca gatttcttat ttcacagata gaagtgagct actgtagtga ttcagtatcc   18900
agccacactg aatattaaca gaatgatgat gaaagagcat aaattgctat atcaatacaa   18960
ctccccttaa ttacatgtga ctgctgtgat tttagctttc ttttttgataa ttaaagatat   19020 taacattttt aaaagatggc attaaaatat gagcttcttt ttttccagct agaaatttga   19080
aagtcaatcg ggtaatttca ctttaatcaa agggaattta atcaaaggga aaacaaactg   19140 ttttttttgtg tgtctttgat ggtgtaggag ctcatttgaa ggggaggctg gatgttctgg   19200
ggtcaagata ctgtgttggt gagcctgacc aaaaggtcac catttcggga agcaaacact   19260
ggttccctca gtggtgttct gcacaccatt tagttaggtg ggttagccaa aatcataggc   19320
ccaagttttt attaaaattt tgttaataag gcagaataga cataaagtat tgagttaata   19380
tagtattttt tgttcagaaa gcatggagcg tcacttttcg gccttttggc tgagatcaag   19440
tgcagaaagc atggagcatt ttatgttgtt actttatttc tatactgttt ggatttagag   19500
gaaaataaag taaaattagt tctctttttt ttttttttttt ttgacaaagg ctcatcctgt   19560
tgcttctcct gcctcagcct cctgagtagc tgggactaca ggcatgcacc accacacctg   19620
gctaattttt gtattttcag tagagatggg ttttcaccac gttggccagg ctggtcttga   19680
actcctgacc tcaggttatc cacccgccgt ggcctcccaa agtgttggga ttacaggcgt   19740
gagccaccac acccagctac ttattctttta taatctttca tttcagagct ctaaatcatc   19800 cctttagtg aactcaaaga ttttaaaacc ccttgaaacc agtgtcttgg gaatgatgaa   19860
tgaatctctt tatttgtttt attttttcatg taccagtatt tttattttca tgaaactttt   19920
atttaaaagt tgggttagta tttacttctt actaaaatct gagttaaatg acatttgtga   19980
aagtgctcca cacccaaaaa aacacccaat aaatgttttcc ttctaatgta ttcaatgcct   20040
atacccccaa atatcttaca agtaagattt ttgtataatc tgtatcatat ctaatttttaa   20100 attatggtaa aaatattaac atgccatcta ccttcttaaa attttaagtg tacagtgtta   20160
ttaactgtaa gcacaaggtt gtacagcaga tctctagaac tttcttctcc atttgttttt   20220
ttcttacctc tcaaaaactg taaatagtgt atttttttcga gataagttgg ggaatattat   20280
ttccccaact ttgttgataa ccaaaagaag ttaaatttgt ttcatgtaat taatcagtga   20340
gtgagctgca ttcaaaaggg aagtaatggg ccgggtgcgg tggctcacac ctgtaatccc   20400
agcactttgg gaggccaaga caggcggatc acgaggtcag gagatcgaga ccatcctggc   20460
taacatggtg aaaccccgtc tctactaaaa atacaaaaaa ttagccgggc atggtggcag   20520
```

```
gcacctgtag tcccagctac ttgggaggct gaggcaggag aatggcgtga acgtgggagg    20580
cagagcttgc agtgagctga gatcatgcca ctgcactcca gcctgggtga cacagtgaga    20640
ctctgtctca aaaaataaaa aagggaagt aatgatcaac tgtgtccaag ttctacttta    20700
agtgtgtgta atattctctg tagacttttc cccacagact tgtttgagat cttcattgac    20760 ataggcatt atgtacgtga tatcagtgct tatgaagaat tggtatccaa gctgaattta    20820
ttagtggtaa gtcctgagtt ttcaatattt tggcaggctg ctatgtagtc aggatgtaat    20880
ttatcacaga aacccatttc ctttttatat tttgattagg aggatgaact gaagcaaatt    20940
gctgaaaata ttgaaagcat taatcagaac aaagctcctt tgaaatatat aggcaactat    21000
gcaattttgg atcatcttgg aagtggagct tttggctgtg tttacaaggt gactttcccc    21060
ttggggaaca tttctgatac tcccaaccaa accggatgtc acacttgcac accgatattc    21120
aattgagtta gaactcttgt cattgaaaaa tagcaaacag atatgaaaat tagaatgatt    21180
gtttttgtcc aacagagata gccacactaa tattgtttta gctgtaagct ctagaaattg    21240
gccactgact ttttaagaca aaaggcatta ttaatctctc acaaaggtat tcaaaatagt    21300
ttctcccaat gcatgatgca atctctaaat taaaaaatgc tactaagtat tgcagactga    21360
cccaggggat accagtgttt tgagctgagc ttaatgtaaa tacagctgga actttaaatg    21420
ctctgtgact tatttatatg acttagttac tcatgtgact ttgttagtct atctctttct    21480
tcctctttct atcttctcct tctttacccct gttccttttg ttgttgttgt gttttcttt    21540 attttaggtt agaaagcata gtggtcaaaa tcttttagca atgaaagagg tcaatttaca    21600
taacccagca tttgggaagg ataagaaaga tcgagacagc agcgtaagga atattgtttc    21660
tgaattaaca ataattaaag agcaggtaaa tgttttcctt gtttctgaag atgttttttct   21720 taaatacatg tcattgcaag aaagtagagt tgtggtgctc ttgtccatgc tgcttatgaa    21780
ctagttccat gtgaaataat tgacactgaa gcagtgatat ttttgccagc ttttttccta    21840
aggcttgaca ttgaagcata aaacactgtc tggagtttat atcagggtca tggatgcaaa    21900
acaatcggat ttacagtaca gaatgcatca tatatgagga atccttttct tttcattgtg    21960
agcatatcta ttcttttctc cttatatttt aggatatttg gttacttagt tacatacata    22020
gaaatatgac taagagtttc ttgacttttg ccaaatggaa ccaagctgtt aacattcctc    22080
aaatatgact ttattagatc taaaatgtag attttcaagt tgggttatta tgtattggca    22140
tgagcagaat actctgatat aatgtaacag ctcaattaac tctcattatg aaagtttgtt    22200
tgaggaggaa gaataaacat ttcaaagaga aatggaattt ctttgtgtga tccaagaaca    22260
cattggtttc tttttcagcc ttccttattt gcacattcat cacgaatact gttcatttat    22320
aattcctgtg gtgcactatc agctttgctg cttttgtcct ccactggtca catttgcata    22380
gcatctgtgt tgggatgtaa caaattccat aaacaaggag accttgttc ataaaaatcg    22440 atagttctac tccagtgtgt acattatagt aaatattatc attaattgtt tattttatag    22500
ttgattttat atactaatag actagacttt aaaaagtttg ttcatgtgta gtttgttcat    22560
gtgtttgtat ggtcatctag ccttccacag tgtgctcttt cattgtagca caaggctaga    22620
acagggcttt tgacctaagc cagtccagtg ttttcatctg gacccaaatt tggttttagt    22680
ccttgtgggt gagccaggtc cagaatatgg ttctggttgg ttacctggtc acatattgct    22740
tacgatctgc tggccacttg ctagttgatg aagtagatta tttgttttag cacatttcct    22800
aagaaaagaa actgtcaaac cagggtcaga taggaagcat atgcttgggc tttgaggtaa    22860
```

```
ctcaaaattg ccctctcact agaggatcaa actgatggaa aggatgataa cattgagtcc  22920
ttaaaggagg aggtagtggc aggcagaagc aaaacaaatg gggctagaat ggagagtaca  22980
ttaagattaa cctgcattaa caaagaggat cccaaatgca ggtgcttaga aagaggactc  23040
acagtacagt gggttatttc tctttcacgg aacaatccca aagtgagtaa accaggttga  23100
aggtgttctc tgctccatgc gatcatttgg ggatgcaggc ttttttctct cttcttgtgc  23160
tgttaccttc tagtgcattg tcttcatctg tgtggttgaa actgccatag ccatgctcac  23220
atccaaggtg agatgaggag gatcatggag ggctattccc aaggtttaga gttcacacag  23280
gaagcacaca tgcttcctct catattccac aggtcagaac tgagtggtag cctcaccccc  23340
agcttcaagg gaggctgaga aatcttctct aactgggaag ccatgtccag cttcaactgt  23400
attgcaatgg gacagcaggt ttttggtgga cagctagcca tctcccttca aaagacttg  23460
cagaaagacc aaaaagagat gcaagcaagc catttgttga tgtgatggtg actgttctaa  23520
gacaaatttt atctagaaac tcaaattata agcaaaaact acaaaattat tagcattctt  23580
ctagaaaatg atctttttta attaaaaaat tagaaattcc actaacattc ttaacttata  23640
tcaaagagaa attgcaccat ttttttaaaaa cggtgaggaa gactttattc aatactattg  23700
caatagaagt caaactattg taatagagga gagagattga acccaactct gaattcgagg  23760
actggacagc tggggactca gagccaatgg tcagggtgag ggagggtcag tggatggaag  23820
tttactaaga ggaacttggt tagatatcaa gggtgagtgg atgagaaact taattggatg  23880
tcaagggtgg gaaattttc cataaactga cttagcagga tataagttgc taaaactgac  23940
agaccaagga tgaggcctag tcacgaagag gactcagagg agcctgacta aagcttggtt  24000
aagtaggaag tccttgtcaa ctgttattat gacttaaact gagtcgactc ttagattatg  24060
ttattttcta ctaatcattt tggagagcat agaaagacag aaatagtgta aataggcaca  24120
aactttccat aaatatttag atggtagaga gaggtaaaga acaatgaata tttgtagtca  24180
acagaagtta ccgcatttca cttttctcct ttatacagtc tgtgtgtcgg gttgtgacaa  24240
ggtgtgctaa agaaattctt aaggttcctt ctacctctat agttctcttg gttaagttcg  24300
atagtaaagt taggtgatag aacgttttta atttttattta ataaagctat agaggattgc  24360
tattttcaga tcagtttata agcaacaagt ttttaaaaat cacaacaatc tcagttcgat  24420
gatatcttga aatgcttagt tttgtaaata aatataattt ctttgtagtt ttcaaatatg  24480
aagtccaact aagtagtcag tgaaaaaact tgtattttga agcagtgcaa tacatgtttg  24540
ttatttattt tcttatagct ttatcatccc aacattgtac gttattacaa acatttctg  24600
gaaagtaagt atgagttttc atgatatttc taaataagga aacatttttg tcacatatat  24660
ttttgtatca gaatgtcaca aaagaaacct aatcaactat tttattgacc tttttttgtt  24720
aatatgacag tagatggtct taagcatcac tttcttgact agtgaaacag tgacctagtc  24780
agtcacctga agatagttat aaaatactta gctgcctgtg tgaaaacgc atgaacaaac  24840
caaatagtt attgctattc tcatatacaa aaaatcact taataggatc aaggaaaaag  24900
aaaactaatg gatggtggtt tccttaagaa agaaagttg ttttttgttga ctcaggtgtc  24960
attttccatc cccaaaataa gttggagaga gctaggtctt tgagatttct tttacctgaa  25020
gttcaggtaa atgccacaaa ggtggcgatg gagcccagac tgattctggc agccaggctt  25080
gctttctgca ggtatgatgg aatgctgaac tagaaccaaa acagataaag ctaaactcag  25140
ccactctttt ttttttttt tttaagtag ggcctatgac agaaataata caagtattgc  25200
taagctttaa tgatatgtgt cacatatgaa atgtcgaaat aaatctccac ttgaagaatg  25260
```

```
atttaaagag acataaggca atgactgggg cttccggact acctcttttt cagtgctatt    25320
gttatttaag aaaacctttt gtgtgtgtat tttgccattt gttacaattt tacccatctc    25380 ccttcccccta gatgactcag aaaaactcag tgctaaaact catgcagtaa atcctgtccc   25440
cttagccatt tgttcttgat attaaaataa ttttctataa tttagtgtat atcccttcaa    25500
aaaaatcaag gttggcttca gacttgtact gaaatgatat aaattgtctt aatataaaaa    25560
acaaaaacgt ttttttactac ctgacagctt ccaaaaagaa ctggaaatgg cggccgggca   25620
cggtggctca cgcctatgat cctagcattt gggaggccg aggctggcga atcacttgag     25680
gtcaggggct cgaaccagc ctggccaaca tggtgaaacc ctgtctctac taaaaaaaaa     25740
aaaaaaaaaa aaaaaagct gggcgtggtg gcaggcgcct gtaatcccac ctacttggga    25800
agctgaggca ggagaattgc ttgaacccgg gaggcagagg ttgcactgag ccaagatcgc    25860
gccactgcac ttcagctttg ccacagagca agactctgcc tcagaaagaa aaaaaaaggc   25920
tgggcgcggt ggctcacact tgtaatccca ccactttggg aggctgagat gggccgatca   25980
cgaggtcagg aaatcgagac catcctggct aacacggtga aaccccgtct ttactaaaaa   26040
tacaaaaaaa ttagccgggc gtcgtggcgg gcgcctgtag tcccagctac tcgggagact   26100
gaggcaggag aatggcgtga accccagagg cagagcgtgc agtgagccaa gatcgcgcca   26160
ctgcagtcca gcctgggcaa cagagtgaga ctccatctca aaaaaaaaa aaaaaaaaa     26220 aaagaattgg aaatggctta aaaatacata aaatatgata aaatagatta ggaaattgca   26280
ataaagagga atgaaggatg agaaaattaa aaataaagct agaggtagta ttggtacata   26340
aatgaatatt tcttgaaatt atgaaaaatt ggaaacaata taaatgtcta tctgtaggaa   26400
aatgattaaa taaattatgg tatacccata ttgtgcaata ccatcaaacc agcagaaaga   26460
atggtatgga tctgtgtgta ctgaaatata aggctgctta atgaaaaaaa gcataaatta   26520
cagaacatga ttccatttt gtcaacattt tctacacaca tattttgtat acatcccaaa    26580
gtttcaaaag acacatatca catcccattg ttaataaacc ctattggttt tagaggagga   26640
agtagaattt actcctttgt tttttggcat ccaaagcaaa aagacaaaca caatcagtca   26700
tgaagttctc tgtatctgta agataaaacc tggagaagtc cagttttgtt ttttttttgtt  26760 tgtttgtttg tttgtttgtt ttgcttttga aaggcataac agaaatttct atcatgtgtg   26820
ttattttcaa ctgtgtcatt gcaagaccat ggcattattc cagtgtaaaa ttctgtaagg   26880
taaatctatc agactatgaa acaatacagt tgaaaatgca attttctgaa tgtctgactt    26940
gatttgagcg taaattttag actactggga ggaaggatgg gcttacggtt tcttcaggga   27000
atcctccatg actggagatc atttacttgt tctctgtggc acctttcaat cattccacat    27060
cctggcatac atagaaaatg atacatttgc cagtgtaaac ttatgctaag gggttgtctg    27120
tagccagaag ataactgtgg ctgggcccca gtttccctaa gacccctca cctccacctc     27180 ttccagggct gagtggatcc atattttagc acatcatccc taattcttta gtgttagtgt    27240
cccgcacaga cactgggaag cttgaactct cattcgtaaa gttttcaag atgcctgtat     27300 tgagtttaaa tttctgtgac cttttgtgat atttatatag atgataggtt gtacatagtt    27360
atggagctga tagaaggagc cccgcttgga gagcatttca gttctttgaa ggaaaaacat    27420
caccatttta ctgaagaaag actatggaaa atatttatac aggtatgctt ttatcttcat    27480
taaatttttc ttaaaacagt aatgttctga gctggcttct taaagacgtg cagtagtcat    27540 cttttggctat atgtatgttg ggggaaataa aatttgtttt ctattcattg tttcaagctg   27600
```

```
tgcttagctc ttcgatactt acacaaggag aagaggattg tccatagaga tctgacacca   27660
aacaacatta tgttggggga taaggacaaa gtaaccgtta gtaagtataa agattttttaa  27720 acttttaact gaagaattcc tgaatactat cctagagtag tagtgtccag tagaactttt   27780
ggcactcatg ggaatgttct ttgtctatgc tgtccaatac agtagccact agccacatgt   27840
ggctattgag cacttgaaat gtgattagtg tgactgagga aatacatctt aaattttaat   27900 taatttttt ttcttcgaga cagagtcttg ctctgtcacc caggctggag tgcagtggta    27960
cgatctcagc tcactgcaac ctccacctcc cgggtttcaa gtgattcttg cacctcagca   28020
tcctgaatag ctgggattat gggcacccgc caccatgccc acctaatttt gtattttag    28080 tagagacagg gtttcaccat gttggccagg ctggtctcaa actcctggcc ttgtgtgatc   28140
caccctcctc gtcctcccaa agtgctggga ttgcaggtgt gagccccaat gcccggccaa   28200
attttactaa attttaattt agacatccct atgtgataag tggctaccat gttggacagt   28260
gactagtata gttctaaatg actgagctat attttgccca tatgagagaa tgaagtactc   28320
ttagaatact taagtatta attccaaaat caatggtttt caggtttttt cttactgtag    28380
aacactgcct catcaacaaa agcttttatg accaacacat gagcacattg ttttgaacca   28440
ttttaccata gtctgtgcct tatgagtgac aaatgtacat atggagggct ataaatcctc   28500
tagccatttg tatatttcaa catagagttt ttatcacaat ttacttcatc tgtagcaggt   28560
aggcctgatg ttggataaaa tttcgcaaat gagaaggctt actttctcct cccagttgtt   28620
gaattcttac tcataactta aaattaagtt tttagcttag gatgacatat tagctttctc   28680
ctgcctgcct catgaacact tgtgttaccc tcatggactt taatggttca ctaactacaa   28740
ttagggagac accttcctaa accagcagtc tccaaatgtt tttcaccgta acatcccagc   28800
aataaaaatt ttttgagaat acactgccaa tatacatagg cttatgtata aattctatac   28860
atatatatta ctgaacaaag attctgtagt aaataacaaa atctacagaa ataaaacata   28920
aaggaataca tttaaaaata aaaatagagg tcttaatatt tttgctgccc ctactcccat   28980
tgggttgcct tagaaactca gtgctggaga ctactgccat caatgttatt gatgtggaga   29040
catcattgat gtcatatgac aacatatgac agcatctaaa gctgagtccc ttggttttag   29100
aatttcagta cccatgaagg caattccaaa tgtacacatt tgctataaca acatgtgttc   29160
aggaatgatg ataagattta ctgtccaaat tttcgtaagt agaacatcat attaatatat   29220
ttgttgaaaa ataaaaaaca acctacaaca gaaactctag ataaccttca atacaaagct   29280
acttggaaat atttcgaagc caatgcattg tgaaataaaa aaagagaaaa taactgtgaa   29340
tctttatctt ggacacacat ttgcttaatc atttgaaatt aattataact ttgtttaccct  29400 taggcttttt atgttttctc tttttataaa ttgaacttat atttcctgaa aattttttat   29460
aatttattta tttgctggaa tgtcaattta taagttaata aggattatta taaattgtgt   29520
gttttaattt tataacaaat agtatatata taacacag ttatgtatat ataacaca      29580 gttatgtata tataacacag agttatgtat atatataaca cagttatgta tatatataac   29640
acagttatgt atatatataa cacagttatg tatatatata taacacagtt atgtatatat   29700
atatatatat atataacaca tttatgtata tatacaacag aacaaatatg tttaatcctc   29760
cttaaatggc tgttcaggcc atatttttctg agtaatagcc aactctgcat tttattttcc   29820
tatgaagatt agctgtaatc atttcctttc attacattta aatgtactaa gcttaatctt   29880
ttattgcagt agcctggttt attttttttct aaacttatat ttactttctt taatcattat  29940
cacgcatcaa aatagtttat aaaataaaaa gcttatagag aaaaacagtt ttatgcccca   30000
```

```
tcccttttgaa actttagttc tgttcccaca aaatggccac gtctccactt tttattcttt    30060
ttcttatggt atttgatttt ctattgtaat gggtgagaat ttagttttct tcttcttct    30120 tccccatcta ctatcctgcc agtacagtta cagcagaatt ttatgttaag tcaatattca    30180
atgtttacat tattgctgct gtgtaattat tgttcgatgt tgattaccta tcctttctca    30240
taggtagttt tgttttttctc agagttaatg attgccttct tttttgtttg tgttcccagt    30300
tttctttgta cctattattt acttttctcc aaatcttcca gaagaattat aaaaccctct    30360
cagtactatt ttccacatgg tcaaacatga taagtactcc cacttttgtt ttcctggact    30420
cctcattcct gcagctgctt gttgcagtgt actctgggtt tcactttagg cctgctgcac    30480
agccattatc atggaactat tgtttgttgg tcttccgatt gtagactcca tttcttatgt    30540
tctgtgtctt tttctttgta aacttccctg ctctgctgaa gtaagtcttc tggtactttt    30600
ctaataaaga gtgctttggg cgttatgttt tttggatgtt cgcttgctac aaatatttt    30660 atgggacccct cttattggac tggtatttgg cttggtgtat gtattctcag atgaaagttc    30720
ttattctctc aagttttaaa ggcatttctc tagtcttctg gtatctagtt ttgctgtcag    30780
gaaatccagt gttcttctga ggcctatttc ttgatacatg aggtatttta tcactctgga    30840
aaatttcaga atgttccctt tatccactgc tttggatggg tctttaaaat tcaatgtgtc    30900
tgtagccacg tgtgctcttc aatctggaga cttaaaattt aagtcctggg aagttttcct    30960
gcattatttc ttcactactt ttctcccctc tgctctctct gttttcattt ttagaatctt    31020
tttagtctta gataccatat gtacaaaatg atctcctaat ttaaaagta attatcttag    31080 tttttaatgt ttgtctcttt gttataatta tttcttcaac tttctttttcc attccattga    31140 atattaaatt tatattatca tattttaatt tcaaaaattt ttgtcttatt ttgtgttta    31200 tttttatgga accctgtttt tattctttct cagggtaata tagactttt tttctttagc    31260 atcctgaatt gtttctgcat cttctgaagg tatatatata tatgcatata catatacaca    31320
cacacacaca cacacacaca caccatatgt acatatacac acacatatac acacacacat    31380
ataaaacata tataactaaa cagtagcata tatacatgtt ttattcctgc ttagtattat    31440
ctgtctttct ggctggggggc ttttctcaac tgtcttgtga ccctgggctg gtctctaata    31500
attttgagga aggcatgaaa aaggctgtca gaagcactgc gagttccagt tgaggctgtc    31560
atctggtgcc cttcattata ataaaatgga aattttcctt tgaagactcc aaaatcagta    31620
tctaaacttt gttttttcta gagaatactc ttcaagtatc ttgcctgggg gtatgtgcgc    31680
ctgtttgctg tcattctgag cagcgtcaac aaacgggct caaggaacca cattcagttt    31740
ataaattttc gtcgaattct accgtgcttg gttccttgct ggtttatttc tttgaaaaat    31800
gaatattttc tgttagtggc agagggtgct tgatttactg gctgtgtgta tgtgggaggg    31860
cacctgggaa cttgatctca attctatgta ttgagctttc tgcttctctt ctcccttgga    31920
tggcaccctg ggctctgcag ggttaaatgg gctcccttaa gccttcctcc tcagatgcat    31980
gggtagcatt tttgctctgc tgagtctgac accatcttct acctgctttc catctgccac    32040
acatttattg gaatatctca tcctctgttg ttgccaagcc cattctcatt gttcctgtgg    32100
gttagtaaca ttccaaagaa tatcccctct cccagctttt ttttttttt ttttttttt    32160 ccatttttagg gggtttgaga tttagaggag ataaaaacat atggtcaatt ccctttttaa    32220
cccacaacac ccagccaatt tttgtatttt aggagagacg gggtttcacc atgttggcca    32280
ggatggtctc gatctgttga cctcatgatc cgcccgcctc ggcctcccaa agtgctggga    32340
```

```
ttacaggcgt gagccaccgc gctcggccta cttccagatt ttaaggccgt ttagctttaa    32400
gtgaagcagt attttcctag tgtcaaataa agaagcagca caggttggtg gcatactggt    32460
gaggctagca gccttcagac acagaagcta gtgagctcag aatgggatcc tagcctagtc    32520
tagtttctct tcactaaagc aattgtgtgg ttagggcatt catgtactcc cattattttc    32580
agtgactata aaatgatttt atgactgaaa agataatcca cagagatttg atgtcattct    32640
ttaaaaaata ctttaaatat aatagtgctg aaatatttt cagtgtctat ctctattgat    32700
ataatgtaaa tatgtccatt agtctcttat ctttaagagg gattatggtt aaattaaaac    32760
cctgcagcat taatttaaaa gtaagtgtat aaaatttcca tattttagga agtggaatgc    32820
agctgcaatt agtagagcct gtgagaatgg gctggctgct gtgggtgtga aagcatgtca    32880
ccacagaggg gcagccttgt tatgttttat ttttctcttt gcttgcgcta gaaggtttat    32940
ttacttccag aaaagaaaca cagaattgcc aaatgatgtt taagatgcat gagacaaagt    33000
gtactgaaaa tgtgatcaga aaaaaagct ttcagaaaac taaaattttc atcttctcat    33060
ttttctcaat ataggtgaat taaatgtttt aagattgagg ttggtttgca cttatttata    33120
gtaagcatgc tggcaggagt ttgctttgat gaggaagcag aatagaaagt actcacatat    33180
tctgctatgc ttggttttgc aaatgctata tattttaag tctaaatata tttccatttg    33240
aaagactatc ttttgatggc atgtgccatg acacatgttc aggtcttgtt ctccatttat    33300
ttgcagcctt tgaaaccatc caaggaaaca gaccccgatt cagtggtaca tggggtgaga    33360
cacagtcaac atttgcccta aatactgtca cttgccaaat aaggtccata ttgtgccatc    33420
acattacaaa atgactcttg agggaatttg gtaaaactga acttacccctt gaacccacca    33480 ttccagatttt cttgaccttt tcaaaaaccc ttatttaat gtaaaccttc catgtccgct    33540
tgcctcctct gctttcaaat aaaaaaggaa aagaaaaaac aaaactcatt taattatagt    33600
taatagattt caggcatgga ctttagtaca tgacacagaa ggtcacatgt tcatcttgca    33660
aacaaacagg ctatgtgaat ttctgttttct caagtgatat ttggcacctg ctctgatgat    33720
aacaacaaga aaaaacctga ttcagtgtaa agtttatcaa aggctccaag gctcttcaaa    33780
tgttatcaca ggtcaggcat tgctgggata gatataagat gaaaagccat ggtttctgct    33840
ccctgagctc acagtcctat ggggaaaacg tctgttattc actcagcaat taccttccta    33900
gctgacacat cctacaagtg agcacagcaa gcatgaagga cataacccct gtcttaatga    33960
agcttataat tctgttacag agtgatgaag gctagaatgt atatgcaaaa tactgtaaca    34020
tgtaataagt aacctgaaat tctcaacagc ttaaaacagt ggcaaaatac agcctaaaac    34080
agtggcaaaa tacagcctgt gggacaaatc aagttgtgac ctattattat atgtcctgtg    34140
agttaagact ggttttata ttttttaaatg cttgttgaaa aaggaagaat acatgacaaa    34200
gaccatatat gttccattta ggcaaagcct aaaatgttta ctatctggtc tttacagaaa    34260
attttgtctg cctctgactt aacaagactc ctatcctgct aatgctacat gtccattatg    34320
tgtcaataag ggagcttcct ctgtacttgc ttctacatcc cagaggcagg aaagacagaa    34380
catgggaaac catgccgtgg ctcttaaaac ttctgtccca agtaacaca tgttacttct    34440 actcagattt cattggtcaa agaaagtcag gtgtagcagg atgtggatgc attcctcctc    34500
cgagagaata tgagtgaata gttatatagt ctatcacagc tatataagca ctggggaaaa    34560
tgtgactaac tgtgccttag ggatcttttg gtgcagagtt aagcaggaag ggtaagagca    34620
gttaatgcag aggcatagca catgcagagg atagagacat gaaggagtat agtgtgtcta    34680
ggaactatca aggtgtttga tgtggcaaga gatgaaggag ccttggtggg tggggagctt    34740
```

```
ggtcaaagac ttatcctcag agatttttca gactagaaat tatatgatca gatctgggag   34800
gtagaaggat tattaaaatg gcaggtgagg gagcatgctg gggaaagact ggacccagat   34860
actcagttta ggacatgtat cagttaggat atgttcaggt gcaaaaagcc agactaacga   34920
tggcttaaac catgaggata tttagttatc tcacaacaag gggtctgaga gtgagtagtt   34980
ccagggtggg ttcagcagct tagggtgatc taggcctttc tgtcctttct ttccagtatc   35040
cccagcagat tgacttctcc atatgtttgt catctcatag tcacaggatg gttgccagag   35100
ctccagacat tattaccaaa ttcaaagatg ggaggcaagg tggctgcttg ggtaaaatct   35160
agaaaaaaaa attgtcttct ccaaatgctg tctcatctgc ttttactgtt aaagaaaatc   35220
ttccaaagaa ggtctccatt agccttctta tattgtgttg actgaaacca agtcatgtga   35280
ctactcctca ttgtaagaga gactgttgag gtgagcttcc agcctctata gttggagatg   35340
agaaagggag aggatttggt tgatggtttt tggagagctg gcccacaatg tttgccactg   35400
aaggctcttg cactttgtc caggaaagtc atgatgtggg ttttccaat gacagaagga   35460 gaagagaatg tgaaaagggg gctcaattca gcagttattt gggacctaga attaaaagga   35520
tttgtcggcc agttaatgag atgtgaggta tgagaacagt tgagaaagag gctgagtttg   35580
tgaagattgc tctgccattg gcagagattt aggtgtaagg ttttggacat gcttagttaa   35640
aatctaatta tgctcttctt ctggttaaaa tccttcaagt aattgccat aatatttaag   35700 ataaagttta gtttccttat ggcacccaaa gccctttctt cgtaatctcc tccttgctcc   35760
ttgctctgac ctcctgggac agattgcact ttcctgaaca ggatgtggct gtatgcctct   35820
gggacttcta acatgccatc cctctgcctg gaatgctctt cctcccttct gccactcagg   35880
tcaaatgccc ttcctccagg tggcatcttt gacatccaca tctgatatgt ccagtttctg   35940
ggacccctta gtacactggg cttgcctgtc tcatagcaca tggcacaaag tattgaaaac   36000
actggcttat tgccatcttc tccttgaggt gagagaaatg aactttcttg accttctttc   36060
tctgatagca cttaatattt ttattcacca aatgaataga agaatgaatg aattaatgag   36120
caaatgaaca aaaacacatc caggtggaaa tattcagaag ccatttaca aatagggagc   36180 agagattgag gtgatacctg ggtttgagat ctccttctga tagccaagat tgtctagaaa   36240
gagtgcttaa aacaagagga gttgaatatt aatgtagaaa ttgcatgcgc acatgggcaa   36300
aggtccaagc agttcccact gtcatcttag caaacagtaa ctcaaagaaa aatttact   36360 ttcttgaatg ccaccaaagt ttcagacatt gaattggacc tacctgtat tgccagaatc   36420 ttcagtattt taaattttc agaggattag aggacttta attgttattg gttggctaaa   36480
ctgtggctga gaaatttgtg tcattatata aaaaaagag ttagtattgc atttctgata   36540
gggaactcaa agtccttatg tgcacattac tcatatactt acaaaacctc ctggtcaaat   36600
acatatatga tggactctat tcatggtttt tgtaggtctg tcgacatgcc ttgctttgaa   36660
cttgttctgt ggtttacttc ccgttaaccg gatatagtgt ctatagagtt tgagctgaca   36720
cgacttgagt actcttaaaa gactacagaa tattgagcca cttgtgttaa atacctcat   36780 agcaactgtt gtaagaagga tcaccatgga attttctca gtcaacagat tggcctcatg   36840
ttagtaagaa agtaagaata tttttgtcaa gttatcacag ttgccttgta ttgccattgg   36900
gtctcataac ataaaaagga aatgtcaaag gaaattcagt caaatccaat ttctgaagta   36960
ctttaaagat tcttcacacct ttggtgggtc attctgcatt tctcagattc tatatttta   37020 agttggctac aagaaaaaga taagaatggg aattcgacaa agttagagcc agatgggtt   37080
```

-continued

```
agtttccaac cctgacaatt gttatccttt tctgatgaga cagtgaactg ggtgagcaca   37140
gaaggagaca ccaaatttt atgaccttag gtgaaagttg gaaatagtaa cctcataatt    37200
gaggtttata aggccaaata aaaacaccga agactaaggt taatacagta gagttcattt   37260
tagtgtgtat ttgggatatg atttggttct ctgagagctt ttaactgaag ggggtggaat   37320
ctgatgtgtg atgtcgtctg gatgagttgt tttcactctg tgagttttcc caaagtgtgt   37380
tttctgaaga aacatagtga gtaggcagta gtacctattt ttgtagagac taattcagtg   37440
gtacagagta ctatgcttct gattatgtca tcagcatttc cagccagcta agtctactaa   37500
agccattgga gcttcagagg tactgccctg atctccatcc taggccttt aagaactagt    37560 atcatgccac acacagtatg tgtgtgtgtg catgtgtgtg tgtgtatgcc tgcatgtgtg   37620
cgcatatgtg aaaaaagag agtgcacccc tgacttccca tccttatagg agtctggccc    37680
ttggcacttt tatgtaatgt tagagctata tgtacagagc tccattattc caactgaata   37740
accagaaaca aaccccattc tgaagaatga ttttagaaga gccctctgtg gtttacttcc   37800
cattaacccc agatacagtg tctatttgag tctgagctaa ggacattagt tttcccaagg   37860
atccagtctg ttgatacaca tcttagagct aggtaatgtt tatgtaccac agatatggag   37920
ttacctagaa ttcagaaagc attcttttat caagtgttga attttcatc atgaagctct     37980 gtgtcatcat aactccatca ataaaatcaa gcaaataatg atgctgttga gaaacagaag   38040
ttccttccct ctccctcatc cctggtggag tctgcactgg agaaggaagc tttggagaag   38100
tggaaagtgg catggtacag gggtccctgg cacaccaaca ccaaacacct gccgcctact   38160 cttttgtttag gaatatctac tttagactta attagcatgc catttgttga attagaaata   38220 atttttaatat taatagtagt tggacttcat ttagctgaag gtcaggaagc agtttgaggg   38280
gcagagatta gaatctgaat gaccttcaga ggaggaagtg tcagtgagac aggggttcgt   38340
tgagggaaaa ctctgagcat tatcctggga aactccttcc cgtccctcac tgactcctgc   38400
actgagagga tgttactgat ggtcctgttg ctgtggacat tgtaggttag ccattccatt   38460
tactgaggca gcaggaaaga gtagagtggt aaatgagctg gagatctta ttctggcctg    38520 tttcacagtt gtgctcaagt agactcctct gtcattgcct agtattatag aggtttcaaa   38580
taatcatttc ccgaaattgt caggtcatta attattttca ttttactcag ggaagacatc   38640
tttaagatga taaaaatttt tagctatgct ttgaagaaaa ggaacaacca cccatagcta   38700
catcccttga gcatttacta tgtgataaaa ggatagatat gcattttctc attcaatact   38760
ctgatgcctt ttaaagatag tgaaaaaggt ttagagagtt tagaaaactt gcttaaattc   38820
cctgtttgta gattgacagt gtcagcaatg aaccatgtct acttctagag gtcatctctt   38880
aaccaagtct ctctctacta ttctctcaga ggaagccatt tcaggtaacg aaaaagacat   38940
gtttgaaagg caccaagatg cttatggtca agtgctgtac aaggatgagt agtttgttgg   39000
aggggacatt ttaatttggg caattatgag agaggtcagt cacctgaaca tggctgcagg   39060
gtcttgcata gcctgtcaat aaccccccatt tggccacgca gttcctcagt agaccatttt   39120
cccttgacca tagggccttt gagcatgcca tttcctctgc ctggaagtct cttcttcact   39180
ttctcctctt acctagataa tgtctgcctt ccttcagatg ttaacccagt caccatttgt   39240
cacagaggct tttcccaatc agctgttttc cttataatac cctctcttaa ccccatatat   39300 ggggaaggt taggaagcag ttgggggca gagattagaa tctgagtgac cttcagagaa     39360
ggaagtgtca gtgggacagg gatttgttga aggtcagtct tctttaatga tcttatcaca   39420
actgtaagtt tacatttata tgtgtgattc tttatttaat gtgtatctac accactggtc   39480
```

```
cctaaagtct gtgtcatcat ggatggtttt tgacctggtt atcatcttat cttgagtacc  39540
tggttcagca cctagaacat atgctcttag tgttggacaa atgagtaaat ggacaatcat  39600
gaagtccaga taaggcagct ggaaactttg taaaaaatag caatcggaag accttctggt  39660
acataagtgg gggcctgatg tgatgaaggc aggtgttggt agattgtttc gttgtcaaat  39720
accctgtagg atggattaaa aggaaaagct ttctaaagaa gtgcatcccc ttttttgcag  39780
gaagagtgag agcctaagct cctggcacat ttaaactata atcagacaaa tcaaagaaa   39840
gatgcagata caagagctgg tgaggggttg aatatagcag caagtgagaa aaggcaaaga  39900
tttcaagccc aggaaatggg gaagatgaga tgccatctgg ttgactggga tatccctgat  39960
gactgaatga tgagcccagt cttgggtggg aagtggcagg tgctttatag ggctggaggt  40020
gaaacccag acaaggctg ggactttaca gctgaatttg gaagtcactg acacatatgt  40080
gatgggtgaa aggttgtgaa cagctgggtt ccctgtggat agggttggga ataccttgca  40140
tctatacagt atttcaaact gcttttcacc tattgtcatg ctgttgttga aacaatcctt  40200
tgcaaacagt aagtaagtt ttataggcca ttttttgaaaa ccagagagca agaatctagg  40260
gactcagcca aagcacacac aacttttcca tctgaaggct ggtaattgta gggctatagt  40320
gtaaacatgc tatagaattt aacattttct gtatcatttg tcctgtcaaa ggggagaatt  40380
tctttggatc ctatttttt tcataatgt gctgtatgca aaatgttttc tattgtcatt  40440
ttgaataccc gtaatggcac atgaatgctt ttatgagtac aatttctgaa ataaaacatt  40500
ttcttcttct ccaaatatga tcacaaatga ggaaagagta atagaaacat ttctgttacc  40560
acccaggtct cccaaatgtc caaacaatat tagttttgc tcattttaag aatacctctc  40620
aactctctgt gttttatgg atatctgtcc aagtgtctgc tattatctaa attaactgga  40680
gtgaataaaa tcattgtaat gctcctcagt ttttgccttt caaaataaat ggcattttag  40740
taagaataag atgactctta catagcatta gaaagaaaag ccaaagcatt attttttggtt  40800
ataagttggt caagaattgt atgctaaaat tatagtgggc tccctaaaaa tattgaagtt  40860
gtgaatattg aatactttt tttttctgta tagtgattgc ttaattttaa ctaattttct  40920
ccagtacata aaaggggaaa gatagcaagc catctagttt gtgaatagtt gttaacacca  40980
ccttatacga tttagtcttc taatatgtcc tatatgtgaa tagtactatt aggtggagag  41040
gttagacaga tagataggta gatagataga tagatagata gatagataga tagatagata  41100
gaagatagat agatggatgg aaagatagat ggatatacat atagttatgc ctatatatgt  41160
acatatacat gtattaaaag atatgtatcc atcagtctac agggataagc aatacaaagt  41220
cctctcatgg atctttcata ctagttagaa atgacagacc ctaaatgaat gaaaaatac   41280
taaataata cataaagtaa tttcagataa tgaaatatgt taagaattaa ataaatgtaa   41340
tagaagaata ttgaaggaga ggactttttt tttatagtgt gtactagaaa agtcattctg  41400
aacgcccaga tcatgtatgg tcgtgtagac cttgtagtag tttggctttt attcttagta  41460
tttatcaaac gtctttgtag agttttaacc ttgtaagtag tgacaaatga gtaaatggac  41520
actcgtgatg gcaactttag atatttaaaa gatcctttg gacctgaagt ggagaattat  41580
atttcatgag gagagatgga gggagggagt ctgttcggga ggaatagctc agtagcctca  41640
gtgagacgtc acagtagcat ggacggatga tggcagttgt attcattatc cattgctggg  41700
taacacattc cccagaaatt tggagggtta aataacaaa tatttatttt cttatcattt   41760
ctgagggtca ggagtccagg agcagtttat ctgggtgatt ctgacttagg gtttctcatg  41820
```

-continued

```
aggctgtagt caaactgtca gccagggatg catcatctga agcctggact ggggctggag    41880
ggtcagcttc caagaaggct caataccatg gctggcaatg ggttctgggt tttgactgga    41940
gtgagtgcct catttctctt ccatttggcc ttttatcctt gagggctgct cttctctata    42000
taacctcttc agcagaataa cctttactat tctacatggt tgctgggttc tgagagagag    42060
tcagtgagca agagagagca caacacaatt ggaagctgta gtttctttat aaccgaacct    42120
tggaagtaac atctcatccg ttctgctata ttcagttcat tagccatgag ttaccaagtc    42180
tcatccacac ataagagaag gacaattaag attcacctcc tgaagggagg aatgttaaag    42240
aactggtgaa cattttccaa aactacaact tcagtggagg tgatgagagg tggcctaatt    42300
cactatatat ataaactttt tgtagaaaca ataggatttt gctgtggtaa aggaaagtga    42360
ggaactatat cagtcaggac tcattcatga gacaggaaca accgagtaat tttaacagga    42420
caagtttcat gtattaaaat gattttaac tagtactaag attaactaca aagagttaaa    42480
gataacccaa taagaacac aggaatagca tatacaggta taccttggag atactgtgga    42540
ctttgttcca gaacaccaca atacagcaaa tattgcaata aagcaagtca tataaacttt    42600 ttggttttc agtttgtaca cgttgtgttc acattatgtt atagtctatt tgtgtgcaat    42660
agtctatttg tgtgtattat gtctaaaaag caatttaggc acatacctca attaaaacat    42720
aattcgttgc taaaaagtgc taacaatcat ctgagcctttc agcaagtcat aatcttttg    42780 ctggtggagg gtcatgactt gatgctgctt actgatcagg gtggtggttg ctcaagtttg    42840
gtgtggctgt ggcaatttaa taaaatgaga caacagtgaa gtttgctgca gagattgtct    42900
cttcttttca caaataaat gtctgtagca tgaaatgctg tttgatagca ttttacccac    42960
agtaaagctt cttcaaaat tggagtcaat cctctcaaac cctgctgcct ccatgtcaat    43020
taaatttatg gaatattcta aatctttct tgtcatttta acaacgttca cagcatcttt    43080
cccaggagtg gattccattc caagaaacct gtttctttgc tcatccagaa gaagcaactc    43140
ttcatccatt caagttttat tgtgagattg caatgattca gtcacatctt caggctccca    43200
ttctaattct agttctcttg ttatttccac cacatctgca gtgagttct tcactgaaat    43260 cttgaaccct tcaaagtcat ccataagggt tgtaatcaac ttcttccaaa ctcctgttaa    43320
tgttgatatt ttgacctctt cccatgaatc atgaatgtac ttaatgatat ctagaatggt    43380
gaatcttttc caggaggtaa acgttgccca gatccattag aggagtcact atctatggca    43440
gctatagcct tatgaaatgt atctctgaat tagtaaaagt agaaatgact ccttgatcta    43500
tggactacag aatggatatt gtgttagcag acatgaaaat aacattaatc tttttttaca    43560
tatccaccag agctcttgag tgatgaggta tattgtcaac aaacactaat attttgaaag    43620
gaatttttta ctaagcagta gttcttaaca atgggcttaa aatattcagt aaaccatgct    43680
gcaaatagaa ggactgtcat tcagactttg ttgttccact tatagacaac aagcagagta    43740
tatgtagcaa cattcttaag ggccctagga ttttcagaat ggtcaataag cattggcttc    43800
aacttaatta ccagctgcat tagtccttaa taagagagcc agcctgttct ttgaagcttt    43860
gaagccaggc attgacttct cctccctaac tatgaaagtc ctagatggca tcttcttca    43920 gtagaaggga attttgtcta cattggatat ctattcctta gtgtagctac cttcatcaac    43980
tgtcttagcc agatctggat aacttgccat agcttctata tcagaattgg ctacttcacc    44040
ttgcactttt atgttatgga aatgtcttct tccttaaacc tcgtgaacca acctctgcta    44100
gcttccagac tttcttctgc agctttctca cctctctcag tcttcacaga attgaagaga    44160
gttagggcct tgctccagat tgggcattgg cttaagggaa tgtgttggtt tgaccttctg    44220
```

-continued

```
tctcagatca cttaaacttt ctctttatca gcaataaggc tgttttactt tcttatcatt    44280
tgtgtgttca gaagtgccac tccactgagt agcactttta atttccttcc agagcttttc    44340
cattacaaca tggctgtttg atgccagagg cctaactttc agcctgtctc agctttggac    44400
atgcctttct cactnnnnnn nnnnnnnnnn nnnnnnnnnn nnnnnnnnnn nnnnnnnnnn    44460
nnnnnnnnnn nnnnnnnnnn nnnnnnnnnn nnnnnnnnnn nnnnnnnnnn nnnnnnnnnn    44520
nnnnnnnnnn nnnnncaatg tatggttatt aactggccta atttcaatat tattgtgtct    44580 aggggataa ggaggctcat agagtagtga aagctgggg gaacagccag tcaatgtagc    44640
agtcaggatg cacacaatgt ttagcaatta agtttgccgt cttatatgcg catggtttgt    44700
agtgtcccaa aacaatgaca atagtaacat caaagtatca ctaatcacag ataaccata    44760 acagatataa taataataaa gtttgaaata ttatgagaat taccaaaatg tgagagacat    44820
ataaagtgag cagatgctgt tgaaaaaatg gtgctcatag gcttgctgga tacagggttg    44880
ccacaaacct tcaatttgta aaaagaatg caatatttgc aaagtacaat aaagtgaagc    44940
acaataaaat gaggtataca tatataagca gctactaccct ctagggctga ggcaaaactat    45000 acaaagaagg agcaaatttt aagacagccc ctctcctcaa gggctgagat ccagactttg    45060
ttggagaggg tatgactata gcccacagat ggcagaaatt gcattgaaat gctgcaggat    45120
aaagctgtca aacagaaagc tgccctgga atgatgacca tgtttttcag gaagccattt    45180
tctggggtat gagtagaact cagtaggaag ctgttggctt gggtgctcct gagactaact    45240
agactgagcc tggctagaat gccggtagaa gttactggga atctacctgt ggaggtgttg    45300
tgaaaacagc tgagatgcca gcagaatttc atggtatgtt gtctgctggg gtgcttgcaa    45360
aacttgccag gaagctggat atagtgccag tggaactgtc tacgaagctg cctctagggg    45420
aagtgagcac cactaagcat cctgcacact gcacaagtgc tacaggagca aggaaagaga    45480
ggaagcatgt cagaacctgg aaaagaagag aagcctctcc tgtagtttct cttcagcaca    45540
ccctctactg acaaagcttt acatcaagcc agctggcgaa ggagagacat tatcaaggtc    45600
cagctccatt aacaaagcag ggcaatgatg aagggtggat tgatgctga aagggaataa    45660 gttgacagct agcacaagaa ctaaggaaag tacctaggtc aatgatggtg ccacttactg    45720
agatgggaaa ccaaggagga gttgtttggg ttaagattga gaattctctt tgagtgtgtt    45780
aattttgaga tgcctaggag acacttaagt gaaagttttg attatccaga tgaatatgta    45840
aatctggtgc tcggagagag gaagggacta tttccaacaa atggtgcagg aacagttgca    45900
aatccccata aaaaaatcag aacctcaacc tacatattgt atcttatata aaaattagct    45960
cagcttggat catagcacta tatgaaactt aaattatgaa acttctggaa gaaaaaaatg    46020
gatatagtct ttgcagtatt gggctaggca aatatttctt agacagcatc aaagccataa    46080
catgtaaaat aaactaataa atttgactta gtcaaagttt aaaacttcta ttctttgaaa    46140
aacgttaaga gaatgaaaag ataagctgca gactagtaga aaatatttgc aaattgtagg    46200
ccgggcgcag tggctcacgc ctgtaatccc agcactttgg gaggccgagg caggtggatc    46260
acgaggtcag gatcgagacc atcctggcta acactgtgaa accccgtctt tactaaaaat    46320
acaaaaaaac tagccgggcg tggtggcgga cacctgtagt cccagctact cgggaggctg    46380
aggcaggaga atggcatgaa cccaggaggc ggagcttgca gtaagccgag attgcgccac    46440
tgcactccag cctgggtgac agagtgagac tctgtctcaa aaaaaaaaa aaaggaaat    46500 atttgcaaat tgtatatctg acaaataatt tgtatccaaa acttaaaaat aagaaaataa    46560
```

```
ataacctaat gaaaaatgca aaaatttgag cagccacttc actaaggaag atacccaggt   46620
gctcactgtg ccagcatata tactaaaatt ggagtgatac agagattagc atggcccgtg   46680
cacaaggatg acatgcaaat gcatgaagtg gtccatttct ttaaatgaag atgcccagat   46740
ggcaaataaa tacatgaaaa gtgttcaaca caaataagct ctaaggaaat gcaaatcaaa   46800
actatactga gatatcacta tgtacctatt agaatggctg attaaacaaa aactgacaac   46860
attaaatgct gatgggatg cagaagcaac tggaacgctc aaatttctgg tgagagaaaa   46920
aactggaaaa cattttgact tggcagtttt tataaaatca aattaaacac atgcttataa   46980
tatgatccag taatcccact ccaaggcatt tttcaaaggg aaatttaaaa ttatgttccc   47040
acaaaaattc atatgcacat attgtactta cctgaatctt caatagaatg ttgactagga   47100
atgctgagaa tggtggacat gttttgtttt tgaacttaaa agggaaacac tcagtttttc   47160
agggttaagt agattattag ctacagcttt ttttggtaga tgctctttat caggttaaga   47220
aaatacccaa ctattcttat tttgctgaaa ggaatagatg ttgaattttg ctgacgcttt   47280
ttgcacatct gttgagatga tcatggtttt ccttctttaa tgtactgatc tggtgaacta   47340
cactgatgat tttttaaaat tattatttat ttatttattt atttatttat ttatttattt   47400
atttagactg attttcgctc atgttgccca ggctggagtg cagtgatgtg atcttggctt   47460
actgcaagct ctgcccgccg ggttccagtg attcccctgt ctcagcctcc tgagtaactg   47520
ggattacagg cacctgccac cacacccaga taatttttt gcattttag tagagatggg   47580 atatccccat gttggccagg gtggtctcaa acttctgacc tcagttgttc cacctgcctc   47640
ggcctcccaa agcgctggga ttacaggtgt gagccaccag gcttggccaa ttaattttta   47700
tttgaaaatt attttggatt caggggctat atgtgcatgt ttgttacatg gatatattgc   47760
atactgctgg tgttcaggct tctattgaac tcacactgat ggatttttaa aagtcaaatt   47820
agccttgtat tcctggcata aaccccactt gatcattatg tattatgctt tttatatgtc   47880
actggatttg atttacttac attttgtcaa taattttgt gtctgtgttc atgaggctct   47940
tgttctgtag ttttctttc ttgtcatgcc tttgactggt tttagaatga tgtaatgttg   48000
gctttatgaa gtgatttggg aaatattccc tcttctattt tctggtagag tttgtgtaga   48060
attggtatat atttcttaaa agtttggttg agtttatcat tgaattgatc tggtcccttat   48120 ttttctatat tggcagtgtc ttggtgagat ttggggcttt agaatcaagc aaccccagat   48180
taatatctca ctttgttaat ttctccctgt gagacattgg gcaagtcaca cattctcttt   48240
gagcctattt cctcatctat caaatgggta attgtgataa ttaaataata atatacatca   48300
tttattcaat actctactac atgtatttat atataataca tacatggggg tggagccaag   48360
atggccgaat aggaacagct cccagcatga gcgacgcaga agacgggtga cttctgcatt   48420
tccaactgag gtactggtt catctcactg aggagtgtcg gaaagtgggt gcaggacagt   48480
gggtgcagtg caccgagcat gagccaaagc agggcgaggc attgcctcac ccggaagtg   48540 taagggtca gggaattccc tttcctagtc aaagaaacgg gtgacagatg gcacctggaa   48600
aatcaggtca ctcccaccct aatactgcgc ttttccaacg gtcttagcaa acgccacacc   48660
aggagattat atcccgtgcc tggctcggag ggtcctatac ccacggagcc tcgctcattg   48720
ctagcacagc agtctgagtt caaactgcaa ggcagcagcg aggctggggg aggggtgcct   48780
gccattgccg aggcttgagt aggtaaacaa agcagccggg aagctcaaac tgggtggagc   48840
ccaccgcagc tcaaggaggc ctgcctgcct ctgtagactc cacctctggg ggcagagcat   48900
tgccaaacaa aaggcagcag aaaactctgc agacttaaat gtccctgtct gacagctttg   48960
```

-continued

```
aagagagtag tggttctctc agcacgcagc tggagatctg agaacggaca gactgtctcc   49020
tcaagtgggt ccctgacccc cgattagact aactgggagg cacccctag taggggcaga   49080 ctgacacctc acatggccgt gtactcctct gagacaaaac ttccagagga ataatcaggc   49140
agcaacattt gctgttcacc aatatccgct gttctgcagc ctccgctgct gatacccagg   49200
caaacagggt ctggagtaga cctccagcaa actccaacag acctgcagct gagggtcctg   49260
actgttagaa ggaaaactaa caaacaggac atccacacca aaaccccatc tgtacgtcac   49320
catcatcaaa gaccaaaggt agacaaaacc acaaagatgg ggcaggaaaa ctggaaactc   49380
taaaaatcag agtgcctctc ctcctccaaa ggaatgcagc tcctcaccag caatggaaca   49440
aagctggatg gagaatgact ttgacgagtt gagagaagaa ggcttcagac gatcaaacta   49500
ctctgagcta aaggaggaag ttcgaagcca cggcaaagaa gttaaaaacc ttgaaaaaaa   49560
attagatgaa tggctaacta gaataatcaa tgcagagaag tccttaaagg acatgatgga   49620
gctgaaaacc aaggcacgag aactacatga tgaatgcaca agcctcagta gccgattcga   49680
tcaactggaa gaaaaggtat cagtgatgga agatcaaatg aatgaaatga gcgagaaga   49740 gaagtttaga gaaaaaagag taaaaagaaa caaacaaagc ctccaagaaa tatgggacta   49800
tatgaaaaga ccaaatctac gtctgattgg tgtatctgaa agtgacgggg agaatggaac   49860
caagttggaa aacactctgt gggatattat ccaggggtac ttccccaatc tagcaaggca   49920
ggccaacatt taaattcagg aaatacagag aacgccacaa agatactcct tgagaagagc   49980
aactccaaga cacataattg tcagattcac cgaagttgaa atgaaggaaa aaatgttaag   50040
ggcagccaca gagaaaggtc aggttaccca caaaggggaaa cccatcagac taacatctga   50100
tctctctgca gaaactctac aagccagaag agagttgggg ccaatattca acattcttaa   50160
agaaaagaat tttcaaccca gaatttcata ggctcaaaat aaagggatgg aggaagatct   50220
cccaagcaaa tggaaaacaa aaaaagggag gggttgcaat cctagtctct gataaaacag   50280
actttaaacc aacaaagaac aaaagagaca agaaggcca ttacataatg gtaaagggat   50340
caattcaaca agaagagcta gctatcctaa atatatatgc acccaataca ggggtacccc   50400
gattgataaa gcaagtcatt agagacctag aaggagactt agactcccac acaataatag   50460
tgggagacgt taacacccca ctgtcaacat tagacagatc aacaagacag aaagttaaca   50520
aggatatcca ggaattgaac tcagctctgc accaagcaga cctaatagac atctacagaa   50580
ctctccaccc caaatcaaca gaatatccat tcttttcagc accaccac acttattcca   50640 aaattgacca catagttgga agtaaagcac tcctcagcaa atgtaaaaga acagaaatta   50700
taacaaactg tctctcagac cacagtgcaa tcaaactaga actcaggatt aagaatctca   50760
ctcaaaacct ctcaactaca tggaaactga caaccttct cctgaatgac tcctgggtac   50820
ataacgaaat gaaggcagaa ataaagatgt tctttgaaac caatgagaac aaagacacaa   50880
cataccagaa tctctgggac acattcaaag cagtgtgtag agggaaattt atagcactaa   50940
atgccaacaa gagaaagcag gaaagatcta aaattgacat cctaacatca caattaaaag   51000
aactagagaa gtaagagcaa acacatttta agctagcag aaggcaagaa ataactaaga   51060
tcagagcaga actgaaggaa atagagacac aaaaaaccc ttcaaaaaat caatgaatcc   51120
aggagctggt attttgaaaa catcaacaaa attgatggac tgctagcaag actaataaag   51180
aagaaaagag agaagaatca aatagacgca ataaaaatg ataaagggga tatcaccacc   51240
gatcccacag aaatacaaac taccatcaga gaatactata aacacctcta cgcaaataaa   51300
```

-continued

```
ctagaaaatc tagaagaaat ggataaattc ctggacacat acaccctccc aagactaaac    51360
caggaagaag tagaatctct gaatagacca ataacaggct ctgaaattga ggcaataatc    51420
aatagtttac caaccaaaaa aagtctagga ccagatggat tcacagccga attctaccag    51480
aggtacaagg aagagctggt accattcctt ctgaaactat tccaatcaat aaaaaaaaga    51540
gggaatcctt cctaactcat tttatgaggc cagcatcatc ctgataccaa agcctggcag    51600
agacacaacc aaaaagaga attttagacc aatatccctg atgaacattg atgcaaaaat    51660
tctcaataaa atactggcaa accaaatcca gcagcacatc caaaagctta tccaccatga    51720
tcaagtgggc ttcatccctg ggatgcaagg ctggttcaac atacgcaaat caataaacgt    51780
aatcctgcat ataaacagaa ccaaaaacaa aaaccacatg attatctcaa cagatgcaga    51840
aaaggccttt gacaaaattc aacaacgctt catgctaaaa actctcaata aattaggtat    51900
tgatgggacc tatctcaaaa taataagagc tatctatgac aaacccacag gcaatatcat    51960
actgaatggg caaaaactgg aagcattccc tttgaaaact ggcacaagac agggacgccc    52020
tctctcacca ctcctattca acatagtgtt ggaatttctg ccagggcaa tcaggcagga    52080
gaaggaaata aagggtattc aattaggaaa caaggaagtc aaattgtccc cgtttgcaga    52140
tgattgtata tttagaaaac cccatcgtct cagcccaaaa tctccttaag ctgatagaca    52200
acttcagcaa agtctcagga tacaaaatta atgtacaaaa atcacaagca ttcttataca    52260
ccaataacag aaaaacatag agccaaatca tgagtgaact cgcattcaca attgcttcaa    52320
agagaataaa ataccctagga atccaactta caagggatgt gaaggacctc ttcaaggaga    52380
actacaaacc actgctcaat gaaataaaag aggatacaaa caaatggaag aacattccat    52440
gctcatgggt aggaagaatc aatattgtga aaatggccat actgcccaag gtaatttata    52500
ggttcaatgc catccccatc aagctaccaa tgattttctt cacacaattg ggaaaaaact    52560
actttaaagt tcatatggaa ccaaaaaaga gcccacattg ctaagtcaat cctaagccaa    52620
aagaacaaag ctggaggcat cactctacct gacttcaaac tatactacaa ggctacggta    52680
gccaaaacag catggtactg gtaccaaaac agagatacag accatggaa cagaacagag    52740
ccctcagaaa taatgccgca tatctacaac catctgaagt ttgacaaacc tgacaaaaac    52800
aagcaatggg gaaaggattc cctatttaat aaacggtgct gggaaaactc gctagccata    52860
tgtagaaagc tgaaactgga tcccttcctt acaccttata caaaaattaa ttcaaggtgg    52920
attaagacg taaatgttag acctaaaacc ataaaaaccc tagaagaata cctaggcaat    52980
accattcagg acataggcat gggcgaggac ttcatgtcta aaacaccaaa agcaatggca    53040
acaaaagcca aaattgacaa gtgaaatcta attaagctaa agagcttctg cacagcaaaa    53100
gaaactacca tcagagtcaa caggcaacct acagaatggg agaaaatttt tgcaatctac    53160
tcatctgaca aagggctaat atccagaatc tacagtgaac tccctcaaat ttacaataaa    53220
aaaaaaacag ctgcatcaac aagtgggtga aggatataaa cagacacttc tcaaaagaag    53280
acatttatga agccaaagga cagatgaaaa aatgctcatc atcagtggcc atcagagaaa    53340
tgcaaatcaa aaccacaatg agataccatc tcacaccagt tagaatgacg atcattaaaa    53400
agtcaggaaa caacaggtgc tggagaggat gtggagaaat aggaacactt ttacactgtt    53460
ggtgggactg taaactagtt caaccattgt ggaagtcagt gtggcgattc ctcagggatc    53520
tagaactaga aatagcattt gacccagcca tcccattact gggtatgtac ccaaagaatt    53580
ataaatcatg ctgatataaa gacacatgca acgtaagtt tattgcggca ctattcacaa    53640
tagcaaagac ttggaaccaa cccaaatgtc caacaatgat agactggatt aaggaaatgt    53700
```

```
ggcacatata caccatggaa tattatgcag ccataaaaaa tgatgaattc atgtctttgg    53760
aggacatgga tgaagctgga aaccatcatt ctcagcaaac tatcgcaaga acaaaaaacc    53820
aaacaccgca tgttctcact cataggtggg aattgaacaa tgagaacaca tggactcagg    53880
aaggggaaca tcacacacca gggcctgttg tggggtaggg ggaggggga gggatagcat     53940 ttggagatat acctaatgtt aaatgacgag ttactgggtg cagcacacca acatggcaca    54000
tgtatacata tgtaacaaac ttgcacgttg tgcacatgta ccctaaaatt taaagtataa    54060
taaaaaatat atataataca tacatgacat ttgcatatat taaattattt aaattttact    54120
ttcatactat tctgtttaca atatatatca gcagtatatt attataatcc ttattttata    54180
gataagaaag ctattggagg ccgggcacgg aggctcacgc ctgtaatccc agcactttgg    54240
gaggctgagg tgggcggatc atgaggtcag gagatcgaga ccatcctggc taacactgtg    54300
aaacccagtc tctactaaaa atacaaaaaa taaaaaaatt agctggacgt gctggcgggc    54360
gcctgtagtc ccagcgactt gggaggctga ggcaggagaa tggcgtgaac ccggcaggca    54420
gagcttgcag taagccgaga ttgcgccact gcactccaga ctaggtgaca gagtgagact    54480
ccgtctcaaa aaaaaaaaa aaaagaaaa aagaaagcta ttggaaaaca agataaaata    54540
acttgcccag ggttactcaa gttgctcata atagagtcag tattcagatt gaggctgtcc    54600
agttcctgag tcctgtcttt taagcactaa gctatactaa tgataatacc tgtctttcag    54660
agtgctatga gtgttaaatg aggcaattca tgtaagtggc tgaatttatg ctagtataaa    54720
cttgttgttt agtaaacgtg tattattatt aataatgcga attttattta tttttgaaatg    54780 aaatgacttt ggaatatttt tgacctgaaa ggtattttag tatatataat caaatactgc    54840
attgaagttt gttccagtga aattccatga gcatttgctg tgctttacaa catgatattg    54900
agaatatcaa agcttatttg gaaaaacaac ttgaattctt gcactggttc tgcattgtct    54960
tttttgtgca atcctggtaa ttaaatttct tgaaatatct gtgaatctgt agcaaacgga    55020
taggaaaaat atctgttttt atcattttga cctaagttgt tgagtggttt ataaaagaca    55080
ggctgggcct ggtggctcac gcctgtaatc ccagcacttt gagaggccaa ggcaggtgga    55140
tcacaaggtc aggagttcaa gaccagcctg gccaacgtgg taaaaccacg tctctactaa    55200
aactacaaaa attagccggg catggtggca cgtgcctgta atcccagcta cttgggaggc    55260
tgaggcacga gaattgcttg aacctgggag gcagaggttt cagtgagccg agatcgcacc    55320
actgcactcc aacctgggtg acagagtgag attctgtctc aaaaaaaaaa aaaaaaaaa    55380 agagagaaaa aagagaagta cctgaagata ttttgaaaag tacaagattg tgctaatatt    55440
acatatagat atttggtgtt ctgtgataaa aatcagaata tgttgttgat atataaatat    55500
tttgagatta ttttgaacat acttgtactg tgattagtac acgttgatgc cagttaattt    55560
taggttttca ggccttcatg gtatttattt gggtgtacct tacttttctt ttagcctgac    55620
aaggtcatga ctgccctatg ccaaatgtta gattcattct gtttacttaa aaattataaa    55680
ggataaccta aaaatggaa tcacagtttc aataagtact ttgtcctatg tttcagtcag    55740
caagacttat tttatgtttt tttaaaatga taaacctcat tatatcaaaa tatatagcat    55800
taagaaaaga aaagcctttg gttatgaagt gtagtagtta ttgtgtagat tgtcaaatgc    55860
taaggaacaa tgataactct gggaaaatat agtaacatat tgcgttgttt tgtgaattgt    55920
agctgacttt ggcctggcaa agcaaaaaca agaaaacagt aaactcacgt ctgtggttgg    55980
aacaatcctg tattcttggt aaggacaatt cttttatggc tctcaaacat catacttaac    56040
```

```
tgatttaggc tttcatttat attattgact tgcaaaggaa agagaatttc aggaaagaaa    56100
gcttatttta taagtttttt caattatcta ggtaatacac attactagaa ttgtggatca    56160
ttatgtatgc ttaaaacaac caccacaaaa ataatctttc ttctaaggta tcatgcccct    56220 catgggatt  acttatatca attgtaaatt gcaatgatcc ttggcatata gtaggtgtgc    56280
aatagttgtt taatgaatct gagaatgaag taatagatat gctacccaac atgatacttg    56340
gaacatttta ttgtaccctc ttgtatgtat gactcttttt ctcttttcta cctataaaca    56400
ttcaagtgca gggcaaggat ttttgtacac taatacctat cctagtatct ggcaaataat    56460
aggcactgaa taaactttat tgtgtgaatg aataaataat gatatgtata cttagacata    56520
tgtttacaaa gtaaattgct tcttagataa atgagtgttt atattttgat aaatcgagac    56580
acttaaattc tttggcatac tttgggggtt cctttgcaag ccattaatta ttatgaagta    56640
agaatcttct tttgctgatc acatgtcatt tgtctgaatc tgctgaaatt agcaaacagt    56700
tatggtaaag agtagaaaag cagatttcag ggaaatattc tgaaatctga ttcaacaggt    56760
caagcaatca agacactttt atttttttt  aaatctagcc tatagttgta caattgagtc    56820
ctggggatag aattaaacac gactcttctt gaggaagagt agaaattgtc taaaaatagc    56880
agcctaattt tacaaagtcc tttcatgcag aagtgttcag aataatgttt taagagggtg    56940
acttttcatt tatcttactg gatatgtttt acatctttat tcttgaaagt ggtttcatga    57000
gaagatgcaa agaaactgtg gcaggctaac atgtaccttg taagctgcaa gcttatatga    57060
tgtctactta tcctcttaac agtaaggctg acctactcgt tactttctga gagaagaata    57120
attttctttt gtttcactgt gtactgtttt tataaaataa acaataaaat ttgatcataa    57180
aagtgtcaag taatcatata tctctgaaca gatttgattg tcaaattgca gaacaattaa    57240
aacacaaact taaatttctg ctggtcatac ttggtgaaag catattttta ttcctgagac    57300
tttgaattaa gtttagaatt gctcatatga tagtatcaac tgtgtgtgtg tgtgtgtgtg    57360
tgtgtgtgtg tgtgtaagag aaagagacag aatccataga atacgtagga agaaatccaa    57420
aacatgccaa ctttttttgcc gtattagcgc aaacacggct tcacattttc atttaatttt    57480
taaattaact gaagggtttg taagctgaac ctactcatat agataagcta ttatttcatg    57540
tatgtgtact atgattgttt taatagcatg tacagtatat cttactacca tttatctttc    57600
tgtcaacttc ttattctttt aaattgcttt aaaaatttct ttctactccc ttctctcatc    57660
tctccgagtt attagaaatg cctcttgtct gataggtttt actatgaatt tgggctcaca    57720
aaccgtcttt cttgctagtt tttgatgtcc ttaactgagt atggagttaa agaactcag    57780 tcctacatca tattgtgttt ctttcttaat ttgggattct ccaaaagcag aatctgggac    57840
aagaatttga gtgaaattgt ttatttagga ggaggtccca ggaaacacta ttaggagagt    57900
ggtgaagtga gattgggagg gaaagcagcc agtacagtga acattaataa ttaggttcat    57960
agagtattat ctgggatata gtgtaaagca ggggtgtcca atcttttggc ttctctgggc    58020
tacattggaa gaggaaaaat tgtcttggac cacacacaaa atacactgac actaaagata    58080
gctgatgggc ttttaaaaat tgaaaaaaac caaaatctca taatgtttta aaaagatttt    58140
ttgagtttat gttgggctac atgcggtccg tgggccgggg gttggactag cttggtgtac    58200
aggatgtctt tgagttgccc tgcgcaccgg atgagaggtt ggagtatttt ttttccaatc    58260
acaaggggga gccctcagca tctgactgag ggctgctctg gggagcttat gcccaggtgc    58320
ttatggcatg ccagggcgtg ggctgggggca ttccaggcag agagctggag ggccattgct    58380
tgaggtatga tgccatagac ttgtactgga aatgtgagta ggagtctggc tagggtcccg    58440
```

```
acattctaga attttttgt aattctataa ttcttatttt cattaatttt tctaagcttg    58500
tctgagccta taaatgtgga cctgggatgt ggacatttgg atgccataga gatgcctagg    58560
cacccctttc ccttccctgc agggtcccca gagtttgatg tccccatgtc attttgccct    58620
ttccatttgc ttttgcttcc tcagatatta acttactgaa tggaagaaag gtctctttgt    58680
caactcttgt aggaagtgcc tcagagcatt tattctgtat tcagctgcta gataaagggt    58740
ttgtgggcac attgctggac cgattgtact agaacagaag gtcagtaaag gttcttttca    58800
ttcatctgat gtgatttatt attaggcagg tatttgttat ccttctcaag ggaaaaaaat    58860
atccaaatat ggtacttgtt tccattttt atctctatgt cttcctccaa ttccagagaa    58920
gaaaattaga caccatcttc aacttcattt tttgggaaga gtatagagtt tgaggctctg    58980
ggaagcattt tcagctagtt cttcacagaa catatatggg atttatgaag ctagtatgat    59040
gtataaaata caataaaagt tttccaataa aaatggaaaa cttcaactat tcctggaatg    59100
ggaattatta gtctatggct tagtataatc ccattcatat tatgacacta gataattaga    59160
agagaagctc atgaacttta aattggatgg atcaaaataa acctgtaggt aaaactgatt    59220
aagtagagac aaagtgaagc atgcctatta actgcacttc ttaaattttt aaaaaaatta    59280
tttttttgat acataaagtt gatagaattc ttaagaaagc tataatacac tcaaaatttt    59340 gagaattta agtggcttaa aacacttaag tgacttccag ctgctcatgc aaagaccaag    59400
ccctcagtat ggccaaagc agacaacctt gcattctctg gcctctgcca agttcttcag    59460
ctttaccaca aaccaaactt taacaattcc tagctgtttc atctgggctc cctctgacca    59520
cagggccttt gcacatgcag ctccctttgc ctggaatact ctttttctatt tgtcatctgg    59580 ttaattctta cctgccttca gctgaacccc cttagacaag gtctatttcc tctgatctac    59640
acactctatg tacttttcct tcacacaatt gaacttttg ttgattttgt gataagcaat    59700
tatgattttg ttcatcacaa tccccagcag tcctaagtct ggtactttaa aactcacaag    59760
taatatttgc tacatgaatg atcaagtact tgcatgatta taaacattag tggaaataac    59820
atattagaaa gaaattatt tcttttttgtt gtaacaaatt tttaattccc tgtccttttcc    59880 cttcttgctg ttccttcaga tctccaaaat actcctcctt ggaatactct tccttcagag    59940
atagctgcag agtttacttc tttacttcat tctgctcttt gcttaaatgc cacttatgta    60000
gagaggattt ccctgatcac ttgccccaaa tagcaacctc ccttcagact gctttatttt    60060
ttcatagtct tgcctctacc tgaccttatg ttgtacttga attggcttat agtgtgtctc    60120
tccactacac acaagctcca taagcatagg acttgcgtct cctttgttca ccactgtttc    60180
cccaggacct agaggagttg actagcagaa tcttaagaaa tactttgaat aattgaagtg    60240
aaaacaagtc atttttaat attaatatga taaaaattag tgtatatttt tattgagttc    60300
tagtatatct ttgaactttt ctgatttta ccctaataaa gcctgaagaa atgcttttc    60360 atttgagata gtaagtacct tgatggtagg gtctatttta ttttgttttc tctttgctta    60420
ttttatcttt atatattaca tagttactac aacagtgagt aaatgagatc aagtaggatg    60480
ttaaacattt taacaaaata aaatgtgtaa agattatata ttacagaaat atgtattctt    60540
cagtgaccaa taaagtggcc ctgagggaaa tttcaaaaaa gagatgtgtt agatcgttct    60600
tggattgcta taaagaaata cctgagactg gataatttat aaagaaaaga ggtttaactg    60660
gttcatggtt ctgcaggctg cacaggaagc atgacgctgg tatcttcttg gcttctgggg    60720
aggccccagg aaacttacat tcatggtgga aggtgaaggg ggagcaggca tatcacatgg    60780
```

-continued

```
ccagagcagg agcaggagag ggaaagtgag gaagtgccac acactttaaa aacaaccaga    60840
actcatgaga acacactcac tgtcagaaca acagcactaa agggatggta ctaacccatt    60900
catgagaaat ccaccccat gatccagtca ttttccacta ggccccacct tcaacactgg     60960
gaataacaat tcaatatgag atttgggcag ggattttcaa aaataagcat aattggaaaa    61020
agaccatggt attgacagag acagggcatt atcaagagca caaactctag aatcagatgg    61080
cctgggttta aattctagat cggctattga gagttttaaa tgattgaatt tttctgtgcc    61140
tcagtttcct catctgcaac ctggggatga taataatagt gcccatgtcc taggattatt    61200
gtgagattaa atgaggtgat acatgtcaca tgctgggaac agtgcctggc tggcatatgg    61260
taagcactca ctagataata gtgattgtta tttcctgtta gtctaaagtt tgaaaggata    61320
gtactcattt aaatgtatat attatattct gcatatatag gaggttatag aacactaggc    61380
ggatttaacc taaagaagac tacctcaagg tatttaataa tcaaactcac aaatatcagg    61440
gataaagaaa ggatctcaaa agcagcaaga gaaaagaaac aaataacatg caatggacct    61500
caatacatct ggcagcagac ttttcagtgg aagccttacg ggccagaaga gagtggcatg    61560
acatattgaa agtgctgaag gaaaaaaaaa atttaccca gaatagtata tctggtgaaa     61620
atatccttca acatgaagg agaaataaag actttcccag acaaacaaaa gctaagggat     61680
ttcatcaaca tctgacctgt cctatgagaa atgctaaagg gggttcttca atcagaaatg    61740
aaagggcatt aatgaggaat aagaaaccat ctgaacatac aaaactcact ggtaatagta    61800
aatacacagg ctgggcacag tggctgacac ctgtaatccc agcactttgg gagaccaagg    61860
caggtggatc acgaggtcag gagatcgaga ccatcctgac taacacagtg aaaccccgtc    61920
tctactaaaa atacaaaaaa ttagccgggc atggtggtgg gcgcctgtag tcccagctac    61980
ttgggaggct gaggcaggag aatggcgtga acctgggagg cggtgcttgc agtgagtgga    62040
gatcgtgcta ctgcactcca gcctgggtga cagagagaga ctccatctca aaaaaaaaaa    62100
aatagtaaat acacagaaaa acaaagaata ttataatact gtaattgtgg tatataaact    62160
actgttagct taagtaagac taaaatgtga atcaataaaa ataactacaa caacttttca    62220
agacatagca caataacata taaagagaaa caataagtta aaaagtgggg ggacaaaatt    62280
aaagtataca gtttttatgt tttcttttg cttgtttgtt tatgcaatca gtatcatcag     62340
tttaaaataa tgggttacaa catagtattt gcaagtttca tggtaacctc aaatcaaaaa    62400
acatacaaca gatacacaaa aagtaaaaag taataaatta aatcatacca taaaagaaaa    62460
tcaccttcac taacaggaag acaggaaaga agaatgaaag agaataccc aaaacaacca     62520 gaaaacataa atgacaaaat ggcaggaata agttcttact tatcaataat aacattgaat    62580
gtaaatggat gaaactctcc aatcaaaaga cagagtggcc cagtggacaa aaaactaaga    62640
cgcaatgatc tgttgcctat taaaaatgca tttcacctct aaagacacat agactgaaaa    62700
taaagagaag gaaaaagata ttccatgcca atggaagcca aaaagagca gaagtagcta     62760 tacttatatc agaaaaaata tatttcaaga caaaaactgt aagaagagac aaagaaagtc    62820
attatataat gataaaggag tcacttcagc aagaagatat aacaattgta aatatatatg    62880
cacccaatac tggagcaccc agatatataa aagaaatatt attagagtga agaaagaga    62940 gatgacaaaa aatataattg tattagtctg ttttcaaact gctataaaga actacctgag   63000
actgggtaac ttataaagga aagaggttta attgatttgc agttcagcgt ggctggggag    63060
acctcaggaa acttacaaac atggtggaag acaggggaag caaggctcct tctttacaag    63120
gcagcaggaa ggagaatgaa tgcaggagga actaccaaac acaaaaccga tcacatgaga    63180
```

```
attcactatc atgagaacag cttgggggat atcgccccca tgattcaatt acctccacct   63240
ggtctctccc ttgacatgtg gggattatag ggattacaat tcaagatgag attttgggtg   63300
gggtgtagcc aaaccattat caacaataat agctggagac ttcaataccc catagcattg   63360
gacagacctc ccagatagaa aatcagtaaa ggatcattgg acttaatctg cactgtagac   63420
caaatggacc taatggatag ttacagaata tctcatccaa tggctacaga atatacattc   63480
ttctcagcac atgaattatt ctcaaggata aaccatatgt taggtcacaa aacaagtctt   63540
aaaacattta aaaaaagtt gaaataatat caaacatctt ctctgactgt aatagaataa   63600
aactagaaat cagtgacaag aggaatattg gatactctac aaacacatgg aaattaaaca   63660
gtatgctcct gaatgaccag tgggtcaatg aataaataag taaattgaaa aaattttga   63720 aacaaataat aatggaaaca caacatacca aaacctatgg gatacagtga aagtagtacc   63780
aagagagaag tttgtagcta taaatgccta aaccaaaaag aagaaaaact tcaaataaat   63840
aacctaatga tgcatctgag agaactagag aagccaaagc aaatgaaacc caaaattagt   63900
agaagaaaag taataataaa gagcagatat aaaagcaatg gaaatgaaga aacaatacaa   63960
aaagatcaac aaaatggaaa gttgtttttt ggaaaagtta aacaaaatta acaaaccttt   64020
agacagacta aaaaaaaggg agaagaccca aataaataca atcagggatg aaaaaggaga   64080
cattacaatt gatactgcag aaattcaaag aataattagt ggctaccacg aacaactatg   64140
tgccaataaa ctggaaaatt tagaagtaag taaattacta gacacataca acctaccaag   64200
atggaaccat gaagaaactc aaaacccaaa cagaccaata acaagtagtg agatggaagc   64260
cataatgaaa agtctcccag taaagaaaac ctgagaccca atggcttcac tgttgaatgc   64320
taccagatgt ttaaagaata actaatacca atcctacaca aactattgca aaaaatggag   64380
gaagagggta tacttccaaa cttacaccgt gaggccagta ttaccctgat acaaaaacca   64440
gacaaagacg cctccagaaa aaaaaaaaaa aagaaaaga aagaaaaga aaattaaaag   64500 aaaactgcag gccaatattg cttgagtgca ggagtttaag accagcctgg caacatggc   64560 gaaaccctgt ctctactaac aatgcaaaat attagccagg catggtggtg tgcatgtgta   64620
gtcccagcta cttggaaggc tgaggcggga ggaatgattt agtccaggag gtggaggttg   64680
cagtgagctg agatcgcacc actgcactgc agtttgggtg acagagactc tgtctcaaaa   64740
aaataaaata aaataaaata aaataaacaa aattctagca aatcaaatcc aacaatacat   64800
taaaatgatt attcctcatg atcaagtggg atttatccca gagatgcaag gatatgtaaa   64860
tcaatcaatg tgatacattg tatcaacaga ctggaggaca acaactatat gatcatttca   64920
attgatgctg acaaaacatt tgataaaaat caacatccct tcatgatgaa aagccctaaa   64980
aaacctgggt acaaaagaa catacctcaa cataaaaaaa gccatttaca acagacccac   65040
agctaatatc atactgaatg gggaaaaatt gaaaacctct tcttgaagac ctagaacatg   65100
acagggatgt taactttcat cattgttatt caaaatagta ctggaagccc tagccagagc   65160
agccagataa gagaaataaa taaaaggcat ccaaattggg aaggaagaag tcaagttatc   65220
cttgtttgca gatgatatga tcttatattt ggaaaaacct gatcttatat ttggaaaaac   65280
ctgacgactc caccaaaaaa ctattagaac tgatcaacaa atttagtaaa gctgcaggat   65340
acaaaatcaa catacaaaaa gcagtagcat ttctatacac caacagcgca caatgtgaaa   65400 agaaatcaa gaaagtaata tcatttatga gagctacaaa taaagtaaaa tacctaggaa   65460
ttaacttaac cgaagaagtg aaatatggga ctaaaaattg tgtgggaata aaatttgtg   65520
```

```
gtgctaaaaa ttaaataatt gaactcatgg agaaagaaca tagaaggatg gtcaccgggg    65580
ctaggaaggg tagtgggcag gggttggggg gattggggtg attaatgggt ataaaaaata    65640
gaattagtga ataagagcta atatttgata gcacaacagg gtgactatag ttaaaaaaat    65700
ttaattatac attttacaat aactgaaaga gtataattag attgttttaa cacaatgctt    65760
gaagtgatgg atatcctatt tactgtgatg tgattattat tcattgcatg cctgtgtcaa    65820
aatatctcat aaacccccata aacatataca cctactatat atttacaagt aaagttaaaa    65880
ataaaaaatt taaaaaatct aaatttactt gaggatgaaa ggttggagga gagagaggat    65940
cagaaaaaat acctattgag tattatgctt actggtgggt gacaaaataa tctgcaacaa    66000 accccccatga catgcagttt acctatataa caaacctgca gatgtacccc tgaacctaaa    66060
agtcataata aaaagggtg aatgtaggta cataatgcca ttgtacatta tgcatttttc    66120
agtctgattt gttctgaact cctcagaatc acaaaacgca agaaagaaag ctctctgatg    66180
attgattctg tcagtggaag tccttgcttc ttttatcaat tggaaattca gaatcattta    66240
tcttcagtct ctatattctt tttctcttgc ccttttatag tctttacttt tacaagtaaa    66300
agtgaatcat aagcactaga tttccttctc catgtttatt tatctacttt gtcattttga    66360
acatttaata cctagtggtt atgtatagta tttctcattt cctattggaa caagattcaa    66420
gaggaaatac atagtgataa gatgtgttac tttaacatgt ttttctgagg gtgggagggg    66480
tgtggtcaaa agaagtttcc tcatgtattt accacaaatt aatttattga ataattaaga    66540
aattagaatc atttgatgat ggagagatgt atatttcaga tatgtattgg atgcataaca    66600
atccatccca aaatttagtt gcttaaaacc acgatggttt atataggttt gcttgatcat    66660
tcctctgttg gttccctga actcatgtgg atgcatttgg ctgaattatt ggcttggctg    66720
ggcagtccaa gatggcttca ttaataaggc agttcgtgtt gatgcttggc tagagtccct    66780
tggatctttt tcaggtggcc tttcgtttac atgacagtag tggagtaaca ttccaagaaa    66840
gtaaaagctg agctgcaagg cccgattggg gctagccttg gatgtcacta aacatcccct    66900
ctgccatatt ctgttggtca aagcacataa gagccagccc aaatgtgtga aatacattta    66960
tctctagatg gaaggaggtg catggtactt gtggccatat tcaacaaatc ataatgcagc    67020
accgtatttc tttaaaaaag aagaagaatc ccccaaatgg cttcaggaat caagacatgt    67080
gaaacaaaga aatagtctat tttaaacact aacggttggc acgttagccc cacatctcct    67140
tagaatgaag tatagcagcc tggatccaac taggagatag aaatgatgca gtgggctaaa    67200
taggggaagt ttaaatatgaa gaacaattat gatgaaagag taactataag atgtaagaaa    67260
actacatggt actttagggt tgagtgacag taccaaggaa ggataaactt ggaagggggtt    67320 cagatttcat tggaaaaagt gtggtagccc aatagacagc agaaaagttg gctagatggt    67380
ccaggctgaa gctgttctgg agctgctagg caagctggga gcaaccctct gaagtgcagg    67440
tgagggagca aggcatcagc atctgcggtg tgggcacata gtgggagtcc agctgccaca    67500
ggtgcccttc agagtttaaa ggccacaggg aagggagaag aggggggcgag tccaggaact    67560 gcacaagcag gaggccttca gagggtgcag gctacacagg ggctctggtt tctgttttga    67620
gaaggttgaa gaaaatgat caccaggctg aggctgcagg gttgcagagg gagaatgggc    67680
tatggttggg ataggctcta ctggttagtc ctataccctat actgcctact cgtggcccat    67740
gtcagaaatt gcaggaaacc tcttcctcct gcagtgtccc tccaatccat gtatagagaa    67800
agcttaatat tgtgctcact ttaaaggaga aatatttaaa gggattccat tgtttattga    67860
ataatacatt aagagacaac aggcaataag ttaataacag acacaataag aaacttcagg    67920
```

-continued

```
gcttggccca gcataacagt ggactgggca actagtagaa tagggccaca tccctgctag   67980
gggatgttca atgcctttaa ttcttctgta aataggtgt tttatttctc tgtgcctcca    68040
aacttttggt gtatctccag agtgtctttt tgaattgtga aaattaaatc tttcagttca   68100
attctgaata ggctcagcgt atttggtgaa aagcaggagc tatagtttgg ctgggttgag   68160
tttgtgctgt gacactggaa gacctagaat tttcctcttg gcattgtaaa gccacagggt   68220
atctctcagc ctgacagtta cttgatggaa atgcggtttt tttggggaa tatctgtgga    68280 atgaaactgg gaaagggaa ggagagatgt gtattcatca ttttatctgt ccctcaagtg    68340
gatattccaa tatttacttc acaggagcag atgacttagt tctttaccac tagaagaatt   68400
caatttaatt tggggacacg gacacacaga cacacacaca cacacacaca cacacaccca   68460
tggtgtcagt caagtgtaga agattaaagg gttagaaaac cctatgatgc ttgtaatgag   68520
tctccaggat aatatagaaa gtagggtaga acagggacct cccagcacag agctgcagaa   68580
ctcgagggaa aggccattgg ggctggggtg gatgctctgt tttctatata ataaatgtgc   68640
catattctat gcactaacta agaatttat aaacagatat attttcctcg aattcagaca    68700
ttatgacagt atatgtatag aagggagtct ggttgacgga taaaatggtc acaagaaatc   68760
aaaaggaaag aagagaaag atagcaaggt gatgagggta aacatataat ggaaagagtg    68820
gagaagtcag aggattcaaa caatgggaa atatgaaagt gaaattacca tattagggc     68880 aaagaatta ataaacatt ttcattattt tgcagggcta catttaattt gtcttattct     68940
tgtgaatgag ttactccaag tgaccttacc agtcatatat ccctttacat caatttattt   69000
cttaactcat ttagctatta gtactttatt aattttttata tttaatttta attattaact  69060
tttttatctt ggcatttcag actgttcata acaaccctag aagtaatgac acgatgctaa   69120
cacaagaaaa ccttcctttg aagtgccaga aattgttttc tctaaaatag tagaatatta   69180
gttagaaggc caatattttg aaattcaagc gtctctttgg agaaggattt taaaaaaatc   69240
ctttaaaaca ttttaaaaca agacaataaa ctgttaaact gtgacaattt tatggcctat   69300
cataaaatgt caaaataaag attttaaaat gttaacttta tgtaaccttg atacattggc   69360
aatactcaac cattttaaaa ccttcatttt cactgaaagg catacttcta ggatcctcac   69420
atttggcagt taagttttga agattttaca tatattggtc aatttcattt tagtactcta   69480
gggttccagg aaggccacat ctattcctca gtaaagcatt tgcctctcag tctgttcagc   69540
tcctcctcac cttaattctt ctgagttcat ctgtaatttt cataacaaag tgtactttct   69600
tcataaattt agtaaataat gctcagaact tcagcagtga gagaagtaag atgccagtgg   69660
acatgggtgc atctgtgcac agtgggcaac tgtgatgtgt ggctgtccct tcccctagga   69720
gccaacagga catagtgcag actctagacc tggattgcct gggcccaatc ctggatctac   69780
accttcctgt ttgactttgg gcaagctact taattttct gggcctaaat ttcctcacct    69840
gaaatggggg cagagggcag taatgataat ttctacaaca tagggttgtt atgaggattg   69900
agaagatagt tggatggatg gatggaagga tggatggatg gcaatagatt gatcaatcga   69960
ttgataagta gatagtatta tctgtagcat agcagggatt taataaacat tacctattgt   70020
caggctggaa gcaacagcct cattcttag gaaatatatt cttccctgcc tttacttcaa    70080
gcacatggtt taaatggctt atacattggg aatactcaaa aaagtatcaa tgccaaaagt   70140
cccattgctt tagagatcct gcctccttgg ccttacatgg tggaacaatt ctagtatgca   70200
tgtccctata gcccaaaatg ttaaaagtag aagtgttttc ttgattcaag tttaaccatt   70260
```

```
cagaattctt tcttgagaac gtgttgagct gaggctcagt taaaagttga agctgggagg   70320
caaaaggccc agcagtgttt tggtggccat ggttgtagcc agggaggaag tcagtctgac   70380
agcatgaggt caatacttag aataagagat ggcaatgtcc aggctcaaga ttccattttc   70440
ttaagtccca gctgcaactt tgctcttcct gcacttacag gagcctatca ataaagtccc   70500
ctatttgcct aaccttgctg ggtttctttc tcttgtctct tagtttgggt tgccctgaag   70560
gcagaccctg agaaagaat tgaagtgcaa gtggtttatt ctggaggtga tcctaggaaa   70620
catgaataaa agagtagggg aagtgagaca gggtagggaa gtaagcagat aaaggatttc   70680
ttgggcaagt taccactgtg ggcaattaga actcaaatct gttgaggtac ttgggagcca   70740
tttatttgaa tacccaaaag gagaaagagc agtatttata cacttgctct tgaagtcact   70800
gggtaaggtc tgtttctggg gtacagtaat tcatcagcac ttcaggctca tcatgttgca   70860
gacacagaaa gtcatgagat taaagaaaat cctcagacaa acctgcaaat ggttggaatt   70920
cagtccagtg tgctcgcaag aagtaagggt caggggatgt taataggaca cctacaacat   70980
ctgcttcaag ttaacaatga aaacaacttt gactgtcaca acagagatat ggttgtaggg   71040
tggcctcaaa gtctgtacat gccagattgt ctgaaaaaat cttattttc cccccatgct   71100
ctctgaacaa attcttctat gctgaatatt tggaagtctt taaagatgtc cctgaagtct   71160
gtttttagat tttcctcaca gttacattga gttgagaatt ttttcccca gtcatgccca   71220
gagagactgt ctgcctccct gtagttctgg ggtgctactc cctgtaccaa cttttgcaaac   71280
aaaatagcaa taccaggctg atgaggtaat gatcatttta aaatagatgt gataggccag   71340
gcatggtggc tcatgcctgt aattccagca ctttaggagg ccaaggcagg cagatcacct   71400
gaggtcagga gttcgagacc agcctggcca acatggtgta accctgtctc tactaaaaaa   71460
atacaaaaat tagccaggcg tggtggtgca cacctttaat ctcatctact cgggaggctg   71520
aggcaggaga attgcttgag cctgggagac agaggttgca gtgagccaag attatgccat   71580
tgcactccag tctggccaac acagtgagac tctgtctcaa aaaaaaaaa aaaagatgag   71640
atagtaataa aagtaaatca gaatgaggta agaatattct cctgtgaggg tctctgctac   71700
cttgaataaa gactatcaaa tgtttacatg gaagttgctc aactgtctct ttttatttct   71760
tagtctgtta aggagcagga atacacattt ttatgtgact ttatatttag agaaaggcat   71820
ttgtataatt atgtattatt gggagattgt attatctttt ttgtgaaatc accataatta   71880
tttagttatg tacttgaatt ttaaaagcta gtgctatttg gcttaatac aaatacaaaa   71940
tatgtgatgt caacctataa tgccagcttt tttttttcta caaaaaatca ttagagacaa   72000
gcaaatggca gttgatgtat aatgagaaat ttcaaggctg ttggatctga atttaatttg   72060
tatttgtgac tcagagtagg caatgctgga aaatcatttg atgactggag tgtaatcact   72120
gggtgaacat aatccatttg tttaattgcc cagactcctc actgtattta cagttaattg   72180
gttcccatta aggtcctctt aatagagacc ataaaacagt aggattagag aaacctgaaa   72240
aggaacattt agtttgagtc ctttcttgaa gccagttgt aacatgtgct catctatttc   72300
attttttacc atcttcataa cagactgagg gagaaaaaga ctctcaggca ggtgctttat   72360
aaattatttt tactgttttg gcctatgaac atttctatag ccagaaaata aaaaaaaatc   72420
tagtgttcct acatataatt gaagtttttc tcttatgact tgaaattctt tttgggttta   72480
gtggccaggc aaagcaaatg gtcactaccc aacatttaat gactcttcat gtactgaaag   72540
gttattttaa gccttttttc cctaaatttc gttgctcatt catagttttt gtaacctttt   72600
gattcagact tctagatatt acatacaaag atcggataga aaacctttca atatcttagg   72660
```

-continued

```
aaagtcatgt gaacccatct gatgaggagg gatacaagtc tcttataaaa tgtgatttta   72720
gtgctgcatt tttaacttac agattttctt tattctccaa agacgggttt atttacttca   72780
ggactgatga agcaaattaa aattataaat tctcctcccc cttccacaga gattttcgag   72840
tctgccttct tctcccttc tcctacccac aattaccctc actacaaatg ctggagcttc    72900
ccttccattg ggctccagcc aatttgggaa aattttgaaa gtaaattagt ttcagtgaca   72960
atataatcaa aatacaaaat tactacattt gaatatttct catcactgat ttttaaaatc   73020
tattgataat attcaggaag ttttacattc tttctgggca cttaacattc ttagttattt   73080
taatttttt tgtgaacttg acattttatt tcttaattca ttttagccaa ttgtgagaat    73140
tatgcattaa aatgggagat tggccccttt ccactgcatc acagatgaaa aatggaaagt   73200
acctttgatt ggtcccctcc cacaagcaat cactggttgt gggccaagtc ttcatgtgta   73260
actttgttaa cttcactta gcctctgatt ggttgactct tgcaaccaat cagactagtt    73320
gtgggccaaa tcttcattta tagagggtat aaccaagtaa ccaatgggaa acctctagag   73380
ggtatttaaa ccccagaaaa ttctgtaacc agtgcccttg agctgcttgc ttcagcctgc   73440
ccctgctctg tggagtgtac tttcatttcc ataaatctgt gctttcgttg cttcacatac   73500
acacacacac acacacacac acacacacac acacacacac gaaaggggag gttggttaga   73560
taaataacac taagctggta atacagtaat gtatttgttg acccagaagc atatttacaa   73620
tattaaataa aaaaataggt taccaatggc atatatttta tgatcctatc acagatagaa   73680
atatctgaaa atattgtcaa gtcaagcaga catcacagac aaaagtgaat tagaaattaa   73740
aggaatatga atacatataa caaaataaaa acaacaaaac ttcaaatctg aaaaaagttt   73800
ataatttgtt gattaaagtt tcttatattg ttttcttatt agaaaatcag tatattctct   73860
gcagaaaatg aagaaaaaat cccattaaga atattcgtaa tcctactaac ccagaaatgg   73920
aaaaaactca cagaaaatag cttattgtcc agattccaaa ttcctttcta tgtgaacaca   73980
caaacacaca tacacaaata ctgatattaa tgagtgcttt tctatagctt cagttttaat   74040
atctggatcg aatcccaata cttggttaaa atcatgattc attcagccaa tctccttttt   74100
ttagatatgc aaattatttc catcttttcc ctaactcata ttacacaggg cacgtattct   74160
tggctaaaac taaattagaa ataagaaaac aaaagttatc tgtggcaaag ttagcctcta   74220
gcacaccatc cccttcttaa tccccaaata aaaaaccctg actacacttg ttggtgaata   74280
ttttgttatt ggctatagta tttacaacct ttctgctgta tgcagctcac taatcttctc   74340
tactcttgag ggtgcggaaa gcatggtgta ttattggtga cacagcccctt tttatacaat  74400
ttcacatatc agagctggtt ttgcaaggat gacttgatga tttgatgccc accatttct   74460
ttactgttaa aaaatttcaa tagttttttgg ggtacaggtg gttttgggat gcatggatag  74520
gttcttaagt ggtgatttct gagactttag tgtacccatc acctgagcaa tgtacactct   74580
atccaatata tagtctcacc ccactcccac ccttcctcac cccactccca cccttcctcc   74640
tgagttccca aaatccatta tatcattctt atgcctttgc atactcacag tttagctccc   74700
actaataatt gagaacatat gatgttgtgg gaagtcaggg accccgaacg gagggaccgg   74760
ctggagccac ggcagaggaa cataaattgt gaagatttca tggacattta tcagttccca   74820
aaattaatac ttttataatt tcttacacct gtctttactg caatctctga acataaattg   74880
tgaagatttc atggacattt atcagttccc aaataaatact cttataatttt cttatgcctg  74940
tctttaatct cttaatcctg ttatcttcgt aagctgagaa tgtacgtcac ctcaggacca   75000
```

-continued

```
ctattgtaca aactgattgt aaaacatgca tgtttgaaca atatgaaatc agtgcacctt    75060
ggaaatgaat acaataacag caattttagg gaacaaggga agacaaccaa aggtctgact    75120
gcctgcgggg tcaggcagaa tagagccata ttttcttct tgcagagagc ctataaacag    75180
acatgcaagt aggagagata tcgctgaatt cttttcccgg caaggaatat taataattaa    75240
tacccagggg aaggaatgca ttcctggggg gaggtctata acggccact ttgggagtgt    75300 ctgtcttatg cggttgagat aaggacagaa atatgccctg gtctcctgca gtaccctgag    75360
gcttattaga gtggggaaaa gatcccaccc tagtaaattt gagatcagac tggttctgtg    75420
ctcttgaacc ctgttttctg ttgtttaaga tgtttatcaa gacaatatgt gcacagctga    75480
acatagaacc tcatcagtaa ctctaatttt gcccttttgcc ttgtgatctt tgctttgccc    75540
tttgccttgt catctttatt gccctttaag gcatgtgatc tttgtgacct attccctgtt    75600
catacaccct ctccccttttt aaagtcctta ataaaaacct gctggttttg cggctcaggt    75660
gggacatcac ggacttaccg atatgtgatg tcaccccctg gaggcccagc tgtaaaattc    75720
ctctctttgt attctttctc tttatttctc agactggccg acacttaggg aaaatagaac    75780
ctacattgaa atattgggag ctggttcccc cgataaatatg atatttggtt ttccattcct    75840
gagttacttc agttagaata atggcctcca gctccaccca agttgctgca aaagacatta    75900
ttttgttcct ttttatagct gagtagtatt ccatagtgta tatatacatt ttgttcttaa    75960
aaatatttca tttatttatt tacttatttt ttaactttta agttcaggtg tacatgtgca    76020
ggatgtgcag gtttgttaca ttgttagtta tatagattat ttcatcaccc aggtattaaa    76080
cttagcatcc attagttatt tttcctgatc ctctctctcc ttccatcctc caccctccag    76140
tagaccccag tgtgccttgt tccccctcta tgagtccatg tgttctcatc atttagctcc    76200
cacttataag taagaatgtg cagtatttgt ttttctgttt ctgcattagt ttgctaatga    76260
taatggcctc cagctctatc catgttcctg caaaggacat gatcttattc tttttttatgg    76320 ttgcatagta ttccatggtg tatatgtatc acattttctt tatatgtatc acttttttt     76380 acccagtcta tcatttttga gcatttacgt tgattccatg tcttggctat tgtgaatagt    76440
gcagcaatga acatgtgcat gaacaagtga atagtgcatg catgtttctt tataatagaa    76500
caatttctat tcctttgggt atatacccag taatggaatt gctgggtcga atggaatttc    76560
tgtctttagg tctttgagga attgccacac tgtcttccac aatggttgaa ctaatttaca    76620
ctcccatcaa caatgtaaaa gcatttcttt ttctccacaa cctcatcagc atctgttatt    76680
ttttgacttc ttagtgatag ccattgtgat gggcgtgaga tgacatctca ttgggttttt    76740
gatttgcatt tctctaataa tcagtaatgt tgagcttttc atatgcttgt tggctgaatg    76800
tataccttct tctgaaaagt gtttgttcat gtcctttgcc cacttttttaa tggcgttgtt    76860 tgtttgtttt gtaaatttgt ttaagctcct tatagatgct ggatattaga ccttcgtcag    76920
atgcatagtt tgcaaaaatt atctcccatt ctgtaggctg tcttttttgct gtgttgatag    76980 tttcttttgc tgtacagaag ctctttagtt taattagatt tgatttgtca attttttgctt    77040 ttgttgcaat tacttttggc atcttcatca tgaaatcttt gtcagtgcct atgtcctaaa    77100
tggtattgcc taggttttct tctagggttt ttatagtttt gggttttaga tttaagtctt    77160
taatccatct tgagttgatt tttgtgtgtg gtataagaaa gggggttcagt ttcaattttc    77220 tgcttgtggc tagccagtga tcccagcacc atttattaaa tagggaatcc tttccccatt    77280
gcttgttttt gtcaggtttc ttaaacatca gatggttgta ggtgtgcaat cttatttctg    77340
aattatctat tgtgttccat tggtctatgt gtctgttctt gtaccaatac catgctgttt    77400
```

```
tggttactat agccctgtag tatagcttgg agtcaggtaa catgatacct gcagctttgt    77460 tcttttttgct taggatctcc ttggctagtt gggcacttttt ttggttccat atgaatttta    77520
aaatagcttt ttctagttct gtgaaggacg tcaaattata gtttcatggg aatagcattg    77580
aatgtatgaa ttgctttggg cagtatggcc attttcacag tattgattct tcctatccat    77640
gaacatggaa tgttttttcca tttgtttgtg tcctttctga tttctttgag cagtggtttg    77700
tagttctcct tatagagatc cttcacttcc cttgttagct gtattcctag gtatttttatt    77760 cttttttgtgg cagttgtgaa tgggagttca tttgtgattt ggatattggc ctgattgttg    77820
ttggtgtata ggaatgctag tgattttttgc acattgaatt gtatcctgag acttttgctga    77880 agttgatcac cagcttaaga aattttttggg atgagacaat ggggtttttct tgatataggga    77940 tcatgtcatc tgaaaacagg gatagtttga tttcctctct tcctatctga acatccttta    78000
ttactttctc ttgcttgatt gtcctggcca gaatttccaa tattatgttg aataggagtt    78060
gtaagagagc attcttgtgc tggttttcaa ggaaaatgct tccaggtttt gcccatttag    78120
tataatattg gaagtgggtt tgtcatatat ggctcttact attttgaggt gtgtttcttc    78180
aataccagtt tattgagaga ttttagcatg aagggatgtt gaatttttatt gaaagccttt    78240 tctgaatcta ttgagaataa tcatgttgtt tttttttcttt agttctcttt atgtaatgaa    78300
tcacatttat tgatttgcgt atgttgaacc aaccttgcat tccaggaatg aagcctactt    78360
cactgtggtg gttaagcttt ttgatgtggt gctggattca gtttgccagt attttgttga    78420
ggatttttgc attgatgttc atcaaggata ttggcctgaa gttttccttt tttgttgtat    78480
ctctgccagg ttttagtatc aggatgttgc tggcctcata gaatgggtta gggaagagtt    78540
cctcctttaa aattttttgg aatagttcca gtaggaatgg taccagctct tctttgtaca    78600 tcttataacca cattttctttt atccacttgt tggttgatgg gcacttaggt tggtttcata    78660
tctttgcaat tgtgaattgt gctgctacaa acatgcattt tcataaaaca acttcttttc    78720
cttttggtag gtacccagta gtgggattgc tagatcaaat ggtagttcta cttttggttc    78780
tttatgtaat cttcttacag ttttccatag tgattgtact agtttacatt cccatcagca    78840
gtgtaaaaat gttcctttttt caccacatcc acaccaacat ctattgtttt ggatttttta    78900
aaaaaacgtt ttaattatgg ccattcttgc aggagtaagg tggtatctca ttatggtttt    78960
aatttgtgtt tccctgatga ttagtgatgt tgagcatttt tcatatgttt gctggttgtt    79020
tctatgtctt ctttttaagaa ctgtctattc atgtgctttg cccacttttt gatgggatta    79080 tttgttttttt tcttgttgac ttgttttgag ttccttgtag attgtggata ctagtccttt    79140
gttggatgta tagtttgtga atattttctc ccactctgtg ggttgtctgt tgtttactct    79200
gctgattatt tatattgctg tgcagaaggt ttttagttta attaggtccc atttatttat    79260
ttttgttttc gttgcatttg gttttgggggt cttagtcatg aattgttttgc ctaagccaat    79320 gtccagtaga gttttttctga ttcaggtgtt agatttaagt ctttgatcca tcttgatttg    79380
atttttgttt aaggtgagag atggggatcc agtttttattc ttctacatgt ggcttgccag    79440
ttatctcaga accgtttatt gaatagtgta tccttttcccc caatttatgt ttttgtttgt    79500
tttgttgaag atcagttggc tgtaagtctt tggctttatt tcttggttct ctattctgtt    79560
ccattgtctc catgcctatt tttataccag taacatgctg tttgctaact atagccttgt    79620
agtataattt gaagtctggt aatgtgatgc ctccagattt acactttttg cttagccttg    79680
ctttggctat gtgggctctt ttttttgttcc atatgaattt taggattttt tttctaattc    79740
```

-continued

```
tgtgaagaat gatgatgata ttttgatgga aattccattg aatctgtata ttgctttgga   79800
tagtatggtc attttcttaa tattgattct tcctatccat gagcatggga tatgttccca   79860
tttgtgcatg tcatctctga tttctttcag cagtgtttgg tagttttcct tgcagagatc   79920
attcacttcc ttggttaagt atattcctaa gtattttatt tgttttgcag tctttgtaaa   79980
aagagttgca ttcttgattt gattctcagc ttggtcattc ttggtgtgta gcagtgctac   80040
tggtttgtgt acattgatta tgtattctga gactttattg aatccattta ttggatctag   80100
gagcttttg gatgagtttt taggttttct gcgtatatga tcatatcacg atgtgttatc    80160
tttttgatat gctgttggat ttggttagct agtattttat tgagaagttt tccatctata   80220
ttcatcaggg ttattaatct gtagttttct ttttttgtta tgtcctttcc tggttttgt    80280
attagggtga cagtggtttc ctagaatgaa ttagggatga ttccctctct ctctatcttt   80340
gggatagttt cagtagaatc aataccaatt cttcttagaa tgcctagtag aattcagctg   80400
agaatcgtc ttgtcctggc tttttgttgg cagtgttttt attactgatt gagtcttact    80460
gcttgttatt ggtctgttca gagtttctat ttcttatttg atctcggaga gttgtatgtt   80520
tccaagattt tgtccatttc ctctatattt cctgatttgt gcatgtaaag gtgttcatag   80580
tagccctgaa tgatctttt tatttctgtg gtattggttg taatgtctcc agtttcattg    80640
ctaattgagc tatttggat cttctctctt cttttcatgg ttagtctcac taatggccta    80700
tcaattttgt ttatctttc aaagaatcag attttgttt catttatctt ttgtactttt     80760
ttgtttcact ttcatttagt tatactctga tgtgtgttat ttcttttctt ctgctgggtt   80820
tgggtttaat ttgctcctgt ttgtgtagtt ttttgaggtg tgacattaga ttatcaattt   80880
gtgctctttc agacttttg atataggcat ttaatgctat gaactttcct tttagcacca    80940
cttttgctgt attccagagg ttttgataag ttgtgtcact gttatcattc atttcaaata   81000
atttttaaat tttcatattg attaatcatt caagagcaca ttatttaatt ttcaagtatt   81060
tgtttgattt ggagggttcc ttttagagtt gatttccagg tttattccac tgtggtttga   81120
gaagatactt catatgattt tgactttctt aaattaattg agagttgttt tgtggcctat   81180
catatggtcc atcttggaga atatttcatg tactgaagag aagaatgtat attctgcagt   81240
tgttgggaag agtgttctgt aaatacctgt taagtccatt tgttctagga tatagtttaa   81300
gtccaccatt tctttgttga cattctgtct tgatgatctg tctattggga gtattgaagt   81360
cccccactac cattgagttg ctatctatct catttttga gtctggtagt aattgtttta    81420
taaatctggg agctccagtg ttaggtgcgt atgtatttag gattgtaatg tcttctcatt   81480
ggactaatcc tttcatcaat atataatgtc cttcttgcc ttttcttact attgttgctt    81540
taaagtctgt tttgtctcat ataagaattg ctattcctgc ttgcttttca tttcttttg    81600
catggattat cttttttcac ccctgtcctt taagtttatt tgaatcctta tgtgttaggt   81660
gagtctcttg aggacagcag atatggtt ggttgttttc tatccattct gctattccgt     81720
atttttaag tggagcatct aggccattta cgttcattgt taatactgag atgtgaggta    81780
ctattctatt catcatgtta cttgttacct agatactttt tttacattgt attattgttt   81840
tataggccct ctgagatgta tgctttaagg tggttctatt ttggtgcaca ttgaacttt    81900
gtttcaagat ttagaagttc ttttagcatt tcttgtagtg ctagtttcgt agtggcaaat   81960
tccctcagca tttgtttgtc tgaaaaagac ttctctctc ctttatttat gaagcttagt    82020
tctactggct atacaaatct tggctgaaaa ttaatttgtt caaggaggct aaagatagga   82080
tcccaatccc ttctggcttg taaggttct cctgagaaat cttctgttag tctgatcggt    82140
```

```
ttctctttat aggtcacctg atgcttttgt cttacttctg ttaaaattct tttcttcatg    82200
ctgattttgg tttgcctgat aactatgtgc ttttgtgatg atcttttgt aattaatttc    82260 ccaggagttc ttcgagcttc ttgtatttgg atatctagat ctctagtaag gccagggaag    82320
ttttcctcaa ttattcccta aaataagttt tccaaactta tttgttcttt tccctcagga    82380
acaccaatta ttcttgagtt tgactgtttt atataatctc atatttcttg gagactttgt    82440
tcatgtcttt tgagtctttt ttctttatct ttgactgatt gggttaattt gaaagccttt    82500
tctttgggct ctgaaattct ttcttctaca tgttctagtc tattgttgaa actatccatt    82560
gcattttgta tttccttaag tgtgtctttc atttccagaa gttctgattg gttttccttt    82620
atgatatcta tctctccgga aaattttta ttcatttcct agattaaaaa aatttcttta    82680
tgttggtttt aaccttcctc tgttatctcc ttgagtaact taataatcaa ccttctgaat    82740
tctttatcta gcatttcaga gatttcctt tagtttggat tcattaatgt ggaactcgtg    82800
tgatcttttg ggggtgttat agaaccctgt tttgtcatat tgccagaatt acttttctgg    82860
ttccttctca tttgggtaga ctgtttcttc agattgttct tgaatttatt tttgatttaa    82920
ctctgttttt caatgagttc ctattttcc ttttaaggat cagactttaa tgtttatagt    82980
ttattatagc ctaatttgat tctttgtact gttaggggta aagactctgt atgagttcct    83040
aagttgtaga ctttgtgcac tggctttcct agatgctggt tgtagtaatt atgtgtttgg    83100
tgtgtgggca aattcactgt cttctattgg gttggaatgg cagggatatc ttgaagctta    83160
tctcattctc ttgaggtgca aactttattt atttatttaa ttttccccta gtattttatt    83220
tactgagttg atgattcacg cttcaggcca gtagggggg tatccctgag taggaaccag    83280
ttgtagctag gtcaggtgcg tagatgtaat acccagtggt aatacctaga ggtcccagtc    83340
tccatgaagg tggctggggg agctctcaat tagatgtgct gaggttttta tcagggagaa    83400
gggtgggagc tacctcagct cctctgccag gccagcagga aaggaatcca cctcccagcc    83460
ttactcctat cccagagttc cagctattca gatcagacag gcatctcttt tcatctgtag    83520
gaacgttgat gttccaagta gggaggaatt gtcactctgc ctcttgtgca agcctgaatc    83580
tggggagtgc tcctcctgtg gggctacaat cattctaaat tgttccagga aggctgtcta    83640
taggttgatg ccctccattt tctcatctga acaacctgc tcccactagc tcctgcctct    83700
tagatcacgt tgtcctgcat gaaacctctt tatgcagctt tcaaatattg ccaagatgtg    83760
atgggccatg gtagaaataa gcagaatgtg ctaattgcca cattttctcc ttaaaaggag    83820
aaaacaacag catctagcta acattattta ctgaaattgt tttggaccac tgagaaaata    83880
gggccagaga gtttctctat aacaggagat agcaagaggg tctgaagaga gcacaaaatc    83940
tgagcaatgg gagggaaagt ggtaattcca aatatattat tttaagtcat catgaggaaa    84000
tgaagagagt aagatgtgta agaagtggag gttggtttaa tatctttgct ttaataacca    84060
aatcacatag ctagtaaatt gggaagtgaa aatttaaact tggtcttgcc tgatacagca    84120
ttaagaaaaa ggaaaggaca gaaagttttt cttagtagca agataatgat taatatgtag    84180
aatatccagt gactaggaat attcattggt gatcgttttc tcatttatc aaggaaaatg    84240 ttcacttctt gactattgca agtttcttcc tgaccattaa agtaataata actagctaga    84300
agttattgtg cccttatatg tgtcagtgtc tgagtttaaa caagatctgc tttaacttgg    84360
atgcttttcg acaaagcagt ttttactcaa attgcctgcc acgctattat accactcaag    84420
agtggccaag ggctataggc aaagtagcca tgcctatggc acttctcaga tcaacaggga    84480
```

```
ccttctactg tttatgtaca attagaaaaa cattttatt attctctgtt tatacctgtt    84540
catatgaata aaataaatgt ttccttggtt atgggtatca cctacttagt gatatttact    84600
ttcaagtttt atgccgttga attgctgaca tacaatgtgt gttatgatgg aatcaagggt    84660
ttatcctgta ccccttcagc caccatgtca gtagggaaca gcagagcaag cctgggaagg    84720
tcacaggagt tgaaggggct gcaggaggtc cgtgaaatgg gaagtcaata tgtgcccgat    84780
gtctgaggag gaggtgtttg actataatta atgtttggat taggaggatt tggcaggagg    84840
aagaagtttt gactctaacc tttatgctaa tgagcctgct ccctacttcg cggagaagct    84900
gggagctatg gaagagaact tccacaagct cctgcttcca tgtctttccc cttacccata    84960
cctgtgttcc tgtaaccgac cttttctcat gcgactctgc ttccatggtc ctggtgaagg    85020
ccacccctcc tcctgtctgt ccatttcctc aagggcatca ctccagcaat tctctgtcat    85080
gtatcaattt ctacacctcc attagtttgc ttctaccaat ttactagcat tctgtcattt    85140
ttctcattag aaaataatc catgaaaaag aggacttggt acatagcaag tgctcagaaa    85200
atgcttgttc aatgaataaa tgaatgaatg aataaatgaa tgaaagcact aagggagta    85260 aggcttttgt aataatttag gggtgggctg atttggactt gttggcaatg agaataaaaa    85320
gaaatgggag gtaggatata cactttgaag aaagaattaa aaatccttgg ttagttattc    85380
tatacatatg taatacagga ggggaaataa cctgtaattt taggattgtg tgtttgataa    85440
taagattatt ttgtggtata actgataagg atatagttga tagaagtggt ttgttttcct    85500
ccttcaagta ttttttatttc cattttttca tatatctttt tttctaagaa taaaaatctt    85560
atcatcttaa tattagatat gtgcattggc cagggaatgt tttcttttaa gatttataac    85620
taatggtaaa ttattaatgt tgagcctgag acgaatttgc ctctgttcac tatgagttgt    85680
aattactctt tggagtcaac tgagggctag aaagaggtga cccagagtta aaaagcattt    85740
agcccacttt gcccagggca tctgaaagcg ttactgtgac ctctgcagca gccgttaggt    85800
ccactcaaga aatagctagt gcactatgga ctacctagac atggaatata ctttgcaaga    85860
attccctcaa taagtagatt attcccacct tcctctttct ctttcagtct ttctttcttt    85920
cttttctttt tttaaaaact gtggccaggc acggtggctc acgcctgtaa tcctagcact    85980
ttgggaggcc gaggcaggca ggtcacaagg tcaggagatc tagaccatcc tggctaacac    86040
ggtgaaaccc tgtctctact aaaaatacaa aaaaagaaa aaaaaaaat agccgggcgt    86100 agtggcgggc gcctgtagtc ctagctactc cggaggctga ggcaggagaa tgatgtgaac    86160
ccaggaggca gagcttgcag tgagccaaga tcatgccact gcactccagc ctgggcaaca    86220
gagcgagact ccgtctcaaa aaaaaaaata ttgtaaccgt atttatttg gtttgggaca    86280 tttcttcaag tagacataca gtgtacattt gtcatatttt ctggctggtc agttaatctt    86340
atgaactcat ttcctatatc tgggggggac ttcctacctt atgaatatct tttccttaag    86400
caagtcaaca gaaaaatgtg taatcttagc ctcccttgca gctgaaacac aaccatgtga    86460
cttagactcc atcaatcaga ttacgtcagc aagacttgga tttgcaagtg agaaatggga    86520
gaaagtatgt attggctaga gtccagtttg gccaggggga aagggtggtg ttggaagatg    86580
gcaggattgg gtctactttc cactgtcagt ggtacaagtt gtgcctgacc caatacaatg    86640
ttggctaaag ctttgtccct ccccgtatgg ccttcaagcc tgactgctgg gtactccagg    86700
gactttgtaa gcttcctaac agcctttaat aagtgttttc ctgtgtaaat gaactttaat    86760
gcttctatag cacaaggtac agtggtaatg gttttaatg tagcacaata aggattaaag    86820
aaaagagggg acattatgtg cacattctcc agtttcttct tcctgtaaca agtgggtgt    86880
```

```
gatggttaat actgagtgtc aacttgattg gattgaagga tacaaagtat tgatcctggt    86940
tgtgtctgtg aggatgttgc caaaggagat taacatttga gtcagtgggc tgggaaaggt    87000
agacccaccc ttaatcttgg tgggcaccat ctaatcagct gccagcatgg ccagaatata    87060
agcaggcaga aaagtgtgga aagagagact ggcctaacct cccagccttc atctttctcc    87120
catgctggat gcttcctgcc cttgaacact ggactccaag ttctttagtt ttggaactcc    87180
gactgactct ccttgctcct cagcctgcag actgcctatt gtgggacctt gcaattgtgt    87240
aagttaacac ttaataaact cccctttata tacatatcga ttccattatc tctgtccttc    87300
tagagaacct ggactaacac agtgggagaa gaatgcaaaa atagctctgg atcttcatgt    87360
agttataatt aatagtaaca agtgacattt tgtgagcact aactatttca agttactgtg    87420
cttttcagat attgtctaat ataatacttt tggtggtcct atgagaagag ccatcattat    87480
ctctattttt agaagagaaa aaatgatgtt taagcaactt gctatcttag cccgggttcc    87540
atagaaaacg gagcttacat gtgagctttt tattggagag gagaggtagt aatcccaggg    87600
tagtgagagt aaggaaaaaa acaagaaaca aagaagggaa ggaaggacag caaatacaat    87660
gtactgttac tgagcttgtc acagctttat taagaagcag catttacttg gtcatgggag    87720
atgtctctgg acagatctta tgggacttct gtgcattaga agagtcgatt gtgggaggga    87780
aggaagaata attcatttcc tgtctctcat tgatgaaagt ttgcccatag gccttattta    87840
acctccagat tcttttggtt actcaacccc actggaagtg ttgtgggggc gggagtatgc    87900
agccagcacc tcttgtagag cagttggcag gggcctgggt acagaagctg ctacagctct    87960
caccagactg ccatgaggga actcatgctg gaagccagcc ctcaccctaa gaagccagac    88020
agctgaaagt gttaagaaat gggactgtcc attgaacagg ctaccaaaag ccggggaggc    88080
agttgggaca ggacagatct gggaagggaa atacttgaca agagacatca ctcttgtctc    88140
tgcctcacct ggcattctct gtgtgtctat gcctgtgtgt ctgttttctc agtacagtag    88200
tcatattgga ttagggccca cccttatgca gtatgacctc atcttaactt gattacctct    88260
gcaaagatcc tctttccaaa caagatcaca ttcacaggta ctgtgagtta ggacttcaac    88320
atatcttttc aggggacaca atccaaccca caaaacttcc tgatgattag agaagacatg    88380
gatagaattt gcagagaaaa ggaagtgatt aatttagttt tgagtatgtt gagtttgaat    88440
tgcttttgag atggtaagac tgttatgtcc aataagcaac ccaaatatgt ttctggagcc    88500
tcaggggagt gtttctggct ggtaaggaga catagggtca tcagcatctg tgtgaaactt    88560
gctgtgaaat agacaagtga tgaataaaac cttgaggagc cacaatgctt aagaggcaaa    88620
cacagagaca ggaaggttgg ggtgacttac aaggagtagg cagacaggaa gttcaaaaga    88680
aaaaaaacta gaagaaagta gtgtcagaca cgatgtgaga aagttcccaa ggaggaacgc    88740
aatgcttttc taagctcagt agtattacag agcagccagg tattgagaat tgttttttata   88800 tggtgatttc atatgcgtcc atgtaaagga tggaagagta tcccttggat gtgcagatgg    88860
acaatggtta tccagagagg tttcagggga gtggtaaggg ctggggtaca gggggatcat    88920
gacaagcaat ggtaggtaga actgtggcaa cagccaatag aggaaaactg tgctatgatg    88980
aaatatgaga acaggaggtg tggttagaaa tcaggagact tgacgatcct tgtttccaga    89040
caggaaagag ccgttgatgg aggaagagga taaagatgtg agaaagggag caagcaaggg    89100
ctcagaatgc agctcccagc ttcaaacaca gcacctttgt tatggcttct tctacatgtt    89160
gagcttctgc acattatttta atatgaagaa agggttctag aaaatcattg gaaactgttg    89220
```

```
aattagatgt cctagctcta aaaagttcta ttaattatta attataccic tacactgagt   89280 aatttatagt aatagcttga atgaccacat tcagataatc ctgggctatt taaggtcatg   89340
ttgccaaaaa aaaacttaat aggaataatt attaaagatg taattatttg catttcagtt   89400
cctgactagc tcttacaatt tggacatgtg taaatttcag cttttaaatt ttggtttgtg   89460
tttgaaaaat aaaagcattt ctcagctgaa ctattaaaat atttgtagag ttttttttac   89520
atgaaaatga gattttaata ctggttcaat ttttaagcca tatattacag tttaaccaaa   89580 atatatttt atagctctct gcttaagtaa agttatgggt agtaatacct ctttgtgaaa   89640
cacatgtatt atttattatc attataaaag aaattcatgt tggttggaag agtttgaaaa   89700
aatgtatata catatcaaga aaaaactaaa atcacaatca catataattt caccacctgg   89760
ggctaagaat tatttcgatg ttttttcattc ttttgtatta tgaaatattt catatgtgta   89820
acaaataccc atttatgcat actaggtttt actacattat ggctttatta tatattctta   89880
agaaaaggtt tttgttttgt tttgttttgt tttttgaga cggagtctcg ctgtcgccca   89940
ggctggagtg cagtggcatg atctcggctc actgccacct ctgcctctca ggttcaagta   90000
attctcccgt ctcagcctcc agagtagctg ggactacagg caccggccac catgcctggc   90060
taatttttgt atttttagta gagacggggt ttcaccatat tggtcaggct ggtcttgaac   90120
tcttgacctc aggtgatcca cctgccccag cctcccaaat tgctgggatt acaggcattt   90180
gccgctgcgc ctggccagga aaagtttttt gaagaaataa tgttacggag tcaattgaag   90240
gctcctcttc atcctacttc cccttcctac ccagaggtaa ccactatctg gaagttttcc   90300
actatctgga aaagtatgt ttttatactt ttacgatgta tgtaactatt cattcaacat   90360
ggagaagtat cactagtagc tgaaagcact gcctcagcca agccctccct aaggaggtct   90420
caactgggac tcctgaaaag ggcctgaact gaagcctctg aatggaagtg cctgagctag   90480
gaaagcagag aagcctatga gcagggctag tgggggtgga gggaccaggc agtgagttct   90540
tggctgcaaa tccctccaga agctgtaaca tactagctgt gtaccaagtc tgatgtggag   90600
atggcagttt cccccaatga ggtctgccgg gcaaagcctt gtaactgtct agggtcctgc   90660
ctgaaagata atacatagga ttttggcctg cagccatact cctcaatatg gtaattctat   90720
gtttaacttt ttgagaaact gccaaattgt cttccaaagt gactgcacca ttttccatттt   90780 ctaccaggaa tatgtgaagg ttccaatctc ctacatgttt gccaatagtt attatttaat   90840
ctgtcttttg gatcatagcc acactagtgg gtatgacatg gtatctcact atggttttc   90900 attgcatttt tctgtaactc atgaagttta acaactttgt ttttgcccat ttttaaactg   90960
ggttacttgt gtttttatta ttgagttata aagttttta cttattttgg aaagcagata   91020
tgtatcagat atatgatttg taagtgtgtt cttctatgtg ttctcttctc attgtcttga   91080
taatgtcctt tgaggcacaa aagttttcaa ttttgatgaa atccaactta ttgatttggt   91140
tgcttgtgct taagagtcat tctaggaaac cattgtgtaa tccaaaatca caaagactta   91200
cacctatatt tctttccata agтттттaтag ttctaattct таттатataгgg tctatgactc   91260

аттагcaтт aatttttgca тagтgтаatga ggtaaggttc caacttcatc cttttgcatg   91320
tgtgtatcca gttgtcccag taccatttgt tgaaataact тcтттттccтa тттgaaтттттc   91380

ttgtcattat tgtcaaaaat cagttgacca тaтaтаataag gtttatttct caaggcttc   91440

tcagttttat tttatcaatc tattgcata tccttatgcc agtctcacac agtgttaatt   91500
actgtagctt tgtagtaagt tttgaaatca agaagtatga gtccttcgtt cttattttct   91560
aaaattatct tggctgttct gtgtcccgtg tgtttctaga taaattttag gatcatcttg   91620
```

-continued

```
tcaatttctg caagaaaaaa aaaagccaat tgtgttgaat ctgtagatca atttgccaat      91680
tgtgataggc agaaaaatga tccccccacc cccgcaagat gtctacattc tagtataatc      91740
cctagaccct atggatatgt tatgttacat ggtgaagggg aattaaggta gcagatggat      91800
ttgaggctac tggacccagt gtaatgacaa atgtctttaa acatgaaaaa gggaggcaga      91860
agattaagtg ccagagtgac atgctgtgag aaagacttga ctggccattg ctgactttga      91920
agatgaaagt gagccataag ccaaggaatg tgggcagtct ctagaagctg gaaaaaggca      91980
aggaaataga ttctctccca gaaccttcag aaagaaatgc agccctacca aaaccttgat      92040
tttagtccag caagaaccaa tttagagcaa ttcaggacta taagatgtgt gttctaaacc      92100
actgaatttg tggtgatttg cacagcaaca agaggaaact aatgcagcca tttaaacaat      92160
ggcaagtctt ctaatttctg aacacaaaat gtctttccat ttatttaggt cttttttaaa      92220 aaacttttt caatgatgtt atgctctttt tagtgtacaa gtcatgtact ttctttgtta       92280
aatttatccc taagttttgg gttttttga agctattgta aataaattgt tttcttaatt       92340
tcatcttgga ttgttcattg ctagagtata gaaatataat ttattttgc atattgattt       92400 tgtgtactat aaacttactg aactcatata ttagctgtaa ttttttgtg aatttcttgc       92460 aattttctac acaaaatatc atagcacctg caaatagaaa ttgtcttact tctttccttc      92520
ccatctggag accttttatt tcccttctg actaagtgac tcaactagaa attccagtgc       92580
aatgttgaat gaagtggtaa gagcagactt ccttgtctta ttcctgatct gaagaagtgt      92640
taggggaata taaattaaaa aacaaatct cttgccaacc cagacaagct caacccaaaa       92700
gtagaaaaga aaacagtttg gattttgaa taaacatgaa accagatgtc attttcaaca      92760
taggcaatcc actaaagaga tagaaaagac agaaagaaat ctcatacagc taagcagatg     92820 taaccttgt catacatgtt ctcaagataa atgataacta gtcttcaagc aagaggactt       92880
gactcaccat ttgtcacaca cagttcatcc taaattcatc tgataattgg ggtaggcatc      92940
tgtgtttact aattgcctta atccaaaaga aaacaaatc tattatatct ttatgacagg       93000
aggtaggttt gtagtttgga cccaggtgcc tgctgagtta ggctgcaccc tcccatggaa      93060
actcccctgg taggtgcatg gtcttcctca ttggcttcat ttcaaagaga tggtggctac      93120
gcctttaagg aaaaggttcc tgggttataa cactgacaag aggcttattt aagttttgga      93180
aagacttaca gagttcattt taaagaggca gagaaagaat gaacaattat aaattttcta      93240
aggcatacgc actaagaaaa ggtggagagt gtggaaaatc tcttacccct cttgtgttga     93300
gggagaacat aggtggttgt atgtatatgt gtgttttca agattcatgt tatttacccg      93360
tctgagtgga agctgttggt ctttaccgtg aagcacaatg ttacctgaga attgtgcaga    93420
tgtctttcat tgggctgagg atgtttcttt ctgttcctag ctgagtgctt ttatcacgaa    93480
agacagttgg actttgtcaa atgctcttgt ctgcatttac taagatgatc cttttttttt   93540
tttttttttt agacttcatt ctgttaatat gatgttttac ctggattgat tttcgtattt    93600
taagccgtcc ttgcttttct gagacaaatc ccacttggtc atggtataca cagtagtccc    93660
gtcttttttt ttttttttt ttgagatgga gacttgatac gttgcccagg ctggagtgca     93720
gtggcgtgat ctcggctcac tgcaacctcc gcttcccagg ttcaagggat tctcctgcct    93780
cagcctcctg agcagctggg attaaaggca tgcgccacca agcccggcta attttgtat     93840 ttttagtaga gcagggttt cactgtgtta gtgaggctag tctcaaactc ctgaccttgt      93900
gatccgcccg ccttggtctc ccaaagtgct gggattacag gcgtgagcca ctgcgcccag    93960
```

```
cccacagtag tcccttctta tccatgattt cactttccac agtttcagtc aactgcagtt    94020
tgaaaatagt aaatggaaga tttcagaaat aaacaatttg taagttttaa attgcgtacc    94080
attctgcgca gtgtggtgaa atcttgcact gtcctgctcc ttctcacctg ggatgtgaat    94140
ctgctctttt tccagtgtat ccacactgca tgctctatct acacagtagt cacttagcta    94200
tctcagtgat caggtcaact gtcatggtat ctcagtgctt ctcttcaagt aacccttatt    94260
ttacttagta atagccccaa agcatcaaag tagtgatgct agaatattgt tataattctt    94320
ctattttgtt attagttatt gttaatctct tactgtatct aatttattaa ttaaacttta    94380
tcatagatat gtatatctag ggaaaaaagt ttgtataggg tttggtacta tctttggttt    94440
caggcatcca ctgggggtct tagaacatat tttccctgga taaggggta ctactgtaat    94500 tcttttata tgttgctggg ttcagtttac tagtatttta ttgaatattt ttgtgtctat    94560
atttataagg gatattggtc tgttttcttt cttgtgattt tacttgcctg ggttttgtag    94620
caggttaata ctgacctcac agaatgagtt gggaagtgac atgatttgga tttgtgtccc    94680
cacccaaatc tcatgttgga ttgtaattcc cagtgtttga ggtggggcct ggtaggaggt    94740
gattgggtca tgggggcgga tgtcccactt tggtggtgct gttttttgtga tagagttctc    94800 acaagatctc attgtttaaa agtgtgtgac acctccctac tctctctctt cctcctgctc    94860
tggccatgcg aagatgcctg ctcccacttt accttctgcc atgagtcaaa gttccctaag    94920
gcctccacag tcatgcctct tctatagcct gtgcgccact taaaactttt ttctttataa    94980
attacccagt ctcagggatt tctttatagc aatgcgagaa tggacgaata caggattttc    95040
ttctttgttt tgtaatgtta tgctagagtt gggttggaaa gtaaatcatg atatgtaggg    95100
ttaaataaaa cccatctgag gccatgactc accagatgcc ttagatagga atttgggcaa    95160
gataaaaaaa tcagaggtta gtcatcattt tcattgtcct tattttctaa gaagcctgtc    95220
agtaaaattt ttttatctttt atcactcata agtaatttat aaaatgtttt ttatttcaaa    95280
gtttttggtt ttttctcttt attcaaagct tatatttat ttggctttac tatgtcagaa    95340
tacagcttgt acaattatag tttagaataa attgataaat tgttcatact ctgatgattc    95400
agataatcat tgcatagcat ttatccccaa cttattggtt taatacaata ataataattt    95460
atttgctcaa attctgcagt ttgaacaggg cttattaata acagcttatc tctgctccgt    95520
gaggcattaa ctagggcaac ttaactggaa tgggaggaat ctcttttaag gaggatattg    95580
gtactggctt ttggctggga gcttacctgg ggatattggc tgggttcttg gtttacttcc    95640
atgtgttctc tttaaatggc tagactgggc tttggttttt tcagtatcgt ggttggaatc    95700
tgagagggaa tgttccaaga ggtagagttc tgaaaatata gcctgcatgt acaggcatgc    95760
atcacaattg ctaatgttcc attggctaaa gccagtcaca tggccaaaac cagaaataat    95820
gtatggaggg actacacaag ggcatatata ctagtaaaag tgttttctca atagatcacc    95880
aaagaatttg ccacacctga tatatagaaa agtttatgta agtttatga attccttgaa    95940 gataatgtgt tttgtttta gactgcagta ctcaatatat atttatccaa ctatatttac    96000
tgtattgaat ttgtaatgat actgtctaga attattttgtc ttttctttga ctattaagga    96060
cccttctctt gggcaggggt tctttttctt ctgtttcttt tctttctcaa tgaccccatt    96120
cacaaagctg gttagtttat acttttcata aatttgagac agtagagaaa aattttaaat    96180
taatgtgtat gtcaatttaa aatcagtgaa actttagtgt tggtacaatc aagtatact    96240 ttctgatatg gtttggatct ttgtccccac ctaaatttca tgttgaattt taatcccgta    96300
tgttagaggt ggagcctggt gggaggtgat tgtattatgg gggcgaattt ctcccttggt    96360
```

```
gctgttctca tgatggtgag ttttcgtgtg atctggttgt ttaaagtgtg cagcacctct   96420
accttcgctc tcctgctcct gctctggcca cataaaacgt gctggctcct cctttgcctt   96480
ctgctatcat tggaagcttc ctgatgcctc ccaagaagca aatgccatca tggttcctgt   96540
acagcctgca gaaccgtgag ccaattaaac ctctcttctt tctaaattac ctagtctcag   96600
gtatttcttt gtagtagtgc aagaacggat tcatacactc tttaaatgtg ataaacaaaa   96660
taaagtacaa tccttatttc agctttgttt accttttgcc tttctctcat ttaaactgcc   96720
aacatccaag gaaagaagag tcaaaactca tctgagtaaa tataaagata ttctatgcct   96780 tatatttaa aaatgtattg catttggcaa ttcttataac acactgaaca ggtcattttc   96840
atattgtata agaaaggaag ttaaggcaca aagcaaatat cttgttttcc acagtcctac   96900
aattttgaag tgtcatttca ttcagccaca ccaggtccat tgctaaaata gtttattctc   96960
tccatataga gttggcatcc catgggttac ccagatagta gttcattcct aaatggaaca   97020
caataaatct ggaactaaat aaagtgcttt atttccctct gttttgaaaa tctatattgt   97080
gcagaaagag agaagaaagg attatcttta tgtgttcaga gattaagact aattttgatg   97140
gtgttaagag ccgaaactat ggaagttttc aagggtaatg cttttaaaga aaatagctcg   97200
cgagacttgc aggggttgga gcgggaagcc ggccaagagg aaagctggag gcgccggtgg   97260
ggaacaggtc ggagttggag cttggccgga agtgggaccg gtgcctggcg gatgtggtcg   97320
tgaagatagg cactggtttt ggattaggaa ttgtcttctc accttcttta aagaagaat   97380 gtggccatta gccttccgtt ctggcatggg attaggaatg gcttactcca actgtcacat   97440
gatttccagg ctccatatct tctacacgga aaatatgtca aagagcagga gcagtgactt   97500
cacctgagaa catcccagtg ggaggacaag agaaattatg tttattcctc aggaatactg   97560
aagtgccgtg aagtaagctg ccattcttct gtaacaatgt tatcagtaat gctttaaact   97620
ccagcacctg gttatgtatt cgaaaccaag tctgtttctt gttttgtatt ttctctctgg   97680
aaatggtgag gaggtggtct taaataaatt aaacaaaaat aggaaaaaaa aaaaaaaag   97740 aaagtaagta aaagctgcct gcattgcatt tgagtgactt gaataagtaa agggaagctg   97800
aggtaggcca ttcagcttct tgcttacagg aggagggaaa ctagcgattt agtgcaggta   97860
aaatgggagt aaatatggac tctcactttt taacttttac ctagaaatta ttgataaaaa   97920
aagccaagct ccgtaaaata cttgaagaga tttgttctga ccacatgtg aggaccgtga   97980 cccgtcaaac tgcctcagga ggtcctgata acatatgcct aggggtggtt gggttacagc   98040
ttggttttac atgttttagg gagacctaag acatcaatca acatacgtaa ggtatacatt   98100
gatttggtcc agaaaggtag gacaacttga agcaagtggc gtgggtggga ttcatagatt   98160
ttctgattga tgattagtta aaactgatat tatctaagac ctggaatcag tggaaacaag   98220
tgtctgggtt aagatatggg attgtggaga ccaaggttct tatcatgtag atgaagttgc   98280
ataggtggct gcccttagag gcaatagatg gcaaatgctt tctattccta cctttaaaag   98340
gttctagact ctcagttaat ctcttcagga tcagaaaaag acctggaaag ggaaggagat   98400
tctctgcaaa atgcatttcc cccacaagag acagctttgc agggccttta aaaatatgtc   98460
aaaggaatat attttggggt aaaatacttt gattttttc agggcctgct atctgtcgtg   98520
tgatgctaca ccagagtcag gttggaattt ggtatcttat tcctacaaag atcagtcata   98580
agacctgtgt tgtaatgtta atgctgatca gctgtgcctg aattccaaaa agaggagatt   98640
ataatgaggc atgtttgagc acccttacct atcacggcct gaactagttt ttcaggtttc   98700
```

```
tttggaattc ccttggccta caggatgggt ccatggattc ggtagagggg cttaaaattt   98760
tagttttggt ttataaaacc taggagtcat atattggaca attgctcatt ttttcaaacc   98820
ttaattttg  gtcacgttag tagaaacgat gaccaattat ggcaaaccag aatgtcaaca   98880
aagcaaaata ccaaggaaaa cggcttgttg tcatgtcaga ggtacagaca gcaaagatca   98940
gttttaataa aatgtgactt aaagttcctc tctctgaaac cccttctttc tttattcccc   99000
ctactctgtc ttttatcttg ttaccagtgg agggagtcca ggttcttggc atcttgaaca   99060
aagaattgga cagaacgcac aaagcaagga aagaatgaag caacaaaaac agagatttat   99120
ttaaaatgaa agtatgcttc acaggtggga gtgggttgag cataggggct caagagccct   99180
gttacaggat tttctggggt ttaaataccc tctagaggtt tccattggtt acttggtgta   99240
tccctatgt  aaatgaagag gatgaagtaa agttacagtc atttaaatgg agaggatatt   99300
tcctgtcata gctaaagtgt ttccattaa  tttagttcta ggaagtcagc atgaattggc   99360
cttatgttcc ctgcctccac actctattct cctgcctcca tctcacactc tagtttgagg   99420
gaaattacga taaagttact ccctgtgtgg ccctggcctc agtatcttat caagctatta   99480
tcttttagtc caccaccaac caacagtcac tgtcaaacat actcaagccc tgggttcccc   99540
atgttttcac ccctcttcct catttttctcc ttatctactt cccggaaata actactatat   99600
aacatagaag aataaatcac taattgtgag aactcacaca ttggcctcag agaagatatt   99660
ttgggtaaag gacattcctt ggtcctcaaa tgtcatcaaa tctgtgtttt ctgttgacag   99720
atgtctttgt atctgctcag caaatgggaa tagggagaca gagtgaaatt ggttgtgagg   99780
aagctgtcaa aggccatggc cattggtttt cgcatattca gtgagggaac ttctgcttca   99840
cagatgaaag aggaatacat ttcttttgtt cttcagccac ataagattac agatttagga   99900
tctagtttgt gcagcatttt ttgagcaaat atggtgatga ttcaggttaa gacatctata   99960
attcttaaaa gtcactttga aatatgcgtt agctatctgt taaataaaa  ataccttatt  100020
ttgcttaaaa atcttaaaac acagacttta atactgtacc aaagcaataa tcaaaaatta  100080
tttacatgtt catgaatttg ttttgataga acaaatttta atttggaaaa tattgttgac  100140
tctgtcctca gcgattaaac cacactgaaa aacaaatgta atctttatct taaaactgtg  100200
catatctgtc acaaaggtat ttttagtctt taatcgatgg acatagcatt tggaacagga  100260
atagatatta caaattatct ctctgtctta cagatgtgag gaaattaata tctacccaac  100320
ctcacctcca aagtcaaaca gcctattaag gccacagaac agtttaaaag tcaattcatg  100380
agaaatgtta ttttaaaaaa tagtctgttt tcttcatggc atctaataaa ttttcaatca  100440
atcaatcaat caattaatta gtatattagt tgtctccttt actggaatgt aaacttcatg  100500
aggccaggta ttttgtgtgt gtttgtttgc tcctgtattc tactacgtgc tcctggcaca  100560
tagtattgct tggagatgaa cgagtaaaca tgccagatat gggtttccat gaactagggg  100620
caaagatcag gagggaggct aacatgggtg ggacagggtg agagtaggct gccactcgtg  100680
ttttgagatc atacatgctt ttaccaaact ggacctaatg gaaaggacaa ctgacacccc  100740
tgtcaccact accaacattt ttacctataa tagtaaaggt tcttggtcta tctgactttg  100800
actttaatag actgagggtc aactatttgg ttgtccactc agaactcctc agaattcagg  100860
aatatgcacag tccgttcttc actaccatat ttattctgct gcctgttttt ttctagctca  100920
cttattgtca cagtccctat gaaatgtgac agatctctct atgtaataat aatgccactt  100980
tgcatttgta tagtacttag tatttttcat ggcacttgca catttattat ctcatgaaca  101040
gattctacat aaattggaat gtcgcatgaa atgatctgaa atcaattgtg tcattctgtc  101100
```

```
aatgtccact gatcctagtg gagaaatgaa aattgagtct gatttgactc atcattttgc   101160
agtaaaaaca agaaactaat taaaggcaga tcaacagcta cactggtaat cacaggtcct   101220
ggtttgcata atgcagtgtc agtctcttct gcttttact  gttatgaaat ttatgtatat   101280
tagatataaa atgtttccct aacttgaaga agtattgcat taatctatca aataatggat   101340
tggttttagt tgtagcagtt atctaccact ctttcataaa aaggacattg acaactcttc   101400
caggtggagt gtcttgtcac tctggttcat aaaatgttat ttagaggtct gaatcatgtg   101460 tagggtgaa  gataacttcc tccttcctca cccttctgaa ggtttgataa tttgagtcta   101520
taaaacaaat gcataataga cagattgata ggagaaaggt atacaaatta ttacttgcac   101580
atgtgtacat aagaacaata tgaaatatga aaactcagga aaggccagat gactgaagtt   101640
ttataccatc cagaagtcgc agaaggaata ggggcttgga ttgtgcaaga caggttatgg   101700
gagggaggga caagaaaagg cctggctagt gaaggtggtc tcgttataca gagtgctatg   101760
gtttgaaagt ttgttccatc caaaacttag gttgaaactt aattccccat gtggcagtat   101820
taggagatgg gacctttaag agatcgctag atcatgagag aagagccctt atgatctagt   101880
gcatcatgag gatccattca tggattaagg aattcatgag ttattatgag aatgggacta   101940
gagggagatc caagtgagca ccctcagccc ctttgccgtg tgatgcctca tggtgcctcg   102000
ggactctgca gaaagtccgc accagcaaga gggccctcac cagatgcagc ccctcatcct   102060
tggattttca gcctccagaa ttgtaagaaa caagttcctt ttctttataa attgtctagt   102120
ttcaggtatt ctgttataag gaacagaaac agaaaacaga ctaagacaca tgaaatttca   102180
caggtagcag ttctcagaaa aaatagatgg tggcctgtgg taaaatgtct ctatcagact   102240
ttcaaaggtg tcatactctc cctctcattc atgtgagtta atctttcctg gattcggata   102300
ggagtggggt gggggtgggc tcagagaaac cctagctgtt tatttcatga atgtagattt   102360
tctctacaga tgcaaatatt ctccacaaaa gacagatttt caagaagatt tctgtggttt   102420
gcagttcctt tgaatagcta tatggaaata tgccaaagaa gtgttttttg ggggtgagat   102480
attctggttt tgttcacatg catgtcccta acacaatcc  acaggagcta ggtgacctaa   102540
taagagggtt tggcatctag aaaccagtcg tggcccacct ttgctgtggg actaaggagg   102600
ctattctgat ggcttctact ccagtttgtt tattatttaa cttaacattt acagagacat   102660
ttggtaaaaa tgtttataaa aactaggcct gaatttaaca tttcatatct tcaaatgtgt   102720
tttgtacttt aagctgctgc ttatatttta aagagctttt aaatcattga tttcattggt   102780
ggttaaggca tgttaatgca tagcttcatg caacatgaga gaaatagaaa gcatttagag   102840
aagtgtccca aatgcccaat ataaacatcc tgctttgcta tttttgtaaa gtaagtgcag   102900
gaaaccatag atagtgttta aatagctctt tttgtgcctt tctagaataa agatgactta   102960
aacactaaca aagaagggta catgaataat actgcaattt aggattgcca gatgaaatac   103020
agggtggcca atgaaatttg aatttttgaat aaacaccaat gaacatttta gtttatgtcc   103080
cgtttactgt atttttagc  atatttttca actattgcat ttttaaaagt aattcaaatt   103140
taactggctg tcctattttt tagtggataa agctgtcaat gctggatgcc gtccaaaagc   103200
aggcaggctc tcaaatttgt gttaaaggtg tgccaatttc ttttagtggc atagtatatt   103260
attccacagc tcttgaatgt gtcatctaat tctcttgtct ctctgtaaga ggtttgtgtt   103320
cagaaaagtt agagctgttt aggtatcaaa tcttttttaac taactgcgta acggcagtag   103380
tcatctgtga gctgagaaca tttccgtgat gccaggctta tagacagcac atgctctgag   103440
```

```
gataaggttt tgagagactc ttcacatctg gaatgatgtt gcccattgaa tatccccaat   103500
tgtggatctt gcagacatac atgaattaat atattccaaa ttgatgtcat ttcttcctgc   103560
acatctgctc cccctgtatc tgtgttaatg actcttatac ccatttagtc accagaacca   103620
aatacttggg atcctagaga aggagggggat catctttccc ttctcttttt ctcttcccca   103680
catccaatca attctgaagt cctgtggctt tcatcttctc atttccctga tcaccacatt   103740
agtgggcttg tccaggcttc cagtctcttt tctggctcaa tccctttact cctccatagt   103800
ggagaatgcc ataaggccga tcagggtgct ctttaatttt tatggccctt gtgggacgag   103860 gttatattt atcaatgcta ttaagtgctt ataataagta ggacctcata gaagaagatc   103920
aaggcatgga tggatctctc tacattcatg attctgccta gtgtcttctc tgctaagcta   103980
tgcttatctc accatatatc tgaatattat gttgctcact ttttccagaa aatgcaccga   104040
gatttatatc cccatggttt ttccaagttt ccgcaccctc attagttctc attaactcct   104100
atcctaccat agtgatggtt ttttgagcca tttctcggca acggtttacc aaccttcagc   104160
aaccataaat atccatggac atgcacacaa acattcacat acacatacaa acacacagac   104220
atccacaata catgcataca cacaaaaata cacacacaca cattttattc atcctatatt   104280
gctacatgct gtacaatgaa ttataattag agcatcattt gattttcagt ctaaataaat   104340
ggtacttact ggcacacaga cttaattatg tcacctcagg tcagaatttt atcctcatga   104400
gtttagatag agttttgcct ccttgagtgc acaaatagtg gatcttaaac cttcagacag   104460
aaggtttatg ttcttttttc agtaacagtg ataagttagt tctctttctc ctttgtattt   104520
aaggtactcc cgggagatga aggtgtgata gccaatacct gagaactaaa tgtacttttt   104580
aatagactca gaattaacac attgcagtgg gatgcagaaa tcccttttct ctctttacct   104640
agtgaagcaa atattattgg ataaataact tcaataagat agacttacag tagtaagtct   104700 attttttattt atttctaaaa tagacttcgt aatagtcttc aaacaattta gccctcactg   104760
tgtcccaaac tccttgagat tctttttatta atattttcta acacttatta agggaacatt   104820
ttcttttatg acatctctaa atgtcattgt ttccaagatg ctatatcatt atattgtcaa   104880
tgagttactt cttcaatgat agttttttcaa tttctcttaa ggttttaatt tcttcttcaa   104940
tttctcatac ctgtgcccta gtatttcttt cagctcatta gtggtgaaaa taagctagtt   105000
cttataaacc cttagttgtc aaatattatc atcttatctt ttgaggaaag aactagcatt   105060
tagaggataa atttaactgc taatgtggta atgctggaca caccaggaat tagggggcaaa   105120 tctgaagcca gcagatgtcc tggaaacatt agctcttgac atcagaaagg ttccctggga   105180
tgcagagtag tcaccctgga gtcttgcaga ttaagaaaaa gctcccatag cacacacaca   105240
tatttaaaag gattgcttga agtgactagg tttgaagtgc aaatggcagc agaagtggaa   105300
gtagaaaaat aaatagaaat gtttcccagg aagtcatgtg ggggcaaaga cagtcacagg   105360
cccagggctt taagatatct cccagggagc tatcttcctg ttgcagatgc tcaggccttt   105420
gtcctgcagg gttgttttgt acacctcaga acagtgctt gaaattcaag aaaataaaca   105480
ttgttgactt gggatgagtt ctccactcta atttataaaa taggcaaatt gtttagagtc   105540
cactgcttta accctatttt cgtcagtgat ttgtaacaga gccttcatct ctgtgcgcac   105600
ttgaggggct tgaagaatgg aaattaggtc tgcgagttac cagcatatgg tttcaatgga   105660
agacttggat gtgaatgaaa ttatccaagg agagagtaaa gtatgaagag aagatgaatg   105720
agtgaatgaa ggaggaagcc actgaagggt cattatatgg tatctgagag ggaggaagga   105780 accattttttt ctaatattgc aacttgccac cttacctcct ctccagacct cctttattct   105840
```

```
agtcgagttt attttcctat agcattttc acttattaaa atacaacatc atttactttt    105900
aagttatttt cttgtgtttt attttatatc ttctctgcct cctgtcccct actagaaagt   105960
gagccccatg agaacagatt ccaagcaggt agaagagtga ctagtacttc tactagtcac   106020
tagtgcttag tcatgtttac tggctgagtg aaaaacatag cagtgtttca agaggaaagt   106080
ctgctacaaa ctgaatgctt gtgtctctct aaaattctta tactgaaatc ctaatctgca   106140
acgtgatggt attagaaaat gtggcctgtg gtaggtgatt aggtcatgag ggctctgccc   106200
tcaccaatgg gattagtgcc cttataaaag agacattgaa aatttatctt tttttcttgt   106260
aaatttgttt gagttcattg tagattctgg atattagccc tttgtcagat gagtaggttg   106320
cgaaaatttt ctcccatttt gtaggttgcc tgttcactct gatggtagtt tcttttgctg   106380
tgcagaagct ctttagttta attagatccc atttgtcaat tttgtctttt gttgccattg   106440
cttttggtgt tttggacatg aagtccttgc ccatgcctat gtcctgaatg gtaatgccta   106500
ggttttcttc tagggttttt atggttttag gtctaacgtt taaatcttta atccatcttg   106560
aattgatttt tgtataaggt gtaaggaagg gatccagttt cagctttcta catatggcta   106620
tccagttttc ccagcaccat ttattaaata gggaatcctt tccacattgc ttgtttttct   106680
caggtttgtc aaagatcaga tagttgtagg tatgcggcat tatttgctga gggctctgtt   106740
ctgttccatt gatctatatc tactgttttg gtaccagtac catgctgttt tggttactgt   106800
agccttgtag tatagtttga agtcaggtag tgtgatgcct ccagctattg ttgcttttgg   106860
cttaggattg acttggcgat gcgnnnnnnn nnnnnnnnnn nnnnnnnnnn nnnnnnnnnn   106920
nnnnnnnnnn nnnnnnnnnn nnnnnnnnnn nnnnnnnnnn nnnnnnnnnn nnnnnnnnnn   106980
nnnnnnnnnn nnnnnnnnnn nnnnnnnnnn nnnnnnnnnn nnnnnnnnnn nnnnnnnnnn   107040
nnnnnnnnnn nnnnnnnnnn nnnnnnnnnn nnnnnnnnnn nnnnnnnnnn nnnnnnnnnn   107100
nnnnnnnnnn nnnnnnnnnn nnnnnnnnnn nnnnnnnnnn nnnnnnnnnn nnnnnnnnnn   107160
nnnnnnnnnn nnnnnnnnnn nnnnnnnnnn nnnnnnnnnn nnnnnnnnnn nnnnnnnnnn   107220
nnnnnnnnnn nnnnnnnnnn nnnnnnnnnn nnnnnnnnnn nnnnnnnnnn nnnnnnnng   107280
ggtgtttatt ggggcatctt tcccaaaaga aaagattggg acccacccca aatgtccacc   107340
aataaagggg gggattaaaa aattggggcc catacccccc ggggaatttt agccccccaa   107400
aaaaaataag gggttcaggc ccttggaggg gacagggata aattgggaaa tcccctttcc   107460
cggtaaactt tcgcaagaac aaaaacccaa cccgggaatt tttcccttaa aggggggaa   107520
ttgaccaatg agtcccccag ggccccagga gggggaattt ccccttttgg gaattttgtt   107580
ggggggggg aaggggggaag gaaaacccttt gggaaaaaac ccaaatgtta aataagaagt   107640
taggggggtgc ggcccccccag ctgggcccag gtaaaaatag gtaattaccc ggcccaaggg   107700
gcccaggccc cctaaacttt aaggtttaat aaaaaaaaaa aaaaaaaaacc cccccaaaa   107760
aaaaaaaaaa aaaaagaaaa tttatctttt gaggagaaaa tggaaagctg tcctccaaac   107820
aagtgcaggt gctggctgtg gggagtgaaa gcacaccaaa gataggaaat gcaaagggga   107880
tttgagggga tatgggtgga acactcacag cttgtgcttt gtgatctttt ggaaatatga   107940
agcaaatctt ctgagatctc agtagatgag aatatgagaa atttgtctgt ggggagccaa   108000
agacattttc tgtgttgagc atgttttctt cttgttaaag cattttttttt ttaacatgag   108060
cagttgataa agggatggca gggaatactt tttgtacatt tagaaccgca gagccctgcg   108120
gaagtctcag ccccaattcc cccatttccg tattattgaa ctgaaaaaca ctaaatatga   108180
```

-continued

```
aaatgcttaa ctgatagacc tagaaatcat acttttcttt gcaaatacat actataaatc 108240
ttaaactagg aattcttctt cctctcaaga acagtaattt gttgattatt tttaagtcaa 108300
tactgatgta tacctgtctt gattgttttg atgccaattt ataaatttct ttataccttt 108360
gccattgtca aagctaacta tattaatctt tactccatta gagtactgag ccagaccca  108420 agtacttatt atggaactga attagcaagc tacttaattt agggtgtgtg tgtgttgagt 108480
acttttagta ctctgttttt tagtgtacat atatgttaga ggaagcttct attagtacaa 108540
aatgttcaag ggaactacac tcgccttcac aaaaattaaa tctaattaaa ttaaaaaata 108600
gattcatgaa ccgttgcaaa ttatttaaat gttgtttaaa ttgtgtggca atttcagaag 108660
cagtgaacat ggtagatatt gtcatttccc gcaacatatt taaatatggt cttcccccta 108720
ctttatatgc tagagctgaa tagcaaaggg aaaggctcta tcagtcagtt ttttccaaa  108780 ttaacacctt atcattagtc accacaaagt ctcagtggca ttcaacttca gaatcacagg 108840
tatgtgagcc tgctaggcta gttctcctgc accctgttgg tatatgggtt gtctggggc  108900 agactggttc tgtgtgtctt atgctgggcc caggctgcaa gggtggaagc tacctgttac 108960
acattctttc tctggtggtg gaccgaagct cctagaagga taaatggaag ccctcagtac 109020
ctgttcagac tgaggctcta atcaggttat tgtcacttcc acattccatt ggtggtcaaa 109080
ggaagaaaac acagtcaaag ccaaaagcag gaatggatga tgagcactgc ccagaagagg 109140
ctaccacaag gatgggatgt acagaagctc ccagagcagc aaagaactgg ggccagcaac 109200
tccatctacc acagtgggct tgctctttct ggaaataaac acccttggat gcatactagg 109260
tgatacttat atgagttact ggtatttagt gcttaagctg gaattgatat gcttcctggt 109320
tcatctaagg ctgggaaatt tcaaacagac tttttgatat cctttcctga aatagtgatt 109380
aagttaaaca tttcagatac ttaaaaaata actccaataa agcttgaaaa ttggatcttt 109440
ctgagcggat tctcccttcc ttagcatgta ttaatgtcct tattttactt cagccccgag 109500
gtactgaaga gtgagccgta tggggagaag gctgatgtct gggcagtagg ctgcatcctt 109560
tatcagatgg cgactttgag tcccccttc tacagcacta acatgctgtc cttggctaca  109620
aaagtaagca acgctgggag acagaagggt ctcgtgtagc taaaaatgca attcttttc  109680 ttattaaaca gatctttgtg atttgtatat aactgcccat taaaagcaag aattgttttt 109740
attaactgca tgatccagtt tattttttcc gctttcttct aaatatatat ctcatgtaat 109800
ggcttatttc cctctataat tgtctttatt tataatacaa aattattttt aaaaagacgt 109860
ttggtcttct attatttatt tatttaattt atttattttt gagacagagt ctcactctgt 109920
cagccaggct ggcgtgcagt gacatgatct tggctcactg caacctccgc ctcctgaggc 109980
tcaagcaatt ctcctgcctc agcctcctga gtagctggga ttacaggtat gtgccaccat 110040
gcccgaattt tttatttttt tttttaggtt tcaccatgtt ggccaggctg gtcttgaact 110100
cctgacctca ggtaatccac ccaccttggc ctcccaaact gctgggatta tagacgtgag 110160
ccactgcgcc cagctggtct tttatttta attgcagtct ggactactca caatccagca  110220
ccttatatta tcccatacac catttttatta tgaatctaag gttaattttt aactcagctt 110280
ggataatata attccagttc aagagctgtt taattgatgc aaatgtttta tttggtcggg 110340
atttctgact aaaattatg tgtgaagtta tcctgcttaa ttagtaactc tcaggttatg  110400
gtcaagtatt aactattcaa agacatccgt ggccccttta cttccatcac tctagtctgt 110460
ttgttttgca gatagtggag gcggtatatg aaccagtccc agaaggtatc tactctgaaa 110520 agtaacaga caccatcagc aggtaattag tcttgcggct tcagacatgt agggacaatc  110580
```

-continued

```
aagaaatacc tcatttctat aataaatcac tatttatgga taaaaggtca tgaagagaaa    110640
gagtccctac ataatccaaa tctagaaaga tgtttgtgca tcatcagtaa cagtgactat    110700
ttggatgcta cttaagtgtc caagaggaag tagagcgttc acttattatg caaccactag    110760
aacgattatt tggaagggtt tgtaacaacc tgtaaaacac attatgatat gtgggtaaga    110820
caaatatgat gtaaagctgt ttgtaaccat gacaaacctc ataaaaatat gcaaaaaatt    110880
ggaaaaaggc cagacaagaa cacatgaaac aaaaagccat gttagatgat aaagttgcag    110940
gtacttttta atttccattt ttaaactgat aatgtgattt atcataattt ttcatagaga    111000
atcaggagct ccagctatca ctatagcagg agtttaatga aagtcattat ttagttgtac    111060
ttccaaagtt ttggccaatc cctgctggcc tgtcacccat gctccctccc acttccccctt   111120
ctgttttctc tgctccagcc acatggtgct tcccactagt cctggcatgc accctccttc    111180
tagacttttg cccttgcttt catggtttcc tagaactctc tttcctcaga tatatgtgtg    111240
acacaggccc tcacttcctc tgggtctctg ctaaaatgtt ccccaccctg atggcccac     111300
tacctcacag tactctctaa cctccttgcc tgctttaaaa agctcacagc actcatcatc    111360
cctgacatat tatacatgtg catacatgag ttttgtttat cgtctgtctc ttccccacca    111420
aaatggaaac tcaagagcag ggacttagtc agttaatttg tagcttttat tgcccaaagc    111480
agtggctggc acagagtaga cccttaataa atattgcttg tatgaataaa tgactcgtgt    111540
atctggctga ttgctatttc tgtaccatct tgggtactta agttgcatct tgagtactta    111600
agttgggtac ttaagttgat gggatttctc catcccatca aactgagtat tttggattgt    111660
agaaattcta gagtcacccc agatagaatc tttttcatc tgccttctga gtcttttaaa     111720
acttgggttg gtatctatac tagcacttag ccccatctct gatgaaatat aatagatgta    111780
ttattgtggc tgtaccccctt tccctttgat ttatccttct agcccattgt ttgtgctaat   111840
attactcctc acctgttttt gtaggatgat atctaaacct ttctttcttt ggcacaatac    111900
taatctacag tcttattttt ttaattgatt tttttaaaat ttttaagttc agaggtacat    111960
gtgcaggttt gttatacaag gtaaacttgt gtcatggggg tttgttgtat agattgtttc    112020
atcacccagc tattaagcct agtgcccaat agctattttt cctgatgctc tccttcctcc    112080
tgccctccac catccaataa ctcccagtgt ctgctgttcc cctttatgga tccaggtgtt    112140
ctcatcattt agctcccact tacaagtgaa aacatgtagt atttggtttt ctgttcctgc    112200
attagtttgc taaggataat ggcctccagc tccagccatg ttcctacaaa agacatgatg    112260
ttgttgcttt ttatggctac atagtattcc atggtgtgta tataccatat tttctttatc    112320
cagtctagaa tttatgggca tttatgttga ttccatgtct ttgctattgt gaatagtgct    112380
gcaatgaaca tatgtgtgca tgtgttttta tgatagaatg attcgtattc ctttaggtat    112440
agagccagta atgggattgc tgggttgaat ggtagttctg ttttatgtc tttggggaat     112500
cactacacat tgttttccac aatggtagaa ctaatttaca ctcccaccaa cagtgcataa    112560
gtgttccttt ttcgctgaac ctttccagca tctgttatt tttgacttttt taataatagc    112620
cattctgact ggtataagat ggtatctcat tgtgattttg atttgcattt atgtaatgat    112680
cagtaatgtt gagctttatt tcatgcttgt tggctacatg tatgccttct tttgtgaagt    112740
gtctgttcat gttcctttgcc cacttttttaa tgggggttgtt tttctcttgt aaatttgctt  112800
aagttcctta tagaaactgc atattagacc tttgtcaggt gcatagtttg caaaaattt     112860
cttctgttct gtagattgtc tgtttactct gttgatagta tcctttgctg tgcagaagct    112920
```

```
ctttagttta attaaatccc acttgtcaat tttgtctttt tttgttttttt tttttttttga   112980 gatggagtct tgctctgtcg cccaggctgg agtgcagtgg tgtgatctcg gctcactgca   113040
acctccacct cccaggttca agcgattctc ctgcctcagc ctcctgagta gctgggactg   113100
taggcctgtg ccaccacacc tggctaattt cttttttgtat ttttagtaga gacgggtttc   113160
acggtgttag ccaggatggt ctctatctcc tgacctcatg atctacgcgc ctcggcctcc   113220
caaagtgctg ggattacagt cgtgagtcac cgcacctggc ccccaacttg tcaattttttg   113280 cttttggtat ctttgtcatg aaatctttgc ctgtgcctat gttctgaatg gtattgccta   113340
ggttgtcttc caggggtttttt atagttttgg gtttcacatt taagtctttta atctgtcttg   113400 agttgatttt tgtatatggg gttcagttca gattttttgta aaggagttca ttttcagttt   113460
tctgcaactg gctagccagt tatcccagca ccatttgtta catagggaat ctttcccccca   113520 ttgcttgttt ttgtcaggtt tgttgaagat cagatggtgg ttgtacgtgt acagccttat   113580
ttctgggttc tcttttctgt tccattggtc tatgtgtctg tttttgtatc aataccatgc   113640
tgttttggtt actgtagccc tgtagtatag tttgaagtca ggtagcatga tgactcaagc   113700
tttgtttttt ttttttttttg cttaggattg tcttggctat tcagttgctc ttttggttcc   113760
atgtaaattt aaaatccttt ttttagtggt gtgaagaatg tcactggtag tttgataaga   113820
atagcattga atctacaagt tgctttgggc agtattgtca ttttaatggt attgattctt   113880
tctatctgtg agcatggggt atttttccat ttgtttgtgt catctctgat ttctttgagc   113940
agtgttttct agttctctct gtaaagctct tttactggtt agctgtattc ctaggtattt   114000
tattcttttt ttggcaattg taaatgggat tgcatgcctg atctggctct tggcttgacc   114060
cacagccgat gttatactga atgggcaaga gctggaagca tttctcttga aaatcagcac   114120
aagacaatac ttcaacatag tattgacgag ttaatgggtg cagcacacca atatggcaca   114180
tgtatacgta tgtaactaac ctgcacgttg tgcacatgta ccctaaaact tgaagtataa   114240
taaaaaaaaa aaagaaagaa agtactggtc agagcagtca ggcaagggaa agaaagggca   114300
tccatatagg aagagaagaa gtcaaactat ccctgtttgc agatgacatt atcctgtatc   114360
tagaaaaccc aatagtattg gctcaaaaac tccttaagct tataaacaac ttcagcgaaa   114420
ttgcaggata caaaaccaat gtgcaaaaat cactagcatt tctatataac aacagtgaag   114480
ccgaaatcta cagtcttaag gcctcaggct ctgaagacag gcctacctgg ggctaagtca   114540
tgtaaacagt tgcaaactct aagaagtgat ttgaggccag gtgcggtggc tcacacctgt   114600
gataccagca ctttgggagg ctgaggcagg cagatcacct gaggtcaggt gtttgagacc   114660
agcctggcca acatggtgaa acccccatctc tattaaaaat acaaaaatta gccaggcctg   114720
gtggtgtgcg cctgtaattc cagctactcg ggaggctgag gcaggagaat cacctgaatc   114780
tgggaagtgg aggttgcaat gagctgagat tgagctgttg cactctagcc tgggtgaaaa   114840
gagcaaaact ccatctcaaa aaatttttt taaataaaaa taaaaaaaaa gagtgatttg   114900
accattattt ctgcgtccct gttttctgat ctagtagaat gagaatcata atagtaccag   114960
tctcattagg ctgatgtgat gattacacaa agtaacatat gcaaatcact taggataggg   115020
cttgcagaat ggtaaatact tgagcaattt tggcaatcat catggttagt attatgggaa   115080
atgagacgaa cctgtctttta aatcatttga ttccacaaac actggatcat gccttgttgc   115140
taatgaatcc aaaatatattt aaactgctca tctctgtgat ttgttcctgt tgtctgttgt   115200
tttttggaaa gtacattaaa aattgacaga gtcgtcagag gtgtcaagac aaaagtacca   115260
tatttgctca tttaatttct ccttttaata ggtatttgag tgccacaaag ggcgagggaa   115320
```

-continued

```
aggtagcgca aataacaagg ttcagagacg ttgctttgat tttgtgaatc tgggcaaata   115380
gactgtaaat ctcttctgaa actaatagac cctggctatg gctacccagg actcttgggg   115440
ttaacatact agtagggggag tcagatagca acattggagt gtaaaggttt agagcgtcac   115500
caagttctgg agtcaactag attctaatgc cccctcttcc actcaattta atttccctga   115560
ggcccaattt tctcatctat gatgtgtggg tagcagtagt aattactttg tagcaggacg   115620
agccacaggc aagaacccct cagatgctga gttgtagaag gaagggctt tattcagctg    115680
ggagcaccgg cagactcacg tctccaaaaa ctgagctccc tgagtgagca gttcctgtcc   115740
cttttaaggg cttacaactc taaggggtc tgtgtgaaag gatcgtgatc aattgagcag    115800
gcaggggta cttgactggg ggctgcatcc actggtaatc agaacagagc agaacaggac    115860
agggattttc atgatgcttt tccatgcaat gtctgaaatt tatagataac acaagcagtt   115920
aggtcagggg ttgattttta actaacaggt ccagggcaca gtgctgggct atttgcctgt   115980
ggattccatt tctaccttt agttttact tctttctttg gaggcagaaa tcgggcataa    116040
gacaatatga gggtggtctc ctcccttaac ttcatgggct tgttttaaag cttaaataag   116100
atagtgcttc tgacccactt aacgcagtac ccagcaagtg gtaggcactc tataaaatta   116160
ggtattatta gtattaataa tgatattgta ttatgtacag aatgaagttt ataaagcaaa   116220
ttgtgataaa tgtgatgaaa atggtaaag ggggcaatga gagattacag aaggacctgt    116280
cttactctgg gaattggcga aaagtttctc tgaaaaaagg acgtgtaatc tgagacctgg   116340
aacattcatt aactctcaaa tagtaagcag catttcgcag accagtatct gtgaaggctt   116400
tgctgaggga aagagcttct caatttgagg ttgcttttgg ttcaaaatac taagatgcca   116460
caataagtta gaactgacaa ttcaacttta tatctgataa taaattaaga ttgcagggtg   116520
cattctgtaa taaatttatt ttcatttaaa gttaagactc ctcattgtct gggtttacat   116580
tccaaataaa gttttatctt tagaaaattt gacttaaaac tgaaatcaat catgaattat   116640
atgcaattgc atatttaatt tgctttggat tttcagtatt aaaaaattga gttctgaaag   116700
aattagggaa caaactcaaa ttttgtattt tcttaaagca acaatgcaag ggacacataa   116760
aggcaagtat tcttaatgat catttatgac tcagcaaaag atcaggctca cagccaatct   116820
ttagtaatt gatagagcct ttgaaataga agacagctct tgacagaaat gtttattata    116880
atcattccta aaaattatat tgtttctaat catatatatc ttctttcctc tatttttacta  116940
tcttctcatt atttttcaca tccttgtcaa gtagagctca cacagtttgc atttctaatg   117000
tgcagcatct ttccttttc ctgtttgctc atgtggtata caagcacatt tgttattgaa    117060
acttgtcttt cctagcaggc cttcaaattg ggagaataac ttagcaaccc tgaggagttt   117120
ggggaagaaa ataaatatat ttttttgttc tgctcagtac taggattact atttttacct   117180
actagtgtac tattaagaga atattgtctg tttacttttt aaaaaggaag aacatttcct   117240
tttatgcata aaatattcta ttaaaatcat tgccttattt ttctttctct gtgcctggtt   117300
gcataagctg cctggtgctt tgcttcagaa gcagtcatga ggactaacaa agttaatact   117360
ttcagctagc tccaaggaca aatggatctt tatatttttc acccctttca attctttgta   117420
tcttaaaaca tgacatgaat gtaattgaat aaggtatcct tctaattctt tccatctggc   117480
cttttcagagt ggagtgggga caaagtggat gaggtgagaa tatcctcaat ttttttagga  117540
ccagatttta tgcttatttg tttacagaat cattggtaga caatctttag catgtattat   117600
gactctgatt cagttgctgt taagaatttc tctgaggccg ggcgcggtga ctcacccttg   117660
```

-continued

```
taatcccagc actttgggag gccgaggtgg gtggatcaca aggtcaggag attgagacca    117720
cgatgaaacc ccgtctctac taaaaataca aaaaaattag ccgggcgtgg tggcgggcgc    117780
ctgtagtccc agctgctagg agaggctgag gcaggagaat ggcctgaacc cgggaggcgg    117840
agcttgcagt tagccgagac tgcgccactg cactccagac tgggcgacag agcgagactc    117900
cgtctcaaaa aaaaaaaaaa aaagaatttc tctgaaatgc ctaagcaggg agtcatttca    117960
gagcaacgag actatcctgg aacttctggt aggaaatgtt cctgggaatc caaaagtcta    118020
tggccaaata ttttgggtta tgggtaggta aacttttttag atgttacgct gagtttgttt    118080
gtggatttat tcattgattc attcgttcat ttgctgaata cctatcagga ctcagattcc    118140
attgtatatg ctgggagatc atagtgaaga ggacacatgt ccctcttctc tagaagtttc    118200
cagtctagtg gtgaaacaga ccattatagt aaaataatta caatagtttt aagtacttaa    118260
gtgcaaatgg tgcaaaaaga atgtacaaaa ggggctcagg atatctgtct gaaggcagtc    118320
caaaagtatt cctaatggag cctggaaaaa tagtgggatt ttggcaagta tataagagat    118380
gatggctgag atgatggctg ggaaagataa gataccatgg gcaaaaaaaa aaaaaaaaa    118440 aaaatcaagc atatggaata aaataagcaa agaaatgggg gtataggaga gacaggtgct    118500
atttggggaa gtgcaggtag ccgcattgga tgtgttgctg gaggagggga aagagtggag    118560
gaagttaagg gccagttcaa gagagacctt gtatagcatt ctgggaattt taattttatc    118620
ctattggacc atgagaacta ttgaagaatt ttgagtagag aaataatata gtcagattta    118680
ggaatagtat tctggttagc agtttacagt acagaccaga ggtaggcaag aaatgagtgt    118740
gttatttagg agactctttc agtagtccaa gtaagtgacg ttgtaatagc caaatagctg    118800
tgggattaca ggggaaggat gtggattcaa gaaatattta gaaagtagaa gtcacaggac    118860
ttggtgtttg ttaaatgtag gaagggatgg aggatacata aaagtgtgga ttttcttttc    118920
aatttattga aattttacaa tgcatgtgca cttcacagag attacctcgt tcaaacacca    118980
taccagttta atgaggtagg tactataatt atcccatttt acaggtgggc tatctgagtc    119040
ttagaagcta tgtaacttgc ccaggatctg actaataaat ggtaaatgag gttttaaacc    119100
ccagcaaaat gatccagagc ctgcatgctg agttatgatg ctaaactgca tcttctttgt    119160
ggtgcctttt ccagtgatgg caaatacagg accaggagag taaccttggg caaggagatg    119220
actatatgct aggagaacga aggtcatttc cattcccatg taccataata tgtagctata    119280
taatttataa aactagttta cgttgctttt tttttatttt taaaaaagtt cagctgatag    119340
ttcagctgct aatattacct tgaagcagct taaacatctg cagtctaaga atttagaata    119400
tccacactaa tgaaaggttt agacactggg cttttttttt ttttttttcca cctgccagtg    119460 agttggcagt gatttcagaa agcagccaac ccatgcagga gaagatggtc ccatctgccc    119520
atcctgagac ccgaagagca tcttcatgct cagcctggaa cccttacctt ccagcccaag    119580
tgcaaagaga ataacgctga ctccttttcc ttccttagct ttccaaatgc cttttgagaa    119640
gtcttggact caaagctgtg cttgatatcc atcttatccc aggttatctt aggtgaaaat    119700
accatagtgg acacacagtg gagtttaacc ttgacccttt acactctgtg gcctgctccc    119760
aacattgacc agagtgttat aattatctca tgttatctta ggtgcctcac tcctgatgcg    119820
gaagctcgtc cagatattgt agaagtcagt tcgatgatat cagatgtcat gatgaaatat    119880
ttagacaact tatctacatc ccagttgtcc ttggaaaaga agctagaacg ggaacgaaga    119940
cgcacacaaa ggtatttat ggaagccaac cggaacaccg tcacatgtca ccatgagctg    120000
gctgttctat ctcacgtaag tgcaaatatt tcaatcggtt catgatgcac tctaatgggc    120060
```

-continued

```
tgtctgaagt tgttcatgct tgttttaagg aacattcatc aaaagttaga aaaatagtta    120120
catgcaatat tgcagtagta tagttacata tttatatcca tttctgtatc ttatatacaa    120180
attaaaataa atataactga ccttcctaag aatgaatcca taatttattt tattttttgca   120240
aaaatcgagg tatcacaaag ttctcttagc gaagtttaag ttacagactg taaaattagc    120300
agtgaatgct tatatttaat ttcttcagca atctgactgc aacttttggg aatatgtatg    120360
aatatgtgag ttaattcaga gaaggaaata acatttgcct ttaaaatttt tcgtattgta    120420
ctttgcaatc tctttcattg ccatttgtgg tattaataat gttgccatgc ttcaaatcag    120480
aatatgtctt atttttcttg ccaagaacct ttagattgtt ttgatattta agtatatttc    120540
tgaacattgc ttggaaaaga gatgccaaag ctacaaatat ccacatgtgc aagcaatggt    120600
gccagtgatg ctcttgttgc tgtctcttat tttctttctt ctgtgtcttt gttgcaatca    120660
caatcagtgt tctgttgttt gctcatgctt tgggcctcca cccagtggcg acctggtaag    120720
gggactttca tcctttttt ttttttcctg ttctgggggt gggcccaagg caattggatc      120780
ataaaactct ttcttagggt acctggtcat taaattcctt cccaggatcc taaggacctg    120840
ctccatctca gctggtaaaa ttatgtatga agttggtctc aaagaggcag ttctgatttc    120900
ttgaataaca gtgttttccag tgaactgctt tctgaaaaga aggaaagtac tactgtttag   120960
tgggtttgtc ttaaggtatt tggaatccag aagttgaaga ctgaatctag ttttcatttg   121020
ggaaggaaac tctttcatct tcattgcctt aaatgctgag cctagatgta attttgcaga    121080
acattccatg atgattattt aagttatatg tttatgtaaa ggagcatata acttggagtt    121140
atagccctta ctgaacacag ttaaatctca gaagggagt tagagctcac tttgcttttt      121200
attttactac ctgacttcat aataactagg caacaatgca tcattctatg tatgtcatgt    121260
tgcattctaa atagagtatt cctagtagac taaaatgcaa gagatttagc tatttctata   121320
tatcttaggt atttggggcc ttctattatt aagttctgca ctgcagagtt acttagctta    121380
tttccagttg tatgtgaaag agtcattca tattagattc atgtggctga tttggggctg     121440
agtggcatta gttacaatc taacagcaga aagtctgtta tctttagcaa acacccttga     121500
gaaggaccat tacttatcta tttatttaca cttctcagct taaaaaattc tttattatgg   121560
aaaacttcaa acgtttataa atgcaaagat tacttcctgt acccatccca gcttcaacag   121620
ttagctatta agggctaatc ctgtatcatc tctattccca cctacttcct tccttcccca    121680
gattatttg aagtaaatcc cagataccat ataatttcct ctatcagtat ttccatatgt     121740
gtttggagag tcattttagc tttagaaata tagatttcag gctatcgcca ggtaaaataa   121800
agggaaagct ctgaaaccaa gggagggatt ttaatgttcc agaggttgta tactcatccg   121860
taaattaagg ggtagaggat attatctacc tcagagagta ctaggataaa tgagttaatg    121920
tgtttgaata tattgtatga ctttaaaagt ggcataaatt gtaagatagc atcagttata    121980
taaatgagca tagcttttgt tagaagaata gtttgttgat ggaacttgtt aatctagtgc    122040
tgacttgtcc aagtagtctc tacattaaat ccttatgtca ggcatacagt taatgcatat   122100
atattagcac ctgctgctag ccagcctcag tgccctcatt gagcattcag gttttatgg     122160
accatagaga aatgctttac ttcaaagcaa agtttatatt cctgctttaa atagtcatac   122220
agtactttct cctttcgcac tatttttaagt ctactgatac attttcattt caaggttaac   122280
caaatgttaa ctaaaaggaa aaaatgcagc tttattaaag aagcaagaag gaagattgca   122340
tttcatcaaa agacagtatg cagttaattg gcatttttct cagtggggac caattattat   122400
```

```
ttttaaaaac ttacatctac accattgctg aagaaaaatt ataggtgtaa aattttatga   122460 ctctttttt  cttaagcagt attatgatta tctcatttca gatatactgg aaagttctcc   122520
cagagcagtt attatcaata atgcagttac acaatccagt gataaattat agtcaaggga   122580
aagagaaatt agtgggttca gtagaacttt atgaattccc aatatcaata agggatcca    122640 ctgtgaatta ctgaaatttt gcaaattagt gggtaagcaa acaattgata agaaacatta   122700
aaggtttcta tttcatgggg aagtattcta tttactttca tattttagtc tattcttaat   122760 tatgcaatt  tttatagtgg cctagtaaac gtaagtacta atatatattt tagaagaaca   122820
gagaagtctt cactaaaaag ttcactctat gtactgtggt ttacccacta tgaaagtgaa   122880 ccaaacctt  ccttttgaag aatgttttct gattcttata acttaaaata agagatcata   122940
aggagagcat agagttgaga atgataagaa tcatgtagag taaaaggaaa taaaatttta   123000
acttaaatgt gtaataatta gaatattgtc atgtagaggg tattgtggca tcataatagt   123060
gaaaatcgtt atccatgttt tggcactgtt cacagtgtag tgaacacaga gaatcattac   123120
cctttcgatc ttatatccct ggcagaaaaa tcaattaaag acatttctga agagtctact   123180
gcttatatct tttccaacaa atacaatagt gtgtattaaa gaaattcagc ctgacaaaac   123240
ctggagaatc aatggaaaac ttcaattcca ttagaattat tgggatttta tagagacagc   123300
tttatgctaa catttaaatg ggtgaaaaaa gcatatttct atgtgtacaa atggagcaga   123360
attgagtgtt ccagggagac tgaagagaat taatgagaga agcatgctgt cagtgtgaga   123420
cttgcaggaa tcacaactac ttttccagtg atatttgaca ggaagtttat cttcaccacc   123480
cctatttaaa ggctgaatga tgatttcttt ttactagttt aataagtttg ttcagtttgg   123540
agaactgctt tcacatctat aacagaaaga gagaaagatt gaaaatgcct gtggtatata   123600
attaataatg aaggaacagg gatttgttgg atgtcttctg aatgtaaggc attatgcttg   123660
gtatagtgaa gcttataaaa aattataaac aatgaccca ttcatgaagt aactgataat    123720
ctacttggaa agacaagata gatgtgcata tgcaggagga actttctaat gattccgaac   123780
attttgggta aataaatgag atgagggaaa tgaattaatg aggcctaggg aggatctcag   123840
agccaaacaa agataggtc  ttgataacta aataaggaag tcactcctgg atggaaaaga   123900
ataacgttaa gtgcagaaac tccagctcag ctcacttaat actaagaatc aaacttagaa   123960
atggaattgt tttatgttt  aattgcacaa ggaaagggaa atcaggagaa gttaaaagac   124020
ttgtccaagt tcatccagct agttagggac agccccagga ccaaaaattg ggtctgctga   124080
ttgacaatgc atattttat  atgtgtagtt tgaaaagcct ggggaagtag gctggagcta   124140
gatgatggat gtttgtgaat acctcattaa gctgtttgaa ttaaatcctg tgggtaacgt   124200
ggactaaaac gttgaatttc tccaaaatac ctaacaagca aattgacaaa ctatgaacta   124260
attctttctt tttttttttt ttttgagatg gagtctcact ctgtcgccca ggctggagtg   124320
cagtggcaca atctcagctc actgcaagct ctgcctcact atgggctaat tatttcttat   124380
tgtacatacc cgcttttaa  tgttttttac tccgcagtgt tttccattac actcctctgt   124440
cctggtttct gtcttctctc tttgaatact cttcctcatt ttctcttcca tcctggcct    124500 tttaactta  aaggttctgc ctctcttacg cttcccttgg tttccatcta gtcccatggt   124560
atttcatttc atatgaattt gggtaaaaat tggtgtgcaa gatggaaact ttattttcta   124620
taattatata tcattttgtt ttgaacccct gtttgtgctg gtagcagaaa atggtagtag   124680
tagtcaggat caattatgtc ggtctctttt ggtctaaaag tttctttgcc atcccaaggg   124740
ttctcttctc cgtgtcctct tccgaagatg gcaacagagt acaggagaaa gcttaagcat   124800
```

```
ccccatgtcg atgagagagg ggcaggggct ctggacttct tctattggcc cctgctgaac   124860
ttagatgaca tgaaccctgt gattttggga tgctgacctc tgtccttatt aaatgtttat   124920
ggcatctgta actcatggcc tcttttatca tcatggctta aacccaaaga attacccatg   124980
atgccccaac tctccccttg gggttactat ttttgatcct ctgagtcttg attgtgactt   125040
tcttggcatt cttagtttaa gcagcctact ctgtggtcct cagtgcagtg atggccaagt   125100
gaactcacct gccagcccca gagctgtctt ctacattggc acaagacaca tgggggcttt   125160
ggattcccat ccacaccaca cacagcccat ggggaactca ctggcactag ggacccctat   125220
ctcagcccca tcagctccag tgccttcttc atccttttct attcttctgt cccaggtgcc   125280
tacaattcaa ttattcattc aacaagtatt tactgagtgc ctaataggtg tcaggcacta   125340
tgtgtacaaa gtataccaca gttagcaaaa tagacaaggc ctctgctctc atgggcctta   125400
tgtatatagt gttatgatga tcatgaagct tcttcaaagc tcccggtctt ttctgtctgt   125460
gccccagttt ccccctcaaa ctctccgtgt atctccatca acagcccaac tctaatccca   125520
aggttcgcat ctgctggagt ggatgtgaga aggaaaaaca aggaggcttg cacttgctct   125580
ttcattttct cttccttctg gcaggctctt attttgagct ccagaagaaa tttccagttc   125640
gcacctttct gccagaagct acccttgcat ctattatatc cttcttttc tccaggtatt    125700 cttttcccct gtcttctcct gggtctataa atctcagcct cataaactgg tcttaacagt   125760
agaagaaaag agctctggag aagtgcacaa aattttctgc gaaggcaaaa tatgttggga   125820
tgtgtttcgc aacataattt ccacacccat ttgctggaga tcaccaaagc tgcctgtctg   125880
atctcagtct ctctgtgtgc cagacctata ttttgaaccg aacattcacc tgcatgtcta   125940
acaggtactt atgctcggca agtccacagt gaatggattc cctcccttg atcagccatg    126000 ttctgtctcc tcatatcacc ttaattgtaa ccttgacatc ttcaattcac tctctctgaa   126060
atcctgtatt cattttgtta gcaagctcta ctaattctgt ctttgaaatg tctggcaaat   126120
ccatcttatc ctttcagttc tcattctcag tatcttgcat tatatcattg caagatccaa   126180 cttttcttgtc tctagttttt tccttacttc taccaagtga ttcagtcagt atatcacctc   126240
tgcactgtcc actaggggcc attaaggaat gtgtgtactg ggggtggggt ggtataattg   126300
ttgtttatca ctgttagcag ccagggatgc tgatatgtca tatacattga cagtcctgca   126360
caaaatgtga gaaacagaac gagcagtaga tacatattca gatatttatt gcaaggaact   126420
ggcttacatg attgtgggga ctgacgaggc aagtgcaaaa tccataggga tggttggcag   126480
gaggaacagg ctggaaatct tggtcatggg ctgaagctgt tttccacagg ctgaatctct   126540
tcctcatctc agagatgcct cagctccact tggagacct gccacctgat taaatcagtt    126600
ccatccagat tatcagggat catctccctc ccttagccat cttccacatt cctacccaaa   126660
ctattttcca aaaaaaatat ctgatcttgg taaattgttt catgcttatg acaataagta   126720
aatgctcatg tagtgagtcc taaaaatttt ctctaagctt ttggtgaatc taaaaaaaga   126780
ttcctatgat aatttgatat tgccagagtc aaaatatggc atacataagt gtcatcttaa   126840
attccatcta ctttggagga gcaggctggt agagcaatta ttagcaaata ttattttta    126900 aattcacaaa ctgttcataa cttcacttct tgtttataaa attcttattg tagttttcta   126960
atctatgatt tttagcagac attgacagat actgatattt tcataaatt ctcagatgtc    127020 tttaaagttg agcatataag aattgaacag atatgtaagc atctagattc tcattttttt   127080
aatgcaaatt aaaaaatgtg ctatttattt atctgggttg ctttattttt attataccat   127140
```

```
atgtcattta caattgctga gcacaccact aaagtcatgt gtctgcaatc ctctgctagg   127200
agattaaatt aagccatgta gaaaatgatg tatttttaaa ggacaatatt tttgtgaaca   127260
tctttgcttt tattgtctgg ttaattgttg actgaatttc tcccaaggct gtgaaaatgc   127320
tacaagtaat gatgtaggaa gagaaaatatc aggaaaaacc atgacttgtt ttggaaatgt   127380
tctatgctca ttatgttata tgaaaataaa gcaatgcctt ataggcttcc tcacaaatac   127440
agacacaatt ctcacatcca cactacaatt ctctcttttt tattgacata taatttacat   127500
gtagtaaaat gtacacatct ttaggtgcct agttcagtgg cttttggcac atgtgtaacc   127560
tccaccccaa acaagagtta gaacattat ctcacctcag aatgttccct taagcctctt   127620
tctatacaat tctctgcccc aggacgtaga ctggtgattt ctgtcactat aaattacttt   127680
gcctgttgtt tgacttcatt taaatcaaac acatgttctc tttagtggct ggcttttttt   127740
ccatgacaaa atatctatga gattcaccca cgtggtgtgt attagtaatt tgttcatatt   127800
gctaggcagt gttaaattat atgactacac cgtaatttgt ttatctgtcc tgttgatgaa   127860
cacttacgtt ttctccagat ttggaatttc ttaacactgt tgaaaaccta tttacaaaaa   127920
gacccataca aaaatgttta taactttttt ctcttagata aagacctaga aatagagttt   127980
cagggttata ggtagttgta tgtttaactg ttaaagaaag caccaaatag ttcttcaaaa   128040
ttgtactgtt taacactttc agaagcagta tatgagagtt ctagacgttc cacatccttg   128100
ccactatttg gtattgtcag tctttccgat tttagccttt gaggtgtaat gatacttctt   128160 tctggttttta gtttgcattt tcctgatgat caatgaggtt gagcacattt atgtttgatt   128220
ttagctattt atatatcttt gtgtatgtgt atgtgttaaa tatctgttca aatctttcgc   128280
ctgtgatttt attggattac ttgtctgttt ttgttgattt gtaggagttc tttatatatg   128340
ccagataatg agcctattgt caaacatatg tattgcaaac attttgtata gtctatggct   128400
tgcctgtttt tttaaattaa tgacattttt tggataaaca gaaaatttta attttgatga   128460
agacttattc atgtaattgt ttgtggtggt cagtgttttt tgcctctttg taatgaaatt   128520
gttgcctacc ctaaggttgc aaaaataaga ttctttatat ttttgtaaat gtttagacc    128580 tatgatccct tttgatttaa ttttgtgtat agaataatga ggagattgac ttttttgtttt   128640 tttttttttgg tcatttgggt atccagtttt tccagcatca cttctttaaa tgtctagtct   128700
tttcccatgg attttgctaa gcatctttat tgaaaattgc ctgacaatat atatgtgat    128760 ctacttactt ttttctttttt tgttttataaa tatttttaaa ttttaaattt taagttttta   128820
attattttga gtacataata attgtacata tttatggtgt acatgtgaaa ttttgataca   128880
agaataaaat gtttaatgat caaatcaggg taattggggt atcagccacc tccaacattt   128940
atcatttgtt tgtgttagaa acattccaat tgcattcatt tagttatttt aaatatacaa   129000
taaattattg ttagctatag ccaccctatt ttgctaccaa acactaaatc ttattccttt   129060
tatcttactg tattttttgta cccaaccgtt cctttttat cccccctctc ctctcctctt   129120
cccagcctct ggtaaccatt attccactct ttatctccat gaattcgata cttttttagct  129180 cccacgtata agtaggaaca ttttgtattt ctctttctgt gcctggctta tttcacttaa   129240
cataatgtct ttcagttcca cccatgttgt tgaaaatgac aagagttcat tctttttttat  129300 gactgaaaat tttcccattt cttttatcaat tcatctttttg atgggtactt aggttgattc   129360
caaatcttgg ccattgtgaa tagtgctata ataaaaatga gcatgcagat atctcttcaa   129420
catacttatt tcttttcttg tgtataaaata cctagcaatg ggattgctgg atcatatggt   129480 atttctatttt ttagtttttta aaggaaactc catactattc attatagtgg ctgtactaat   129540
```

```
ttacattccc accaacagtc tgcaagggtt cccctttctt gcaggtctat ttctgaactc    129600
tattctgttc catggattat atgtctcttc ttagaccaat accacaccgt tttgattttt    129660
gtagctttta aaaaatgttt taattttaat tggcaaaaaa ttatatatat tgtatacaac    129720
atgatgtttt gaatatatat acattgtgga atggcttaac ggagttaatt aacatatgca    129780
ttaccacaca tatgctttac cacataacat atgcattacc acacaatata attttgtgg     129840
tgagaacact taaaatccaa tctcagtatt tttcaagaat acagtatatt gttattaagt    129900
ataatcatca tgctgtgcaa tagatctctt gaacttatcc tcccatctca ccgaaactct    129960
gtatcttttg atattgtagc ttttaataa gtctcaaaac aagccctgta agtcctccaa    130020
ctttgttgtt ctttgtcaaa tttgatttgg gtgttctagg tctgttgtat ttccttatta    130080
attttagaat aagtttgtct aatttcttca aaaaatcata cctacaattt ttattttac     130140
cccttgtttt aacatggaga atcttggcaa cattttaaaa aatcagtctt ttattttact    130200
tattcaacaa aatttattaa gcatttattc tttcctggga cctattctag tattctcctg    130260
atacagtagt gaaccaaaca gccacagact ccctccttca tagtgagaga agacaaaataa   130320
tagataaata aaactatatt taagtgctat gaacaaaaat aaaagaaggc aaggtaatag    130380
aaagtgattg tagacacagg gagacaggct attttaaata gggatgtcag tgaagggctt    130440
tataattaca tgacatttgg gcagagacct gaatacagtt gacctttaaa caatgtgggt    130500
ttgaactgca tgaatccact tatacatgaa ttttcttctg cctttgccac tcctgaggca    130560
gcaaaaccaa cccctcctct tcctcttcct cgtcttcagc ctacccaatg tgaagatgac    130620
aaagatgaag acctttatga tgatccactt ccacttaatg aatagtaaat atagtttctc    130680
ttctttgtga ttttcttaat aacaagctag aggaaagaaa atgttattaa gaaaatcaca    130740
aggaagataa actatattta ccatatgaca tatcaagtat gtattaattg tttatgttat    130800
tggtaagctt ctagtaagca gtaggctatt agtagataag tttttagaaa gttaaaagtt    130860
atacatagat ttttgactgc atggagtatt ggtgcccctc actcccatgt tgttcaaggg    130920
tcaactgtac attaaaggga taacctctgc aaatatctga aggcacaaca ttggtagcag    130980
aaggagtagc atgcccaaag atcctgaggt aggagtgagc ctgccaagct cggggaacag    131040
caaggaggcc tgtgtgtcca gcgtgcggtg aagcagggag agacagttgg acatgcaggt    131100
gccatagtcc ctggcatgca cttgagtaat atgagttctg agcaagccaa ggtggcacca    131160
ctaggcttta aaatgatata ggtggccgct gagtaggaat aaaccactga gagccaagaa    131220
tgaaatcagg gaaattggtt aagaagagat tgcagtgggc caagcaaaag acaatggtga    131280
ctctttttct tgacttttaa ttctttctct actggcaatt aatcagtttg gaattttgac    131340
aacatgtgca aaatgtgcag tttaacaaga actagacctt tccttatgta actctgtgtt    131400
aaaaatgaaa cagtcaatga ggttctaatt tggtgtttca ttcctgttga taaccactca    131460
tttctaattc catactcttt aattccttaa gcattggtaa atttcaatga cattgttttt    131520
ttgagaaaca aaaaatttct taaaacttgc ccacttgatt gttctctgta cattgttcct    131580
tcccttttcct ttcctttccc tcccttttccc ctccccctccc ctccccttcc cttcccttgt    131640
cttttctttt tgagatacag tctcactctg tcacccagga tggagtgcag tggtgtgatc    131700
ttggctcact gcaacctcca cctcccatgt tcaagtgatt ctcctgcctt cgcctcctca    131760
atagctgaga ttataggcac gcaccaccat gcctgtctaa ttttttatatt tttagtagag    131820
atggggtttc actatttggc caggctggtc tcaaactcct gacctcaaat gatcggtcca    131880
```

```
cttttggcct cccaaagtgc tgggattaaa ggcatgagcc accatgcctg gcccattgtt    131940
tctttctttt tttctttttt ttcttgagac agagtcttgc tctgttgccc aggctggagt    132000
gcagtagtat gatctcagct cactgcaacc tccgcctccc aggtttaagc aattctcgtg    132060
cttcagcctt gcgagtacct gggattacag gtgcctgcca ccatgtctgg ctaattttg     132120 tattttagt agagaccagg tttcaccttg ttggccagac tggtctcaaa ctcctgacct     132180
caggtgatct gtctgcctca gcctcctgaa gtgctaggat tacaggtgtg aaccaccacg    132240
cccagccccc attgtttctt ttaaatgtta aatagaatta cctgatcctg gcctcatttg    132300
aaatgctttt aaatatattg gtatatacat ttagttctat tggcatgtta gtctgctgtc    132360
ttggaaaaac atggtggtca gtattgttgt gatggaccag atcttctgta ttcttaacaa    132420
atgataattt cagattatga cattgttttc cttctcctct ttgttagtat tattccttct    132480
agaaaacctg tatttgagtt aaaagtgata gaaaatccac tcatttctga tacagtacta    132540
ggttagttat gggataacag tgaaacattt ttaaccataa taaatttgat actggagttt    132600
tagattgaat tgtaatgacc aatttattcc ctaatttatt taatttaatc acagctcatt    132660
aatatgtaat agtgctttta agacgttcta attaagatag tataataatg agataataac    132720
tatgtcatga cagtaaaatt tttagctttg tgtaaatatt taataagttc aaaataaata    132780
agatccaacc taaagagaat attttcttta ttatataatc catataaatt agttatttt     132840 agggccccaa acaccagtt tttctggttt agatttaact attgctctct taactgtatg     132900
tagagaatgg gagaagggaa attcttcaag attccctgat gaaaatagac gatgttacca    132960
tccaaaccat tttgggaaag ctggacacag tggtgtgcct ctgtatttcc agctactcag    133020
aagaccgagg caggatgatc ccttaaaccc ggaggttcaa gaacagcctg ggcaacatag    133080
tgagaaccta tttctaaaaa acaaacaaaa actaactttc aggatcaaag attaaagatt    133140
tccatctacc actgggtagg gggtgggacc aggctccagg cttattccat cagcccacct    133200
ctctgatgtg gcaaagccaa gtcttccata gggaggcctg gagaaaaggt tcctatctca    133260
ccactacagt gagcagttca ctcagctatg gtcagtcca caaggttcct taatcatctg     133320
accacactgg ctgattttta aaaatatacc ttaaaatgta gggactaagt ttatttacaa    133380
tagtatgcag tcaatggcct gtctcctagt ttgaattttc tttgtgcaat catccatgaa    133440
aagcatagaa tgcggtgcca ctgataaaag atcacctcag ctggatgaat ttctagcacc    133500
tggtagcact aaattgagat atttaagggt acagtttatt aacaaaacag atggaagaaa    133560
ctgggtaaaa atatacctaa tagaatatga atatttcaga acacaaagaa atagtgcatt    133620
ttttagagtt ctaaagtaaa gcatctatag gatatagctg ttgttatgct ttatatttat    133680
ttcttgattt tctttctctc ctaaaacttt ctggcaattt taaaaattgc actgatttta    133740
ataaaataga tgcccttaat tttcctactg tagcagttaa tttgggtaat gtcagtctgt    133800
tactgttaga attgctattc aactgaaaat gtattatgat ctgctgcaca cataaaaata    133860
ttacattata atgcgcaaaa ccgagctaaa cataattgtg ccaatactag cgtggtgaca    133920
ggaagcatct tctataatgg tgctgatttc catatcagtg ataattttat tgtgtgattt     133980
gcgttgtatt ctccttgccg ccgtattgat atccggaatg tgtctatcca ttcctaggat    134040
agatgcatgc agatgccaaa aaactagtt aactccctct cctactcctt gaaaatctct     134100
agtaattaga aagtgaaaaa gattatagca gccaaattct gtctccaaaa actttgcctt    134160
ttttcttgcc taaatccctt taataggtta atgtacttgc tggatgtgtc ttctgaggac    134220
aacttaatgg ctcaactatt tattgagcct ttgctatgtg taaggcattg tgcaaagcac    134280
```

-continued

```
taaaggattt aaaatggact aaagtgcccc cagttcttca aggaacaatt ttataaagag 134340
ttggatactc aaatactcac agtgaaaaac tccagaaatc acagtaggga aaatgtgtgg 134400
catatggttt atggcaaggt caaaaattat atcaattttt ttttgaagca aaaactgctg 134460
caagggattg ttatagaaat atatatattt tttttttttg agacaagagt cttgctctgt 134520
cacccaggct ggagtgcagt ggcacaatct cggctcactg caagctccgc ctcctgggat 134580
catgccattc tcctccttca gcctcccgag tagctgggac tacaggcgcc caccaccatg 134640
cccggctaat ttttttgtat ttttagtag agacagggtt tcactgtgtt agccaggatg 134700
atcttgatct cctgacctcg tgatccacct gcctcagcct cccaaagtgc tggaattgca 134760
ggagtgagcc accatgcctg gcctagaaat acaaattttta aacccaaact atccatctat 134820
attatcatat ttttatgcat acagagtctg aaaaagcatc tctctcagat tgtaaattcc 134880
cctttatcag aatttatgca aacagtcaat tacccgtgga tgaaattttg gcagttacaa 134940
gtgactattg atttatgacc caattggttc ttgggttttg attgcaagtc cagcgtcctt 135000
aagtctcgaa ttgccttttt cagcggggac tccagcttct cctgactctt catttgttca 135060
aagaaaaatg ttttcctctg atgttttatc catgcctgtt cttaagagac acaaagcctt 135120
tgttaaagtt ttactagttt tagggatatt tgaattccag catcttaatt gcatcgacag 135180
aataaaaagt tttctcaatt caaaaattct ccttcatctt ttttcaacct tggtaatgtt 135240
gacacatctt gggtgtaaag tcctgaaaag gttgcagatg ccagctgtgg tcttcaggat 135300
agggtagaag atgatttact tagaataaaa aaggtcataa gaaggaaaag gccttgaatt 135360
gggtttttac ttctgtgtaa atttctaatg acttcagttg aggatagtta gaggaagaag 135420
ggttttgtgg tttgggacga agaaaagagg taggcatgga agaagttgag ttggttttgc 135480
aataaagttt tgagccttag aaagagctcc tggatttggt atcagggtt gagtgtggca 135540 gagctgaggc tggacttaga agcccgatac tagcctaggg cattgaaaaa atttctgagt 135600
agcatatatc ttttgccaga gagcggccaa agcatttcct gtctcaggtt gtaagttagc 135660
caaccagggt ggacctcaga agcagaaatt aacaactcag agtcataaaa cagcctttga 135720
acattggatg tactaattat ggaaaatcaa agttaaaata cttcttcacc tgcaaattaa 135780
cttcaacaaa acaaggagct tggtgaaact ttgaagaatc actgaaaaga atctcaggga 135840
aaagaaataa acagcaattg atcagacagt ttgcaatgca caaatgtttt ttgtatttta 135900
aaaatctttt catcttacct atagaacata aatatatgaa agcttttaga ggtttatttc 135960
tgattctagt tatccctaag atcttaggtt ttcttcatct gcaaattcta ttattatgga 136020 gttttttagaa acctgtgcct tggagctgtg tcattttact gtaggaaaaa aataaaaaac 136080
acataaatct gaaataaata aggctgtctc tgaaatgagc atcattggag ccttttttagt 136140 caagaagtgc taggtaattt gtgactaaat catcttggac acaattcata gagggaattc 136200 tttcccctttc aataaatgca cctttttctt tcttctcaca ctctctgcct gttatccttt 136260
cctccatcac agcctttctt tgtctttttg tctacctgat ctgtagcttt actttgccag 136320
cactgtttag ccccacggcc taaaaaggct cttcacgctt gctgcgaata gtcccataca 136380
atgaacatct taggagttgc ttgggtaaag aaacaagtgg tacttttta ctgattcata 136440 gtcattcctt ccgcatggtc tttctcttag aaaaatgaaa acttccagca tcagtggcat 136500
taattaatta attttttattg acccttgaga cataatttt gcagtttcta atactattat 136560
ttagggaaat atggaattac acaaccagat tgatgacttt gtagtgctat cataatggaa 136620
```

```
atgcatccat ccgtttggga ggattcagga ggaccctgtg gctagttctg cagagagtgt 136680
tcaagccagg cagtagtgta gagtcccaag tggtttgtaa gttctgttct ctgtagctcc 136740
ttttttttgga aaaccttgcc tctcactctc catggcctgg ctttgtctgc tactaatttt 136800
cctggagttt tgaagagaat aagccttact tatttgctgt ggtactgaga ggatttgata 136860
gcaaatgttt ttgaaaaaac ttaagggaga gaaatttctc ctaaattaat atagtctatt 136920
tctagaagta catatttccc cccgctactg ggttatatgg gccttttcta ctgaacactc 136980
ttgccacttc catcctttt gatccaatgt agcttataga cctgcatctt tttgtattta 137040
tggactgaat agattctgta acaggtgtat aggtggaact actgatgcgt cttctgcatc 137100
aaacatttat attgatattt gaagcagtta atatatgttc taacaagatt taggtcctat 137160
agaaggaagg atagagaaag aggctatgaa aaactgaatt tctctttcca ggagaccttt 137220
gagaaggcaa gtttgagtag cagcagcagt ggagcagcca gcctgaaaag tgaactttca 137280
gaaagcgcag acctgccccc tgaaggcttc caggcctcct atggtaaaga cgaagacagg 137340
gcctgtgacg aaatcctgtc agatgataac ttcaacctgg aaaatgctga gaaaggtact 137400
gctagtggca gtgtgtcaac gtaggtactg ctagtggcag tgtgtcaaca tgaatgtatt 137460
ctggactcct tcctgtttca agactcattt gcttttttat tgttttatt aatgtgcaga 137520
tacatattca gaggtagatg atgaattgga catttcggat aactccagca gctccagttc 137580
aagccctctg aaagaatcta cattcagtaa gctttctgtt atcaatttgc tgtttgtggg 137640
attccggaag acagtggttt ggaaatcata cttgagtcaa gcaaatatca ccatatacat 137700
aacccagtgg tttgtttttc aggtgcagtg ctaattagga cagatgtgtc tgtctctctg 137760
acagagccca aaggttagcc agcacagtgg ttttatattt tctcagctgt caaatgaata 137820
gttttactat ttctaccagc aattgcaggt tctaactaga gagtcaagat atctaacttg 137880
gagacagcca ataaccaca ggagtaatgg acatgacctt ttatgagcct gttggttaga 137940
tgaattcaaa gcctgtagaa gaaattggtc ctggtataga ctaattttg tgcaattta 138000
tttatataaa tctaaaggga tgtgttacat ttaaaacaat aaaataaaag aaatttttt 138060
agagttatta aaaatatgac atataaattc cgtccataat gttaatcttg actcttaatt 138120
taaaacagta aagaaaatag tcatactggg atatgggaaa gaaaggaaa aggtatattt 138180
agataaagtt taaagattat aaagagagat agaataaaat acatggaaca aacctgaaac 138240
ttaaagagaa gttaaaatag aaaatgaagg gaaacaattt ttttaaaaaa gagtaagttg 138300
ataaaatatt aaaaaccata gatagaaata ttctgaaata aattaagtga aaataattct 138360
ctctcctcag tgactatact atgaaaatct cataaaagaa catttaaaat agcttctcta 138420
aggatcaaag tagaaccta aggatttagc tacattcttt gtccttttcca aacttaattg 138480
gtccatcgaa atgatgatta gatgttccat atttctgggg acaaccccag ttttcaatat 138540
tctgtcctat tttctccgta gatccctgcc ttctaggtgt attaatttgt gattgggaaa 138600
acatgaagct catatgggaa aaaatattta tgcatataaa catgtataac aaattccaga 138660
agaagtttat tactgactgt tttgagataa gttcagtgtt ctatatacct ggcagcaatg 138720
gtgggagggt tagtggggag gtaggaaaga gatgcttgac ccttaaattt gcatatggta 138780
acttggcaag gatggttatg acattttatt gcatgacatt ttattgtgtt ttgttagata 138840
ttaataacag ggttgttttt gtttgtttag cacatttgct ttagagaaaa gcccttaaa 138900
caaacctgac aaataaataa caatttgtaa catattttag ttcatgcttt cataatcaaa 138960
gacaatttt acagtatgta caattgctca ggtaaccgaa attcagtatt gtttttttgtt 139020
```

-continued

```
gttgttattg tggtttacca tgaataaagc catgtttgtt tcttgaatgt tgtttgactg    139080 cttt catgct acaatggcag cagaattcag ctgtgacaga catagtatgg cttgcaaagc   139140
ctagaatatt tcctacctac catttacaga gataagtttg actttagaac aatatgagag   139200
tgtttataga caaagccatt catggaatat atatattctt tattattttg aattttataa   139260
aaaacttatt taaaattttt tctgatatat aatatatttg tacctattta tggatacttg   139320
tgatattttg atatatgcat agaatgtgta gtcattaaat tatacattgt atgggtaatt   139380
cagatattga tcacctcaaa catttatcat ttatttgtgt tggaaacatt tcaaatctcc   139440
ccttctagct atttttaaat atttaaacat tttctttatc cattcatctg ctgagggata   139500
cttagtctga tttcatatcc tggtggttgt gagtagtgct gcaataaaca tgagagtaga   139560
gatatctttt tgatatacta acttcccttc ttttggatat ataccagtag tgggattgct   139620
ggatcatata gaagttctat ttttagtttt ttgaagagaa actttattta tttatgtatt   139680
ttaagttttt tttttttttt tttttttttt tgagacgggg tctcgctctg tcaccaggct   139740
ggagtgcagt ggcacgatct tagctcactg caacctccgc ctcctgggtt caagcgattc   139800
tcctgcctta gcctcccgag tagctgggac tacaggcatg ctccaccaca cccagctaat   139860
ttttgtactt tttagtaggg acggggtttc atgttggcca ggaaggtctc gctctcttga   139920
cctcatgatt catctacctc ggcctcacaa agtgctggga ttacaggtgt gagccaccac   139980
acccggccga aacctttat actgttttcc ataatggcta cactaattta cagtcccacc   140040
aacagtgtat gagttccctt ttctctgcat cttcaccagt atttgttgtt cagtattgtt   140100
ttattaaaac ataaaaaata aaagatttgc agaggaaata atgtaaagtt atttctatt   140160 tctcgtctca gacattttaa agagaagttt tagtgcttca ggaggagaaa gacaatccca   140220
aacaaggtag gtgcaaattg aactcctaga aatatttttt gattttgcag agctgagtaa   140280
taactcagct gaattgaaac ctgatagcca gaagtttcca tgtgcctgcg gaaataggag   140340
ttagagctta cttgcccaga actgtttata gttcaccaag tagcatactg aaacaggtac   140400
tgatcttgga cctgggtctt agtctagctc tgccttttc tagctttgtg accttgagca   140460
aatcagttag cctctctgag ctcaagggtg ggccggcggg gtagggcagc tgtgctccat   140520
gaggtcatct ggagccctgg tcttatatct tgttcttcca tatccccagg gtataggttt   140580 catcttttttg accaatatga cttatgagac cgcatcctac ctccaagcca gcaagaagaa   140640
gaaaggggaa gtagagacac ccctctttct tttaaggata tgaccgagat gttatgctca   140700
tcacttctgt tcacatacca ttggccagaa cttcctcata tgaccacagc tagttgcaag   140760
ggatggtgaa atatgtttga gagactgtct tttaaaggca aagcaaaatt gttattttgg   140820
gacagctagc tgtgtcagtg acagttgttt cttagagtag ggactgaaac aaaactatta   140880
gattgagcct tctgcaagtt ctcctgacct tcactggcac tgggtgagat tagagggagc   140940
agaaccttga ttacaatgtt ccagaggcag agataggagg catttaagaa gttgagaaat   141000
gagctgggag aatgagctgg tgggaatgt ttgatggaaa aggacctcct agaatcagga   141060
tgaactcagg gcatttggga cagaggaagg agaagagacc aatggagagg agaaatgaga   141120
gaggaaaaga gataactgac agtatacagt tgcatcatag accagagcca gaggagtggg   141180
cctggaaaag atgagtggca acgccttctt tgtgtctgga gaaggggagg tgaagataaa   141240
attaagctag tgaaataggg aaaggcagat taaggaagaa atatacttta tggtttctgt   141300
atattattat tattattgtt gagatagaat cttgctctgt cacccaggct ggagtgcagt   141360
```

```
ggcgtgatca ctgcaacctc tgccttccag gttcaagtga ttctcctgcc tccgcctccc    141420
gagtagctga gattacaggc acctgccacc atacctggct aattttttgta tttttaggag   141480 aggttgggtt tcaccatgtt ggccaggctg gtatcgaact cctgacctct ggagatccac   141540
ccaccttagc ctcccaaagt gctgggatta caggcattcg ccactgtgcc cagccagttt   141600
ctatgtatta gttgatattc taggccaata ttctagacag ctgagaggac tgtctagatt   141660
tgtggagtat attcagctag gagcagccaa tgttgagatg agaactgggc agagaatggt   141720
ggaaggactg ccagactgct ctgaggctgg ggcacctgtt gaggttgggc acatataag    141780 tggtgatgcc aggcagggct cttcagagct gtgggatgac ccccactcag gaggtggcag   141840
catctgtgta acaaaaggct aaggctgcga tgtgctatag caggcagggc ttttggata   141900 caagcaaagg agcctgactt tagctaactt atgtgacagg gggttcttta gacgtcattg   141960
tggggcttgt gtaatttaga ctctggagga tcaagcttgg gaaggcatag gagccagttc   142020
agtccctgaa gtctataaag gagacatttt tgggaggctt ataagggcac aggaactctg   142080
ggataaatga actcccagct tgtttattcc attctcatgt caccttttct taggattcaaa  142140 atcctgagag agagagagcc agattggcct ggctgggatc aggttcctgt ttactgcctt   142200
gaggagagct gagatccttg actagtccat caggggtgct tgctgaaggg agcaggtgtt   142260
agtgctgggc agcctcaatg gaaccacctg gatctacctc tggtttgag ggtgctggga    142320 atcacataac ataaatgaag ttcagaagaa cctgctcagc aaattcctgg gggattcagt   142380
taggtgacaa acgaaggttt ctatagacaa atcctttttct tgtttagtca aagatgcatc  142440
actgatacat ttatcttcaa atgaagatca ggaggagtta gggtggagcc ttttaatttc   142500 ctaactttt ttccagtgtt tctgggaata aaaacccaag gaaaacttat caacagggtg     142560
tatgatctat cagaaagata ttcgataaaa ccctgtaaga cctcatgacg ttctttagtg   142620
ggccaaagtg cagaggagtc atggtcagaa gtaatgggga gggcagggga aagaaaagta   142680
ctccaaaatg ccaaagagaa ccacagtggg tgtttgtggg gactggagat ctgagttaga   142740
agatattcca aaggatcttt agggcttgct agtacccaac attcctcatt cctcacttac   142800
tgactttcta ttgctaacaa agcaagtatt ttagttcaaa agtaaattat gatatatgat   142860
gtactcccaa ttaagtgagt tttatgttaa aatgacaatt tccaatcaga tgaatgtagg   142920
tatcttggcc ctgtcaaaaa taattctact atttttttaa aggatccatg gaaaattgtc   142980
ttatttgcac aaatccggtt gatgtccacc ccttcaaaac caaacaaaaa ccccatatgg   143040
tctatatctt ttagagcttg agatggcttt taaaaagcta gtcattaact aaatacttta   143100
taacaaattg gataagctag aatcagcaga aaggcaaggt ttaatctgaa gatcattgaa   143160 acagggtat agaacaagct ttaacttggg gttatgacca agtcaacaga tggatatgga   143220
aagtggccca tacattgaag ttgatgtttt ggaaagtatg ttccaaggtg aacaggacct   143280
gacctaaagc aacatttgta aaattgtgcc atgaaatgtg gtaatacagc gtgacatgcc   143340
accagggaac acaggtttgt ttaagacaag ctgtcttcct tcagggagct cacagcaaaa   143400
tgggaagaca agggccgact tcagaagaaa ataaatgata aaagacagcc tttgatttat   143460
gccaaataag aggagagaaa attaataact tttgactccc tcccaggtaa tccctgggc    143520 ttctctgaat taaaggaga caatcccaaa atgtatttat aattctttaa agaacgttaa    143580
atagagctaa agttatttgc agtctaattt gtttaggatt ttcctgggtt tctttgttta   143640
ttaatgtgaa atgtgaaccc atcctgcaaa atatttagaa gctaaataag aagttttgaat 143700 ataaagaag atagcaaagc tacataatag aataaaaata aattgaaaat caagcctgta   143760
```

```
gagggttttc ttttttctttt ttttttttcc tattctgtgc catgtataaa atggtataac   143820
aatttcaagg agaccctagg cagctctccc acttggggac ccttactgac tcttttaaaaa  143880 ggcccaatga gagaagtcac agggaagtac atacctgttc tgaccacagc ctccaaaata   143940
tagaagtcag acgtggccct ggctaaatat taatagtacc aagagaaagc ttaagcataa   144000
actcataact ttggtcagat atcagatatc aggagccaga tttaaaccaa ttgcttgcgg   144060
aaaaactaac gtaactccct aataacttag gatatgcttt tgggcaaatg agccagacaa   144120
atggatacaa catgagcaaa tggaactagg agggatagcc cctgcctgct cagaaaagtt   144180
ttgaagtctc aaggctggag aataatatta gaactggaag gcacctcgga atccaagcca   144240
tcatcagttg ataaaacttt ttttaaggaa tatagttaat ggcaagatca agagaggaat   144300
aagccccaat ttctttgaaa tttccaactt taatcatttt caaacttgat atgaaatctt   144360
ttatatctat tactatttgc taggaaggca ttaagaatgg gcttgacttt taccagtttt   144420
tatgcgagtt tcataggctg acctagtata tacacattga ggattctaat ccagcaagtc   144480
atagcatgtt atttcaactt ataaataaaa tactctgtat agtggaactt gataatgctc   144540
actgggcttt cagcctcttt atcacatatt ctcaggtcct agtaaaattt agtcattgtt   144600
ttacgaccat cttaagaacc ttcattcatt tgtttaattg atggatattt attactgtgt   144660
gccaggcctg cgccaaacta tgcctaattc atctttgcat tctccagggc acagtgtatt   144720
gcacataggt accaacctac agatacttgt taattaatag atgaatgact gtgactgtta   144780
tctcagtgta aattctttat ctcattacca aggactgaaa tcttgcctac tgacagcctt   144840
tgccatagcc acagcttaag gcacattttt ttttttttaa aggatcctgt tgctccggca   144900
accagatttc tccacgtctg cttgccttct gtcaccaagg caacaggta  tagttggcag   144960 gctggtttga gacactggat gtttgtggta tcagagatgc ctgtggttca caactttttt   145020
gattcatcag tgtatgcata attgtatttg gcagtgtgct cctaagtcta aatctttttt   145080
tttttgagac agaattttgc tctttcaccc aggctggagt gcagtggtgc catctcagct   145140
cactgcaacc tcggcctgct gggttccagc ggttctcctg ccccagcctc cctagtagct   145200
gggattatag gctcctgcca ccacacccag ctaattttg  tatttttagt agagatgggg   145260
tttcaccatg ttgaccaggc tggtctcgaa ctcttgactt caggtgatcc acccgcctgg   145320
gcctcccaaa gtggtaggat tgcaggcata agccaccgtg ccaggccttt ctaagtctttt  145380 atatgtgaag atgattgtgg atgtttgtga caattcagct tcatatttgt gactggaaag   145440
acctcgtgta ttttcaggac ctgtggatct tgcctcttaa aagcggaagt cttgcttatt   145500
tttacttata gctcttctcc ctccatcttt tttataatct gtatctggtt ttactttggt   145560
tgaataaata ctgcatgatt actccttgct agaatcaacc tggcccatct gctaatgtct   145620
cactccaaca gccttaaaac aaacaaacaa acaaacaaac aaaaaaacac atagtaagac   145680
cactttgttt cttttctgta atagttctat actttcctgg tttattgctc atttgtttct   145740
agctgttatt ggagtaggag gggatagcca caggaacatt atactacttt gttgtcatga   145800
taccaactct attaacatta tagataaata ggagaactca aagctacata atgttgctta   145860
ttcacacagg acatatttat gaatgtcact gcctgaaaga gagcttcagc tataaaatgc   145920
tcattagctc acatggtgtg gctgcagtag tttcggaagg cattaccttta ctattgtaag  145980 ccaaaccctct catttcataa ggtttaatta ttttttatcaa tatcaaatag cattgatact  146040
tttcacaatt gaattaaatg atggaataca cttataatgt atttgaaaat gttttctttg    146100
```

-continued

```
ttcagataca tatttcaagg aattcttatg agagatgata ttctagggct tcatcttctt 146160
cttggccagg actctgctgg caaaattatt atccaaataa ttcaccgtgc tcttgactta 146220
attcagcgaa aagtctattt aaaaaattac gatgctaatt cctagattat tcactttatc 146280
tgttagtgtt ttggggtgga aattgtaggc taacactcat tttcagcact tcagtttctc 146340
ttttgcctta ttaattccag atgaggtcac actaggtctg aagagagctg aagggatgg 146400 cctttttagaa ttctttcagc cttctatttt tctgaaattc ttccattggc ctgaagtgct 146460
gttggtcaat gcccatttca aaattttcag agaacacaaa cagtaatatg ttaagcctct 146520
tcaccagaaa ctatttctgg aatgttctct gtgtgaaacc actttggtat attttccagc 146580
ttgtgatacg atgggaacac caccctctgt agccgtaatg ctctattggg cataaacatt 146640
caatgtggtt caatctagag gcagacttcc cccaggctct gcataatttc aaccattgt 146700 ccatctgtga acccaacaat tgcatagtta aaagctgtca cttctggtga caatgagtct 146760
gttctatttt gaaatttcag atgactatat tttcttgcgg ttagtgatat aatttccaga 146820
gaaattgaca ttttatttc tgctatctct atgcaatctt gtaaattcta agactgtgga 146880
aactatttat tttcaccatc ccatctccag tgtctagcat ggtggctaca catcgtgggc 146940
atttaataaa tatttcttga atgaatgaat gaatgtgtaa ttgttctttt tgaagattcc 147000
ctaaagttta ttaaagagga atttaaaatt atataaagga atagcaaaag cggcagcaac 147060
tcagcattgt cagggtgttc tatgtcacat atcccactag cacacattat gcataacatt 147120
tgttaatatg taaaaatgtt tgaaacgtta gattcttcag gacatctgga atagtcatct 147180
tgcaaactca tcatgtgagt gattatcagc ttttcaagaa catgtataac ctgatggata 147240
caagtttgcc acaagttgca ttttttattca cttttttaaga gagtgggatt caggaggtat 147300
tgcaggttta gcagctacat ggcatgaatg taataaatgt atgaagacaa tgaccaacac 147360
ttaaggaagg gcctggacca cattgttaag tatggaggcc actgggcaca tgtgactctt 147420
gagcagctta aatgtggcca gtgcaactga gggactgaat ttttaatttt gtttaatatt 147480
aattaagatg taaataata agatttcaat ttgtatatgt tgaaataata ttttggatat 147540
ttttgattaa ataaaataga tttatttcac tttattcttt ttacttttg aaaatgtggc 147600 taccagaaaa cttaaaatta tgtttgatgc ttacaatcgg tttccattag acagtactag 147660
cttcatctag aagggtaagg ggcaaagtta ttcggaaagc atttgctggg gtatggcatt 147720
tgtgcaggca tacaaggaac tggaacagat gctctgctcc tcagctcagc cctggggctg 147780
tcctgcctac acatgggcac tgctgtcatc atgcctcttt tcaaactttc tgagggcagg 147840
atcagcttca tttctttttt taaacatgct ccttatctca ggttagggaa agtatataaa 147900
ctgttaaagg ctggcaggtt ccatttactt ttcaaggctc tggaaacttg agctcagaat 147960
ggaacagaat atattatgag atcaagagag tgttagcctg gtgaggatca agagggaatg 148020
gaaaggaaca gggaagaaac tcataggtgg atgcaaagat tttggtatta ttctagtgct 148080
taagttgggt ggtaggtaaa tgagtgccaa ttttgttacg cttaataact taggtaggtg 148140
ttgcatgcat gtatcaaaaa ttctatgatt aaaacgaaaa ggttgggaca agagaattat 148200
cagccatgtt tacttgtatt tgaattccta tatttattcc tacttaacaa ataacctatc 148260
atgtgcctta tacctagtac atgtatgata tattttgtt ggatttcatt aagtttaaga 148320
atgattctta caacttgtca gggcacagat gtttcttatt tcattccaga aaactattaa 148380
aaacttggtt ctaggccggg cgtggtggct cacacctgta atcccagcac tttaggaggc 148440
tgaggcaggt ggatcatgac gtcaggagat cgagaccatc ctggctaaca tggtgaaaca 148500
```

```
ctgtctctac taaaaataca agaaaattag ctgggcgtgg tggcgggcac ctgtagtccc 148560
agctactcgg gaggctgagg caggagaatg gcgtgaacct gggaggtgga ggtttcagtg 148620
agctgagatc gcgtcactgc actccagcct gggtgacaga gctagactcg tctcaaaaaa 148680
aaaaagaaaa attggttcta gggtacagtg gaaaaaacaa ggctgaaggt gatttacaga 148740
tatccctggt ggggtctaag gccacctcca cagagtagaa gacactgaga ccaactcgta 148800
aaatgatcaa ataacctaga attttggggc aaggcaaaca agggatgtta ataacactgg 148860
caactttagg aaagataatt attttcaatg caaaaaacat tttataggag gaggtataag 148920 gtttttttg ttttttaat agagcaggga caaatcatag aaaatactat atataacatt 148980
ttaaatctta tatccttta gtgcaaaatc atattttgag tttaagtgta actagaaaat 149040
tattcaggat cctaaaattt aggctcttag tcatacttag agcctaaaaa ctgtggtggg 149100
acgattctgt catttgtcag tagaatgtca attgtactgt ttattgcaat atatttattt 149160
ccctcttaat taaactcttg agagcatctt gagggaaaat aatctctatt aatctttata 149220
atgtagacca tagcaagatg taggctctta gtttgtcaaa tccaagttga acaggtcatt 149280
ctaatggcct gtaattctat tttcagggac ttcactggag gaacaggatc aagaccaaga 149340
ccaggtaact tagtgttggt agcaataaaa tcaaacacaa ctctctaaaa ttcaatgtaa 149400
tttatgttac agtttcatat cttccccct tttatttctt cagctttgct gcctcttgac 149460
ctgcttctga agtgccacc ccacatgctc agggcccaca ttaaggaaat agaggctgag 149520
ttagtgacag ggtggcagtc ccatagcctt cctgctgtga ttcttcgaaa tctcaaagat 149580
catggtagta cttactagat cacattgatg ttaagcacac aatgggcaaa tgcagaatta 149640
tagttgggcc tgagatgtct gaacgatgct tgggtggtaa ttttaataca aagagcggag 149700
aattctgcct tgtttgttca ccattattag tttggcgatt tgatggtaac aaaatgcctt 149760
ctgtgttcac tgttggttga aatattatgg gctgtttttt ccaaaatttg catttctgcc 149820
gtggcgggaa tgttaaccag ttgacctatt gatgcttcaa gtacatacct acaaacaaaa 149880
aatagtaacc atgttttaca taggtatttc tgtaaactct acacctacat gatacatgta 149940
gaatgaagaa agtaagtcat atttttttct atctcctcta cccttacaca ataattatc 150000 ttttacttat ttatgtttct tttcttttct tttttttttt gagacagaat ctcactttgt 150060
cacccaggct ggagtgcagt ggcacgatct cggctcactg caaccttcac ctcccaggtt 150120
caagtgattc tcctgcctca gcctcctgag tagctgggat tacaggtgcc tgccaccatt 150180
cctggctaat ttttgtattt ttaatttaga tggggtttca ccatggtggc caggctggcc 150240
ttgaactctt gacctcaggt gatccgccca cgattaaaat gacatatcac attgtttccc 150300
taataattga aaaattatag atccttaaac ataaagttt ctaatagagg tttgggaaga 150360
atgtgttaat gtttctaatt tttgtgaaag aggaccaaag tccatcagta acatttaaat 150420
tattagctaa acctagacaa ttcagaaaaa agtttgatga ttatgctttt atcatatgtg 150480
tgagcataca actcttgagc atagagttct actttactat tggttaattt gggattattg 150540
tttaatgcta ttttcacttc agcttccttg attcacattc ttttgtagag ctaatgttta 150600
tagtgaatat aggcaaactg actgtaatgt tagcccatgt ctccacattt attaaatttg 150660
ctttggatga gttattgaca gtttgaggcc attacaatgt cagcatagat gccaaaaatg 150720
atggttttat taagatgcct gaaactatca tgttgaccat gctctgctcc tgttattttg 150780
aaaaggtaag ttcaaaatat aattatgaaa ttaagatgat tgttattaat tgatgttcca 150840
```

```
acagcaagaa tggaacacac atatatatgt aagcaattga cagttctgtt gtaatccata    150900
ttagaaattc ttttcctaa acagtatgtt gacttagttc agtgcaagac ttgattttat     150960
gtcggtggca ctgatcagat ctctggacct ttaaacaaac tatttacatt atggcagagt    151020
ttacatacat ttctttctta tccctacagt ttgctatatc atctaattct ttaaaatctg    151080
ctgattcata tattgttaaa acttgtatca gaatacacaa aagcatttt tatttttttg     151140 agacagagtc tccctgtgtt gccaaggctt gagtgcagtg gtatgatctc agctcactga    151200
agcctcctcc tcctgggttc aggcaattct cctgcctcag cctaccgagt agctgggatt    151260
acaggcgtcc actaccatgc ctggctaatt tttgtatttt tagtagagat ggggtttctc    151320
catattggcc aggctggtct ctaactcctg acctcaagtg atctgcccac ctcggcctcc    151380
caaattgctg ggattacaga tgtgagccac cactcctggc catttgtta tcagtgagtg     151440 ctagatttg tacataaaaa gagtggttag gttttgctaa tattgtacaa cacattaatt     151500
cacagggaac atttgggtta ccacctgaga gttactctac tttcatgtca gaaaatgaga    151560
actttatttt tctcaacctt catatgaagg ttttttccat taactataaa actcatacct    151620
tttaagtgtt gcaagtcaat ttggatgatt ggttgcttta tcaaattata aacagctggt    151680
gccagtgcca ttcacttagg tcaccacatc tgcaaaccat gctgtaatcc agtcattacc    151740
ttggtatctc tgtcttaact aaagtataga gaagtgacat taatctggta gtccaacaat    151800
aaagtagtac gtttggacca aggtgtcatg agacgttgtt ggtcctgtca gtagcgagtt    151860
ataccttaag catttgttat gaaaaatagg taaagcactt aaatttgtga atgatttatt    151920 tttttaaaa aaataagctg attatattag tgtattttca tttacttaac atttggtctc     151980
gctttcttgg atagaaagga acatgttgga acttatgcat aaccaacatt tacagccctg    152040
tattgcctaa atgttccgga aaaagcagaa aggggagaat tttgccaaaa tcagggcatt    152100
tccccaggaa tatatctagt atgtgaacat tatttcccat gtattatggc agaatacagg    152160
gttggaacca ttatttaga gtgccaagtg cctatattgt aatatgatct tgcctgtatg     152220
gtactcctaa aagctgaact tctaggttca tgtcatggta ataacagcag tacctccaaa    152280
ctcttctaga acaaataaca atgaaactat tttacattac ttgtattaaa aatcccttg     152340 ttctatcttt tattactaaa ttgtatcaat aatttatttt ctacaaatta tttcaattaa    152400
ataatagatt gcaattccct gccaatagaa aacttaggaa ttcatatatt atacaaatga    152460
aaatattacc agtaattaat atgaataact gaatgaagaa acattttaac atgttaatta    152520
ttttagctct gttttcccag ctttagtcac tagtgaatta ccatggtaca aatttgccta    152580
tgtctgagaa ctatatgtac tataattttc ctgatatttt tctttacatc gactaactca    152640
atttaaattc attttagag gaaagttgtt attatttctg taaatgagaa ccagtatagt     152700
atcacttgcc ataagtagat aaccattgta aaagtaaata caaatctaag aaagacaaca    152760
ttaaattcca ggtagatatt gttttctgct tatgctgagg tctgttgtct ttgctgtaaa    152820
ggaacattac ctaatatttg agaaatgatg aaaacatact tgcacgatac tgaaacttaa    152880
tccttgatat aaacaacaga aagaaaactg taaaggaat acgtttccta ctggactatt     152940
tcatacctga tatacctact aatgaaatta ggctgtgtag gtgtccccag ttctttaaaa    153000
atagattgat tctgtggtct gtaaagtcaa atcagttaat caaacaactg gatattacca    153060
agtatttgga attggggaaa aaggtctcag gtctgtcttg tataaaaaag aaataatcgt    153120
ttcctttcaa gacaagggaa atgatatata tttgtgaaaa ttaaatcaca caaaatata     153180 acacaggaaa cgtgttcttt tcaagtacat actataatgt tatggattct attagtgtgg    153240
```

```
gtcaaatgta aattttTggg tgtgtaagtc aaacctaaat tttcaagtgc aaatataatg   153300
tcaactaaaa atctggccta atttgactgg attaacactg acattttccc ctcccttgct   153360
caggttttta tttagacagc acctgacacc caggcgctga accgatgtat gggttcttat   153420
gcactgcatt ttgaatagaa attgtcactt tatgatttct gggtccttaa ttatgttttc   153480
ctattggatg actatgaatc tattttTatg tttccatttt gttagtaaag gcaaatctaa   153540
atcaaattgt caatgtttTt tattttTtgc tcaaatattc tagaaagcat agctaacatt   153600
ctagttgtcc ttatacgaac aacttTtagt agtttacttt caagtTaatt attaacataa   153660
agtacttaaa actcatcttc acaattgcca aagtgatttt aagtacatac cttcttttat   153720
tatgttgcat agcattttta atcatataaa aatttgctca caggtTttag tcaaaacttc   153780
tatgatacta gtctatacta tataatttgg catataatta tatacattgt tgggatttgt   153840
gaagtattaa ctatgttttc caaccagatt gtaagcacct tcattgcaac tttgatagat   153900
ataggtgtat ctcacagata ttgcaggttc cgtcccggcc aacagcaata aagcaaatat   153960
cacaattaaa catgtcacct gaattTtttg gttTtccaat gcacataaag gttatgttta   154020
cactatacta agtctattaa gtgcacaata atattatgtc taaaaatata tatactataa   154080
ttaaaaatgc cttgttgcta aaaagtgcta aagatcatct gagacttTta acaagacata   154140
atcattttgc tggtggaggg tcttgcctcc atgtaggtgg ctgcagattg atcaggctgg   154200
tggttgctaa agattggggt ggttgtagca attttgtaaa ataagataac aatgaagttt   154260
gctcaatcaa ttcagtcttt cacaaaagtt tctctgtagc gtgcgatgct gtttgatagc   154320
atcttactca cagtagaact tcttacaaaa actggagtca gtcccctgaa acctactgct   154380
gctttatgaa ctaaatttat agactattct aaatTatttg ttgccatttc aacaatgttc   154440
atagcatctt taccaggagt agattccatc acaagaaacc actttTgttg ctcatccctA   154500
agaagcaact gctcatccat tcaagctttt ggatgagact gcagcaattc agtcacatct   154560
tcagtctact tctaattTta gttctcttgc tatttctact acatttgcaa ttacttcttc   154620
tactgaagtt ttaaaccctc aaagtcatcc atgagagttg gaaccaactt cttccaaact   154680
cctgttactg ttgatatttt gaccattcat cataattttT taaattttTt aaatttcttt   154740
ccataagtta ttgggtaca attctttagt ggtgatttgt gagatttTgg tgcacccatt   154800
acctgagcag tatacactgc accatatttg tagtcttcta ttcctcaccc cttTcccact   154860
cttccccccA agtccccaaa gtccattTta tcattatcat gcctttgcat ccttatagct   154920
tagctcccac atatcagtga aagatacaa tgtttggttt tccatTcctg agttacttca   154980
cttagaataa tagtctccag tctcatccag gtcactgcaa atgctgttaa ttcattcctt   155040
ttttatggct gagtagtatt tcatcatata tatatatata tatatatata tatatatata   155100
tatatatata tatcagtT tctttatgca ctccttgatt gatgggcatt tgggttggtt   155160
ccacaattat gcaattgtga attgtgtggc tacaaacatg catgggcaag tatctttttt   155220
gtattatgat atcttTtcct ctgggtagat acccagtagt gggattgctg gcttaaagaa   155280
cttTtagttc tttaaggaat ctccacacta ttTtccatag tgattgtact agttacattc   155340
ccaccagcag tgaagaagtg ttccctgatc actgcatcca tgccaatatc tactgttttc   155400
tgatttTttg attatggtca ttcttgcagg agtaaggtgg tatcgcattt tggttTtgat   155460
ttgcattTcc ctgctcatta gtgatgctga acatttTttc gtatgttcgt tggtcatttg   155520
agtatcttct tttgagaatt gtctattcat atctttggcc cacttTttga taggattgtt   155580
```

-continued

```
tgttttttac ttactgattt ttttgagttt gttgtagatt ctagatatta gtcctttgtc 155640
acatttatag attgtgaaga ttttcttcca ctctgtgggt tgtctgttta ctctgctgac 155700
tgttcctttt gccatgcaaa agctctatag tttaattagg tccctgctat ttatctttgt 155760
ttttattgca tttgctttta gtttcttggt cattaaatcc ttgcctaagc caatctctag 155820
aaggattttt ctagaattct agaagatcta ggatcttcta gaattttat agttccaggt 155880
cttaggttta agtccttaat ccatcttgag ctgattttg tatggggtga cagatgaggg 155940
tccagtttct tttcctactt gtggctagcc aattatccca gcaccatttg ttgaaaaggg 156000
tgtcctttcc ccactttatg ttttttgtttg ctttgttgaa gattggttgg taagtatttg 156060
ggtttacttc tgggttctct attctgttcc attggtctat gtgcctattt ttataccagt 156120
accatgctgt tttggtgact atggcctttat agtatagttt gaaatcaggt agtatgatgc 156180
ctccagatttt gctctttttg cttagtcttg atttggctat gcagactcct ttttggttgc 156240
atatgaattt tagaattgtt ttttctaatt ctgtgagaat gatggtggta ttttgatggg 156300
gattgcattg aatttgtaga ctgttttttgg aagtatggtc attttcacaa tattgattct 156360
actcatccct gagcatggga tgtgtttcca tttgtttgtg tcatctatga tttcttccag 156420
cagtgttttg tagttttcct tgtagaggtc tttcaacttc ttggttaggt atattcctaa 156480
gtatttatt ttattttatt ttattttatt ttatttattt ttatttattt ttatttattt 156540
ttttgagatg gagtctcact ctgttgccag gctggtgtgc agtggcgcaa ttttggctca 156600
ctgcaacctc cgcctcccgg gttcaagtga ttctcttgcc tcagcctccc taatagctgg 156660
gactacaggt gtgtgctacc acacccagct gattttgta tttttagtag agacagggtt 156720
tcaccatgtt ggccaggatg gtctcgatct cttgacctcg tgatctgccc accttggcct 156780
cccaaactgc tgggattaca ggtgtgagcc accacgccca gccagtattt gtacttttg 156840
cagctattgt gaaaagaatt gagttcttga ttggattctc cacttggttg ctgttggtgt 156900
atagaagagc tgctgatttg tgtacattaa tcttgtatct agaaaattg ctgaatgctt 156960
ttatcagttc taggagcttt ctggaggagt ctttagggtt ttcaaggtaa atgatcatat 157020
tgacagcaaa cggtgacagt ttgacttctt ctttactgat ttggatgccc tttatttcct 157080
tctcttgcct gactgctctg gctaggactt ccagtactat gttgaagagt agtggtgaga 157140
gtgggcatcc ttgtcttgtt ccagttctca gagagaatgc tttcaacttt tccccactca 157200
gtattatgtt ttctatgggt ttatcataga tggcttttat tacattgagg tatgtcccctt 157260
gtatgccaat tttgctgaga gttttaatca taaagggatg ctggattttg ttgaatgctt 157320
tttctgcata tattgtgatg atcatttgat tttagttttt aattctgttt atgtggtata 157380
tcacatttat tgacttgtgt attttaaacc atccctgtat ccctggtatg aaatccactt 157440
gattatcgtg gactgtcttt ttgatatatt gttggatttt gttagctagt attttgttaa 157500
ggattttacc atctatattc atcaaggatt tcagtctata gttttctttt ttgattatgt 157560
cctatcctgg ttttggtatt agggcgatgc tggcgtcata gaatgaatta gggagggttc 157620
cctctttctc tatcttatgg aatagtgtca gaaggattgg taccaattct ttgaatgtgt 157680
ggtagaattc tgctgtgaat ccctctggtc ctggaccttt ttttgttggt aatttttaag 157740
ttaccatttc agtctcactg cttgttatag gtctgttcag ggtaactaat tcttcctgat 157800
ttaagctagg aggttgtatt tttctaggaa tttatccatc tcttctaggt tttctagttt 157860
atattcataa aggtgttcat agttacctga atgatgtttt gtatttccat agtgtcagtt 157920
gtaaatatctc ctgtttttgtt tcttagtgag gttatttgga ttttctctct tttcttgatt 157980
```

```
aatcttgata atggtctatc aatttattt atattttcaa agaattagct ttttgtttca 158040
tgtatctttt gtatatttt tgtttcaatt tcatttaatt ctgctttgat cttggttatt 158100
tcctttcttc tgctgggttt gagtttggtt tgttcttgtt tctatagttc cttgaggtgt 158160
gaccttagaa tgtcagtttg tgctctttca gtcttttcga tgtagttgtt tagggctatg 158220
aacattcctc ttagcaatgc ttttgctgta tcccagacct tttgataggt tgtgtcatta 158280
ttgtcattca attcaaagaa ttttaaatt tccatcttga ttgtgtttct gacccattgc 158340
tcattcagga gcaggttatt taatttccat gtatttgcat ggttttgaag gttccttttg 158400
cagttgattt ccacttttag tccactgtgg tctaagagag tgcttgatat aatttcaatt 158460
tttaaacatt tattgaggct catttttatgg cctatcatat ggtctatctt ggagaaagtt 158520
ccatgcactg ttgaatagaa tgtatgtttt gcggttgttg gatgaaatgt tctgtatata 158580
tctgttaagt ccatttgttt caaggtattt agttaaatcc attgtttctc tgttgacttt 158640
ctgtcttgat aacctgtcta attgtgtcag tggagtactg aagtccccgc tactgtctgt 158700
ctcatttctt tttttttttt tttttgagat ggagtctcgc tctgtcgccc aggctggagt 158760
gcagtggcac gatcttggct cactgcaagc ttcgcctccc aggttcacgc cattcttctg 158820
cctcagcctc ccgagtagct gagactatag gcgcccgcta ccatgcccgg ctaatttttt 158880
gtatttttag tagagatggg gtttcaccat gttagccagg atagtctcga tctcctgacc 158940
tcatgatctg cccacttggc ctcccaaagt gctgggatta caggcatgag ccaccgcgcc 159000
tggccattct catttcttag gtctattagt gttttataaa tttggaagct ccagttttag 159060
gtgcatatat atttaggatt gtgatatttt cctgttggac aaggccttt accattttat 159120
aatgtccctc tttgtttctt ttaactgctg ttgctttaaa gttttttttg tctgatataa 159180
gaatagctac cttgctcact tttggtgtcc atttgcatga aatgccttt tccaccccctt 159240
tactttaaac ttttgtgagt ccttatgtgt taggtgaatc tcctgaagac agcagatggt 159300
tggtgagttc tgatccattc tgtggttctg tatgttttaa gcagagcatt taggccattt 159360
acattcaatg atagtattga aatgtgaggt gctgttgcat tcattgtgct atttgtttcc 159420
tgtgtacttt tgttttttt ttgttttttg gttttgcttt ttaacttgta tttttgtttt 159480
agagggtttg atatatgctt taagtaggtg ctgttttgat gtgtttccag gatttgtttc 159540
aagatttaga gctccttta gcagttcctg tagtggtggc ttggtagtgg tgaattctct 159600
tagcattttgt ttgtctgaaa aagattgtat ctttccttca tatatgatgc ttagttttgt 159660
tggatacaaa gttcttggct gataattgtt tagtttgagg aggctgaaga tagggctcca 159720
atcccttcta gcttgtaggg tttctgctga gaaatctgct attaatctga taggttttcc 159780
tttataggtt acctggtgct tctgcctcac agctcttaag attctttcct tcatcttaac 159840
tttggataac agatgacaat gtgcctaggt gatgatcttt ttgcaatgaa tttcccaggt 159900
gttctttgtg cttcttgtat tttcatgtct aggtctctag caaggctagg aattgttcct 159960
caattattcc cccaaatatg ttttccaagc ttttagaatt ctcttcttcc tcaggaatac 160020
caattattct tggtattggg ttgtttaaca taatcccaga cttcttggag ctttgttca 160080
tattttcttg ttcctttttc tttgtctttg ttcgagtggg ttaattcaaa gacctcgtct 160140
ttgagctcta cttgttcaat tctattgctg agactttcca gagcattttg catttctata 160200
agtgtgtcca atgttacctg aatttttat tgttttact ttaaactatc tatttccctg 160260
aatatttctc ccttcacttc ttgtattgtg ttttggattt ccttgcactg ggcttcacct 160320
```

```
ttctctggtt cctccctgat tagctaagta actaacctcc tgaattcttt ttcaggtaaa  160380
tcagggattt cttcttggtt tggctccatt gctggtgaac aagtgtgatt tttgggggt   160440
gttacagagc cttgttttgt catattacca gggctggttt tctggttcct tcttatttgg  160500
gtaggctctg tcagagggaa tatctagggc taaaggctgt tgttgagatt cttttgtccc  160560
atggggtgtt cccttgatgt agtactctta cccttttcct atggatgtgg cctcctgtga  160620
actgaacctc agtgattgtt gtgtctcttc tggatctagc cacccagcaa gtctacccag  160680
ctccaggatg gtactgaggg ttttctgcac agagtcctgt gatgtgaacc atctatgggt  160740
ctctcaaccg tgggtgccag tgcctgttct ggtggaggtg gtggggcggg ggttgcaatg  160800
gactccataa gggttctttg gtggtttaat gctctatttt tgtgctggtt ggcctccttc  160860
cgggaggtgg tgttttccaa agaccatcag ctatggtagc atggagaggg actagcggtg  160920
tgtgaggcct tagaactccc aagattatac gtcctttgtc ttccgctacc agggtgggta  160980
ggaaagaacc atcaggtggg ggcagagcta ggtgtgccag agctcagact ctccttgggc  161040
agatcttgct gcagctggag catttggggt gtctcctagg tcctgcagga gcagtctgct  161100
tccttcagag ggtctgtgaa tcctctcagg attcctagtt tgttcttgga gttgatctgg  161160
agctaaaatg catacatgtt tttaatgaca tctagaatag tgaatccttt ctgggaggtt  161220
ttcaatagac tttgcctaga ttcatcagag gaatcactat ctattgcagc tatagcctta  161280
tgaaacggat ttctgaaata ataagacttg aaagtcaaaa tgactccttg atcattggac  161340
tgcagaatgg atgttatgtt agcatacatg aaaacaacat taatatcctg tacctcctca  161400
tcacagctct taggtgacca agtattttgt caaagaacat caatattttg ataggaatct  161460
ttatttcagg gcagtagatc tcaagagttg gcttaaaata ttcaataaac agagtgcttt  161520
catccaggct ttgttgttct atttatagag cataggtaga atagatttag tacaattctt  161580
aagggctcta gtattttgg aatggtcaat aagcattggc ttcaacctaa gattacctgt   161640
tgcgttagct cctaacaaga gagtcagcct gtactttgaa gccaggcttt gatttctcct  161700
ccctagctat gaaagtccta gatggcctct acttgcaata aaaggctgtt ttgtctacct  161760
tgaaaatcta ttgtttagtg tagccatctt catcagttat cttagctgga tcataagaag  161820
atcttacctt gctgcaactt ctatatcagc atttacagct ttgccttgta cttttatgtt  161880
atggaaatgg cttctctcct taaactgcac gaaccaacat ctactacttc tagctttcct  161940
tctgcagctc tctcacctct ctcagacttc atagagttga agagggttgg ggccttcctc  162000
tggattctgc tttggcttaa gggaatgttg tggcaggttt gatcttttat cttctaaatc  162060
tttctctata taagcaataa ggctgtcatt gttattattc atgtgttcac tgttgtagca  162120
cttctaattt tccacaaaaa tcttttctct gcattcacag cttggctaac tatttgatgc  162180
aagaggccta gctttctggt atcttggctt ttgacatgcc ttcctcacta agctttatca  162240
tttctgcctt ttgattgaaa gtaagagaca tgtgactctt ttttccactt gaacaattag  162300
aggccattgt aggattatta actggcttaa tctcagtatt gttgtgtctc agggaatagg  162360
aaggcctatg aagaagggaa agatggggga atggctggtt gatggaacag tcagagtaca  162420
cacaacatcc atccattaag tttactatct tatatgagtg cagtttgtgg tgccccaaaa  162480
caattacaat agtgacatgc aggatccgtc atcacagatc atcacaacag atctaataat  162540
gaaaatgttt gaaatattgc aagaattacc aaaatgtgac acagaggcat gaagtaaatg  162600
catgctacta gaaaatggt gccagtagcc ttgctcaatg cagaattgac acaaaactta   162660
aatttgtaaa aaaatttaaa aaaagcaaca tctttgaagt gcaatataat aaggtgcaat  162720
```

```
gaaatgaggt atacttgtaa ataccttgga gtatttcctc tgagatcagg cccttgaaaa 162780
ctatttattg agtaactgat ttagacccat cactgtataa actcttgttt atctttgcta 162840
ttgtattgag agcaactgca taagtaatca gaagcagtga gggaatcact gattttttg 162900 tattagactt ttaaaatatt ttatttttat taaatttatt ttattatatt aaaatatata 162960
catatatatt ttagatttca gattgagata agaaatttcc tttaccaatg attatttgct 163020
tcctcattct tcatgccaag ggaggtgcca aacgactgtg tacagggtcc caggaggatg 163080
cttcttggag atgtagattt ttttcatggt cattttaggg taatgtgttt tcaaatggat 163140
actcatctca caagagttac tggtggttcc aattcaagcc taaatccaaa ttgcatatca 163200
cctgttaaat ggcaactcac actcatgcca tttgggtttc tgcctgggag gaaaggctaa 163260
aggaagtaag ggttgaaagg tatcccactc tctggtagga gtaaagggag gtaggtcagc 163320
atgacttggg tgatgattgt agcatggtgt gtaaaataat tgaattaaca gcgaaaagca 163380
tcaccctcaa attccaaatt gccattatta gtaatttata gtggatttta aaatatgtt 163440 aaaagtattt acaaatatgc tttgaattag tttgttgcat tgaccaattt gagaattgag 163500
gacagtgaca gaagggccaa ttataagaag aagaaacctg gatatcaaag accttaggtt 163560
catgtggagt ctgttgcaca tgagccatac cattttggac atacatatgg acatctaatc 163620
aaattattcc tgtgtagaaa tgtaagcacc agtagctaag aatctatcca tgtgttggct 163680
cctgtctggg gagtagtttt tttaaggatc tcagagtaca tttaaaccat aagggagtat 163740
taatcattga atcagtcatt aagcttctat taattcccctt tcttcaagaa aaatgttgat 163800
acaactaagg ctgtgtccaa accattctat aatggttgct acagcagttc cctctcctga 163860
aagcaagagg cctctttctt ctctctggga tacctgcctg ccctccacta tagctggaac 163920
cttgttcatt cttaattgac tctgctcagt atggattcaa taatttattt gggatgtttc 163980
atatagtgtg tcaattaaaa attttttctgt ttatataact acttattatt tttatattg 164040 gggtgcaaaa gcacaattct taaagttgtt cttttggcaag tgtctgagtt ttattcaatg 164100
cattgatgat agaaccaggt ggaagacaaa aatgctgatt caagagcatt tgaagaacag 164160
agatttatgt agttaggcaa gaaagaagag ctgacataag attgctaaat taagcgtaag 164220
actggtagaa cttctatagg gcaataaaat gataccatt ttgtgatcaa gttcttgact 164280
gggtgtaaaa tcataccagt atattaattt ctgcaggtta acctctaacg ctacaggcct 164340
gtaaactgtc tgctccttta ttggtgtaga ttgttagtta aatatactgt gacattaccc 164400
attatgggaa tataagacac attacttaaa agaggctcag ccagaattca agagttaagg 164460
acttcaaagc agccttgcct ctggcctttta aacagcttat tcctgaagtt tcaaatgaaa 164520
ggaagtttgt tgcctgatca cccagaggtg aaaggagctg atgctttgac tcagcttcct 164580
gccattctgt gagaaactct gccggaggct agggtagcag gggcatctag gcctagactg 164640
ccaagctcct tccaaacact ttttgtctga ttatagaatg gtctactggt ctgtgttggg 164700
aagtttccat tgtccatgca tcatatcctc tgtcacttcc ctctctcttc tgatggaaca 164760
tcatattctc agtgtctcag tcccaagctt cagcagtcct tggctcctgc tccccatgtg 164820
gaaacagcta cagtgcactg tagattgatt caccccacaa cgtgtatgac ctcagccccc 164880
ttggttctag tcccattttt accattctgc catttcatat gaagaaacta aggcccaaag 164940
aagttgtgac tttctgaaaa ccatattgca atgcaagcca ggcctctgac ttcaactgta 165000
tgatcctctt cccgtgagat caccttttcct gaaatacagt cagccttatt gtttctcacc 165060
```

```
atcgtgtatg gtccctggct acctctccag ctgtatacat actgtacttt ttttattgta  165120
ctgcacacca gctaaactga acagtttgct gttcttcagt tgcagccctc acttagctga  165180
cttcactctt tgctggaatt attccttctc ctaagaaccc acactcacat acaacttccc  165240
tcacacccaa tacatttcct gtgctatcga agaccttcta attcttcctg gtcttctcaa  165300
attaacattt gaatttgctc tttagcctac atccatggtt gtctggqtga accttctatg  165360 aaatccttat gagttcaaga ttcttcatct aaccagggac acagggattg attgctgaac  165420
acttacagat ttgaactaca attacgttac tttatttcat tgttatgata gtaaagaggt  165480
gagagtaaat ttgtattgta gtttgacaac actgttggtc caatatagag aagctcatgt  165540
gtgttttggc cccccattca tgaaaacaat atatttttg cttcttcatg gatttccttc  165600 cttaacccett ttttctcca gttgtccaaa agttcctgat ccttagctga gagaattcag  165660
aaaaataatg cattgatacc atattttgat caattgggag agtacagtgt aacccacttt  165720
tttgggttta atttgtagtt attaacagct tcaaagtgta tattgtgaat tatagtttca  165780
atagaatgga catatagtat gtgtcaagtg tcaagtgtca aagcaccagg gatgggcaac  165840
taacttggct attttattat gcaatgatat actaaagcag aatgtagtgc acagcactag  165900
ctgtaaagac ctaatgcttc cagcttatta tgtctacatg cttccaaaa ataattaatt  165960 aaatgttgag agagatagat agaacatcgt gttaaaagta gcagtccttt taagaagaga  166020
aataatattt cattatggga aggagatatt gttttgtatt tgcagtaacc agaggcgcct  166080
tctagctgtg tccttgcatg gtagaagggg gtgaccacct ccctctggcc tcttttataa  166140
tggcactgat tccattcatg aggcctccgc ccttaggacc taatcacctc ccaagctcac  166200
ttcctccaaa tgccattgcc ttggggatta ggatttcaac ctgtgaattt tggtggttca  166260
gaagcattta gaccacagca ctcagtctcc tcatctgtaa aatgggggta gaatctacac  166320
caataaagga gcagacagtt tacaggcact gggaggtgtt ttatgcattt agtctcctct  166380
gtggattaaa gcagactaaa tgtgtaaaac acctcccagt ttctcaccca agttcttgct  166440
aaaaaagaag gactgctctt cttgcaagtc ctctgaccta acactgcaaa ggggaaacaa  166500
aatagctctt tagcgtcatg cttgcaacag agtaagctag caaatataat tatgtaatga  166560 cttttttgacg cttttaagta aattgcctct tataagaaat ttcgtagttt ccttctaagt  166620
tttaaaacac tagccaaatt tactatttta ataaaaacta taaagaata caaagtatcc  166680 caatatttta aactttgatt ttatttaaat tttaaggaga ccaaatattg tgtatatatt  166740
ttgcagtagg aaataccaca tagatatgaa tcatgggcat attatgtatg actgacattg  166800
cacatgaact gtgatcagcc tcaccgatgt ctctttaata aaaaattgtt ttaatacaaa  166860
tattctcagt ataaaattga taatataaat atatgctgct ttttttttt tggtgaacag  166920 tcagaaagtg tagcgttttc agtgggctaa tctaaaagat atactgagag agaatgtttt  166980
taaagctaga caaaatgtta tggctaacat ttgccaaatg tttggcagtt aataacattt  167040
aaatgaagaa taaaaataca ctttgggagg tcgaggtggg tggatcactt gaggccagga  167100
gttcaagacg agcctgtcca atgtggtgaa accctgtctc tactaaaaat ataaaagtta  167160
gccaagtgtg gtggtgcatg cctgtggtcc cagctacacg ggaggctgag gcaggaggat  167220
tgcttgagcc caggaggcag aggctgcagt gaactgtgat catgccactg cactccagcc  167280
tgagtgacag agtgagaccc tgtttcaatt ttttaataat gtaataaaag gatgagtatt  167340
cagaatatct aaagagcatt tacaaatcaa taagaacaaa gaactatgga tacaagcaag  167400
aaatttacca aagaagtaca gcaacctcac tagcgtttag ataaatacaa aagcaatcag  167460
```

```
attggcacag tggaaaagtt tgataatata tattgttgac cgaggtgtag aaaaatggat  167520
tcttttctgg tcagagtgta aattgactca gccacttaaa aatgtatttg ttacaatgta  167580
tccttgggtc cagctatttc acttcactgt gtctaccctc aaataactct tgtacttacg  167640
cacaatgagg catgccggtg tatattcact gcagcatcac ttattatcat gagaaattga  167700
aagcaaagga agtgtccact aggacagaag tggctgtgta aactacagtg catccaggac  167760
acatagtagt cttcagcggt tacagagaat gggctagaac tgcatgtgtt gataataaac  167820
catctccatg atagactaag tgaaaaaaat aaattgtaca acagtttatg tgatgtgata  167880
tgtcaccatt tgtttacaaa ggaaggcaag gaaggaggga ggaaagaagg gaggaagagt  167940
gcaagagaga aagagaggaa aggaggaagg gaggacggac agactgctat agattttcca  168000
taatagtagc tttcaaatgc ttggaaatga ctatcaatag aaaacgcatt ttatgtcttg  168060
gctgagtgga cccttccaat gtactctgaa attttaaaat ctagttccga ttcatttgat  168120 atcattttc aaaatgctga tcataacatt aaaattggct tcaggactca agtatggttt  168180
gaaaaacact gttttgaagt gtacatttat gtatgtaaat ggatagagaa gtgagtggaa  168240
gtcaacacac ccctctgata tcacaggtta tttctgggga ggtggctgtg atgggtggtg  168300
gctcctggga gccttgaatc tcatttgtac aactaacatt tttgtttgtt tgcttgcttg  168360
tttttatagg ggcatgcgta attaaatatt tttaacttta ttttttaata actaagtaat  168420
caaaagtatt tccagaagtc aaggatgtgt tgggattgtg agggtagtgg tcaaagggtc  168480
tcaataaaaa taattttga gttaaaaaaa ttgcatagtt gattaattca gaaggaagac  168540
attctagcta actctttgtt tttgtattta gggccacaga tgggcacatt cttgtggcaa  168600
ggtagagtca aacctatgtg atatcccatt caaaatgtca tcacagatct aagaactctt  168660
tgccatgttg tgagatttta actcattaaa atctatgaat ctataaacta tgaatgttgc  168720
atctacaaat cagaaacata gtataaaaat gattttaaaa aatcaagctc tccatttca   168780 gagaatgcaa agttaatttt tctgtagcaa taacaacttg gtcatgttac acactgtcta  168840
gtatttgttt tgggtctaga cgaacagtta cattttaaga attatttctc caagaagcac  168900
tactgtagaa aatatggcat gtgtacactt ggccatctcc acaagatgga gcagacaact  168960
ccagctctct gttttctatt ttagagctac attaactctt tctatttgcc tctttacatt  169020
tttatcccaa gggtatttat taaacctcat attaataatc aaataattca tattaaaagg  169080
agtaaacatt gtgtccatgg gatagagact ctttaaattt caaacattta acaaggtat   169140 taactgcaga tgagctagaa ctagattatt tcttgtgcta aattctaaac taactcagta  169200
aagatatctg taaagaaagt agtatttctt tgaatgttta tattttattc ttttttgcat  169260
tttatgtctt aaatatacat tttcatgtgc ttataataaa acaagttgac tcttttaaat  169320
gactgcattg aatgttctct ttaaatgtct tgaaaacaaa atatttatgg taaaatatgc  169380
aagctttctc aggaagtgct tataatagaa gcgttttaa agatgtttag ctgttgttaa   169440
agcaataact atattcatgt ttaacttcat agtagctcaa tgttgtgtga agggaagaaa  169500
agagggtctt tggaactttc atctttttt ttttttaaa aggaaattag caagagaagt   169560
tttattgcgg aaagcacact ctaggttaag gggaggaaag gaaagagaaa gagaaggaag  169620
agaaaggaag gaagataatg cacatcacat atctgaagtc tcttttttgtt ttatccagtg  169680 tggttctgtg ggtgaaaaga ggcagaggtg gccttgtagg taatctagag aaaagagtca  169740
ttcctttaaa tagtttttata gtcctcaggt taagaacaga ctgtgggctat ggcagaggac  169800
```

-continued

```
gctgggaaag caactaatat gtaatttgac actgaattag tctgaaaact gtgaaggtgg 169860
tgtggctgta tgatgagaat tcaggataaa ttataaatgt gccctactta gacatggaga 169920
gaaatctatg tgaaaattat aatttgtaat aatcaaaggt ttgaaagtta tttaattcta 169980
gctaaaagaa ttttcatttt tttttgctct gtaagaatgt tcagtgatta cattttatag 170040
ttttgataaa attagtctta aaatatgtta tggaaggcat aatgaattta aaagttaaaa 170100
gcatgatagc ctcttaacta tacatgtctg aagcctggct tttcagtggc tactgtatct 170160
aaggcactgc tgactcctga tggcagcctg ctgtaattgc cagcaaaata tccaagtgat 170220
aagcagtctt tcagatgtta ttatagataa tatcattgtg ttacttagaa gtctgagaag 170280
taaagggaag atatttttta ttccatgtca taaaatgttg aagtattaca gggtctctgc 170340
atattgtctc attgataagg tgaagtcttt gctttaaaat ttgtgttaga attttacttc 170400
attttttcac taatgtaact tttgaaagag aacttgacta actacaaaat ttatcaccca 170460
cagcatcagc aggaattgct gtgtcccaga ggaaagtgcg tcagatcagt gatcctattc 170520
agcagatatt aattcagctg cacaaaataa tctatatcac acaggtcagt gttctagctt 170580
tttatttcct tttcatctta aatgcaagtt tggtgctaat attgctgaag aactattttg 170640
gaggacttta gattgaattc ttgttcttat cctccccagc tacatacatg tgggacact 170700
ttagtttagc agcagagctg ggaaggcagt agagtaacaa agcaaatata tgggattttc 170760
cctatgattc ctaacatcct ctcttactgt tagtgcccaa acaaaccaaa cttcaccata 170820
aatggccctc ctgtagggt gcaagtggag acggagttgg gattctttgc tcttaagcag 170880
ctttactcta agaaagaaag aggaaaatag tgcccacaca ttaattctga gaatgctagg 170940
ttgaaaatag gacctttcag agagtgaaag ccaaaaccac acaaaatcca gaattgttaa 171000
aattttctac ttgtaaatct cagtgattcc tagcactgag aaaataatca gtgctaaaaa 171060
atggctatta attattgaca gaaatatgtc tagaaataac ttgaaggctc tgttatatat 171120
ggttaataaa atcttttttt tagacaaaga agtgcagaag acctttggac atgaaagtca 171180
ctgttatttt gaagtctaaa attgtgtatc ttatgtggtt tattcattca ttcactcact 171240
tgacatataa ttattaggtg cctactatgt gccagatgct attctaggga cttgggatac 171300
atccacgagc aaaacataaa cattgccttg ctctagattc aaagaaccaa tgggggatgc 171360
tgtcagctgc cagttttggc aattccaact aaatattcag atactgaaga gaaataccac 171420
aagttaaatg gaccaactgg gcccattggg ctcatatttc atttaactaa ccccatccc 171480
tacccaaaac atcccaaaac aaaaaatcat taaaaatggt gtaccacagt aacatgataa 171540
gactctagga atcttgatgt cagttttgcaa ccagtgtcta gtatttgctg aaagcctgtg 171600
tatttccttt tccccagtaa acagtcactc tagtaaatgg ctgcggttct ccttggggga 171660
ggtttggagg aaaatgtata gtgtgcactt gtagtaatat ttcagggggcc ttcctcaagg 171720
ggtcccagct ttccacttaa tcaagggggct ttgagtcttt gaattgactt gcatctgaa 171780
actgtgtgag aagctataac tcttcactgt agcaatggca acttagggca ggtttctgtc 171840
taccacacct agataatctt ttctgttaaa ctgatcaagg aatactttaa taggcagacc 171900
atctatttct tttccaggaa caccctagtc aactaaccac tgccaaagat ctctgttggc 171960
taaggcattc taaataatag tacctccctg ctgcccttta tggaagatgc tctcagtttg 172020
ctattagtgg tcaagtgctg tcagttggcc cctgacaact ggatacattg aaatcatgta 172080
tcgttcggtg tcatacctgg cctccaaagg agagcaacca cagggctttt caaggatgct 172140
ggtgctcccc tttccaatgt atttctcaat gtcttagtga aaggaatggc ttctggatgt 172200
```

-continued

```
tcttgctgaa tgtggttagg gagtgggtgt gcaagtcaca catggtaaat ctaccccaat    172260
gagcccgtct ctctgagcct ttgaaatcac cccttcacat gccagagaag ctctggcatt    172320
ttaccctcat caaacacaga ccatggttaa gtacaagttt tactcaaaca accagttaaa    172380
ctacttccag ctgcatgaac taacatgtga atctggagt ctgtagtacg tgcacccata    172440
tcaatgaatt cagcctgatc tagtgctata gttttaccc ttcttggcct acccttctta    172500
gaatccactc ctgtacatgt tctctgggtt gctgctgaaa tgtaatagca aaatcttgca    172560
attcttttcc tatttcatac tgggtcatgg tgtacatgaa ttcccctgga tcatattgaa    172620
ataggaccct agttatggat ttgaccctca ttgtgttgga tctcatgagg aaatgaacat    172680
cccttttaaa gacatttgtc ctagatgagg ttatcatagg gttttcaagc aaagaaaggt    172740
tcatgttctc agacacagag tggcaagcta tttttaattg ctatgaaggc tcagagtgac    172800
cttggtttta ggattgttag ttttacttgg gtagtctcaa caagatgttc ctattccaag    172860
ttttagaatt cttttttttt ctaactttca catgagaaat ttgataacat gtgacttcat    172920
ccgaccttgt aatttagtaa gctgctcgat taaatttcga ttatcagcca tatcagcact    172980
gtagcagaag aaagcaatgg attcttttag ggctatcttg ggatctttcc acgtctcaga    173040
ccatgacttc agctgagctg taaaggaccc aagcttgtca ttttctttct gtaagtgctc    173100
caatgcattc aaaagaaccc attctgtgcc atagtccttg tgttcttcat tactgtttac    173160
tagtcaagaa cagcagctat ttgggcttcc aaggcacctg cttcagttgg cacttcatca    173220
ggataacctg attaattgtg atgcaactgc atgccatgga ttactagcat cccatgtcct    173280
attggcaaca agcaaaggaa caaacaaaac tcagcactgg gctcagttcc aagggcacag    173340
tcaaaccagt tcccaaatcc tatctgtatg gctcttctg ggacattcct aaaacctgta    173400
tctgtatcag tgagggtcta gtcagaaacc ataccatagt ttcaacaggg aaggtttaat    173460
gtaaagaatt attaactatg atgagtatta tctactaggg aggggaagag aaatctaaag    173520
gatgtaggaa gagcacaaaa agaagtcaca acctctaggg ctgaggcaga gcacccaaga    173580
aaggaacaaa tatagaattg ggcactccca cactaggtcg aagtcctgac cttactgaaa    173640
agatcagaaa aattagtaag gtgctatact ggagaaactt gaagcgaagt gtccctctgg    173700
gggacctggg caagccctcc acagtgaggt actgtgccct ggaacttact gggaatcagc    173760
acttgagggt attgtgctgg gtagcaccct ccatgggacc aggggaggcc accctgagtt    173820
aggtgttgct ccatggaatt ctctggggag cgacctgcag agttggtgcc actggatttg    173880
actgggggtt agcaccaacc tctagggtc ccacatgtgc tgtttgctat gagctgccgc    173940
agcaaggcaa cgcaggagca tcactggagc caggaaacaa gatccatcct ccttcagcat    174000
ccctccaggg ctctcttctg atagagctta gcatcctgct agatggcaag ggagaaatgt    174060
tccagtatca caagctggat aatgaaaggg tggacttgga gctgacaggc tgcttactga    174120
cacacttaac ctagggact agacaaggaa ccgccttctt tggtgtctcc ctacctctga    174180
gttctccttg ctttccttt agcctgggta gtctttaagc ctggggctga gtagcctggg    174240
tcttatctat caagttttgt ccaaactctg gtgttctttt ttctttcccg atggctgcct    174300
tttggagatg caagagtcta aaactgatca cttttctatt ttctgctgtc aagctttctc    174360
ttaggcaacc acagaattgt ctaactaatt acgtaaaaga gggtgaagga gtacaggaa    174420 atattggggg aagcttgact aatacatcaa aatataatct gccatatcta tattgagtaa    174480
agtggttata ttaatgcatg tccatttaaa tactgatata gaaatatgga aaaagcattc    174540
```

```
ttaactttag tgttacggaa atagctttaa atagctttt  agttctctta actattaact 174600
attcaattga gagaaatatc ctttgaaatt taaatatagt tttcatatgc ctgtcttgct 174660
aatttttatg taataaaaaa ctttataatg tataccattt tcttattgga tttcaaagta 174720
gtttaaagca agagtaaaac tattataaat atcttattat tatgctcttg aactgccagt 174780
gtaacaaatg atttcatttt ttttggcaga atggcattcc ttgctacaag ttcaaatata 174840
actatcgtga tttttaaaat gtatttccag aatactctaa agtttatgac attgcacata 174900
gtcgggaatg attcctcttt gaggaacttt aacttatagt gctaaacaaa gtcaatgact 174960
ttcaaataaa aagaaaaaat acatgtaaat attatactag tgtatttgct ataggttaaa 175020
gaccaagatc agttactttg ctaattgcaa aggaagactg aaagtaagaa tgaattggaa 175080
aaacaaacaa aaagacaata ttttcacata tttatttact agtcaaactc tctcagactt 175140
aacacttggt agctgcccta aactgagggg ccacatatct cctgacaacc agcagatgaa 175200
cttaacaagg aaaacttctt acttttggtt ggtggtggcc ttttctgtct cgtttccatg 175260
gagacagatc agtgaaaatc atcaaaagc  aactatttta gaaggcagga tgttaaaatc 175320
cttaccttgc tttctaactg atttgacctc tgttttatc  aaagctgaaa tggtaatcgt 175380
aagaccagca agctaagtat gaaatcagtg gtttacttct attgctggaa ccccaaatct 175440
acctttggac atataaggtg actaaagtac atatgttacc tttgagtatg agtctttatg 175500
tgttattgct taggtcacac ctgcacagcc cagtgaagca ctggatttaa ctttatactt 175560
acatttagat tgtttttgtta aatagatgct ttgaaaatca ggatatatag catcttttaa 175620
aaattaaaca ttggggccgg gcgcggtggc tcacgcctgt aatcccagaa ctttgagagg 175680
ctgagacagg tggatcacaa ggtcaggaga tcgagaccat cctggctaac acagtgaaac 175740
accgtctcta ctaaaaatag aaaaaattag ccgggcgtgg tggtgggcgc ctgtagtccc 175800
agctactcgg gaggctgagg caggatagtg gcgtgaacct gggaggtgga gcttgcagtg 175860
agatgagatg gcgccactgc actccagcct gggtgacaga gcaagactct atctcaaaaa 175920
aaaaaaaaaa aaaaaaaaaa aatcgatctc ctagagaaca ggcaagccat ttatttgaag 175980
cgcctttgaa ttgtttgtct tcacaaccac agttattgcc aatggaaaaa aatgtagttc 176040
agaatagcaa tgtgttgtcc tccaatgaaa attatactac tgactgtcat tggtgaaacg 176100
ttctgtgttt tttcagcagt agtgatggat aagactagaa ccatccatac ctgctcatct 176160
ggatctcctg tactaatggc aagggtgacc tagatttaac agaataagat atttaggata 176220
aagttgtatt tcttaaattg actgccattt tcagggtttg taaattctaa gagaagtgtt 176280
atgttttgtg tatttagttt gataacagtc tttgaacatt ctgttttagc atttagggaa 176340
atatcctctt atgcagtaat gtcaaaataa cttttaaaa  aatagaatta ggaactaact 176400
taaatcactt tttatcaaat ggagtcctgt gaacaatgga tagtcttctg atgtattctt 176460
ggagatacta gagaatatag caagttcttt aaaagaatcc atatattctt ccatatgtag 176520
aaatctatat attcttttcc aatattaata ttatgcaagt ttgagaaaac ctagtataaa 176580
acatgcagat cggctttcat tattttgtta ctttgtgtag tatagtaaaa acaagcaaac 176640
aaaaaccaag cttttaggtg tgtgactttg aggaagtaat tatcttttta agagtcactt 176700
tcttcatttg taagatgggg gagcttatga gactacttgc ctcaaatgaa ataaagtatg 176760
taaaaatgtt tgtttatttg tttctttatt ggagatggat cttgccatgt tgcccaaggc 176820
tggtcttgaa ctctcctggg ctcaagcggt cctcccacct tgcctccca  aagtgctggc 176880
aatacaggca tgaaccaccg tgcctggctg aaaatgtttc taaactataa agtgctatcc 176940
```

```
tacagtaatg ctagtcatgg tggcatctgt tctagaataa tggctgtgct agaagacgct    177000
gctcagaaag tattcttgca tgttacataa tgtctttaag ctctgacttc ctcacctata    177060
aaatagtact tgctttataa gtttgtcgtg gagaaaaaag tgagactgcg cataaatgag    177120
tagtcatagt gtctggctca atgaatcat agacattaat attctattct tagtattata    177180
gtccttacgt ataatatatt attatgttta tatcacctgc aattaaacta tgcatgagtc    177240
atcattttgt gtaaaatttt aaattcttgt atgaaaaaac ttcaaagatg gggtgctgtc    177300
cattgtaata attattccag taagatcaat agctttctaa tatatatgca gcttaagttg    177360
actgaatgtt aacttactca atgagtttt tgaggcttaa ttcagaccat caggagcagt    177420
aaaaacaatt ctaacttaac tagaggcttc tcaagttaaa taaatcgcaa gaattctcag    177480
agtacctgaa ttaataatct gatactcata gcttccagta gtgggttaag tcccctttga    177540
aggaagctat gagcccactg gtgttccaca ctttcaaaag tttgtcatag cagagaaggc    177600
tcgctgcctt tctgtttgac agccccttgc agtcagctgg gcagcagcta gagggttctg    177660
ggccaacact gccctctggt gtttggtttg gggaagtggc aacttttggt gcattacaaa    177720
agggaattat caaacctgtg ctctgtccag gtactttctg gtcccctcat tactccatcc    177780
catcttcctg ctaggaatat acatgcacat gctcctcacc ttcatgtctg tttctattct    177840
aagttaaatt catttctctt ttgcttttct ctctcacaca catatatcat ttatactcat    177900
tttccttctc atctgtcttt gatttgctcc ttaatgctga gaaatctctc tctctctccc    177960 tgcaccccc ttcctctctt ttcttttctct cttccacatt tttttaaatt tcctcctttc    178020
atttcatgtg aaaggacaat aataattatg actatttgct gggagccgag gaagggatcc    178080
catctggatt aaggcaaaag aaactataat attgacctga aaagaggtca gaggagactc    178140
agtgctgcca acctacaaaa catttcagag tacactgaag tgcttcagta tctccagaag    178200
agtcttattt cttcgctaat taacgtattt tgactcaaac actaggataa aagatacatt    178260 tttatttt tgagatggag tttcgctctc attgcccagg ctggagtgca atggcattat    178320
ctcagctcac cacaacctcc acctccgggg ttcaagcaac tgtcctgcct cagcctccca    178380
agtagctggg attacaggca tgcaccacca tgcccggcta attttgtatt tttagtagag    178440
atggggtttc tccatgttgg tcaggctagt cttgaactcc ttacctcagg tgatcctcct    178500
gcctcggcct cccaaagtgc tgggattaaa ggcataagcc actgcaccca gccaaagata    178560
tatttttaaa aacattttc aattgaatta ttttcctgtt ttatataatt acagtacttc    178620
ataatgggcc ctacattcta ctatatttgg gatgatgaaa agtttttatt tggctgtgca    178680
atcagtgttg tgagccctc cctgtaggcc ctattctttg ctctgccatt atctttata    178740 tgtcctcctg tctgacaaaa cttgagtaaa taagataagg ttaagtcatg ctgaacgaac    178800
agttacaccc tgaaattcct tggcttgaca caatagaggt ttatttctta ctcagttcca    178860
ttcgggctgc tcaggtggcc ctgttccttc ttgtggctgt gcagtcagaa taggatggta    178920
atgccaagct ccttgcagta gggaggacag tggtggagaa acacactga ctttgaattg    178980 tcttatcctc agagtgacac acatcatttt tattgaccaa aagtagtcac atggtactaa    179040
ctaagcctgt aaaggagcct agaaaataga gcagggttgg ggtaataatt atttctgata    179100
cattcttctt tcttttgatc tgagctttga attatattct tgtttaatat tgagatctct    179160
tactatcaca ttttccttc cacttagcca tcttttttct gactggttcc tctttctctc    179220
ccttcaagtt ctttccataa tttaaacaaa accaaatatt atttccactc tgagacccct    179280
```

```
ttaatcctga cccaatttct tttctattat ccttcttcta aatgtcactt catctttctg 179340
tgctttccag gacttttgat tttcttgtag agatccaacc tacaaagcat gacaaatcat 179400
ttttttaatc cccattttttt ttgttaccat gttttctaag gtcctaccat gactttctac 179460
tactcactta ctaaatgtaa ctcatcctag tctggtctta atatatgcta atctatcctc 179520
tctttcttct ggaatgattg gtacctaaat ctgacctctc tgcagctgaa ttttcaggag 179580
cactccaaga caggcatctg actatatata ctactaaagc agatatgtgt ttcctggtcc 179640
aaagtgtcag atcctatagt accaaggcta cagtgtttgg catagttcta ggcatattat 179700
aagcacctaa acatctgata aaagtgcacc attctgtgtc aagactgttc ttcacaaaat 179760
tcagtatatg tgtgcaatta atgaataatt tgttaaatga aaataatat caatcaatga 179820 agaaacaata agataaatgg aagcagccat ttgaaaaaga gcaaataat atattccttc 179880 tgaatcgcag ggtaaaaatt atagcatcta gtcatgctat ttgcagtaaa atttaaattc 179940
ttacatagtc ctattgagtg aatattgtta catgggccct cagcgaatgc ttttttgtagt 180000 cagctgtgta gtgttaacaa tttgtttata atgattgttt tcttattta tgcagcttcc 180060 tccagctttg caccacaatt tgaaaagaag ggttatagag agattcaaga atccctctt 180120 cagccagcag agtaacccctt gtaatttgaa atctgaaatt aaaaggtat ggtattctat 180180 atataggaat tcttttgctg acaaaaccac atcataagag gtacatttta tacctccttt 180240
acttcgtact ttaagctcta tcctctatta aagtttctta ttgctgcttt acatactaaa 180300
ttgaggatat gtcttttgctt ctgatttttct ctatttccgt ggcccttatt tttagataac 180360
aaatggatag ctttttcagt atttttgtat gttttcctaa gaaaaagtaa tatttaattt 180420
gaaatgtgta tattttagcc tcttctagag aattatattc tgatatttta ttagaataat 180480
cttcaataag ctccaaaatt gagatttgtc actctgaaga agtcatttaa ccatctgggg 180540
ccattgattt tttattatct atgaaagctg actgaactat ttctaaggtt ctttccatct 180600
tagatattct acaatcttct agaccttaga tactagcaga catttctgtc catacatata 180660
gcaactaaac tacaaaaata ctaaatcaac tgggcagaaa gaaaattgtt tacctctggt 180720
taacaaaact tgatattgga aaatccccttt gtcctggttg gtagaccttt cgatacagcc 180780
ctggaagtgg ccataagctc ccctgaaagg cccaaggtac aagcaattca ggcccaccta 180840
ggtaaagaca attggtagca ctccaatttc atatttttta aaaagtttca tcatattttt 180900
aaatgggtag catagtcatg ctgccagtga acttttcctt taaggtttca cgttcccttta 180960 atgcatcaaa gcttcagcat taacttactc attatttaga aaatatgata ggctctttga 181020
taagaaatgc aaacaacatt ctttagcttt gttgtttcac atcactggta tctgcacata 181080
caccaaaaac agatggggga aaaagacaca gctgcaggta aacaaaacat aaagcctgct 181140
ccatcagaga ttagagagca aggtttcttt cctgggttgt gttggcaaat agggccaaga 181200
aacaaagctg aaggagatca aagcagtaga agaggcttca gatatttatc ttatgatatt 181260
tatatattgt atcataataa acacattttt aaaagataaa agcttaaatc tcccatgaaa 181320
agataatatg ttgcttggtt ttttattctt attaaggtca tataactctt attcttattt 181380
tatattctta ttaaggtcag aataatctgg tttgagcata gacttatttt aacagaaatc 181440
ctagttttat gagatgaaag catctgctac aaactgtctg agacataaag gtggcttcaa 181500 ctccccactga gtgattttcc atcagtgctt ctctttattt tctcgtttat tacttatgtt 181560
tttggttttg caactcttcc tcactttctt tcctctcctg atagagaaga ttttgttggt 181620
taaattctcc cacccactcc ttgtcttcct tcctgtgtat tgtggcagca tctctcattg 181680
```

-continued

```
ggcatttacc ttctgataca cctcgtctgg gaaaataaaa acaggaattg gtagggtggt    181740
aggagatgtt tgggaagcat gggtgagaga accctcagga atagactcat ccttattatt    181800
aacttgttta agaggcagat tatactctcc tataaagact gccatggttc tcttgtctga    181860
tactacaagc ccatggtggt ctttgggaca tcttgtatgg acctttaggt agggaaaggc    181920
cctatatatt gctttagggc tcatgatcaa cagaagtgtg gttccattcc tctacaggca    181980
gcttcaggct tgcgccatct ccccatgaag ttggatgata ccttcatggg ggtgtatcct    182040
cttagtcaga gaggcaggcc tcctgggtgc taaagaaatc ctcagcttgg gatattaaaa    182100
cacttcctat tctttaccac caaactgaaa aaaatagctc tgacaaaaaa aaaaaacctt    182160
tcttaatttt ccctgtccag aattaatctt acctttctct atgggtgaat ccactttttc    182220
acctgtatta ttgtgtttta aatagctttt tatctaccct acattctgtt tcccccaaag    182280
ttggtgggtg tgtcttattt atctttgatt ccccagggcc ttgcacagtg cctggcatgt    182340
ggtaggtact taatgtttaa taattggaga taggatatat aatacattaa tatatattct    182400
gtataatata tagttgttcc attctttatt ggtatactga taaaatatat tcatatatgt    182460
aactttcctg ccttcatcta aacttaaatg agaagagttt gtgacctcca ttttttacccc    182520
ttttctggta taatcttttg atagcaacaa cttctgttca taaatggatt tttcattccc    182580
tgtgtaacca tagaggagtg gccaattagc ctttgactga cacagtcacc ccataccagg    182640
gccataggag cagtaagtgg tgacagccca taaatgcact tgatttctac ctttctcact    182700
gaaacttcta aaacccacgg gccctgtgtc cctagtttga aggagccatt atgggatgac    182760
tgtgcctact tactaatagc ctaagaccca gaaggataca gaagattcaa aaagtgcaaa    182820
aggccttttc taagacatta agctctttat ttatacctca cctaagttag tcttcaatcc    182880
agtctgctca atcttggcta gaattgcgag gggagtaaag caaccaagta attgtatagg    182940
tacccttggg aactaggatt ttcagcatgg aggaaagggg aaacagaagc aagatagcag    183000
agattcatct aaattggaat tggaagtatc agtgtgaatg aatatgagtt catgataaat    183060
ctcatctatt aaaaaatata cacatttcct aatattttca ttgaaatagt cgagaaacta    183120
atcaagcagc aatgagctcc tccacccatg actccttggg gatataggtg attttggtct    183180
agagcaggaa ctgtacaaga ttagactgga atatttggac atacagatag catagtaagt    183240
atggtgtcaa ggactactga gagtatatca aaagttctca agagccaaat tgaagaggct    183300
cccactggct atttatggga taattggaac atcaataaga ataataaatt gaaagcatta    183360
aataaggttt aaacccaaga gttcataata ccaaaaaaga aaaaaaaaaa tccctcattg    183420
gttaccttttg gaagatgcta agtaaccagc ttattatatt gaaaattgtt tacataggaa    183480
agaagaaagc ttttattctg cctttccttt atgaattcta tcgcatgtta acaaaatcat    183540
tgagaggaaa agtttcttat tgtagaagta cttaagctaa taagtgccaa agggataaag    183600
aatattcctg ttttgcagtc cctgtttaaa tgatagcacc tagatatgat caccaatggg    183660
cgttaatgtc acaagaagga caatcaggca ttatatgcca cctgatggga gtgtacagca    183720
ctgtctatga aatattcttg ctaaaagctt gaatctacat ctgattaagg ctgtagatta    183780
gaagtcagca aattacagcc ctcaggccaa tcatttctga tgcctgtgtt tgtaaataaa    183840
gtgttgttgg aacgcaactg cagaggttca cttaatactg tctatggctg cttttgttta    183900
cagacaaagt tgaatagcag ttacagagac catatggcct ggaacgccaa aaatatttac    183960
tatctgatcc tttacgggaa aagtttgtct gtccctgctc tggatctagc tatctacttg    184020
```

```
cagcaaataa ggggacaaca gaacatgttt aatgacatca gggggataat cagcaaaatc 184080
cagccaggaa atccatagga aaagtgacct gttttcttca ataaataaat ttcaggaaga 184140
ggggaggagg agagaagaag ggaagaaaag ggagagaaag agtgtggaga agcggagagg 184200
gattgcctgt aaagattaaa gcattttagg gaaaataacc acttgcaata tatgaaatta 184260
tttcttcctg acttaaacat agaaactcta aaagtgtttg aaatatatat ttacaagaaa 184320
gttgggaaaa ttaaaacatt gattatatat ttgttagaga gtcatgcacc acataatgat 184380
gttttggtca gtgatagact ggatatatga cagtggtccc acaagattat aatagcataa 184440
ttttactgta cctttctgt attcaaatat gtttagatac ataaatacca ttgtgttgcg 184500
gttgcctaca gtatttaata cagtaaaatg ctgcatagtt ttgtagcata ggaacaatag 184560
gctcctattg ctcctattgc cagcatatag cctaggtgtg tagtaggatg tactatctag 184620
ttttgtgtaa atacactcta tgatgtttgc acaatgatga aattgcctaa tgatgtgttt 184680
ctcagaatgg atttctgttg ttaagcagtg catgacagta ttcaggaatc aataacctct 184740
taggtgggat aattatattg tggttttgtt ttttaaaaag aaatccatct cttttaaaga 184800
gccatgctga aatattacgg atagtatgat atgttgtaca ggatttgctt tccaattctt 184860
gagagtgaga caaggtagga agggaagtgg gggagattta aatgaagcaa gattgaacat 184920
gttttaactg ggtgacgggt acgtggaatt cattgaattg ttatctttac ttttgtaaat 184980
gtttgaagtt ttttataata aaaatattta tgggttttt gtttgtttgt ttgtttgttt 185040
tagtgtattc cgggcttctc ctagatcaat tactgggcat tagcattttg aaaacagctc 185100
tcccatcaaa gctgccagtt agaattggac aggttatttt ctgttcaaga gcacctggat 185160
gaagagactg actggggttg cgtcctccgg aagaagggag tgactttttc taatttgcac 185220
taagacacaa tagggctag ttggctgtct aggagttgga tcaaggtttg ttgttgtttt 185280
ttttttgctc ccaggtgatt ctaatttgca gccaagggtg agaatcagtg gcctggtagg 185340
atcagggttt ctcacatttt attgtttata tcaatcatct ggggatcttg ttaatgtgtg 185400
gattctgatt cagtaggtct ggggaagggt ggagattgtg ctcttccaat catcttccag 185460
gtgatggctg ctgctgctgc tgatccaggg acacactttg agtggcaaac ctataaaata 185520
tagtacctgc ccactgtgaa cttatggtat atccaacagg cttgagactt tttattagaa 185580
agacaggtta tctaataggc caaatattta tccagatgca attgtatcct ggacccaata 185640
ttctgcattt ctgtctagtt cccttatgtt actgatgctg taattctata gatcacgctt 185700
ttgataagaa agcccagaca aaacccagta acatttcccc tgtgttatta cccagattgc 185760
ttcctgtagg catgggcctt tctgacattt ctgtttagtt cctaatctct gtttcaatgc 185820
agatcagcaa ggccaagttt gctttatta gcagctggca cttcctttaa ttcctaactc 185880
caggttttca gctcttctcc aagtaggcag attgcttagg tgctcagact tgaattaacg 185940
gctctttatg catataataa tcatgactta ggtttgcaca acccttatta gggcccatg 186000 gaggcattgt gaatcagcag tgcccagcag caacctgttt tgaacaagta gagaagctcc 186060
tatagcaggg ctctccttcc cagccaggtc aagccaccgt tcactcttcc ttgacatcac 186120
cttcagtgtt gagtcaagtt cctgggagga tgagctcctg gttgtaagta gtgtagaaca 186180 gtggttttc agccttcttt tagtttaggg attttctgtt aggaacacaa tccttgctgg 186240
aaatgtaaac accacagcaa caggaatact tttggcagaa acggggatga gtgtgaggtg 186300
tacatccctg gggcttagaa agtgtggtgg agccagtgat gggccatgca tgtatgggtc 186360
cacatgcata tgtgcatttg tgtgtgtatg tataagaaaa tagtaagtag gaatactgga 186420
```

```
catttctgtt aacaaaatgt cccatagaaa gctaataaaa actcatatgg agaagctgta   186480
tgttagaaaa gataaaaaaa ttaggcaata tgttgtatct tataatagtg tagttcagtc   186540
aaagaagata aggaaaatct gagggaagta agaccagaag actggcgagt gcagagtgat   186600
gaaatgtgtt gaaaattttc tcacttctgg caccctcattt tatttatgtt tggctcagtt   186660
tccttcagag ttctacctca gttgattaga ttcccaaata ttgtgtgtaa ttgttctaca   186720
gtgaggataa ccctatttta tcatatgaaa aagatgttgt ttgggaaatt taataaatat   186780
tacatgtata gtttctttat tttttctatt taggttttgc ctagaaagta ctatattctc   186840
aattgaccaa ataaatgata aaattgctca atacttgctc aaaaatcagt gttttttggg   186900
gggagaggta gtaacaatga tacagtctgt tctccttaat atatttactt agtttagttc   186960
gaaagtatat tcagtcattt gctctttaga actgtaggtg tctattcaga gcaggagggc   187020
cctattattg tcaactcaga aggagctct tacacattct ttcaaacaga gtttgaatgc   187080 taaaaggag gtacaactat aagctgaatg ctcatgaggc aaaaaaaagg gttcacacag   187140
cacttgcatt ggactactga accatctcat ggcctcatct agccattggg gcctctgctt   187200
aaagatgttc tgctgtgtcc tccatatttc cacctgctgg gtgaacattt actttgccat   187260
ctggcatgtc gggaattaga ctcaccacct tcctccccct tcctgtgtcc acatcagttt   187320
ccttgaaagc atccgttttc cttcagctaa ttctttaaac ctcacgcttt ttcacctgct   187380
ctgcttcatt tcttttaccc gctaagtcat taatgcctga gtagtctgta gtcactaagg   187440
ttctgaccct tgatgtaaga cagccctagc ttctggccct ggttctgcca cttaatagct   187500
gtttcttgtg taaattactt tccttctcca tttccttgtt tgtaaagggg ggtaatactt   187560
gccttagagg gtagttgtaa gaatcagcta gaatatctac tgtgtctaga atgttgtaag   187620
tattcaatac atgtcaatta gtactactat tgtaaataa gaatattcag tcttccatat   187680
ccattccttc ctttggttgc catctagtct aagctctggg cccttctctc ttgcattagt   187740
gtcacagctt ctttgctgat cttcttgttc tccaatctat cttgtcagac taatagttat   187800
taagcatttt tttattagca tactcaaaaa ccttagtaga ttcctgtttt ctgtctcacc   187860
atctaaactc tgggatccag cttttccaggc cccccttact tgtaggagcc tcttaatagt   187920
ctgtctgcat tcaccctgat gttcccaacc ccacttaaac tgttttgtgt attacatcca   187980
ggatgaacct ttcaaaacag atcatgtcac acttgtacac acacacacac aacacagaaa   188040
atccttcaag gaactcagta taaaatgcca aaatcaggtc taactcctgc ccttctgttc   188100
accctcatct tgtatcactc ttgccccttg ctgtctccac gtcagccacc aggcctttc   188160 taaaatttgt ttatctagca tgctgcttcc ttcgtagtct tgtacatgct ttttcctctg   188220
cctgtaatgt tcttctcgcc ccatctactc attcttactc attctttcag ctcttggcat   188280
aaatgtcact ttttcatgga agcctttgct gactaagtca atctatctg ctacctccta   188340 aagtcacaaa cctgtctttc aatgcattta gaacagttgc aatttttacat gtatctaggt   188400 ggacatttca cagacatatt tctccctaag tagttagcga actccaagag tataattttt   188460
atccattaat gtgttttttc attgtttgga tctgtgcttg gcacaaaata attgattaaa   188520
aatactaaat taatgaatgg aacttgtttt cctcatttca tcatgaatgc ccatataaca   188580
tggaatcatg tcatatcccct ttcatcattt ttccattaat atgcaatgcc caacctttac   188640
ctccaagttc cccctacctg gaatgtccac tttgattgct gtgatttacc taaatttatc   188700
cttcaaagat cagctccagt gtttcttcta cagaaccctct aaaaaaacca agctagtctt   188760
```

```
catgaaggac ccttctttt  gtaagtttac aaatcactat ttcatttcat ggttcatgat  188820
ttatgatatc acccttattt tgctcattat tatcctgttg tcctagtcag attgcaagtc  188880
tcacagaaac cagattattt ctgcatcctg ctcagatcat aaaccatgct gtccaacata  188940
cactggggc  aaaaaatagt ttgctaaaac aatgtgtata tctagaaact gaactgcaaa  189000
aagtagttct gggaagttcc tagaatgaaa gtcagtgtat ctggattcg  tcaaaaaatg  189060
aattttagtc cttgccttca tccgtgtgcc gatctctcta agaatttcca gttcttaagc  189120
tcagtgagac taccagtgtg acataagcac tggaaatgaa aactcctctc ttcagagttt  189180
gagatgaacc ctgaaagatg acttgtcctt gtcatcttaa aatagcaatc ttgacctctc  189240
caagtcacaa ttcatgtaat ttttttgag  gctttaaata tctttctgtc tttgaaatct  189300
ttagaattcc aaggtataaa cttaataatt aaattaagta agctttttat aattaggatg  189360
agatttcagg cagccagtta ctcctacgct aaaccatatg aaaaattcca tctgaagtca  189420
tttgaaaggt aataccagga aatcattttc agcatcacaa gacattaaaa agcttatttg  189480
tagccaccta caagctggga tatgagatat acagaatgct cagggctacc tccatgaaac  189540
cctgcagcac agatgagaaa gttttaagt  gtgtgactgt cagggcttcc tgtattacag  189600
tatttataat cttacaatct tgtcatatta cagatgggtt atatattagt ccattctcag  189660
gctgcatgaa gaaatgcccg agacttggta atttataaag caaaaggct  taattgactc  189720
acagttccac atggctgggg aggcctcagg aaacttacaa tcatggtgga aggcacttct  189780
tcacttcttc actgggcggc aggagagaca atgagtgcaa gcaggggaaa tgccagacac  189840
ttataaaacc atcagatctc gtgagatctc acacactatc atgacaacag catggggaa   189900
accacccca  tgatccaatt acctcagtta tcagttatca ctgataaaaa tggatataat  189960
catatatttt tttccttaga gggtagtagg tgtttgtcaa catggagact aggaaaccca  190020
caaatgattt gtatttacaa tatccaaagt ccattgatgg aaaaaattaa ttttttaattg 190080
ctaatataaa atattttaag gtataaattc atagtgagta caatgaggta catatacagc  190140
ctcatgaagt tttatgaaca cattttcacc catacgacca ccaccacat  caatatatag  190200
aatatttcta gctctgcaga agacccctt  gtacggccac attacatctc ctgccacaat  190260
gtaatcatta cctgatttct gttacccttg gttagttttg tctgattgta ttagtctatt  190320
ttcatgctgc tgataaatac gtacccaaga ctgggaaatt tacaaaagaa agaggtttaa  190380
ttggacttac atttccacgt ggctggggaa gcctcacaat catggcagaa agcaagaagg  190440
agcaagtcac atcttacacg ggtggcagca ggcaaaaaga gagagagctt gtgcaggcaa  190500
actccagttt ttgaggctat cagatcctgc gagactttt  cactatcacg agaacagaca  190560
ggaaagaccc acacccatga ttcaattacc tctcaccagg tcctcccatg acacatggga  190620
attgtgggag ttacaattca agatgagatt tgggtgagga cacagccaaa ccatatcacc  190680
gatgatgaaa atttctaaga atgaagtcat acactatgta ttttgtttct ggcttctttt  190740
ctccaacact gaaccgtgtt gctctgagta tccatagttt gttcttttt  attgctttgc  190800
agaattccat tgtatgaaca caccatgata tatatctatc cattctttc  tccacggaca  190860
attgggttt  ttctagattt tagttattat gaaaaaaaga tggcatgaat attcttatac  190920
atgtcttttg atgggacata tgcacttatt tctctcatat aaatccttaa gagtcagatt  190980
gctgggtcat agggtaggca tatattatta aaatgtagtg tctattgcaa atagttttct  191040
caagtgattaaacaatgatg tattttaact cataaacaaa gtatatgaat acaagctaac  191100
tactatagca tagtacaaat tatgccattt tttctgactt attattatga atttatattt  191160
```

```
taaaagtaat ttaggcacta aaatttggcc agcccaagtg ataattggaa ttaaaggtga    191220
aaggaggttg aaaaacgttt acggtctaaa attctacttt aaaaattcag ctttatagaa    191280
aggcattaaa tgattgaaac tttaataaat accgtcattt ggcaaattac tctttccatc    191340
agagtgctgg gaattaatat ttggagatta aaattaatta atagtaattt cgaaaaatgt    191400
attaagaaac ttatttggcc aggcgcggtg gcttatgcct gtaatcccag cacttcggaa    191460
ggccaaggtg ggtggatcag ctgaggtcag gagttcgaga ccagcctggc caacatggtg    191520 aaacccccatc tctactaaaa aaaaaaaata caaaaattag ctgggcatgg tggtgggtgc    191580
ctataatccc agctactcgg gaggctgagg caggagaatc ccttgagcat ggaggtggaa    191640
gttgcagtga gccgagattg tgccactgca ctgcagcctg ggcgacagag tgagacactg    191700
ttgcagaaaa aaaaaaaga aaaagaaaa agaaacttac tttccttggt caaacaaaaa    191760
ggaattattc aaagcagata catgaaaaaa aaatagtgat ttgggctaag catattgttc    191820
tgttgaataa ttggagttta ttcctcccat gcctgataaa aataacatct tgacatccca    191880
gcttcatgcc agtattttta tattcatttt tcttttgctc tcataaggcc ataaagtata    191940 tttttttcata tgaccagaga attgtccaac ttgctttcac tgtaattttg ctgcatccaa    192000
tttataaatt cttttggaaa gaagattatt tctttatcta tttacaaggg attgaaaacc    192060
acagaacact aaattttctg tgcagagaca tagggaaatg aaaaacccca cacagaggtc    192120
tcctgccatt tccttctgag tgtaaactaa gatgtgattt tgcttttct atttcagtta    192180 tctcagggat ctccagaacc gattgagccc aacttttttca cagcagatta ccatttatta    192240
catcgttcat ccggtggaaa cagcctgtcc ccaaatgacc ctacaggtaa tagtgatcaa    192300
catgggtaac ctggctttca tgaagaaata tattgtttgg atcaacagct atttctaaaa    192360
gattatctcc aattttttt taaatagagc ttgttttgat tatttatagc aatagttgga    192420
aggcacatat ggtaggaatc tagaaattcc ctgaaattta tcttacccag ttgtggcagc    192480
ttccttgatc atttattaat atcataaaca aacagcagaa tctgtgtggg tgagttgtat    192540
ttccttttat ttcttttttgc ttatctgatg atgggaaatc aaattcccta aagcatgtag    192600
ggagataaag agcagaaata aggagtttaa atattcaaaa tagagaaacc cttgaaactc    192660
acctaaagaa tccacattag acacttgaat ttttttctct tttacataaa attcacatag    192720
ggaggcagta tagcatagg atttaaaggc acatattctg gaaacctggg tgcctagatt    192780
caaatcttgg ctaaaccatt tagtagctga ctatggacaa ctatttaacc tctctgaacc    192840
ccagtttcct tgcctgtaaa atggggataa atacttgcat cacaaggtta tagtgaggat    192900
tagagtaaaa ataaaaactg cctgtctatt agtagggct cagcataatt gaactcttct    192960
tgtcatatct gaattctaag aggaagcttt caagctactc tgaggtttca gtactcctaa    193020
ataatttttg aatctttata aacggtagct atgtcacttg gaggagtgga tagaagtgaa    193080
gattttacag ttaaatgaag acttgccatc tctttagctt ggaaaaaatg ctcacttttg    193140
ttgtgctttt gttgctgact gaacaaatta tttcatgaat taattgacaa actttccttt    193200
ggtcttctgg gataaagcta aaccctatgt atgcagaatt ttatttaaaa taatctctga    193260
gaaatccaag ataaaaagtt gtttaaagta atttgctttt aaaatcattt ccaagacagg    193320
gaagtttatc tgcaggtcaa acttctccgc atcatagaaa ctctgatgaa atgaagaact    193380
ttgataaaaa tctctcaaaa acctgagggt gagttgacaa actccccca gggcagctgg    193440 atgccccact ccagagctga ctaggcttgg cccatgtcac agctggctgg gcaaaagcaa    193500
```

```
aaacagcaga gcctgccagt actgtggggt atgcctttaa agatgagcca ccagtactca   193560
cattttcaca tctcttcttg accctaaacc cattctctct tctctatttg aattggcaga   193620
gaagtggcct aggcctctac atgtcagtgt tgattggttt gagtgaaagc tggtcaacac   193680
ggctttgggt ggcatcggag tgtgttaagg tgctggtata ccaaattctg atcaaccatc   193740
ataaagtctg tccagcaaga caatcccaag caaaaaggac aaagctggag gcatcacatt   193800
acctgacttc aaactatact acaaggcttt agtaaccaaa acagcatgga ctggtacaaa   193860
aacagacaca tagaccaatg gaacagaata gagaactcag aaataggacc atacatctgg   193920
aaccatctga tctttgacaa acctgacaaa acaagcaat ggggaaagga ttccttattt   193980
aataaatggt gctgggagaa ctgactagcc acatgcagaa aattgaaact gggccccttc   194040
cttcacccct atacaaaaat taattcaaga tggattaaag acttaaatgt aaacccaaa    194100 attataaaaa ccctagaaga aaatctagac aataccattc aggacatagg cctgggcaaa   194160
gatttcatga cgaaaatgcc aaaagcaatt ataacaaaag caaaaattca caatgggat    194220 ctaattaaag agcttctgca cagcaaaaga aactatcatc agagtttaca gacaacctac   194280
agaaagagaa aattttttgca atctatctat ccgacaaagg tgtaatatcc agaatctgca   194340
aggaacttaa acaaatttac aagaaaaaag caaccccatt aaaaagtagg caaaggacat   194400
gaacagatgc tactcaaatg aagacattta tgccggccaac aaacatatga taaaaagctc   194460
aacatcattg atcattagag aaacgcaaat caaaaccaca atgagaaacc atcttgtgcc   194520
agtcagaatg gcaattattt aaatgtcaag aaacaacaga tgttggcaag gctgtggaga   194580
aataggaatg cttttacact gttgctggga atgtaaatta gttcaaccat tgtggaagac   194640
agtgtggcta ttcctcaaag acctagaacc agaaatacca tttgaaccag caatcccatt   194700
actgggtata tacccaaaga aaataaatc attcccttat aaagatacat gcacacatat   194760
gttcattgct atactattca caatagtgaa gacatggaat caacccaaat gcccatcaat   194820
gatagactgg ataaagaaaa tgtggtacac atgcaccatg gaataccatg cagctataaa   194880
gaggaatgag atcatgtcct ttgcagggac atggatggag ctggaagcca ttatcctcag   194940
caaactaaca cgggaacaga aaaccaaaca ccaaatgtcc tcatttataa gtgggagctg   195000
aacaatgaga acacatggac acagagaggg gaacaacaca cactgggcc tgttgggtg    195060 gtggagtggg tgaggggagg gagagcatca ggataaatag ctaatgcatg ctgggcttaa   195120
tacctagcta ctgagttgac aggtgcagca aaccatcatg gcacacattt acctatatta   195180
caaacctgca catcctgctc atgtatcctg gaacttaaa ttaaattaaa ttaaaaaaaa    195240
aaatctggcc agccatggtg gcacatgctt ataatgtaca gacgttggaa ggctgtaggc   195300
aagaggatga cttgagctca ggaattcaag accaacctgg gcaacatagt gagaccctat   195360
ctctacaaga tgatgatgat aataataata atagtaataa taaacatttt aaaagtcttc   195420
tggcaataaa tatattttt ccctctaggc agctatatga aagggtcaga tctttggtct   195480
ctttacatct gtatctgcct ccctgtaaga atcaattttc tttctaacgt atatttattc   195540
ttcttagcct gtagattagg gagagtttct taatcagaaa acacccatca ggtaatttgc   195600
attgggaatc acccctcact tgcccttaac acatacacac acacacctct aactttattg   195660
gacactatga gcaatgcccc ttaatcttca tatatcattt tgtgatgccc atgcccaagg   195720
aagtcagtta ttaaagaaag gaaaacaaaa cacttgaata ttcaaagcca aggcagatgc   195780
tttggaattt gcttgttcca tctttatcat taagaaattg acctgtttgc cctgtggttg   195840
aagtcataat tgccagtaaa gaataactaa gaaaatgtga acccaaatgt cagacttttcc   195900
```

```
ataatttatc ttttttaggt ttaccaacca gcattgaatt ggaggaagga ataacatatg    195960
aacagatgca ggtgaggttt ttgcagtgtc tctgaatgat tttattttgt tacttctaat    196020
tcaatactaa cctgattttt aaaattttag actgtgattg aagaagtcct tgaggaaagt    196080
ggctattaca attttacatc taacaggtaa gagctagagt ttgccttcaa ttgtgaaaga    196140
tgaattgagg tcatcagatg ttagatctaa tttctttatc ctttattcca gagggatttt    196200
ttttcagatt ttatttaaa tactttata aaatatcttg cttagacta gatacatcta       196260 taagtagaat atatgtgccc atcttttgtg tggacacagt tgctgtattc tcagttgaaa    196320 caaaagggt gattgcttag tagaaattta ttcccataaa aaatcataaa tataagtaaa     196380
tggaaaaagc atttctagat tggttttta aacatcaaat atttgtttgt ctcattctag     196440
aagagctgaa aactcactcc tatcacttaa atctacccac tatttgcaca gaaggctagg    196500
gacaaagtgc aactgaacaa agaatcattt cttgtgaatt taagatatat ttgtggagaa    196560
gagactttgc tattgtatgt tgccatttgt ttaccctaaa taaaaaacct ccatttactg    196620
gagctgtatg ttatcttcca atatagctat cgttggtgtt ctaagagtat atgctatttt    196680
atcaattgca tcaattttta taattttagt tttggaaata gtgttggcac aacaatttga    196740
gtacaattag tttactatga agttattcaa gaaaggtttt ataatcaagc aaattagcat    196800
tgtaggtgat tgaagcctga tcccactggg gaaatctaag agctgatata gaatatgtac    196860
cagggccatc ccacacaaag agtgagagag ctgaggtatt tatcctccaa tctccatcag    196920
tcattgttta aggcctttcc ctaggaagtg ttaatgccct gttttttttct ggccttttgt    196980 aaatatgaac aaagaagact ccaggggtca gagaaatcct caggaaaaga agtgcaggta    197040
ttccattatt gaatttcttt atatattagc aggtagaaat ctgccagcgt gctttgaagt    197100
ggaatagata ggggtatggg tgtttacaat gtctgctaca caagagttgt ctgttgactt    197160
acctaaggag cctactcata gctgagtcat caaattggtt gcaagtatcc acacacacac    197220
tctatctggg ccacagttgt tttaggaggc atagtccttt ggagtatatt ctctcaaagt    197280 ggtctttat gcctggaggg actgccttcc ttttcaatta ttgaagctat tttgtgacca     197340
ctatttaaat tattccagaa gtcttcacca aagatgacta gtaacaacgg gaagagaaag    197400
agggctcaag aacatcctgt taaggtcatt atatagaaat tagattcttt tctaaggtta    197460
gttcagtctc cagtgtttct tctccttttt cttctacttc tcccatttca aggagttttt    197520
cttatgagtc acaagtaaaa ttattcaact acttgctctt ttgacttgat aacagtttca    197580
aaatactacc tttataaatt tagatctgtt gtgatttgta actgcagagg aacaatgagt    197640
aattctcatt ttctaaagat ataccgtcaa tagaaattac catctccaca actactctcc    197700
tcccaccatc cctggagaga tttttgaatt ttcattttct attcaagggc tgagtatatg    197760
cattaggaaa agaaaatggt aacaggaaca gaaagagcag caaggacctc tgaccaagtt    197820
tggatatttc tcatttctgg gcttccggga aaagggagc taggactgag ttggaaggaa     197880
gaaagctgtg taaagaaagt taagaaggt cataaaggct tggccagcct cgtagctctt     197940
cccaaagcag gctctatttt tgatcatttg catggttgta tgataaatta cattttacat    198000
acataagcat actatcatgg atagtatgaa tgtttctgtt tttaactgtg agcctcatta    198060
tttcaagtgc ccttggcttg tactggggaa aagatgactc ttgtcatttt atctgcattt    198120
tctcagagac ttgggatcat gggcaaggaa tgtcttcata tttttgcag aaaatcattt     198180 aaatatcaag aaaaactaag tgtgcaagga acttaaggaa gctcttacaa gaactttat    198240
```

```
tttcccttta ttaaaaaata tttgtcttat ttttggaattt atcattattc tttttcaatt    198300
ctactttcat taggttttaa accgatctag ttccaaagac atatggcttt attaaaagac    198360
attgcaaatt ttcttattat gataaacaga taataagatg ccttataaca aaggcaaaaa    198420
attattcagt tatatttgta attgtgaatc tattatgaag gtatgatgaa acagtcaagt    198480
ttaagcaata taagttgggt attgcattaa attttcttaa agtgctccaa attaaaatga    198540
atcacattta aaaatccata tatccatggt attcccttt tggcttcttt ttttttttt    198600 ttttttttg agatggaatc tcgttatgtt gctcaggcca ggctgaagtg caatggtgcg    198660
atcttggctc actacaaact ccacctcctg ggttcaagcg attctcctgc ctcagcctcc    198720
cgagttgctg ggattatagg cgccaccac cacacctggc taattttttgt atttttagta    198780 gaaacggggt ttcttcatgt tggccaggct gatcttgacc tggcctcagg tgatccacct    198840
gccttggcct cccaaagtgc tgggattaca ggcatgatcc accacacccg acccccttt    198900 ggcttctaat agcaatgata gaacatatct gggagaaaaa actctccaga atttgtttgt    198960
aaaaataacc cttgtttgtg cctaaagcca ctctttgttt actagtattc caaataatt    199020 tccaagaaat aagtcaggct tcaattagaa gcacctacta atccacaaac tgtgaataac    199080
acataactcc aagtacaaat cagattagct ggtactgtca tgctttttc cacaaaggat    199140 ggagggtgct aaatgtcaca gcatatgtag aggtatttag aatcagtatt tagaattagt    199200
agactgcatt tttccccaat aggtttcata gaatgggcaa tattatcaaa gatgtcaata    199260
gatagtctct gaaaaataaa gtttcatggc cacatatatt tgggaaactc agaatgtaca    199320 atttttata tttggagaat gttgacacct attactatat taaagactct gagatgtact    199380
ataagaaaga aatctgttga ccttgtttgt tgacctcagt gttttcctca ctctttacat    199440
ggaatacaat tgaggaaagc tgttttagct atgtggttgg aaatgaggaa caccgttttc    199500
actccttcac cagggtctac ccagatctct gttgttctca ttgacatggt catcattgtc    199560
atcatcgtca ttgcaaaatt tgttcttaaa tgaattaagc accgtgctga gaaagttaca    199620
tatataattt cggtgttatt caagtttaca atttaagact atcagtttga atagtacaca    199680
catcatctag ccagccagtc actaaaggat taattcaaga taaggtacat ttttggttta    199740
aattataggg tttatattta gttaaggaag agaatagaa ggtgccattt tcagactgaa    199800
agtctcagga taaagccatt atctatctgt tagctatctt tgaggaagat ttctggaact    199860
gtttaaatca tgaggagact gcttggacag ttaggaagaa tgtctcaggc ataaaatgct    199920
gcattaggaa aagaaaatgg taacaggaac agaaagagca gcaaggacct ctgaccaagg    199980
ttgggtattt ctcatttctg ggcttctggg aaaaagggag ctaggactga gttggaagga    200040
agaaagctgt gtaaagaaag ttaaagaagg tcaaaaaggc ttggccagcc tcatagctct    200100
tcccaaagca ggctctattt ttgatcattt gcatggttgt atgataaatt acgttttata    200160
tacataagca tttagcttgc ttaccagaag gatgcaactt aatatgcctt aattttatca    200220
ttgttgtttg tgaggataaa atcatttgag tcatgaataa acagataatg agcatataat    200280
ctttatgaat atacttatgt attacattaa tatttatttt ttaataataa aatgtgttga    200340
gaaataacag tatacaagat aacaaatcta cattgaatca acttgaattg ttttatttcc    200400
ccaattgact gataagcgtg taaattagtt atttttaacct acacaggtat tcaagtatac    200460
aagctatttt gaatgaatat ttgttttctct actacaaagt gttatcagtt cctattgagt    200520 tcataaatttg agaaaggcct tgttagcacc agacttcagc caaaggcagc ttttaaaaa    200580 tgtcccccatc ctaacaaaaa taatcgtctt tttatttact gtgatttatt tacttatatg    200640
```

```
cctgagcccc agtttttgaa attgaatgta tgaactaaaa tatttgtaac tatagagaat 200700
tctttccact tctgaatctt ataggtatca ttcctatcca tgggggacca agaatcaccc 200760
aaccaaaaga tgaaaatgct gcattttgag tggacttgat tttctcagtg aagttcaagt 200820
tctggacttc agccgctatt gcaagatgcc caaggattgg gtgctgctag agggtgtgga 200880
aaagaccaag atgccatggg gcctgcagga cttctttctg ggggtcctgt gctggagtat 200940
atgacagctg cggtacttga gggcttcatt gccagaacac attatataca ggatgtcaga 201000
gctaccagtg tgctgctggg agaaaatgct gcaaaattca tcttttggag ggtgggggga 201060
aaacccaaaa acaacaacaa aaaaactctc ttacagaatt ttccttaaca ttaaaaaaaa 201120
cttgtcatat ttttcaaagg cacatttgat actcagaatt gctaaaagta tatttaaaga 201180
catctagcct tccatatgta aaaatatttt tagataaaga cagttacagg actcagaata 201240
atatattggg tgattcactg tatcctccat ttttacattt aaagaaattc aaaatacgtg 201300
attaaatttt tttttttttta atggatgggt tggttctcgc ttaaccactt gggtgctagt 201360
ggtcttgaac tgtgatacag tgtagacagt atttgtaacc ttgcacagcc tctgggggta 201420
actgtcaaac tgtcagattt aacttagact aatagaaat attgctgtac agtgtgtgta 201480
tatgtttata tatgagggcg gaaggagaga ggttttgatt agactaatgc tttgctgcta 201540
atcaaactta tagtattttt agagcacttt gaagagttta tagaatctat gaaaagatg 201600
caatattcct catcctaaat ccctccttat tacaattacc taaattgttt atgaattgtt 201660
taggattttg aaatgaaaat aagttaaatc ccttttttac tcattgaggc agctcaatgg 201720
aagtgaaatc agaatgccaa actgtgtatc atcctttatg ccgggagaat tatgatgaaa 201780
atctgctaga ttctcactgg gcttaaactc cttctcttca atcagcttct taaaactctg 201840
gtgtaatgtc aagaaatacc cttattgcga aatctgtcta cacttctagc tacctaaaga 201900
gcaatttatt ctacataatt agtaatctga aagttgaaat tatactttt atttacttt 201960
catggagttc tgtcatcttt atttacactg aattttttta gtatgattga atcgatttta 202020
gttcaatgta tttacagtgg ttgaaagacc ataaccttct ttctgtatag tatgaaaatc 202080
tacactattt ttaaatgagc atatttaata cttaaattat atccaaattc cctttaatca 202140
tgcactaatg cttttgaaga ttgtcaatgg atctttcttt aagccaaatt aacaattaca 202200
gatacactgt aatgtaagat aatagatgca aatacagtaa tgaaaatttc agtttcagct 202260
ttcaaactaa ttctatccat atgtgaaatt cataaaatca aaatgctatg atattgattt 202320
acccaggcaa aatttatttt ctgttccaag ttaatttgaa cctgcactta taattctttt 202380
tatctttcag tgtatgaaag gggcacattt cttcttcatg caggaagcac agacctggag 202440
gggcacaaat tctaattgtg gggtgagagt ttgaaatcaa gttatttccc aaatggtagt 202500
atatagtaaa cagaatttag gaaagaatag tattcaaaag gtgtaccgtg gtaagggaag 202560
ataaatggtt tacttgaaga tgttttaaag tgtatatagt tggccttatt gaccagaaag 202620
tgagcaaaat gtttccatct aactcttttt tttttttttt ttttttaaga cagagtctca 202680
ctctgttgcc caggcttgag tgcaatggcg agatcttaac ttactgcaac ctccgccacc 202740
caggttcaag caattctcct gcctcagcct cccgagtaac tgggattaca ggcatgtgct 202800
gccatgccca gctaattttt tgtgttttag tagagatggg gttacaccat gttggccagg 202860
ctggtctcaa actcctgacc tcaggtgatc tgcctgcctc ggcctcccaa agtgctggga 202920
ttagaggcgt gagccactgt gcccagccat tgcatgtaac tctttaggt gataggaatg 202980
```

```
ggcatttatt atgctagaag tcagtgaaag ttaagtaagc agaagctgtc ctttttaaca 203040
acagcttcag gcctatcaac tctatgtgga tagatgtatt gttttgctaa aagtatgaat 203100
atgctctatt tgaattctcc ctaaactacc acaatcactg agtctatatt ttcccatgtc 203160
tctaagagaa agtcaggctc tggcaaaagc accattttgt acatagagtc catcccaac 203220 agagaagtta acttttcaga agcctttcta acacaaatat ggagcacctc ccctcatgac 203280
caagaatgat cattttgttt tgattctcca aactgtctat tagtgcaaag gagttgttac 203340
atgaacttca tagacctctt aatcttttct tgattgcatt tatatatttt ttcccttttct 203400 cttgtataat ttttaatgat ttgttgtgca atgaaattcc tatgaatgca cctaatttcc 203460
gtaactgaat atttgcatgg aatagaatat gaatcagtct tttcagatta cttttgaaac 203520
acaaatgctc ccgttaatta tgtttcgacc caccagctct ttctgaatta tgtgtacttg 203580
aaaccttaat ttgctttttta aaagcaaaat gtttcattct cagggaagtg actgcagcag 203640
gaatatttgc ttgcttgtta actttatctt cctccaggca tgtagtcttc aaatggagtc 203700
ttcaagggaa tagtaacgtg gacacttgga cccactgctt gtggatgaat ttcagaaacc 203760
tagagaaatg ctgcttgttt attgtggaca cttgtatggc attaggcagt gtttacagaa 203820
tgtttaggca ttctaaagca gaacacaatt aagaaacact gttaggaaat ttactcaaat 203880
gatataattg attaagagtt aggtcttcct ataagtatca tctatgactc attaaatact 203940
atgaattttg atgtccaaaa acaaatacag gtctgattat gtacaattcc agaaatatca 204000
ttaattaatc accactcatt tttaagatgt gtgaagactg taatattggc tagtgaattt 204060
tatcagtatt aatatgcata gaacccacat tcctcttttt gatttgatgt attatagcat 204120
gtatgtattg ctattttctc ttttttttga agtggtgagg aatcatgcac agtcaatatg 204180
ctgggttcct ttagaaatga ctttagctcc tgtctgaagg caggaaaaac ttcttttttaa 204240 ggaactttca tcattgcctt ttacttttttc tatgatggtt ttcatgagca ctgaaatcac 204300
ttggagaggc aatgcaaaga aatctatctg aaacagcttc ttggcaccct ggagttacag 204360
ctatgaaggg ctccaacgta agggaagctt aatgcttccg aatattgaca ttgactcctt 204420
gggtgaaatt ttgtccaaat ataaaattct tcatgttcaa caactaaatg taataaatga 204480
atttcatata tacttacatg atatctttga gattaaatta attatccttt tgtaggaact 204540
gacagctttg ggtagattat tttttcagtt gaaatgtgtt gctaacaata tgcttacact 204600
tgaacgctgt ttttcatatt gataggaaga cacaaatttc tcaggaaaac agctttgtga 204660
taaaggaatt cttatgtgtg tcattacagt aaattgcata ttgtaaatat gactgttgtg 204720
gttgattata gtcctgctgt gatgttgttt tgagatttgc aagagggaca ggaaagattt 204780
tatgagtttc atgggtgtc tgatggatat tgccaattta catattttct gagttcatgg 204840
gcaatagttg tttttaaaaa tgaagatcac gtaccctaaa atcacagctg catacttgct 204900
atgtgaggta tactagatgc tttattgcat gtatgtaaca attgtctaat aatataaaaa 204960
atttaagata cagttcattg ctttatccta aaagtaaatg aactgtagtc ttaattcaaa 205020
actgaatgtt attcctcaaa acatgagaaa ctgcctttt ctctcctttc cttttgtact 205080
gtgaagatgt gcactggccc cagctactgt atttagcgat aacagaagta cgtgactgtt 205140
taaatgctgt catttggaaa tagcttacct ttctttctcc taaacaaaga tagaattttg 205200
tctttatgta tggaggatta tggctgactg tcattttgac aatcaacaaa tccagatgga 205260
tacttggaat tgatatggtg agttcacaaa tgaaaaatta gccgaagttt ttgcaaacat 205320
gtgaaaaact ggtcccataa aacatgcaga gagaagtttg tgccagaaat aacaaaccaa 205380
```

```
gaggaacaac tgctttaagg ccttggcacc tttaaggcag actgtgaagg tcacttacaa 205440
aatgatattc ttaacccatg atttagctct gcatttcaag tgccatttga gtcaagattc 205500
tgaaatagaa tataaagctt gtaaatggct attaaatttt agctaaaact gttgccctcc 205560
atattctgtg tgtttgcctc atactgcagt gaattttgga ggaaatggag ctggtttagg 205620
gatacttcat gtcatgacaa acacatgaa gtatttacat gaacctaacc ttactttgag 205680
ggaggttaat aagtataagt actcagaagg gaaaccttga cttgctaaag attaaggata 205740
gatctttcat ggaggtggaa catcttcaaa tagaaattat gttttgagaa gttggagagc 205800
aagaaggcaa gaaattccct agtgcctggg tcgcccagca ggctgccac taggggtga 205860 gcaatggcaa agggtagctc gggagccttc cgtgattcct gctgctgggt ttcccagaag 205920
cagctgacca gatgcttccc cagcatgcag ctattgttga acttttagcc aggcaccgtc 205980
accaacaagt tgaccaccca gagcggtagc aaaaggcccc aaagtctctt cataacctgc 206040
tggctggtgg aatccgtagg acaggatccc taggaggcat tccaaagaca ttagactcct 206100
caaagaagca gttttatctg ccattaagtg agtgtgattc tgccccaggg gttatgttcc 206160
ccatctttca tccatgggct caggcccatt ttgtctgaca atgcacattt tacaagaagt 206220
atatgtgaga tgtaaatgga taagtgcagg cagatttgaa tatacttgta ccagttaaat 206280
tagaaaagaa acattgcaag caattttagc tgtttgcaag caaaccagtt gataatcagg 206340
ctgtagaaag attctattat ttcactcttc cacactgaaa acaaaaatt acttgaaaaa 206400 ttttggggtg cattttgctt actgacattt agtgggtcaa acaaaaact atagtgcttc 206460 ctgtattcca tcgttcacac tggtgacttt gtgaggataa aaagaacag agctgtcctc 206520 tgaaggaag agaaacccct aatctcatgt tgcccagagc ttttattttt tggacagccc 206580
aggatccaag acaaaggcct gtgcccacag aagcaaaaat acctgcaatg tgcttttttt 206640
tccctattag cctctaacat agtatctttt tgttgttgtt ctagcacccc tcccatgcgg 206700
gtctctcccc tgacacctct tcccctccca ctattcctac ccaaggaaca aacaaggttt 206760
cctgcacaga gctgtgttat tagagggaat gaatgttcca tagttattta atggtgtgcc 206820
ttgtggaagg cagagggaag tacttctctg tacgtgattt ctatctttct aaaacctccg 206880
caacacttcc ttcatgagca cacctactct agaatgacct caaagtcaga gatcctcaag 206940
agaagaagaa agaaatgatt ctataaaaga tttatataag atatgcaagc agcttttatt 207000
tttgctatga ttaaatatgc cctgtaaaat gctaaaataa tttaaaaagt tattttcaat 207060
tttattggaa aatgatttct cttttattga gaatttacag taaatgatca tctcttttct 207120
ctcaccagct tccccaattt cttgttttat gctcttaagt cttttgatta aaaaaaaatt 207180
tccagaaagc aatcatatat gtgtgaaagc tcaaatgcat acctcagctt tcattggtgg 207240
gtccctgtag caattatcta ttgctacaca tgttgtataa caaagcacct aaaaacttag 207300
tggtttaagg tagcaaccat ttattttttt cttatgagtt catgggtcag ttggaagttc 207360
tgcctatctg agcagagctc cactgatctc tgctagactt tctcctgtgt ctatggttag 207420
ttggcaggtt ggctgaagtc tagctgattt aggattgacc tagagggac aaatcagttc 207480 tcttccctgg tctcacacgt gttttcagca acttagccca gatgtgtttt tgtggcagta 207540
gcaagagttg aaaagagaat gcagaaatgc actcctattt tgacaagcca cttcttgtgt 207600
tgttttcttc attctcaatg gtcaaagcag gtcacacggt caaatctatc attagtgtgg 207660
ggagctgtat gaggctttca ctgctgtgca accagttgct ataagtttaa cagttttaaaa 207720
```

```
taacacacat ttattagctc acaatttctg tgtgttggaa gtttgagcag ggcttacatg 207780
gtcctctgct cagtgtctca caactataat cagtgtcggc taggtctggg gtctcacctg 207840
agcttgggga tcattttcca agatcatgtg attattgaca gggtttattt ccttgtgttt 207900
gtaggactga ggtcctgagc agctagatac catagatgcc acctgtagtc ccctgccatg 207960
tggccctctc cggagacagt tcccatcaag gcagctggct gcttcaaggt ccacaggaga 208020
gtctcttct ctctctctag tctgctaaga tagaatctta taaccaaatc acaggaatga 208080
tatcctgttg ccatattcta gtgggtaaaa gcgagttaca ggtgtactct acactcaaag 208140
gaagggatt atacaagagc aaggtcattg gggtcacctt ggattgtgtc tgccgcagag 208200
tgcaatacca aagaatgcaa aaaagtaga cctgaaaaat tggggccatg aagtaccaaa 208260
tgccacaata tcaaattacc acatgataaa aaggctggag aaacgcctag agccctatat 208320
tcgatgggag gtctctggat ggtgtcacac agggtcctga gcagatgcct ccccgctgcc 208380
ttcctttgcc cctgagctca ggtgcatatg gccacctgta ccctggctgc ctaggtgtgt 208440
ggcccccaga accttggcgc tcgcacacat tcgtcccct catgtgggat catggctctt 208500
ctgcccagac actgcatccg attccttcct ccctcccaaa cagctctgat ggaagactgc 208560
tcgatggtct ggagaagaaa gaattgtgtg gtagtcttat gaaaatgacc tcagagtgca 208620
ggacataaat tccagaatgt ttccagtccc catcccagga ttctgttaga tgtatccagc 208680
aggctatttg aaaatcattt ctaatccacc aagcaaacag acaaacctca gtcagtggaa 208740
tgagaagcag gaatgaaaat tattctttct ctagaagcca gaggagcttt cagtagcatc 208800
atagtaaaca tccttcacct ccttaaaact cgttgtgttg caatctgcta ttcttatttt 208860
agtcatttat caaatgggga catattgact gttctcagta attatgttca tatagtagag 208920
aacaggacta cataaatgaa ttatagagta tagcttgata taaatacaaa ctacaatctt 208980
aacagaaaac ccttataagc catgaataaa ggaaaatgtc tcccaagtct cccaaattta 209040
aagattctgt ctctcttctc aagattgagc atcgaatggt atcttcattc tacattcgct 209100
acgatgcggc atcaacaagg cgggtgggag ttcgcatcac accaggtagg ctagttgctc 209160
gtatccatgg ctcctacgcc gacgcggagt agaaatctct tgagccatgc tgtttgtcac 209220
agacattcta accatctttg ggatgtgcca aaaagttgtt tatataactc aggaaaatac 209280
ttgtaatttt cataagtata taggtactta tattgtacat tgttcaagga tcaagaaaca 209340
aatcacttaa aggctagaat ttcctaaatt tatttgcaca taatataata agcaagcatc 209400
attaagaatt taggccctga gcacacatag acttggatct gaatgccagc tccatgatat 209460
tctacttgta taacttctga ccaaggactt aacttttcta atgcttagct ttcacatcta 209520
tatcatgaag aaaatagtag attccacttt aaaaagttgt taagcatagg cttgacacaa 209580
gaattaaaca ctataatagt ggcaaggaat tcaagtgcaa tgtcagccta gagcagactt 209640
acccagtact tggtgtactg gcctcctggt acagctcctt tttcaacagc ctgcatctgt 209700
ttgtctttgt ttttgttttt tcttttttttt gagaccgggt cttgctctgt cgcccaggct 209760
ggagtgcagt ggcacaatct cggttcactg cagcctctgc ctcctgggtt caagcaactc 209820
tcttgcctca gcctcccaag tagatgggat tacaggtgcg tgccaccaca cttggctaat 209880
ttttatattt ttagtagaga cggggtttca ccatgttggc catgctggtc tcaaactcct 209940
gaccccaagt gatccgcccg cctcggcctc ccaaagtgct gggattacag gtgtgagcca 210000
cagagccttg cctgtctttg atgggaactg tcctcaggtt ggtggaacca gcatttcctg 210060
ctggcaatag taacggcctg cagaggctgc ccctatccca tgagaaagag gtgcatggga 210120
```

```
accaatcctc cagcaccctc actcctgatt aggacagctc tgagttgtac tcttcgctct 210180
cacagtttcc ctgcagaacc gagccaaagg cacccttgt tggactgaac ctaatgaggc 210240
atccctggct gggcttcctt cctgtcctga tctgacttca cttatcggtt ttcctggcaa 210300
tacttcctga caaatccatc aagggtgca cttctgagga accgcatctg aagcatcttc 210360
agaacatgaa caacctaatc agtattagcc caaaatatct gtgtcaaaga gtgtggattg 210420
gcaacctctt catgatacac atgtgaaagg aataattca ttgattggtg ctactggggt 210480
gcatcctgca atagcatcac cattaagcag agatgaaagt aggcatagtg gtcaatagca 210540
gtgaccacac ccctgcctcc tcttcctatc ccagtcagca gttaggtgtg gctctcagtg 210600
ggatggcaga gctctgtggc ataattaaag gatagagtca cagtccacaa catctcccca 210660
gcctcctcac atggtttggg ggctcttcct tcctgtcctt agggagtggg gctgcctctc 210720
tctgtgattt cattgttata ctatagatca aggtggggtc agaattccaa aaaaagatgt 210780
cacaggaact ggggagaccc ctaaaacagg tatggtcttg cctggcctcc attcaccaca 210840
aagtcatctc agatttgggg aacctccatg ttgtctgtga tagaagaaaa ggctggctga 210900
cactcatttg gtctctaaga cagatggaat gcttttctct taggtccttc accaattctc 210960
ccgagagtgt ttttttcctt ccaaataacc gcaaccaaag taatgagtgt cttggcacct 211020
gctaatttat ttctaaaatg cttttgaatt atgattatta actccactgt gaacttttta 211080
gatgatttta tcacctgtct ttccaggaaa ataattctca tgacaaacat ttaacttta 211140
gtatgaaata tataagaaat gacttaattc tacgcaaatg cttaccatct ttgatcagtc 211200
acacattagg aactattttc attggaaata tttttcatga cagcgaaggt tgtcatatcc 211260
cacgtttgtt gatctcaact gcctggttgg ttcttgtcag tagggccatt aacatttgac 211320
aataggtgct ccagtttggg aagattattc caaagtcacg gttattattc caaatctgct 211380
tgccctaaa gtgcatgcgt gaggaggaag agctttctca cttggccgtg ttctttgttc 211440
cggatatgag taagtgggag aattgccgct aaaattcttt ggcctcttct acttcctatg 211500
cttgtccttc ctgcccccgc ttcctacaca acatacacac acacacac acacacacac 211560
acacacacac acacacacac agaaacacac gcacgcatac acaccccac cccacacttc 211620
aaggaggaca taatcttcct tgcattggta accatttcct actggttacc attgtcattg 211680
gataactgag gtaaccattt cctactggtt gccattgtca ttggataatt gaggtagcat 211740
gaagattcat gttggccaca tttccaaatc actactcaag tctttctttc ttttcccct 211800
ttttcttcat tctagaattt ggggtgcatt tcttcatata ttatctctgt ctaactctgt 211860
ttctaatagg aaaaatatct ctctctgtct acataacaca atgacttcaa gagtcaatac 211920
tgtttatatt gtttaatatt acagcttgtc ttcttttcta cattttaat attttaatgt 211980
gtatttcata ctttaagaga tatgaaatgt catggaaact ttgtttctca gttttctcct 212040
gtagatttca taacccagtc tcaggagtat ttatagaaca atcattttaa tttatttcc 212100
ctcagaaaca atacagatga attgctaact ttaaaataaa attctgcttt catctttaac 212160
tagtatttaa aaagctttat ggagctatat agagttttaa aaacaaacac acaaataaga 212220
gtttgacaaa taacttaata tttaaatcag aagttctgtt cacttagagg ttaattggat 212280
caatttaaag gagtgctaga tttacagggg accatgtgtt catgaggata atttctaaaa 212340
ttctcaccag aaaatcagtc ttcttacctt cccctggaga gggagagatg tgttgaatgg 212400
ttactatgtg gtacgcactg tgcaaggcac cttatttatt cattataaca gccactctga 212460
```

```
agggttataa ctaacactat tgtagatatt tttaaaactg aggttcgagg gcattaagaa    212520
gacaacagct agttgtaaaa aacaaaaaaa ggcagaatgc aaggaaaaga acctagattt    212580
tacattgctc caatacccat gcttttttc cccatttaca ctaagcaaaa ccctgtttat     212640
atcgtagaga taagattatt aaaattatgg gatttaaaca ttctatatgg gccttattgc    212700
cttgcctctt actcttagtg gccattttgt gcgtgtcatt gatgcgtatg attataaata    212760
gttgtaagga aaaaatgctc tattaattct tttcaaaagc agaaatgtag cctacatagg    212820 atttttttt ttttttttt tttggagaca gagtttcact cttgttgccc aggctggagt     212880
gcatgcaatc tcggctcact gcaatctcca cctccctggt tcaagtgatt ctcctgcctc    212940
agcctcccga gtagctggga ttacaggcac ccatcaccac acctggctaa tttttatatt    213000
tttagtagag atgggtttca ccatgttggc caggctggtc tcaaactcct aacatcaggt    213060
gatccacccg cctcggcctc ccaaagtgct gggattacag gcttgagcca ccgcacctgg    213120
tgcctacata gcatttaaat aattatttta ctactagagc ctgagcctcc ccagactact    213180
cacaacccag gctttttat gttttcattt ggacccaact ttccacaaag tgctttggta     213240
actctgctca tgtcaactct tgatatataa tgagagctca agtaatatta ctaattaagt    213300
ggctcaagaa tcagtcaggc attttgactc ttaaactcaa tggactgaaa gaaaaaagt     213360 caatggactg aagcatttcc tttcagagac aaagtgagag atatactggc cgtttgacct    213420
aaggtgaatg acttaaacca ctctgaacct cagttttcta agatagtagt gctttctatt    213480
gtattatcat atgattaaat gtagtatcat atgattaaat gtaaattaaa ggtggtgact    213540
aacatgagaa atgataagtt caatgtgctg accaaagaaa caaataaata gaaacaatga    213600
gttttattaa gctgtaattt cccaaagatg agggaatgca cttgctgact ttttttgtct    213660
cattttcctc atttaaaaaa tgacccagcc agcattgcct cctctgttgc ggatgtccag    213720
ctctgaagat gtctgtttca gtgcgacagt gtcagaggac tgctgatact ctagcatcct    213780
gttcaattct tagttgcgag agatagaatg ccaactggtt caataagtaa aagggaattt    213840
attggctttt ataattgaaa tgataattgt ccacaaaagg acaagcttga ggcattgcta    213900
aatgcaagaa gatatcaaca ggtctctctc tctctctctt tctactgtcc cctgcctctt    213960
tctgctttca ttttttggcct ttgctctcct ccatcatggc cttactctca agtaggttcc    214020
cttcttccca cgatagttcc caggaacact gagatgaaac cctttccagg ccatcagaag    214080
attcccttat cagtttgacg gaagttccag aatcaagtct taataggcca aagtgagtaa    214140
cagactcagt gctttagctg ggagaagatg gtataatggg atatgccaat tgcctgtgtc    214200
atgggccaaa cctgagccaa tcactggcca agggaatgca gtgtccatcc ctggagccca    214260
gatcggagga gccctggaac accatggttt gagagtggga aggaacaaca ctgtgaggat    214320
gctgttgggg gaaatgatga gtctaaggat aatgaggaac taggttttg gtagatgaaa     214380 agcagatgtt tatgaacttg gcttagtctt acaagaaagc atttgtatct gatcattggc    214440
tgggactcct gaccaattgc tcctgccttc ctcttccatc acctcagtta gcttaaaagt    214500
actgagataa accattgctt aagcaaaaca tatcagcaga gaagcataat caaggcaggc    214560
taggaagtct gggaaaaaat gaataatatc tgcatagctc ttgtgtttca tttgtcacag    214620
agcccactga gtaagggtgg acagaatagt aacactaaac gagctgcaag aatatgcaaa    214680
tgccctgtgg tcagttttcca gctttgctgc tgtaacacct gttaactccc tgttttcag    214740 ttttacaaaa ctcagctcaa aagggatgtt gtttctgtgc agggatgcca ttatttctct    214800
tcaccaccct cctccttctg ggtgaaagca tgctccagct tttctctaaa ctcctctcct    214860
```

```
cagtctgcac catcgattac taacctacag gctcagtcct tcaaactttg ggcccatctt    214920
aattagggca gccagcagta tattgctggc caactcagag ccacacaaaa cttctcccac    214980
ctcttgcaac tgttaagatc ttgcattact cctgctgggc taagtcaggt atgtcacaca    215040
gatccctgaa catccacata ggtccctgtg ttagcctgtc ctctaacctt cttcagggg    215100 ttacctgcct gattgtaacc caaatcctgg tctggccttt gactccaacc catttggttg    215160
aatccaaaac aaacttacct tctagaatct aaaacctagc ctgctgtaac tccttgcaaa    215220
tggctcaccc agatcaagcc caagttttca acatgaaatt tgggcagcaa ccctcactct    215280
ttcagttcac aaaggtccca cttttcctgt tcactcacct caattctgta cccatgtgtt    215340
tctgaggtcc cagtgtaaaa tggcaccaag cctgcttaca tgatctatgg cactgggtga    215400
tgttggtgag ttggggtggg aattctcctg tgtaaacaca gcaaaaccgg agtatcctga    215460
tggggagcct ctagtgaact aatggtgttc attcactcat ttattcatac aatgaatatc    215520
aatcacataa tttagtgctt ctgaaacttg agtatgtata caaattcctg tggatcttat    215580
taaaatgcat attctgattc agtagggctg ggattgggcc tgagattctg cattttaaca    215640
cgctcccaga tgatgtgcat gctgatgttt tatgaaccag aatttgggta gcaaggacta    215700
tagaaactca ggaagtattt gttgaacgtt aaatgaatga aaatctgaat aaaagctttg    215760
aataatcgtt tcagtttaga tagaaaagag aagtataatg ttgatggagt tactggtaaa    215820
tgacagttaa tgggtcaaat gctttagcct ttgccaatga gtcttccctg gtgttgtccc    215880
ctcattaccc atcccaatgg actttgaccc atttcccctg cctcttgcta agggaataag    215940
agagccaact tcagactagc attccaattg cctgttaaag cctgttcttt ttgaaccaca    216000
cccatagttt ttcaatgttc tcaacagaag catggctttg tagtcacata cacacacaat    216060
gcccaattac tggcaatttt ggtataacaa ggaatgtaca tccccaaccc tactggatat    216120
caagaccttt tatggcattt catgtctgtg tagattctca acaatgccaa agaaactcaa    216180
aacgtgaaaa gaggaagtac tagaatacca cactagagac aaaacctctt cccctatttt    216240 ttttttttt ctgctgaatg tttctggctt gatttctttg ccaacacaga tttcttactg    216300
gacaaagcaa acactctgtt gtactctcag aaagttccat ttttagctca cagcataatg    216360
tgtggtgtgg tttgttctct aaagaaggaa cacagcaggt aaaaggtaaa ttatttcaca    216420
aaggtcagct gtgagcccgt tctctttga taataggaat cttgccttgt ggagagctca     216480
ttagaggtcc ccaagaggcc caagaagag gctgggatca ggagatgggg gataaaaatg     216540
cctgctgaaa atgttagggc tgtcattcct accccagaac tctggctctc catttaatga    216600
acaattttcc cttaacaaaa actcactgga aatgatggaa tgctcatgca ttagttatct    216660
ccccgcctct ctgccaaatg cctctctttg ctgctttctt gtctagacca tagactccat    216720
agtcccagac aggaattgta gagacttctt gttcctcaga tatgtcgagt tggagctata    216780
tctttgaaag tcaaatttta tgttaagaga acatcacctt aaacaacttt ggctttgctc    216840
ctaagtccaa ccccataata tattaaattt catttgttct ctctggagtg ggctctcttt    216900
ccaacttaga tagcaagtga gaaaagtata gttcttgttc agctggcaca ccatttccat    216960
ttaaactgct gtcaacttga gcttagctga ggttatgaat agaaaatgtg cacgtccat     217020 gaccacaatg gaacaggctt taggaaacaa cccacgacac acaacaactt cctgaatagg    217080
cagcagctga ccacagtttc aacgtcctaa ctgtgataac cattataact ttaataggca    217140
tcctggggca gaaactactc tctgtcaaca gttaaaggtc cctccacaaa gagtcaccaa    217200
```

```
attgtgaact tttattgcag aaagggctca gagagaagaa ttctaaggct tcactctgca 217260
gggtcaaaaa cttgtcaaat gtcacaccac ttcggactag tgaaagaatc acagattggg 217320
gggagccctc aggctgaatt tggaaggata aattgaaaaa gtcatacttg aattaaaaaa 217380
tggcttgagt tggacttgtt ccatgaatgc aatttagctt tttactgtgg ctggtgacaa 217440
tgtggtattt tcagcttctg agttgattga cagtggcaaa atactggaag atttatttta 217500
ataagagtgc cattgttatc tctacattag acaacttct ttctctggta caatcacttt 217560
ttttttaaag ttaaaactca ttttctcttc tgtattcccc ttcccctggg aaggaaaaga 217620
atacatgcac aaagaagaaa aaatgtaaaa cacaaccctg ccatttagga cttttttccag 217680 gcttatatgt tgctattatt ctttaaggat actatatgct tcctaatgtg attttttttt 217740
cactaatcaa tataatgtgg gcatctttat atgtcaagga gaannnnnnn nnnnnnnnn 217800 nnnnnnnnnn nnnnnnnnnn nnnnnnnnnn nnnnnnnnnn nnnnnnnnnn nnnnnnnnnn 217860
nnnnnnnnnn nnnnnnnnnn nnnnnnnnnn nnnnnnnnnn nnnnnnnnnn nnnnnnnnnn 217920
nnnnnnnnnn nnnnnnnnnn nnnnnnnnnn nnnnnnnnnn nnnnnnnnnn nnnnnnnnnn 217980
nnnnnnnnnn nnnnnnnnnn nnnnnnnnnn nnnnnnnnnn nnnnnnnnnn nnnnnnnnnn 218040
nnnnnnnnnn nnnnnnnnnn nnnnnnnnnn nnnnnnnnnn nnnnnnnnnn nnnnnnnnnn 218100
nnnnnnnnnn nnnnnnnnnn nnnnnnnnnn nnnnnnnnnn nnnnnnnnnn nnnnnnnnnn 218160
nnnnnnnnnn nnnnnnnnnn nnnnnnnnnn nnnnnnnnnn nnnnnnnnnn nnnnnnnnnn 218220
nnnnnnnnnn nnnnnnnnnn nnnnnnnnnn nnnnnnnnnn nnnnnnnnnn nnnnnnnnnn 218280
nnnnnnnnnn nnnnnnnnnn nnnnnnnnnn nnnnnnnnnn nnnnnnnnnn nnnnnnnnnn 218340
nnnnnnnnnn nnnnnnnnnn nnnnnnnnnn nnnnnnnnnn nnnnnnnnnn nnnnnnnnnn 218400
nnnnnnnnnn nnnnnnnnnn nnnnnnnnnn nnnnnnnnnn nnnnnnnnnn nnnnnnnnnn 218460
nnnnnnnnnn nnnnnnnnnn nnnnnnnnnn nnnnnnnnnn nnnnnnnnnn nnnnnnnnnn 218520
nnnnnnnnnn nnnnnnnnnn nnnnnnnnnn nnnnnnnnnn nnnnnnnnnn nnnnnnnnnn 218580
nnnnnnnnnn nnnnnnnnnn nnnnnnnaat atgcggtgtt tggttttttg ttcttgcgat 218640
agtttactga gaatgatggt ttccaatttc atccatgtcc ctacaaagga tatgaactca 218700 tcattttta tggctgcata gtattccatg gtgtatatgt gccacatttt cttaatccag 218760
tctatcattg ttggacattt gggttggttc caagtctttg ctattgtgaa tagtgccgca 218820
ataaacatac gtgtgcatgt gtctttatag cagcatgatt tatactcatt tgggtatata 218880
cccagtaatg ggatggctgg gtcaaatggt atttctagtt ctagatccct gaggaatcgc 218940
cacactgact tccacaatgg ttgaactagt ttacagtccc accaacagtg taaaagtgtt 219000
cctatttctc cgcatcctct ccagcacctg ttgtttcctg acttttaat gattgccatt 219060 ctaactggtg tgagatgata tctcatagtg gttttgattt gcatttctct gatggccagt 219120
gatgatgatt attattgtga taacagctga tacagagggg ttgcccttc catagttct 219180 cttgcctatc atctacaaaa ctatactcac agagcccgag acttcaagac cacacagacc 219240
atctaatgga acttgacagt ggggcacact ccattatcga gctccaaatt tgcagcccta 219300
gcaattgctg aaaacaagga ctgagagatg aactatcttc caatggtttt gtcctttggc 219360
tcagcgtaca ccacatcctt ataaaaacac cttcattcaa aagtcagcct gtggagccag 219420
cttggagata accagtgtgg tttgactggg gggcttgtgt tatatctttt atgagtttgt 219480
catgacacca agagtaaaata atcaaatcca gcctttaata gcccagggtt tggtagctgc 219540
ctcttctcgg gtgatggagg ctgccatgga tggaatgtgg caagttaagt tatttctgtt 219600
```

-continued

```
tcaggtttct ctttagccag ggcctgaagc agtctgctat gcttctgcta tatagcacta 219660
ggtctaagcc ctaagttcct caggacccce ttcataacct gatatatgct gggcattttg 219720
tctaaagtag cctccatctc ttttcacaat gcagagagaa aagctaaaat gtaaaacaga 219780
aaagtgtggg ggacatttat ctggtatctt cacttgttaa ccacttctta tggccctaaa 219840
acatatgtgt ttacgtatat ttactcgaag gcaaatataa tctttaatat tattaatatt 219900
aattatatta ggtgtatatg tgttatatac acctaatatt aataatcttt atatatacct 219960
aatattaata atatatgtat gtatacactt aatattaata atatcaaaga ttctgcttga 220020
aaaaacctag ttgattttgt atataagctc ggctttcttt tctctgtgtg ggataacctg 220080
gcactgcact taatcctagt gggacaagtt ctgttggctt ttttctcttc cacgccagtg 220140
gaaaaggtga cttcccagcc agtcagagac taagtaagag aatttatata atgaaatgct 220200
atacagcaat ataatgact gagctactga tgcatgccca ggcaaatctc aaaagcattg 220260
tgctaagtga agaagccag acacaagagt ccatttacat gaaattctag aaaaggcaaa 220320
actatggtga aagaaaatag attagtggtt attaggggcc ttggatggga tgggattgag 220380
ataatctttt ggaacgatga ccatcttcta tgttttgatt gtggtgtggt aacataaatg 220440
tatacggctg tcaaaattta ctgaagtata aactcttcaa ataggtgcat tctgtaatac 220500
ataaatgata ccttaataaa tttgaagtga tgaaaaagaa gtaaaggaag gaatttgggt 220560
tgatttatga atgtgtggct tgaacattta tatgggtggt ggttccattg gacattagac 220620
aataacaaac aagagcgcaa atataagagg tggtgaggag gatgatgggc acaattttgg 220680
gcctgtcaag ttgagagaca cccaggtgaa gagtccaagt tttggactgg atacgaagat 220740
tttggaattg ctagtgcatt ggtgagagta gactctaaca atgtgcatga agtggaaag 220800 aaagagaaga ctccagaaat aagggcctat cctgaagaac acccatgcgg aatccactag 220860
```

<210> SEQ ID NO 4
<211> LENGTH: 854
<212> TYPE: PRT
<213> ORGANISM: Homo sapiens

<400> SEQUENCE: 4

```
Met Arg Val Leu Phe Asp Glu Ser Val Leu Pro Pro Thr Val Tyr Phe
1               5                   10                  15

Lys Asn Cys Ser Ile Leu Phe Leu Ala Ser Leu Cys Ala Phe Gly Val
            20                  25                  30

Leu Thr Gly Leu Leu Val Trp Ser Phe Met Gln Tyr Met Glu Ile Val
        35                  40                  45

Ala Asn Glu Tyr Leu Gly Tyr Gly Glu Glu Gln His Thr Val Asp Lys
    50                  55                  60

Leu Val Asn Met Thr Tyr Ile Phe Gln Lys Leu Ala Ala Val Lys Asp
65                  70                  75                  80

Gln Arg Glu Trp Val Thr Thr Ser Gly Ala His Lys Thr Leu Val Asn
                85                  90                  95

Leu Leu Gly Ala Arg Asp Thr Asn Val Leu Leu Gly Ser Leu Leu Ala
            100                 105                 110

Leu Ala Ser Leu Ala Glu Arg Leu Thr Ala Glu Leu Leu Arg Leu Leu
        115                 120                 125

Cys Ala Glu Pro Gln Val Lys Glu Gln Val Lys Leu Tyr Glu Gly Ile
    130                 135                 140

Pro Val Leu Leu Ser Leu Leu His Ser Asp His Leu Lys Leu Leu Trp
```

```
               145                 150                 155                 160
        Ser Ile Val Trp Ile Leu Val Gln Val Cys Glu Asp Pro Glu Thr Ser
                        165                 170                 175

Val Glu Ile Arg Ile Trp Gly Gly Ile Lys Gln Leu Leu His Ile Leu
                        180                 185                 190

Gln Gly Asp Arg Asn Phe Val Ser Asp His Ser Ser Ile Gly Ser Leu
                        195                 200                 205

Ser Ser Ala Asn Ala Ala Gly Arg Ile Gln Gln Leu His Leu Ser Glu
                        210                 215                 220

Asp Leu Ser Pro Arg Glu Ile Gln Glu Asn Thr Phe Ser Leu Gln Ala
        225                 230                 235                 240

Ala Cys Cys Ala Ala Leu Thr Glu Leu Val Leu Asn Asp Thr Asn Ala
                        245                 250                 255

His Gln Val Val Gln Glu Asn Gly Val Tyr Thr Ile Ala Lys Leu Ile
                        260                 265                 270

Leu Pro Asn Lys Gln Lys Asn Ala Ala Lys Ser Asn Leu Leu Gln Cys
                        275                 280                 285

Tyr Ala Phe Arg Ala Leu Arg Phe Leu Phe Ser Met Glu Arg Asn Arg
                        290                 295                 300

Pro Leu Phe Lys Arg Leu Phe Pro Thr Asp Leu Phe Glu Ile Phe Ile
        305                 310                 315                 320

Asp Ile Gly His Tyr Val Arg Asp Ile Ser Ala Tyr Glu Glu Leu Val
                        325                 330                 335

Ser Lys Leu Asn Leu Leu Val Glu Asp Glu Leu Lys Gln Ile Ala Glu
                        340                 345                 350

Asn Ile Glu Ser Ile Asn Gln Asn Lys Ala Pro Leu Lys Tyr Ile Gly
                        355                 360                 365

Asn Tyr Ala Ile Leu Asp His Leu Gly Ser Gly Ala Phe Gly Cys Val
                        370                 375                 380

Tyr Lys Val Arg Lys His Ser Gly Gln Asn Leu Leu Ala Met Lys Glu
        385                 390                 395                 400

Val Asn Leu His Asn Pro Ala Phe Gly Lys Asp Lys Lys Asp Arg Asp
                        405                 410                 415

Ser Ser Val Arg Asn Ile Val Ser Glu Leu Thr Ile Ile Lys Glu Gln
                        420                 425                 430

Leu Tyr His Pro Asn Ile Val Arg Tyr Tyr Lys Thr Phe Leu Glu Asn
                        435                 440                 445

Asp Arg Leu Tyr Ile Val Met Glu Leu Ile Glu Gly Ala Pro Leu Gly
                        450                 455                 460

Glu His Phe Ser Ser Leu Lys Glu Lys His His Phe Thr Glu Glu
        465                 470                 475                 480

Arg Leu Trp Lys Ile Phe Ile Gln Leu Cys Leu Ala Leu Arg Tyr Leu
                        485                 490                 495

His Lys Glu Lys Arg Ile Val His Arg Asp Gln Thr Pro Asn Asn Ile
                        500                 505                 510

Met Leu Gly Asp Lys Asp Lys Val Thr Val Thr Asp Phe Gly Leu Ala
                        515                 520                 525

Lys Gln Lys Gln Glu Asn Ser Lys Leu Thr Ser Val Val Gly Thr Ile
                        530                 535                 540

Leu Tyr Ser Cys Pro Glu Val Leu Lys Ser Glu Pro Tyr Gly Glu Lys
        545                 550                 555                 560

Ala Asp Val Trp Ala Val Gly Cys Ile Leu Tyr Gln Met Ala Thr Leu
                        565                 570                 575
```

-continued

```
Ser Pro Pro Phe Tyr Ser Thr Asn Met Leu Ser Leu Ala Thr Lys Ile
            580                 585                 590

Val Glu Ala Val Tyr Glu Pro Val Pro Glu Gly Ile Tyr Ser Glu Lys
        595                 600                 605

Val Thr Asp Thr Ile Ser Arg Cys Leu Thr Pro Asp Ala Glu Ala Arg
    610                 615                 620

Pro Asp Ile Val Glu Val Ser Ser Met Ile Ser Asp Val Met Met Lys
625                 630                 635                 640

Tyr Leu Asp Asn Leu Ser Thr Ser Gln Leu Ser Leu Glu Lys Lys Leu
                645                 650                 655

Glu Arg Glu Arg Arg Thr Gln Arg Tyr Phe Met Glu Ala Asn Arg
            660                 665                 670

Asn Thr Val Thr Cys His His Glu Leu Ala Val Leu Ser His Glu Thr
        675                 680                 685

Phe Glu Lys Ala Ser Leu Ser Ser Ser Ser Gly Ala Ala Ser Leu
    690                 695                 700

Lys Ser Glu Leu Ser Glu Ser Ala Asp Leu Pro Pro Glu Gly Phe Gln
705                 710                 715                 720

Ala Ser Tyr Gly Lys Asp Glu Asp Arg Ala Cys Asn Glu Ile Leu Ser
                725                 730                 735

Asp Asp Asn Phe Asn Leu Glu Asn Ala Glu Lys Asp Thr Tyr Ser Glu
            740                 745                 750

Val Asp Asp Glu Leu Asp Ile Ser Asp Asn Ser Ser Ser Ser Ser Ser
        755                 760                 765

Ser Pro Leu Lys Glu Ser Thr Phe Asn Ile Leu Lys Arg Ser Phe Ser
    770                 775                 780

Ala Ser Gly Gly Glu Arg Gln Ser Gln Thr Arg Asp Phe Thr Gly Gly
785                 790                 795                 800

Thr Gly Ser Arg Pro Arg Pro Gly Pro Gln Met Gly Thr Phe Leu Trp
                805                 810                 815

Gln Ala Ser Ala Gly Ile Ala Val Ser Gln Arg Lys Val Arg Gln Ile
            820                 825                 830

Ser Asp Pro Ile Gln Gln Ile Leu Ile Gln Leu His Lys Ile Ile Tyr
        835                 840                 845

Ile Thr Gln Leu Pro Pro
    850

<210> SEQ ID NO 5
<211> LENGTH: 2562
<212> TYPE: DNA
<213> ORGANISM: Homo sapiens

<400> SEQUENCE: 5
atgagagtat tatttgatga atctgttttg ccacctacag tttattttaa gaactgcagc    60
atcttgttcc ttgcttcctt gtgtgctttt ggtgtcctga ctggcttgtt ggtttggtcc   120
ttcatgcagt atatggagat tgtagccaat gagtacctcg ctatggaga agagcagcac    180 actgtggaca agctggtcaa catgacatat attttttcaaa aacttgctgc agtcaaagat   240
caaagagaat gggtcaccac aagtggagcc acaagacat tagtaaattt acttggtgcc    300
cgagatacta atgttctatt gggttccctt ctggctctgg ctagtttagc agaaagacta   360
acagcggagt tgctgcgcct actttgtgca gagccccagg tgaaagagca ggtgaagctc   420 tatgaggga taccggtcct cctcagtctg ctccactctg accacttgaa gctcctctgg   480
```

| | |
|---|---:|
| agcattgtct ggattctggt acaggtttgt gaggaccctg agaccagcgt ggaaattcgc | 540 |
| atttggggag gcatcaaaca gcttcttcat attttacaag gagacagaaa ttttgtttct | 600 |
| gatcactcct ccattggaag cctgtccagt gcaaatgctg caggccgaat ccagcagctt | 660 |
| catttatcag aagacttgag ccctagggaa atacaagaaa atactttctc acttcaagca | 720 |
| gcctgctgtg ctgccctcac tgagctggtc tcaatgaca ccaatgccca ccaggtggtt | 780 |
| caggaaaatg gtgtatatac aatagcaaaa ttaattttac caaataagca aaagaatgca | 840 |
| gcaaaaagta atctattaca gtgttatgct ttcagagcct tgagatttct cttcagtatg | 900 |
| gaaagaaaca gaccactctt taaaagactt ttccccacag acttgtttga gatcttcatt | 960 |
| gacatagggc attatgtacg tgatatcagt gcttatgaag aattggtatc caagctgaat | 1020 |
| ttattagtgg aggatgaact gaagcaaatt gctgaaaata ttgaaagcat taatcagaac | 1080 |
| aaagctcctt tgaaatatat aggcaactat gcaattttgg atcatcttgg aagtggagct | 1140 |
| tttggctgtg tttacaaggt tagaaagcat agtggtcaaa atcttttagc aatgaaagag | 1200 |
| gtcaatttac ataacccagc atttgggaag gataagaaag atcgagacag cagcgtaagg | 1260 |
| aatattgttt ctgaattaac aataattaaa gagcagcttt atcatcccaa cattgtacgt | 1320 |
| tattacaaaa catttctgga aaatgatagg ttgtacatag ttatggagct gatagaagga | 1380 |
| gccccgcttg gagagcattt cagttctttg aaggaaaaac atcaccattt tactgaagaa | 1440 |
| agactatgga aaatatttat acagctgtgc ttagctcttc gatacttaca aaggagaag | 1500 |
| aggattgtcc atagagatca gacaccaaac aacattatgt ggggggataa ggacaaagta | 1560 |
| accgttactg actttggcct ggcaaagcaa aaacaagaaa acagtaaact cacctctgtg | 1620 |
| gttggaacaa tcctgtattc ttgtcccgag gtactgaaga gtgagccgta tggggagaag | 1680 |
| gctgatgtct gggcagtagg ctgcatcctt tatcagatgg cgactttgag tccccccttc | 1740 |
| tacagcacta acatgctgtc cttggctaca aaaatagtgg aggcggtata tgaaccagtc | 1800 |
| ccagaaggta tctactctga aaaagtaaca gacaccatca gcaggtgcct cactcctgat | 1860 |
| gcggaagctc gtccagatat tgtagaagtc agttcgatga tatcagatgt catgatgaaa | 1920 |
| tatttagaca acttatctac atcccagttg tccttggaaa agaagctaga acgggaacga | 1980 |
| agacgcacac aaaggtattt tatggaagcc aaccggaaca ccgtcacatg tcaccatgag | 2040 |
| ctggctgttc tatctcacga gacctttgag aaggcaagtt tgagtagcag cagcagtgga | 2100 |
| gcagccagcc tgaaaagtga actttcagaa agcgcagacc tgcccctga aggcttccag | 2160 |
| gcctcctatg gtaaagacga agacagggcc tgtaacgaaa tcctgtcaga tgataacttc | 2220 |
| aacctggaaa atgctgagaa agatacatat tcagaggtag atgatgaatt ggacatttcg | 2280 |
| gataactcca gcagctccag ttcaagccct ctgaaagaat ctacattcaa cattttaaag | 2340 |
| agaagttta gtgcttcagg aggagaaaga caatcccaaa caagggactt cactggagga | 2400 |
| acaggatcaa gaccaagacc agggccacag atgggcacat tcttgtggca agcatcagca | 2460 |
| ggaattgctg tgtcccagag gaaagtgcgt cagatcagtg atcctattca gcagatatta | 2520 |
| attcagctgc acaaaataat ctatatcaca cagcttcctc ca | 2562 |

<210> SEQ ID NO 6
<211> LENGTH: 2043
<212> TYPE: DNA
<213> ORGANISM: Homo sapiens

<400> SEQUENCE: 6

| | |
|---|---:|
| agaaataatg tatggaggga ctatacaagg gcatatatac tagtaaaagt gttttctcaa | 60 |

```
tagatcacca aagaatttgc cacacctgat atatagaaaa gtttattgtg cagcacctct      120
accttcgctc tcctgctcct gctctggcca cataaaacgt gctggctcct cctttgcctt      180
ctgctatcat tggaagcttc ctgatgcctc ccaagaagca aatgccatca tggttcctgt      240
acagcctgca gaacccccg aggtactgaa gagtgagccg tatggggaga aggctgatgt       300
ctgggcagta ggctgcatcc tttatcagat ggcgactttg agtccccct tctacagcac       360 taacatgctg tccttggcta caaaaatagt ggaggcggta tatgaaccag tcccagaagg      420
tatctactct gaaaaagtaa cagacaccat cagcaggtgc ctcactcctg atgcggaagc      480
tcgtccagat attgtagaag tcagttcgat gatatcagat gtcatgatga aatatttaga      540
caacttatct acatcccagt tgtccttgga aagaagcta aacgggaac gaagacgcac        600 acaaaggtat tttatggaag ccaaccggaa caccgtcaca tgtcaccatg agctggctgt      660
tctatctcac gagaccttg agaaggcaag tttgagtagc agcagcagtg gagcagccag       720
cctgaaaagt gaactttcag aaagcgcaga cctgccccct gaaggcttcc aggcctccta      780
tggtaaagac gaagacaggg cctgtgacga atcctgtca gatgataact tcaacctgga       840
aaatgctgag aaagatacat attcagaggt agatgatgaa ttggacattt cggataactc      900
cagcagctcc agttcaagcc ctctgaaaga atctacattc aacattttaa agagaagttt      960
tagtgcttca ggaggagaaa gacaatccca acaagggac ttcactggag aacaggatc       1020 aagaccaaga ccagctttgc tgcctcttga cctgcttctg aaagtgccac cccacatgct     1080
cagggcccac attaaggaaa tagaggctga gttagtgaca gggtggcagt cccatagcct     1140
tcctgctgtg attcttcgaa atctcaaaga tcatgggcca cagatgggca cattcttgtg     1200
gcaagcatca gcaggaattg ctgtgtccca gaggaaagtg cgtcagatca gtgatcctat    1260
tcagcagata ttaattcagc tgcacaaaat aatctatatc acacagcttc ctccagcttt    1320
gcaccacaat ttgaaaagaa gggttataga gagattcaag aaatccctct tcagccagca    1380
gagtaaccct tgtaatttga aatctgaaat taaaaagtta tctcagggat ctccagaacc    1440
gattgagccc aacttttttca cagcagatta ccatttatta catcgttcat ccggtggaaa    1500
cagcctgtcc ccaaatgacc ctacaggttt accaaccagc attgaattgg aggaaggaat    1560
aacatatgaa cagatgcaga ctgtgattga agaagtcctt gaggaaagtg gctattacaa    1620 tttttacatct aacaggtatc attcctatcc atgggggacc aagaatcacc caaccaaaag    1680
atgaaaatgc tgcattttga gtggacttga ttttctcagt gaagttcaag ttctggactt    1740
cagccgctat tgcaagatgc ccaaggattg ggtgctgcta gagggtgtgg aaaagaccaa    1800
gatgccatgg ggcctgcagg acttcttttct ggggtcctg tgctggagta tatgacagct    1860
gcggtacttg agggcttcat tgccagaaca cattatatac aggatgtcag agctaccagt    1920
gtgctgctgg gagaaaatgc tgcaaaattc atcttttgga gggtggggg aaaacccaaa     1980 aacaacaaca aaaaaactct cttacagaat tttccttaac attaaaaaaa acttgtcata    2040
ttt                                                                  2043
```

<210> SEQ ID NO 7
<211> LENGTH: 2043
<212> TYPE: DNA
<213> ORGANISM: Homo sapiens

<400> SEQUENCE: 7

```
agaaataatg tatggaggga ctacacaagg gcatatatac tagtaaaagt gttttctcaa       60
```

| | |
|---|---|
| tagatcacca aagaatttgc cacacctgat atatagaaaa gtttattgtg cagcacctct | 120 |
| accttcgctc tcctgctcct gctctggcca cataaaacgt gctggctcct cctttgcctt | 180 |
| ctgctatcat tggaagcttc ctgatgcctc ccaagaagca aatgccatca tggttcctgt | 240 |
| acagcctgca gaaccccccg aggtactgaa gagtgagccg tatggggaga aggctgatgt | 300 |
| ctgggcagta ggctgcatcc tttatcagat ggcgactttg agtcccccct tctacagcac | 360 |
| taacatgctg tccttggcta caaaaatagt ggaggcggta tatgaaccag tgccagaagg | 420 |
| tatctactct gaaaaagtaa cagacaccat cagcaggtgc ctcactcctg atgcggaagc | 480 |
| tcgtccagat attgtagaag tcagttcgat gatatcagat gtcatgatga aatatttaga | 540 |
| caacttatct acatcccagt tgtccttgga aaagaagcta aacgggaac gaagacgcac | 600 |
| acaaaggtat tttatggaag ccaaccggaa caccgtcaca tgtcaccatg agctggctgt | 660 |
| tctatctcac gagacctttg agaaggcaag tttgagtagc agcagcagtg gagcagccag | 720 |
| cctgaaaagt gaactttcag aaagcgcaga cctgccccct gaaggcttcc aggcctccta | 780 |
| tggtaaagac gaagacaggg cctgtgacga atcctgtca gatgataact caacctgga | 840 |
| aaatgctgag aaagatacat attcagaggt agatgatgaa ttggacattt cggataactc | 900 |
| cagcagctcc agttcaagcc ctctgaaaga atctacattc aacattttaa agagaagttt | 960 |
| tagtgcttca ggaggagaaa gacaatccca aacaagggac ttcactggag aacaggatc | 1020 |
| aagaccaaga ccagctttgc tgcctcttga cctgcttctg aaagtgccac cccatatgct | 1080 |
| cagggcccac attaaggaaa tagaggctga gttagtgaca gggtggcagt cccatagcct | 1140 |
| tcctgctgtg attcttcgaa atctcaaaga tcatgggcca cagatgggca cattcttgtg | 1200 |
| gcaagcatca gcaggaattg ctgtgtccca gaggaaagtg cgtcagatca gtgatcctat | 1260 |
| tcagcagata ttaattcagc tgcacaaaat aatctatatc acacagcttc ctccagcttt | 1320 |
| gcaccacaat ttgaaaagaa gggttataga gagattcaag aaatccctct tcagccagca | 1380 |
| gagtaacct tgtaatttga aatctgaaat taaaaagtta tctcagggat ctccagaacc | 1440 |
| gattgagccc aacttttca cagcagatta ccatttatta catcgttcat ccggtggaaa | 1500 |
| cagcctgtcc ccaaatgacc ctacaggttt accaaccagc attgaattgg aggaaggaat | 1560 |
| aacatatgaa cagatgcaga ctgtgattga agaagtcctt gaggaaagtg gctattacaa | 1620 |
| ttttacatct aacaggtatc attcctatcc atgggggacc aagaatcacc caaccaaaag | 1680 |
| atgaaaatgc tgcattttga gtggacttga ttttctcagt gaagttcaag ttctggactt | 1740 |
| cagccgctat tgcaagatgc ccaaggattg ggtgctgcta gagggtgtgg aaaagaccaa | 1800 |
| gatgccatgg ggcctgcagg acttcttcc ggggtcctg tgctggagta tatgacagct | 1860 |
| gcggtacttg agggcttcat tgccagaaca cattatatac aggatgtcag agctaccagt | 1920 |
| gtgctgctgg gagaaaatgc tgcaaaattc atcttttgga gggtgggggg aaaacccaaa | 1980 |
| aacaacaaca aaaaaactct cttacagaat tttccttaac attaaaaaaa acttgtcata | 2040 |
| ttt | 2043 |

<210> SEQ ID NO 8
<211> LENGTH: 1601
<212> TYPE: DNA
<213> ORGANISM: Homo sapiens

<400> SEQUENCE: 8

| | |
|---|---|
| tttattagtg gaggatgaac tgaagcaaat tgctgaaaat attgaaagca ttaatcagaa | 60 |
| caaagctcct ttgaaatata taggcaacta tgcaattttg gatcatcttg gaagtggagc | 120 |

-continued

```
ttttggctgt gtttacaagc tttatcatcc caacattgta cgttattaca aaacatttct      180
ggaaaatgat aggttgtaca tagttatgga gctgatagaa ggagccccgc ttggagagca      240
tttcagttct ttgaaggaaa acatcacca ttttactgaa gaaagactat ggaaaatatt      300
tatacagctg tgcttagctc ttcgatactt acacaaggag aagaggattg tccatagaga      360
tctgacacca acaacatta tgttggggga taaggacaaa gtaaccgtta ctgactttgg      420
cctggcaaag caaaacaag aaaacagtaa actcacctct gtggttggaa caatcctgta      480
ttcttgcccc gaggtactga agagtgagcc gtatggggag aaggctgatg tctgggcagt      540
aggctgcatc ctttatcaga tggcgacttt gagtcccccc ttctacagca ctaacatgct      600
gtccttggct acaaaaatag tggaggcggt atatgaacca gtcccagaag gtatctactc      660
tgaaaagta acagacacca tcagcaggtg cctcactcct gatgcggaag ctcgtccaga      720
tattgtagaa gtcagttcga tgatatcaga tgtcatgatg aaatatttag acaacttatc      780
tacatcccag ttgtccttgg aaaagaagct agaacgggaa cgaagacgca cacaaaggta      840
ttttatggaa gccaaccgga acaccgtcac atgtcaccat gagctggctg ttctatctca      900
cgagaccttt gagaaggcaa gtttgagtag cagcagcagt ggagcagcca gcctgaaaag      960
tgaactttca gaaagcgcag acctgccccc tgaaggcttc caggcctcct atggtaaaga     1020
cgaagacagg gcctgtgacg aaatcctgtc agatgataac ttcaacctgg aaaatgctga     1080
gaaagataca tattcagagg tagatgatga attggacatt tcggataact ccagcagctc     1140
cagttcaagc cccctgaaag aatctacatt caacatttta aagagaagtt ttagtgcttc     1200
aggaggagaa agacaatccc aaacaaggga cttcactgga ggaacaggat caagaccaag     1260
accagctttg ctgcctcttg acctgcttct gaaagtgcca ccccacatgc tcagggccca     1320
cattaaggaa atagaggctg agttagtgac agggtggcag tcccatagcc ttcctgctgt     1380
gattcttcga aatctcaaag atcatggtag tacttactag atcacattga tgttaagcac     1440
acaatgggca aatgcagaat tatagttggg cctgagatgt ctgaacgatg cttgggtggt     1500
aatttttaata caaagagcgg agaattctgc cttgtttgtt caccactatt agtttggcga     1560
tttgatggta acaaaatgcc ttctgtgttc actgttggtt g                         1601
```

<210> SEQ ID NO 9
<211> LENGTH: 21
<212> TYPE: DNA
<213> ORGANISM: Homo sapiens

<400> SEQUENCE: 9

```
aatgagtacc tcggctatgg a                                                 21
```

<210> SEQ ID NO 10
<211> LENGTH: 21
<212> TYPE: RNA
<213> ORGANISM: Homo sapiens

<400> SEQUENCE: 10

```
ugaguaccuc ggcuauggau u                                                 21
```

<210> SEQ ID NO 11
<211> LENGTH: 21
<212> TYPE: RNA
<213> ORGANISM: Homo sapiens

<400> SEQUENCE: 11
uuacucaugg agccgauacc u                                          21

<210> SEQ ID NO 12
<211> LENGTH: 21
<212> TYPE: DNA
<213> ORGANISM: Homo sapiens

<400> SEQUENCE: 12
aagactaaca gcggagttgc t                                          21

<210> SEQ ID NO 13
<211> LENGTH: 21
<212> TYPE: RNA
<213> ORGANISM: Homo sapiens

<400> SEQUENCE: 13
gacuaacagc ggaguugcuu u                                          21

<210> SEQ ID NO 14
<211> LENGTH: 21
<212> TYPE: RNA
<213> ORGANISM: Homo sapiens

<400> SEQUENCE: 14
uucugauugu cgccucaacg a                                          21

<210> SEQ ID NO 15
<211> LENGTH: 21
<212> TYPE: DNA
<213> ORGANISM: Homo sapiens

<400> SEQUENCE: 15
aagatcgaga cagcagcgta a                                          21

<210> SEQ ID NO 16
<211> LENGTH: 21
<212> TYPE: RNA
<213> ORGANISM: Homo sapiens

<400> SEQUENCE: 16
gaucgagaca gcagcguaau u                                          21

<210> SEQ ID NO 17
<211> LENGTH: 21
<212> TYPE: RNA
<213> ORGANISM: Homo sapiens

<400> SEQUENCE: 17
uucuagcucu gucgucgcau u                                          21

<210> SEQ ID NO 18
<211> LENGTH: 21
<212> TYPE: DNA
<213> ORGANISM: Homo sapiens

<400> SEQUENCE: 18
aactcacgtc tgtggttgga a                                          21

<210> SEQ ID NO 19
<211> LENGTH: 21
<212> TYPE: RNA
<213> ORGANISM: Homo sapiens

<400> SEQUENCE: 19

-continued

```
cucacgucug ugguuggaau u                                          21

<210> SEQ ID NO 20
<211> LENGTH: 21
<212> TYPE: RNA
<213> ORGANISM: Homo sapiens

<400> SEQUENCE: 20
uugagugcag acaccaaccu u                                          21

<210> SEQ ID NO 21
<211> LENGTH: 21
<212> TYPE: DNA
<213> ORGANISM: Homo sapiens

<400> SEQUENCE: 21
aatagtggag gcggtatatg a                                          21

<210> SEQ ID NO 22
<211> LENGTH: 21
<212> TYPE: RNA
<213> ORGANISM: Homo sapiens

<400> SEQUENCE: 22
uaguggaggc gguauaugau u                                          21

<210> SEQ ID NO 23
<211> LENGTH: 21
<212> TYPE: RNA
<213> ORGANISM: Homo sapiens

<400> SEQUENCE: 23
uuaucaccuc cgccauauac u                                          21

<210> SEQ ID NO 24
<211> LENGTH: 21
<212> TYPE: DNA
<213> ORGANISM: Homo sapiens

<400> SEQUENCE: 24
aagctcgtcc agatattgta g                                          21

<210> SEQ ID NO 25
<211> LENGTH: 21
<212> TYPE: RNA
<213> ORGANISM: Homo sapiens

<400> SEQUENCE: 25
gcucguccag auauuguagu u                                          21

<210> SEQ ID NO 26
<211> LENGTH: 21
<212> TYPE: RNA
<213> ORGANISM: Homo sapiens

<400> SEQUENCE: 26
uucgagcagg ucuauaacau c                                          21

<210> SEQ ID NO 27
<211> LENGTH: 21
<212> TYPE: DNA
<213> ORGANISM: Homo sapiens
```

-continued

```
<400> SEQUENCE: 27
aacaccgtca catgtcacca t                                            21

<210> SEQ ID NO 28
<211> LENGTH: 21
<212> TYPE: RNA
<213> ORGANISM: Homo sapiens

<400> SEQUENCE: 28
caccgucaca ugucaccauu u                                            21

<210> SEQ ID NO 29
<211> LENGTH: 21
<212> TYPE: RNA
<213> ORGANISM: Homo sapiens

<400> SEQUENCE: 29
uuguggcagu guacaguggu a                                            21

<210> SEQ ID NO 30
<211> LENGTH: 21
<212> TYPE: DNA
<213> ORGANISM: Homo sapiens

<400> SEQUENCE: 30
aatagaggct gagttagtga c                                            21

<210> SEQ ID NO 31
<211> LENGTH: 21
<212> TYPE: RNA
<213> ORGANISM: Homo sapiens

<400> SEQUENCE: 31
uagaggcuga guuagugacu u                                            21

<210> SEQ ID NO 32
<211> LENGTH: 21
<212> TYPE: RNA
<213> ORGANISM: Homo sapiens

<400> SEQUENCE: 32
uuaucuccga cucaaucacu g                                            21

<210> SEQ ID NO 33
<211> LENGTH: 21
<212> TYPE: DNA
<213> ORGANISM: Homo sapiens

<400> SEQUENCE: 33
aattgctagt gcattggtga g                                            21

<210> SEQ ID NO 34
<211> LENGTH: 21
<212> TYPE: RNA
<213> ORGANISM: Homo sapiens

<400> SEQUENCE: 34
uugcuagugc auggugagu u                                             21

<210> SEQ ID NO 35
<211> LENGTH: 21
<212> TYPE: RNA
<213> ORGANISM: Homo sapiens
```

```
<400> SEQUENCE: 35
uuaacgauca cguaaccacu c                                              21

<210> SEQ ID NO 36
<211> LENGTH: 21
<212> TYPE: DNA
<213> ORGANISM: Homo sapiens

<400> SEQUENCE: 36
caatgagtac ctcggctatg g                                              21

<210> SEQ ID NO 37
<211> LENGTH: 21
<212> TYPE: RNA
<213> ORGANISM: Homo sapiens

<400> SEQUENCE: 37
augaguaccu cggcuauggu u                                              21

<210> SEQ ID NO 38
<211> LENGTH: 21
<212> TYPE: RNA
<213> ORGANISM: Homo sapiens

<400> SEQUENCE: 38
uuuacucaug gagccgauac c                                              21

<210> SEQ ID NO 39
<211> LENGTH: 21
<212> TYPE: DNA
<213> ORGANISM: Homo sapiens

<400> SEQUENCE: 39
cagctgtgct tagctcttcg a                                              21

<210> SEQ ID NO 40
<211> LENGTH: 21
<212> TYPE: RNA
<213> ORGANISM: Homo sapiens

<400> SEQUENCE: 40
gcugugcuua gcucuucgau u                                              21

<210> SEQ ID NO 41
<211> LENGTH: 21
<212> TYPE: RNA
<213> ORGANISM: Homo sapiens

<400> SEQUENCE: 41
uucgacacga aucgagaagc u                                              21

<210> SEQ ID NO 42
<211> LENGTH: 21
<212> TYPE: DNA
<213> ORGANISM: Homo sapiens

<400> SEQUENCE: 42
cagcactaac atgctgtcct t                                              21

<210> SEQ ID NO 43
<211> LENGTH: 21
<212> TYPE: RNA
```

-continued

<213> ORGANISM: Homo sapiens

<400> SEQUENCE: 43
gcacuaacau gcuguccuuu u                                              21

<210> SEQ ID NO 44
<211> LENGTH: 21
<212> TYPE: RNA
<213> ORGANISM: Homo sapiens

<400> SEQUENCE: 44
uucgugauug uacgacagga a                                              21

<210> SEQ ID NO 45
<211> LENGTH: 21
<212> TYPE: DNA
<213> ORGANISM: Homo sapiens

<400> SEQUENCE: 45
caagcatcag caggaattgc t                                              21

<210> SEQ ID NO 46
<211> LENGTH: 21
<212> TYPE: RNA
<213> ORGANISM: Homo sapiens

<400> SEQUENCE: 46
agcaucagca ggaauugcuu u                                              21

<210> SEQ ID NO 47
<211> LENGTH: 21
<212> TYPE: RNA
<213> ORGANISM: Homo sapiens

<400> SEQUENCE: 47
uuucguaguc guccuuaacg a                                              21

<210> SEQ ID NO 48
<211> LENGTH: 21
<212> TYPE: DNA
<213> ORGANISM: Homo sapiens

<400> SEQUENCE: 48
caggatgtca gagctaccag t                                              21

<210> SEQ ID NO 49
<211> LENGTH: 22
<212> TYPE: RNA
<213> ORGANISM: Homo sapiens

<400> SEQUENCE: 49
cggaugucag agcuaccagu uu                                             22

<210> SEQ ID NO 50
<211> LENGTH: 21
<212> TYPE: RNA
<213> ORGANISM: Homo sapiens

<400> SEQUENCE: 50
uuccuacagu cucgaugguc a                                              21

<210> SEQ ID NO 51
<211> LENGTH: 21

<212> TYPE: DNA
<213> ORGANISM: Homo sapiens

<400> SEQUENCE: 51
gagacagcag cgtaaggaat a                                              21

<210> SEQ ID NO 52
<211> LENGTH: 21
<212> TYPE: RNA
<213> ORGANISM: Homo sapiens

<400> SEQUENCE: 52
gacagcagcg uaaggaauau u                                              21

<210> SEQ ID NO 53
<211> LENGTH: 21
<212> TYPE: RNA
<213> ORGANISM: Homo sapiens

<400> SEQUENCE: 53
uucugucguc gcauuccuua u                                              21

<210> SEQ ID NO 54
<211> LENGTH: 21
<212> TYPE: DNA
<213> ORGANISM: Homo sapiens

<400> SEQUENCE: 54
gaggcggtat atgaaccagt c                                              21

<210> SEQ ID NO 55
<211> LENGTH: 21
<212> TYPE: RNA
<213> ORGANISM: Homo sapiens

<400> SEQUENCE: 55
ggcgguauau gaaccagucu u                                              21

<210> SEQ ID NO 56
<211> LENGTH: 21
<212> TYPE: RNA
<213> ORGANISM: Homo sapiens

<400> SEQUENCE: 56
uuccgccaua uacuugguca g                                              21

<210> SEQ ID NO 57
<211> LENGTH: 21
<212> TYPE: DNA
<213> ORGANISM: Homo sapiens

<400> SEQUENCE: 57
gaacaccgtc acatgtcacc a                                              21

<210> SEQ ID NO 58
<211> LENGTH: 21
<212> TYPE: RNA
<213> ORGANISM: Homo sapiens

<400> SEQUENCE: 58
acaccgucac augucaccau u                                              21

<210> SEQ ID NO 59

```
<211> LENGTH: 21
<212> TYPE: RNA
<213> ORGANISM: Homo sapiens

<400> SEQUENCE: 59 uuguggcag uguacagugg u                                                    21

<210> SEQ ID NO 60
<211> LENGTH: 21
<212> TYPE: DNA
<213> ORGANISM: Homo sapiens

<400> SEQUENCE: 60
gatctccaga accgattgag c                                                   21

<210> SEQ ID NO 61
<211> LENGTH: 21
<212> TYPE: RNA
<213> ORGANISM: Homo sapiens

<400> SEQUENCE: 61
ucuccagaac cgauugagcu u                                                   21

<210> SEQ ID NO 62
<211> LENGTH: 21
<212> TYPE: RNA
<213> ORGANISM: Homo sapiens

<400> SEQUENCE: 62
uuagaggucu uggcuaacuc g                                                   21

<210> SEQ ID NO 63
<211> LENGTH: 21
<212> TYPE: DNA
<213> ORGANISM: Homo sapiens

<400> SEQUENCE: 63
gacttcagcc gctattgcaa g                                                   21

<210> SEQ ID NO 64
<211> LENGTH: 21
<212> TYPE: RNA
<213> ORGANISM: Homo sapiens

<400> SEQUENCE: 64
cuucagccgc uauugcaagu u                                                   21

<210> SEQ ID NO 65
<211> LENGTH: 21
<212> TYPE: RNA
<213> ORGANISM: Homo sapiens

<400> SEQUENCE: 65
uugaagucgg cgauaacguu c                                                   21

<210> SEQ ID NO 66
<211> LENGTH: 21
<212> TYPE: DNA
<213> ORGANISM: Homo sapiens

<400> SEQUENCE: 66
gagtatatga cagctgcggt a                                                   21
```

```
<210> SEQ ID NO 67
<211> LENGTH: 21
<212> TYPE: RNA
<213> ORGANISM: Homo sapiens

<400> SEQUENCE: 67
guauaugaca gcugcgguau u                                              21

<210> SEQ ID NO 68
<211> LENGTH: 21
<212> TYPE: RNA
<213> ORGANISM: Homo sapiens

<400> SEQUENCE: 68
uucauauacu gucgacgcca u                                              21

<210> SEQ ID NO 69
<211> LENGTH: 21
<212> TYPE: DNA
<213> ORGANISM: Homo sapiens

<400> SEQUENCE: 69
gaggattgag catcgaatgg t                                              21

<210> SEQ ID NO 70
<211> LENGTH: 21
<212> TYPE: RNA
<213> ORGANISM: Homo sapiens

<400> SEQUENCE: 70
ggauugagca ucgaaugguu u                                              21

<210> SEQ ID NO 71
<211> LENGTH: 21
<212> TYPE: RNA
<213> ORGANISM: Homo sapiens

<400> SEQUENCE: 71
uuccuaacuc guagcuuacc a                                              21

<210> SEQ ID NO 72
<211> LENGTH: 21
<212> TYPE: DNA
<213> ORGANISM: Homo sapiens

<400> SEQUENCE: 72
gagttcgcat caccagat c                                                21

<210> SEQ ID NO 73
<211> LENGTH: 21
<212> TYPE: RNA
<213> ORGANISM: Homo sapiens

<400> SEQUENCE: 73
guucgcauca caccagaucu u                                              21

<210> SEQ ID NO 74
<211> LENGTH: 21
<212> TYPE: RNA
<213> ORGANISM: Homo sapiens

<400> SEQUENCE: 74
uucaagcgua guguggucua g                                              21
```

```
<210> SEQ ID NO 75
<211> LENGTH: 21
<212> TYPE: DNA
<213> ORGANISM: Homo sapiens

<400> SEQUENCE: 75
tagtggaggc ggtatatgaa c                                          21

<210> SEQ ID NO 76
<211> LENGTH: 21
<212> TYPE: RNA
<213> ORGANISM: Homo sapiens

<400> SEQUENCE: 76
guggaggcgg uauaugaacu u                                          21

<210> SEQ ID NO 77
<211> LENGTH: 21
<212> TYPE: RNA
<213> ORGANISM: Homo sapiens

<400> SEQUENCE: 77
uucaccuccg ccauauacuu g                                          21

<210> SEQ ID NO 78
<211> LENGTH: 21
<212> TYPE: DNA
<213> ORGANISM: Homo sapiens

<400> SEQUENCE: 78
tattacatcg ttcatccggt g                                          21

<210> SEQ ID NO 79
<211> LENGTH: 21
<212> TYPE: RNA
<213> ORGANISM: Homo sapiens

<400> SEQUENCE: 79
uuacaucguu cauccggugu u                                          21

<210> SEQ ID NO 80
<211> LENGTH: 21
<212> TYPE: RNA
<213> ORGANISM: Homo sapiens

<400> SEQUENCE: 80
uuaauguagc aaguaggcca c                                          21

<210> SEQ ID NO 81
<211> LENGTH: 21
<212> TYPE: DNA
<213> ORGANISM: Homo sapiens

<400> SEQUENCE: 81
tatatgacag ctgcggtact t                                          21

<210> SEQ ID NO 82
<211> LENGTH: 21
<212> TYPE: RNA
<213> ORGANISM: Homo sapiens

<400> SEQUENCE: 82
uaugacagcu gcgguacuuu u                                          21
```

```
<210> SEQ ID NO 83
<211> LENGTH: 21
<212> TYPE: RNA
<213> ORGANISM: Homo sapiens

<400> SEQUENCE: 83
uuauacuguc gacgccauga a                                              21

<210> SEQ ID NO 84
<211> LENGTH: 21
<212> TYPE: DNA
<213> ORGANISM: Homo sapiens

<400> SEQUENCE: 84
tatgacagct gcggtacttg a                                              21

<210> SEQ ID NO 85
<211> LENGTH: 21
<212> TYPE: RNA
<213> ORGANISM: Homo sapiens

<400> SEQUENCE: 85
ugacagcugc gguacuugau u                                              21

<210> SEQ ID NO 86
<211> LENGTH: 21
<212> TYPE: RNA
<213> ORGANISM: Homo sapiens

<400> SEQUENCE: 86
uuacugucga cgccaugaac u                                              21
```